US008541569B2

(12) United States Patent
Srivastava et al.

(10) Patent No.: US 8,541,569 B2
(45) Date of Patent: Sep. 24, 2013

(54) PHOSPHORAMIDITES FOR SYNTHETIC RNA IN THE REVERSE DIRECTION, EFFICIENT RNA SYNTHESIS AND CONVENIENT INTRODUCTION OF 3'-END LIGANDS, CHROMOPHORES AND MODIFICATIONS OF SYNTHETIC RNA

(75) Inventors: Suresh C. Srivastava, Burlington, MA (US); Naveen P. Srivastava, Burlington, MA (US)

(73) Assignee: ChemGenes Corporation, Wilmington, MA (US)

( * ) Notice: Subject to any disclaimer, the term of this patent is extended or adjusted under 35 U.S.C. 154(b) by 382 days.

(21) Appl. No.: 12/708,827

(22) Filed: Feb. 19, 2010

(65) Prior Publication Data
US 2011/0137010 A1   Jun. 9, 2011

Related U.S. Application Data

(63) Continuation-in-part of application No. PCT/US2009/005063, filed on Sep. 8, 2009.

(60) Provisional application No. 61/191,065, filed on Sep. 6, 2008.

(51) Int. Cl.
*C07H 21/00* (2006.01)
(52) U.S. Cl.
USPC ..... 536/25.3; 536/25.31; 536/26.7; 536/26.8; 536/27.1; 536/27.13; 536/27.2
(58) Field of Classification Search
None
See application file for complete search history.

(56) References Cited

U.S. PATENT DOCUMENTS

| 6,043,353 | A | 3/2000 | Pon et al. |
|---|---|---|---|
| 2010/0324278 | A1 | 12/2010 | Srivastava et al. |
| 2011/0015382 | A1 | 1/2011 | Srivastava et al. |

FOREIGN PATENT DOCUMENTS

WO   WO 2010/027512 A2   3/2010

OTHER PUBLICATIONS

Matteucci et al. JACS (1981), vol. 103, pp. 3185-3191.*
Carroll et al. The Journal of Biological Chemistry (2003), vol. 278, No. 14, pp. 11979-11984.*
Lin et al. Organic Letters (2001), vol. 3, pp. 795-797.*
Ogilvie et al. Can. J. Chem. (1978), vol. 56, pp. 2768-2780.*
Aramini et al. Biochemistry (1996), vol. 35, pp. 9355-9365.*
Notification of Transmittal of the International Search Report and Written Opinion of the International Searching Authority from counterpart International Application No. PCT/US2011/025488, date of mailing: Nov. 18, 2011.
International Preliminary Report on Patentability for International Application No. PCT/US2009/005063 dated Mar. 8, 2011.
Notification of Transmittal of the International Search Report and the Written Opinion of the International Searching Authority, PCT/US2009/005063, mailed Apr. 20, 2010.
Wagner, T. and W. Pfleiderer, "Nucleotides, Part LXV, Synthesis of 2'-Deoxyribonucleoside 5'- Phosphoramidites: New Building Blocks for the Inverse (5'-3')-Oligonucleotide Approach," *Helvetica Chimica ACTA*, 83(8):2023-2035 (Aug. 2000).
Matysiak, S., et al., "Acetal Oligonucleotide Conjugates in Antisense Strategy," *Nucleotides & Nucleotides*, 16(5&6):855-861 (Jan. 1997).
Schwartz, M.E., et al., "A Universal Adapter for chemical Synthesis of DNA or RNA on Any Single Type of Solid Support," *Tetrahedron Letters*, 36(1):27-30 (Jan. 1995).
Ravikumar, V.T. and R.K. Kumar, "Stereoselective Synthesis of Alkylphosphonates: A Facile Rearrangement of Cyanoethyl-Protected Nucleoside Phosphoramidites," *Organic Process Research & Development*, 8(4):603-608 (May 2004).
Srivastava, S.C., et al., "RNA Synthesis: Phosphoramidites for RNA Synthesis in the Reverse Direction. Highly Efficient Synthesis and Application to Convenient Introduction of Ligands, Chromophores and Modifications of Synthetic RNA at the 3'-End," *Nucleic Acids Symposium Series*, 52(1):103-104 (Sep. 2008).
Van Boom, et al., "Chemical Synthesis of Small Oligoribonucleotides in Solution," Ch. 7 in Oligonucleotide Synthesis—A Practical Approach, M.J. Gait (ed), IRLS Press, Washington, DC, 1984, only pp. 153-183 supplied.
Becket, et al., "Enzymatic synthesis of Oligoribonucleotides," Ch. 8 in Oligonucleotide Synthesis—A Practical Approach, M. J. Gait (ed), IRLS Press, Washington, DC, 1984, only pp. 184-197 supplied.
Guzaev, et al., "A Conformationally Preorganized Universal Solid Support for Efficient Oligonucleotide Synthesis," *J. Amer. Chec. Soc.*, 125(9): 2380-2381 (2003): CAPlus Abstract No. 2003:98281, CA Doc. No. 138: 287895; see CAPLUS search of record for Abstract and structure.
Anon, Sigma Catalog—Biochemicals and Reagents, St. Louis, MO, 2002-2003: only p. 1424 supplied, see items R 4142 and R 6895.
Non-Office Action mailed Mar. 23, 2011 for U.S. Appl. No. 12/584,625, "RNA Synthesis-Phosphoramidites for Synthetic Rna in the Reverse Direction, and Application in Convenient Introduction of Ligands, Chromophores and Modifications of Synthetic RNA at the 3'-End".
Final Office Action mailed Dec. 5, 2011 for U.S. Appl. No. 12/584,625, "RNA Synthesis-Phosphoramidites for Synthetic RNA in the Reverse Direction, and Application in Convenient Introduction of Ligands, Chromophores and Modifications of Synthetic RNA at the 3!-End".

(Continued)

*Primary Examiner* — Patrick Lewis
(74) *Attorney, Agent, or Firm* — Hamilton, Brook, Smith & Reynolds, P.C.

(57) ABSTRACT

The present invention provides building blocks and methods for synthesizing very pure RNA in a form that can efficiently be modified at the 3' end. Reverse RNA monomer phosphoramidites have been developed for RNA synthesis in 5'→3' direction, leading to very clean oligo synthesis that allows for the introduction of various modifications at the 3'-end cleanly and efficiently. Higher coupling efficiency per step have been observed during automated oligo synthesis with the reverse RNA amidites disclosed herein, resulting in a greater ability to achieve higher purity and produce very long oligonucleotides. The use of the reverse RNA phosphoramidites in the synthetic process of this invention leads to oligonucleotides free of N+1 species.

32 Claims, 47 Drawing Sheets

(56) References Cited

OTHER PUBLICATIONS

Notice of Allowance mailed Jun. 29, 2012 for U.S. Appl. No. 12/584,625, "RNA Synthesis-Phosphoramidites for Synthetic RNA in the Reverse Direction, and Application in Convenient Introduction of Ligands, Chromophores and Modifications of Synthetic RNA at the 3'-End".

International Preliminary Report on Patentability from counterpart International Application No. PCT/US2011/025488, "Phosphoramidites for Synthetic RNA in the Reverse Direction", Dated Feb. 19, 2010.

Srivastava, S.C., et al., RNA Synthesis by Reverse Direction Process: Phosphoramidites and High Purity RNAs and Introduction of Ligands, Chromophores, and Modifications at 3'-End:, *Current Protocols in Nucleic Acid Chemistry*, 3.20.1-3.20.39 (Jun. 2011).

* cited by examiner

| UV -200nm Results | | | |
|---|---|---|---|
| Time | Height | Area | Area% |
| 17.367 | 2830 | 16392 | 0.45 |
| 17.663 | 7726 | 56557 | 1.57 |
| 17.729 | 8696 | 59447 | 1.65 |
| 17.788 | 6589 | 13327 | 0.37 |
| 17.883 | 2591 | 11215 | 0.31 |
| 18.288 | 5460 | 36314 | 1.01 |
| 18.333 | 5684 | 17932 | 0.50 |
| 18.358 | 5244 | 9679 | 0.27 |
| 18.392 | 4241 | 13766 | 0.38 |
| 18.542 | 3130 | 10727 | 0.30 |
| 18.613 | 3767 | 29016 | 0.80 |
| 18.692 | 3198 | 15183 | 0.42 |
| 19.033 | 7751 | 138415 | 3.84 |
| 19.712 | 5169 | 129375 | 3.59 |
| 20.171 | 6366 | 164372 | 4.56 |
| 20.550 | 5723 | 37498 | 1.04 |
| 21.837 | 85024 | 2847215 | 78.95 |
| Totals | 169189 | 3606430 | 100.00 |

FIG. 1C

| UV -200nm Results | | | |
|---|---|---|---|
| Time | Height | Area | Area% |
| 17.550 | 617 | 14699 | 0.30 |
| 17.892 | 3270 | 84889 | 1.71 |
| 18.896 | 884 | 42940 | 0.87 |
| 19.079 | 1609 | 30490 | 0.62 |
| 19.804 | 1764 | 59025 | 1.19 |
| 21.058 | 3925 | 112388 | 2.27 |
| 21.550 | 6191 | 142628 | 2.88 |
| 23.046 | 110750 | 4414791 | 89.09 |
| 24.904 | 198 | 53425 | 1.08 |
| Totals | 129208 | 4955275 | 100.00 |

FIG. 2C

| UV -200nm Results | | | |
|---|---|---|---|
| Time | Height | Area | Area% |
| 17.654 | 3340 | 12127 | 0.47 |
| 17.688 | 3452 | 9191 | 0.35 |
| 19.188 | 1584 | 9953 | 0.38 |
| 19.908 | 2163 | 9338 | 0.36 |
| 20.192 | 3111 | 11230 | 0.43 |
| 20.217 | 3348 | 9631 | 0.37 |
| 20.333 | 2004 | 14702 | 0.56 |
| 20.683 | 3015 | 28095 | 1.08 |
| 20.750 | 3029 | 26439 | 1.01 |
| 21.313 | 6686 | 155191 | 5.95 |
| 22.396 | 85829 | 2320510 | 89.03 |
| Totals | 117561 | 2606407 | 100.00 |

FIG. 3C

| UV -200nm Results | | | |
|---|---|---|---|
| Time | Height | Area | Area% |
| 17.304 | 1410 | 20826 | 0.60 |
| 17.663 | 1508 | 12887 | 0.37 |
| 17.762 | 1385 | 16366 | 0.47 |
| 19.208 | 1113 | 16037 | 0.46 |
| 19.929 | 1225 | 16374 | 0.47 |
| 20.383 | 1568 | 19428 | 0.56 |
| 20.967 | 908 | 10362 | 0.30 |
| 21.329 | 1635 | 17295 | 0.50 |
| 22.613 | 113518 | 3311035 | 95.29 |
| 23.383 | 1236 | 9540 | 0.27 |
| 23.879 | 1061 | 11808 | 0.34 |
| 24.271 | 820 | 12711 | 0.37 |
| Totals | 127387 | 3474669 | 100.00 |

FIG. 4C

UV – 200nm
Results

| Time | Height | Area | Area % |
|---|---|---|---|
| 17.867 | 2612 | 124390 | 3.14 |
| 19.767 | 2308 | 125679 | 3.17 |
| 22.879 | 114213 | 3710219 | 93.69 |
| Totals | 119133 | 3960288 | 100.00 |

| Peak No | Peak Name | Ret Time (min) | Peak Area (counts) | Result (Area %) |
|---|---|---|---|---|
| 1 | | 2.441 | 316307 | 0.19 |
| 2 | | 3.060 | 76365 | 0.04 |
| 3 | | 3.484 | 113880 | 0.07 |
| 4 | | 3.758 | 241658 | 0.14 |
| 5 | | 4.032 | 74999 | 0.04 |
| 6 | | 4.444 | 228289 | 0.13 |
| 7 | *3'-DMT-2'-Si-Adenosine (n-bz) OP | 5.067 | 50914964 | 29.99 |
| 8 | | 5.852 | 154261 | 0.09 |
| 9 | *3'-DMT-2'-Si-Adenosine (n-bz) OP | 6.391 | 116966520 | 68.90 |
| 10 | | 6.751 | 375067 | 0.22 |
| 11 | | 7.395 | 213522 | 0.13 |
| 12 | | 7.842 | 49721 | 0.03 |
| 13 | | 9.450 | 46789 | 0.03 |
| | Totals | | 169772352 | 100.00 |

Method Notes
Column: ChromSep SS (4.6 x 250mm) with ChromSep Guard Column OmniSpher 5 C18.
Detection: UV @ 254 nm
Solvent System:
Eluent A- 95% ACN in 0.1M TEAA [pH 7.5]
Eluent B- ACN
Gradient: Increse B (0-50%) in 25 min
Dissolved in: ACN
Flow Rate: 1.5 ml/min Sample Amount (mg): _____
Solvent Amount (ml): _____
Solvent: _____
Lot Number: _____
Exp. Date: _____

Analyst Initials: _____
PASS / FAIL

FIG. 11B

| Peak No | Peak Name | Ret Time (min) | Peak Area (counts) | Result (Area %) |
|---|---|---|---|---|
| 1 |  | 3.555 | 58277 | 0.02 |
| 2 |  | 4.644 | 162346 | 0.07 |
| 3 |  | 6.565 | 159521 | 0.07 |
| 4 |  | 6.860 | 314210 | 0.13 |
| 5 | *3'-DMT-2'-TBDMS ibuG OP | 7.418 | 136478720 | 56.37 |
| 6 | *3'-DMT-2'-TBDMS ibuG OP | 7.754 | 104749944 | 43.27 |
| 7 |  | 9.366 | 76431 | 0.03 |
| 8 |  | 9.755 | 99522 | 0.04 |
|  | Totals |  | 242098960 | 100.00 |

Method Notes
Column: ChromSep SS (4.6 x 250mm) with ChromSep Guard Column OmniSpher 5 C18.
Detection: UV @ 254 nm
Solvent System:
Eluent A- 90% ACN in 0.1M TEAA [pH 7.5]
Eluent B- 95% ACN in 0.1M TEAA
Gradient: Increse B (0-50%) in 20 min
Dissolved in: ACN
Flow Rate: 1.5 ml/min

FIG. 12B

| Peak No | Peak Name | Ret Time (min) | Peak Area (counts) | Result (Area %) |
|---|---|---|---|---|
| 1 |  | 2.238 | 51545 | 0.02 |
| 2 |  | 2.906 | 257959 | 0.11 |
| 3 |  | 3.171 | 73365 | 0.03 |
| 4 |  | 3.378 | 761764 | 0.32 |
| 5 |  | 3.769 | 328242 | 0.14 |
| 6 |  | 3.971 | 178872 | 0.08 |
| 7 |  | 4.201 | 291630 | 0.12 |
| 8 | *3'-DMT-2'-TBDMS Cytidine (n-ac) OP | 4.618 | 118156432 | 49.60 |
| 9 |  | 5.264 | 101551 | 0.04 |
| 10 | *3'-DMT-2'-TBDMS Cytidine (n-ac) OP | 6.064 | 117767928 | 49.44 |
| 11 |  | 6.872 | 112221 | 0.05 |
| 12 |  | 7.346 | 67182 | 0.03 |
| 13 |  | 10.956 | 51009 | 0.02 |
| Totals |  |  | 238199696 | 100.00 |

Method Notes
Column: ChromSep SS (4.6 x 250mm) with ChromSep Guard Column OmniSpher 5 C18.
Detection: UV @ 254 nm
Solvent System:
Eluent A- 95% ACN in 0.1M TEAA [pH 7.5]
Eluent B- ACN
Gradient: Increse B (0-50%) in 20 min
Dissolved in: ACN
Flow Rate: 1.5 ml/min Sample Amount (mg): _____
Solvent Amount (ml): _____
Solvent: _____
Lot Number: _____
Exp. Date: _____

Analyst Initials: _____
PASS / FAIL

FIG. 13B

| Peak No | Peak Name | Ret Time (min) | Peak Area (counts) | Result (Area %) |
|---|---|---|---|---|
| 1 | | 2.239 | 1713140 | 0.91 |
| 2 | | 2.672 | 42783 | 0.02 |
| 3 | | 2.958 | 157395 | 0.08 |
| 4 | | 3.209 | 130255 | 0.07 |
| 5 | | 3.354 | 127776 | 0.07 |
| 6 | | 3.861 | 317837 | 0.17 |
| 7 | *3'-DMT-2'-TBDMS Uridine OP | 4.213 | 103188256 | 55.05 |
| 8 | *3'-DMT-2'-TBDMS Uridine OP | 5.098 | 81737304 | 43.61 |
| 9 | | 6.314 | 31376 | 0.02 |
| | Totals | | 187446128 | 100.00 |

Method Notes
Column: ChromSep SS (4.6 x 250mm) with ChromSep Guard Column OmniSpher 5 C18.
Detection: UV @ 254 nm
Solvent System:
Eluent A- 95% ACN in 0.1M TEAA [pH 7.5]
Eluent B- ACN
Gradient: Increse B (0-50%) in 20 min
Dissolved in: ACN
Flow Rate: 1.5 ml/min Sample Amount (mg): _____
Solvent Amount (ml): _____
Solvent: _____
Lot Number: _____
Exp. Date: _____

Analyst Initials: _____
PASS / FAIL

FIG. 14B

UV - 200nm
Results

| Time | Height | Area | Area % |
|---|---|---|---|
| 18.929 | 453 | 2418 | 0.05 |
| 19.004 | 550 | 2554 | 0.05 |
| 19.692 | 868 | 2721 | 0.06 |
| 20.042 | 8898 | 143692 | 2.92 |
| 22.408 | 140089 | 4552901 | 92.63 |
| 22.933 | 659 | 139402 | 2.84 |
| 23.087 | 3128 | 21046 | 0.43 |
| 23.142 | 3459 | 13274 | 0.27 |
| 23.329 | 1344 | 2550 | 0.05 |
| 23.354 | 1197 | 3151 | 0.06 |
| 23.517 | 834 | 3423 | 0.07 |
| 23.692 | 919 | 2454 | 0.05 |
| 23.729 | 1006 | 3436 | 0.07 |
| 23.900 | 828 | 3525 | 0.07 |
| 24.288 | 829 | 2412 | 0.05 |
| 24.333 | 1100 | 3250 | 0.07 |
| 24.717 | 1151 | 2318 | 0.05 |
| 24.771 | 1473 | 7753 | 0.16 |
| 24.821 | 861 | 2754 | 0.06 |

| Totals | | | |
|---|---|---|---|
| | 169646 | 4915034 | 100.00 |

FIG. 15C

UV - 200nm
Results

| Time | Height | Area | Area % |
|---|---|---|---|
| 21.879 | 1374 | 5992 | 0.97 |
| 21.925 | 1346 | 3836 | 0.62 |
| 21.958 | 870 | 2521 | 0.41 |
| 24.087 | 34498 | 607012 | 98.01 |

| Totals | 38088 | 619361 | 100.00 |
|---|---|---|---|

FIG. 15E

SEQUENCE LISTING

<160> NUMBER OF SEQ ID NOS: 11

<210> SEQ ID NO 1
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(21)
<223> OTHER INFORMATION: All c's, a's, g's and u's are ribonucleic acids
<220> FEATURE:
<221> NAME/KEY: misc_feature
<222> LOCATION: (1)...(21)
<223> OTHER INFORMATION: Internucleotide linkage formed by BTT (5-Benzyl
      thio-1-1H-tetrazole) activator
<220> FEATURE:
<221> NAME/KEY: misc_feature
<222> LOCATION: 1, 20
<223> OTHER INFORMATION: Adenosine is
      N6-Benzoyl-2'-O-Me-3'-O-DMT-adenosine-OP
<220> FEATURE:
<221> NAME/KEY: misc_feature
<222> LOCATION: 21
<223> OTHER INFORMATION: u is 2'-O-TBDMS-3'-O-DMT-uridine-OP
<220> FEATURE:
<221> NAME/KEY: misc_feature
<222> LOCATION: (2)...(19)
<223> OTHER INFORMATION: All a's are
      N6-Benzoyl-2'-O-TBDMS-3'-O-DMT-adenosine-OP;
      all c's are
      N4-Acetyl-2'-O-TBDMS-3'-O-DMT-cytidine-OP
<220> FEATURE:
<221> NAME/KEY: misc_feature
<222> LOCATION: (2)...(19)
<223> OTHER INFORMATION: all g's are
      N2-Isobutryl-2'-O-TBDMS-3'-O-DMT-guanosine-OP;
      all u's are 2'-O-TBDMS-3'-O-DMT-uridine-OP

<400> SEQUENCE: 1
aacagcauac aucucgacca u                                                  21

<210> SEQ ID NO 2
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(21)
<223> OTHER INFORMATION: All c's, a's, g's and u's are ribonucleic acids
<220> FEATURE:
<221> NAME/KEY: misc_feature
<222> LOCATION: (1)...(21)
<223> OTHER INFORMATION: Phosphorothioate internucleotide linkage
<220> FEATURE:
<221> NAME/KEY: misc_feature
<222> LOCATION: 1, 20
<223> OTHER INFORMATION: Adenosine is
      N6-Benzoyl-2'-O-Me-3'-O-DMT-adenosine-OP
<220> FEATURE:
<221> NAME/KEY: misc_feature
<222> LOCATION: 21
<223> OTHER INFORMATION: u is 2'-O-TBDMS-3'-O-DMT-uridine-OP
<220> FEATURE:
<221> NAME/KEY: misc_feature
<222> LOCATION: (2)...(19)
<223> OTHER INFORMATION: All a's are
      N6-Benzoyl-2'-O-TBDMS-3'-O-DMT-adenosine-OP;
      all c's are
      N4-Acetyl-2'-O-TBDMS-3'-O-DMT-cytidine-OP
<220> FEATURE:
<221> NAME/KEY: misc_feature

```
<222> LOCATION: (2)...(19)
<223> OTHER INFORMATION: all g's are
      N2-Isobutryl-2'-O-TBDMS-3'-O-DMT-guanosine-OP;
      all u's are 2'-O-TBDMS-3'-O-DMT-uridine-OP

<400> SEQUENCE: 2
aacagcauac aucucgacca u                                              21

<210> SEQ ID NO 3
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(21)
<223> OTHER INFORMATION: All c's, a's, g's and u's are ribonucleic acids
<220> FEATURE:
<221> NAME/KEY: misc_feature
<222> LOCATION: (1)...(21)
<223> OTHER INFORMATION: Phosphodiester internucleotide linkage
<220> FEATURE:
<221> NAME/KEY: misc_feature
<222> LOCATION: 1, 20
<223> OTHER INFORMATION: a is N6-Benzoyl-2'-O-Me-3'-O-DMT-adenosine-OP
<220> FEATURE:
<221> NAME/KEY: misc_feature
<222> LOCATION: 21
<223> OTHER INFORMATION: u is 2'-O-TBDMS-3'-O-DMT-uridine-OP
<220> FEATURE:
<221> NAME/KEY: misc_feature
<222> LOCATION: (2)...(19)
<223> OTHER INFORMATION: All a's are
      N6-Benzoyl-2'-O-TBDMS-3'-O-DMT-adenosine-OP;
      all c's are
      N4-Acetyl-2'-O-TBDMS-3'-O-DMT-cytidine-OP
<220> FEATURE:
<221> NAME/KEY: misc_feature
<222> LOCATION: (2)...(19)
<223> OTHER INFORMATION: all g's are
      N2-Isobutryl-2'-O-TBDMS-3'-O-DMT-guanosine-OP;
      all u's are 2'-O-TBDMS-3'-O-DMT-uridine-OP

<400> SEQUENCE: 3
aacagcauac aucucgacca u                                              21

<210> SEQ ID NO 4
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(21)
<223> OTHER INFORMATION: All c's, a's, g's and u's are ribonucleic acids
<220> FEATURE:
<221> NAME/KEY: misc_feature
<222> LOCATION: (1)...(21)
<223> OTHER INFORMATION: All a's are
      N6-Benzoyl-2'-O-TBDMS-3'-O-DMT-adenosine-OP;
      all c's are
      N4-Acetyl-2'-O-TBDMS-3'-O-DMT-cytidine-OP
<220> FEATURE:
<221> NAME/KEY: misc_feature
<222> LOCATION: (1)...(21)
<223> OTHER INFORMATION: all g's are
      N2-Isobutryl-2'-O-TBDMS-3'-O-DMT-guanosine-OP;
      all u's are 2'-O-TBDMS-3'-O-DMT-uridine-OP
<220> FEATURE:
<221> NAME/KEY: misc_feature
<222> LOCATION: (1)...(21)
<223> OTHER INFORMATION: Phosphodiester internucleotide linkage

<400> SEQUENCE: 4
```
cacagcauac aucucgacca u                                          21

<210> SEQ ID NO 5
<211> LENGTH: 75
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(75)
<223> OTHER INFORMATION: All c's, a's, g's and u's are ribonucleic
      acids.
<220> FEATURE:
<221> NAME/KEY: misc_feature
<222> LOCATION: (1)...(75)
<223> OTHER INFORMATION: All a's are
      N6-Benzoyl-2'-O-TBDMS-3'-O-DMT-adenosine-OP;
      all c's are
      N4-Acetyl-2'-O-TBDMS-3'-O-DMT-cytidine-OP
<220> FEATURE:
<221> NAME/KEY: misc_feature
<222> LOCATION: (1)...(75)
<223> OTHER INFORMATION: all g's are
      N2-Isobutryl-2'-O-TBDMS-3'-O-DMT-guanosine-OP;
      all u's are 2'-O-TBDMS-3'-O-DMT-uridine-OP

<400> SEQUENCE: 5
acgcgggcuu gucccugaac uuggaccug ggagucuauu uuucagacua cgagauggcu    60
gacucgauag gcccg                                                   75

<210> SEQ ID NO 6
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(21)
<223> OTHER INFORMATION: All c's, a's, g's and u's are ribonucleic acids
<220> FEATURE:
<221> NAME/KEY: misc_feature
<222> LOCATION: (1)...(21)
<223> OTHER INFORMATION: Phosphothioate internucleotide linkage
<220> FEATURE:
<221> NAME/KEY: misc_feature
<222> LOCATION: 1, 20
<223> OTHER INFORMATION: Adenosine is
      N6-Benzoyl-2'-O-Me-3'-O-DMT-adenosine-OP
<220> FEATURE:
<221> NAME/KEY: misc_feature
<222> LOCATION: 21
<223> OTHER INFORMATION: u is 2'-O-TBDMS-3'-O-DMT-uridine-OP
<220> FEATURE:
<221> NAME/KEY: misc_feature
<222> LOCATION: (2)...(19)
<223> OTHER INFORMATION: All a's are
      N6-Benzoyl-2'-O-TBDMS-3'-O-DMT-adenosine-OP;
      all c's are
      N4-Acetyl-2'-O-TBDMS-3'-O-DMT-cytidine-OP
<220> FEATURE:
<221> NAME/KEY: misc_feature
<222> LOCATION: (2)...(19)
<223> OTHER INFORMATION: all g's are
      N2-Isobutryl-2'-O-TBDMS-3'-O-DMT-guanosine-OP;
      all u's are 2'-O-TBDMS-3'-O-DMT-uridine-OP

<400> SEQUENCE: 6
aacagcauac aucucgacca u                                          21

<210> SEQ ID NO 7
<211> LENGTH: 21

```
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(21)
<223> OTHER INFORMATION: All c's, a's, g's and u's are ribonucleic
      acids.
<220> FEATURE:
<221> NAME/KEY: misc_feature
<222> LOCATION: 1, 20
<223> OTHER INFORMATION: a is N6-Benzoyl-2'-O-Me-3'-O-DMT-adenosine-OP
<220> FEATURE:
<221> NAME/KEY: misc_feature
<222> LOCATION: (2)...(19)
<223> OTHER INFORMATION: All a's are
      N6-Benzoyl-2'-O-TBDMS-3'-O-DMT-adenosine-OP;
      all c's are
      N4-Acetyl-2'-O-TBDMS-3'-O-DMT-cytidine-OP
<220> FEATURE:
<221> NAME/KEY: misc_feature
<222> LOCATION: (2)...(19)
<223> OTHER INFORMATION: all g's are
      N2-Isobutryl-2'-O-TBDMS-3'-O-DMT-guanosine-OP;
      all u's are 2'-O-TBDMS-3'-O-DMT-uridine-OP
<220> FEATURE:
<221> NAME/KEY: misc_feature
<222> LOCATION: 21
<223> OTHER INFORMATION: u is  2'-O-TBDMS-3'-O-DMT-uridine-OP
<220> FEATURE:
<221> NAME/KEY: misc_feature
<222> LOCATION: (1)...(21)
<223> OTHER INFORMATION: Phosphorothioate internucleotide linkage

<400> SEQUENCE: 7
aacagcauac aucucgacca u                                            21

<210> SEQ ID NO 8
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(21)
<223> OTHER INFORMATION: All c's, a's, g's and u's are ribonucleic
      acids.
<220> FEATURE:
<221> NAME/KEY: misc_feature
<222> LOCATION: 2, 21
<223> OTHER INFORMATION: a is N6-Benzoyl-2'-O-Me-3'-O-DMT-adenosine-OP
<220> FEATURE:
<221> NAME/KEY: misc_feature
<222> LOCATION: 1
<223> OTHER INFORMATION: u is 2'-O-TBDMS-3'-O-DMT-uridine-OP
<220> FEATURE:
<221> NAME/KEY: misc_feature
<222> LOCATION: (3)...(20)
<223> OTHER INFORMATION: All a's are
      N6-Benzoyl-2'-O-TBDMS-3'-O-DMT-adenosine-OP;
      all c's are
      N4-Acetyl-2'-O-TBDMS-3'-O-DMT-cytidine-OP
<220> FEATURE:
<221> NAME/KEY: misc_feature
<222> LOCATION: (3)...(20)
<223> OTHER INFORMATION: all g's are
      N2-Isobutryl-2'-O-TBDMS-3'-O-DMT-guanosine-OP;
      all u's are 2'-O-TBDMS-3'-O-DMT-uridine-OP

<400> SEQUENCE: 8
uaccagcucu acauacgaca a                                            21

<210> SEQ ID NO 9
<211> LENGTH: 21
```

```
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(21)
<223> OTHER INFORMATION: All c's, a's, g's and u's are ribonucleic
      acids.
<220> FEATURE:
<221> NAME/KEY: misc_feature
<222> LOCATION: 2, 21
<223> OTHER INFORMATION: a is N6-Benzoyl-2'-O-Me-3'-O-DMT-adenosine-OP
<220> FEATURE:
<221> NAME/KEY: misc_feature
<222> LOCATION: 1
<223> OTHER INFORMATION: u is 2'-O-TBDMS-3'-O-DMT-uridine-OP
<220> FEATURE:
<221> NAME/KEY: misc_feature
<222> LOCATION: (3)...(20)
<223> OTHER INFORMATION: All a's are
      N6-Benzoyl-2'-O-TBDMS-3'-O-DMT-adenosine-OP;
      all c's are
      N4-Acetyl-2'-O-TBDMS-3'-O-DMT-cytidine-OP
<220> FEATURE:
<221> NAME/KEY: misc_feature
<222> LOCATION: (3)...(20)
<223> OTHER INFORMATION: all g's are
      N2-Isobutryl-2'-O-TBDMS-3'-O-DMT-guanosine-OP;
      all u's are 2'-O-TBDMS-3'-O-DMT-uridine-OP
<220> FEATURE:
<221> NAME/KEY: misc_feature
<222> LOCATION: (1)...(21)
<223> OTHER INFORMATION: Phosphorothioate internucleotide linkage

<400> SEQUENCE: 9
uaccagcucu acauacgaca a                                              21

<210> SEQ ID NO 10
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(21)
<223> OTHER INFORMATION: All c's, a's, g's and u's are ribonucleic
      acids.
<220> FEATURE:
<221> NAME/KEY: misc_feature
<222> LOCATION: (1)...(21)
<223> OTHER INFORMATION: All a's are
      N6-Benzoyl-2'-O-TBDMS-3'-O-DMT-adenosine-OP;
      all c's are
      N4-Acetyl-2'-O-TBDMS-3'-O-DMT-cytidine-OP
<220> FEATURE:
<221> NAME/KEY: misc_feature
<222> LOCATION: (1)...(21)
<223> OTHER INFORMATION: all g's are
      N2-Isobutryl-2'-O-TBDMS-3'-O-DMT-guanosine-OP;
      all u's are 2'-O-TBDMS-3'-O-DMT-uridine-OP

<400> SEQUENCE: 10
uaccagcucu acauacgaca c                                              21

<210> SEQ ID NO 11
<211> LENGTH: 76
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(76)
<223> OTHER INFORMATION: All c's, a's, g's and u's are ribonucleic
```

```
         acids.
<220>  FEATURE:
<221>  NAME/KEY: misc_feature
<222>  LOCATION: (1)...(76)
<223>  OTHER INFORMATION: All a's are
       N6-Benzoyl-2'-O-TBDMS-3'-O-DMT-adenosine-OP;
       all c's are
       N4-Acetyl-2'-O-TBDMS-3'-O-DMT-cytidine-OP
<220>  FEATURE:
<221>  NAME/KEY: misc_feature
<222>  LOCATION: (1)...(76)
<223>  OTHER INFORMATION: all g's are
       N2-Isobutryl-2'-O-TBDMS-3'-O-DMT-guanosine-OP;
       all u's are 2'-O-TBDMS-3'-O-DMT-uridine-OP

<400>  SEQUENCE: 11 gcccggauag cucagucggu agagcaucag acuuuuuauc ugagggucca ggguucaagu     60
cccuguucgg gcgcca                                                    76
```

PHOSPHORAMIDITES FOR SYNTHETIC RNA IN THE REVERSE DIRECTION, EFFICIENT RNA SYNTHESIS AND CONVENIENT INTRODUCTION OF 3'-END LIGANDS, CHROMOPHORES AND MODIFICATIONS OF SYNTHETIC RNA

RELATED APPLICATIONS

This application is a continuation-in-part of International Application No. PCT/US2009/005063, which designated the United States and was filed on Sep. 8, 2009, published in English, which claims the benefit of U.S. Provisional Application No. 61/191,065, filed on Sep. 6, 2008.

The entire teachings of the above application(s) are incorporated herein by reference.

BACKGROUND OF THE INVENTION

Defined sequence RNA synthesis in the 3'→5' direction is now well established and currently in use for synthesis and development of a vast variety of therapeutic grade RNA aptamers, tRNAs, siRNA and biologically active RNA molecules. The chemical synthesis of RNA is desirable because it avoids the inefficiencies and limitation of scale of synthesis such as by in vitro transcription by T7 RNA polymerase (See Helm, M., et al., *RNA*, 5:618-621, 1999, the entire teachings of which are incorporated herein by reference). Chemical synthesis of RNA is desirable for studies of RNA structure and function, and many useful modifications can be achieved selectively, such as site specific introduction of functional groups; viz., disulphide cross linking as a probe of RNA tertiary structures (See Maglott, E. J., Glick, G. D., *Nucl. Acids Res.*, 26: 1301-1308, 1999, the entire teachings of which are incorporated herein by reference).

This approach utilizes a ribonucleoside with suitable N-protecting group: generally 5'-protecting group, the most popular being dimethoxytriphenyl, i.e., the DMT group; 2'-protecting group, out of which most popular is t-Butyldimethylsilyl ether; and, a 3'-phosphoramidite, the most popular of which is cyanoethyl diisopropyl. This component is then coupled with a nucleoside with a suitable N-protecting group, 2' or 3' succinate of a ribonucleoside attached to a solid support. The coupling of component 1 and 5'-OH-n-protected-2',3'-protected-nucleoside are also achieved in solution phase in presence of an activator leading to dimers and oligoribonucleotides, followed by oxidation (3'→5' direction synthesis), also leads to a protected dinucleotide having a 3'→5'-internucleotide linkage, Ogilvie, K. K., *Can. J. Chem.*, 58: 2686, 1980 (scheme 1).

A number of such synthetic RNA require a modification or labeling of the 3'-end of an oligonucleotide. The synthesis of 3'-end modified RNA requiring lipophilic, long chain ligands or chromophores, using 3'→5' synthesis methodology are challenging, difficult to synthesize and generally result in low coupling efficiency and lower purity of the final oligonucleotide, in general. Additional purifications are generally required. Therefore, new synthetic methodologies are needed to synthesize RNA molecules quickly, and cleanly and in a form that allows for modification at the 3' end.

SUMMARY OF THE INVENTION

The present invention provides building blocks and methods for synthesizing very pure RNA in a form that can efficiently be modified at the 3' end. Reverse RNA monomer phosphoramidites have been developed for RNA synthesis in 5'→3' direction, leading to very clean oligo synthesis that allows for the introduction of various modifications at the 3'-end cleanly and efficiently.

Higher coupling efficiency per step have been observed during automated oligo synthesis with the reverse RNA amidites disclosed herein, resulting in a greater ability to achieve higher purity and produce very long oligonucleotides. The use of the reverse RNA phosphoramidites in the synthetic process of this invention leads to oligonucleotides free of N+1 species. The N+1 species leads to impurities that broaden out the desired peak during HPLC analysis/purification or Gel purification. The N+1 species arise by addition of the two nucleobases within the same coupling cycle rather than just one nucleobase.

In one embodiment, the invention relates to a compound of Formula Ia, Ib, Ic, or Id:

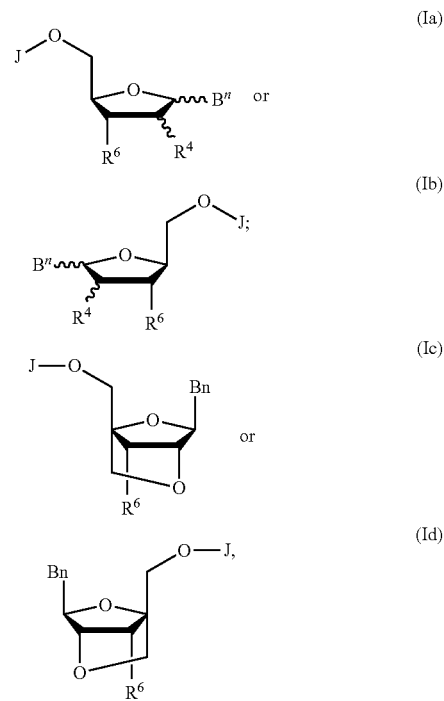

or a salt thereof, wherein
J is H,

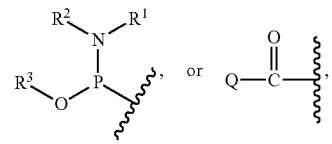

wherein ⌇ indicates where J is attached to the O atom;

Q is a) a support comprised of a linking group and a spacer that can be cleaved to form a hydroxy group; or b) an aliphatic chain, aromatic group, substituted or unsubstituted aromatic, a substituted or unsubstituted phenoxy, or levulinyl;

$R^1$ is a substituted or unsubstituted $(C_1-C_{12})$alkyl group, a substituted or unsubstituted $(C_3-C_{20})$cycloalkyl group, or a substituted or unsubstituted $(C_3-C_{20})$cycloalkyl$(C_1-C_{12})$alkyl group, wherein the alkyl or cycloalkyl groups optionally include intervening heteroatoms independently selected from NH, NR$^7$, O and S;

R$^2$ is a substituted or unsubstituted (C$_1$-C$_{12}$)alkyl group, a substituted or unsubstituted (C$_3$-C$_{20}$)cycloalkyl group, or a substituted or unsubstituted (C$_3$-C$_{20}$)cycloalkyl(C$_1$-C$_{12}$)alkyl group, wherein the alkyl or cycloalkyl groups optionally include intervening heteroatoms independently selected from NH, NR$^7$, O and S;

or R$^1$ and R$^2$ taken together with the nitrogen atom to which they are bound form a 4-7 membered non-aromatic heterocyclyl, wherein the heterocyclyl formed may optionally include intervening heteroatoms independently selected from NH, NR$^7$, O and S;

R$^3$ is a phosphate protecting group;

R$^4$ is a -halo, —R$^5$, —NR$^7$R$^8$, —OR$^9$, —SR$^{10}$, or 2'-blocking group; or when Structural Formula Ia or Ib is:

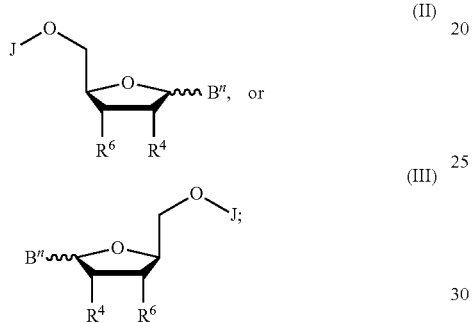

wherein R$^4$ is further selected from O—Si(R$^{11}$)$_3$ or O—CH$_2$—Si(R)$_3$; or when Structural Formula Ia or Ib is:

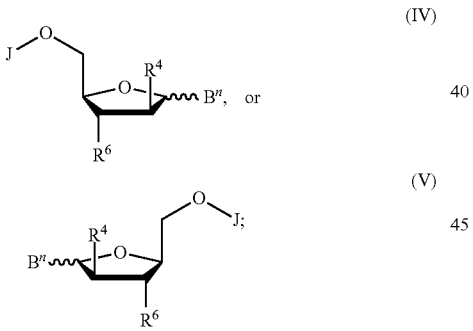

R$^4$ is further selected from —OC(=O)R$^{12}$;

each R$^5$ is independently a substituted or unsubstituted (C$_1$-C$_{12}$)alkyl group, a substituted or unsubstituted (C$_2$-C$_{12}$)alkenyl group, a substituted or unsubstituted (C$_2$-C$_{12}$)alkynyl group, or a substituted or unsubstituted phenyl, wherein the alkyl, alkenyl, alkynyl and the phenyl groups optionally includes intervening heteroatoms independently selected from NH, NR$^5$, O and S; and may optionally terminate with —NR$^7$R$^8$, (C$_1$-C$_4$)alkylamino, di(C$_1$-C$_4$)alkylamino, —OR$^9$, (C$_1$-C$_6$)alkoxy, benzyl or substituted benzyl, —SR$^{10}$; or —S—(C$_1$-C$_6$) alkyl group;

R$^6$ is —H or —O—Z;

each R$^7$ is independently a fluorenylmethyloxycarbonyl; —C(=O)—(CH$_2$)$_{1-16}$NR$^8$C(=O)CF$_3$; —C(=O)—(CH$_2$)$_{1-16}$NR$^8$C(=O)-phthalimide; —C(=O)—(CH$_2$)$_{1-16}$-phthalimide; NR$^8$C(=O)-phthalimide; a substituted or unsubstituted (C$_1$-C$_{12}$) alkyl group, a substituted or unsubstituted (C$_2$-C$_{12}$) alkenyl group, or a substituted or unsubstituted (C$_2$-C$_{12}$)alkynyl group;

each R$^8$ is H or a substituted or unsubstituted (C$_1$-C$_{12}$)alkyl group, a substituted or unsubstituted (C$_2$-C$_{12}$)alkenyl group, or a substituted or unsubstituted (C$_2$-C$_{12}$)alkynyl group;

each R$^9$ is independently —C(=O)—(CH$_2$)$_{1-16}$CH$_3$, a substituted or unsubstituted (C$_2$-C$_{12}$)alkenyl group, or a substituted or unsubstituted (C$_2$-C$_{12}$)alkynyl group;

each R$^{10}$ is independently —S(C$_1$-C$_6$)alkyl, —C(=O)—(CH$_2$)$_{1-16}$CH$_3$; a substituted or unsubstituted (C$_2$-C$_{12}$) alkenyl group, or a substituted or unsubstituted (C$_2$-C$_{12}$) alkynyl group;

each R$^{11}$ is independently a substituted or unsubstituted (C$_1$-C$_{12}$)alkyl group, a substituted or unsubstituted (C$_2$-C$_{12}$)alkenyl group, or a substituted or unsubstituted (C$_2$-C$_{12}$)alkynyl group;

each R$^{12}$ is independently a substituted or unsubstituted (C$_1$-C$_{12}$)alkyl group, a substituted or unsubstituted (C$_2$-C$_{12}$)alkenyl group, or a substituted or unsubstituted (C$_2$-C$_{12}$)alkynyl group, or a substituted or unsubstituted aryl group;

Z is an acid labile protecting group;

R$^n$ is hydrogen or an optionally substituted nucleobase optionally functionalized at each exocyclic amine with an amine protecting group, wherein the nucleobase is selected from:

N6,N6-dimethyl adenine, N6-benzoyladenine, N-1-methyladenine, 7-deazaadenine, 7-deaza-8-azaadenine, 3-deazaadenine, ethenoadenine, isoguanine, N1-methylguanine, 7-iodo-7-deazaguanine, 7-deaza-7-iodo adenine, 7-deaza-7-iodo-6-oxopurine, 5-iodo-5-methyl-7-deazaguanine, 7-deazaguanine substituted with —C≡C(CH$_2$)$_{1-8}$-pthlamide, 7-deaza-8-azaguanine, 8-methylguanine, 8-bromoguanine, 8-aminoguanine, hypoxanthine, 6-methoxypurine, 7-deaza-6-oxopurine, 6-oxopurine, 2-aminopurine, 2,6-diaminopurine, 8-bromopurine, 8-aminopurine, 8-alkylaminopurine, 8-alkylaminopurine, thymine, N-3 methyl thymine, 5-acetoxymethylcytosine, 5-azacytosine, isocytosine, N4(C$_1$-C$_6$)alkylcytosine, N-3(C$_1$-C$_6$)alkylcytidine, 5-propynylcytosine, 5-iodo-cytosine, 5-(C$_1$-C$_6$)alkylcytosine, 5-aryl(C$_1$-C$_6$)alkylcytosine, 5-trifluoromethylcytosine, 5-methylcytosine, ethenocytosine, cytosine and uracil substituted with —CH=CH—C(=O)NH(C$_1$-C$_6$)alkyl, cytosine and uracil substituted with —C≡C—CH$_2$-phthalimide, C$_6$)alkyl, 4-thiouracil, 2-thiouracil, N$^3$-thiobenzoylethyluracil, 5-propynyluracil, 5-acetoxymethyluracil, 5-fluorouracil, 5-chlorouracil, 5-bromouracil, 5-iodouracil, 4-thiouracil, N-3-(C$_1$-C$_6$)alkyluracil, 5-(3-aminoallyl)-uracil, 5-(C$_1$-C$_6$) alkyluracil, 5-aryl(C$_1$-C$_6$)alkyluracil, 5-trifluoro methyluracil, 4-triazolyl-5-methyluracil, 2-pyridone, 2-oxo-5-methylpyrimidine, 2-oxo-4-methylthio-5-methylpyrimidine, 2-thiocarbonyl-4-oxo-5-methylpyrimidine, and 4-oxo-5-methylpyrimidine;

wherein any substitutable nitrogen atom within the nucleobase or on the exocyclic amine is optionally substituted with fluorenylmethyloxycarbonyl; —C(=O)OPh; —C(=O)(C$_1$-C$_{16}$)alkyl; —C(=O) CH$_2$CH$_2$CH=CH$_{21}$; —C(=O)(C$_1$-C$_{16}$)alkylene-C (=O)OH; —C(=O)(C$_1$-C$_{16}$)alkylene-C(=O)O(C$_1$-C$_6$)alkyl; =CR$^8$N(C$_1$-C$_6$)alkyl)$_2$; —C(=O)—NR$^8$—(CH$_2$)$_{1-16}$NR$^8$C(=O)CF$_3$; —C(=O)—

(CH$_2$)$_{1-16}$NR$^8$C(=O)CF$_3$;  —C(=O)—NR$^8$
(CH$_2$)$_{1-16}$NR$^8$C(=O)-phthalimide;  —C(=O)—
(CH$_2$)$_{1-16}$-phthalimide; and

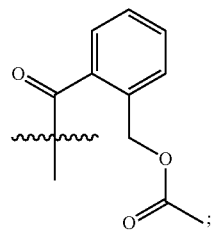

wherein any substitutable oxygen atom within the nucleobase is optionally substituted with —C(=O)N(C$_1$-C$_6$alkyl)$_2$-C(=O)N(phenyl)$_2$.

In another embodiment, the invention relates to a compound of Formula Ia, Ib, Ic, or Id:

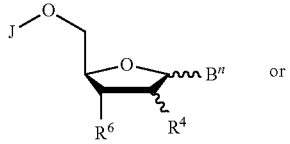 (Ia)

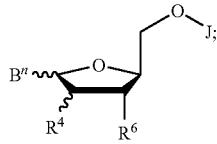 (Ib)

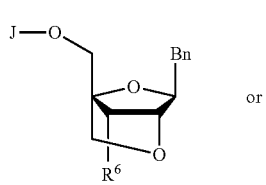 (Ic)

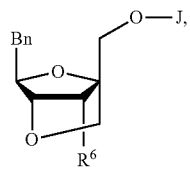 (Id)

or a salt thereof, wherein
J is H,

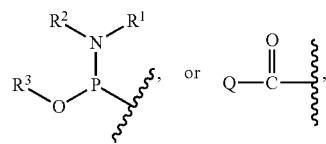

wherein ⸽ indicates where J is attached to the O atom;
Q is a) a support comprised of a linking group and a spacer that can be cleaved to form a hydroxy group; or b) an aliphatic chain, aromatic group, substituted or unsubstituted aromatic, a substituted or unsubstituted phenoxy, or levulinyl;

R$^1$ is a substituted or unsubstituted (C$_1$-C$_{12}$)alkyl group, a substituted or unsubstituted (C$_3$-C$_{20}$)cycloalkyl group, or a substituted or unsubstituted (C$_3$-C$_{20}$)cycloalkyl(C$_1$-C$_{12}$)alkyl group, wherein the alkyl or cycloalkyl groups optionally include intervening heteroatoms independently selected from NH, NR$^7$, O and S;

R$^2$ is a substituted or unsubstituted (C$_1$-C$_{12}$)alkyl group, a substituted or unsubstituted (C$_3$-C$_{20}$)cycloalkyl group, or a substituted or unsubstituted (C$_3$-C$_{20}$)cycloalkyl(C$_1$-C$_{12}$)alkyl group, wherein the alkyl or cycloalkyl groups optionally include intervening heteroatoms independently selected from NH, NR$^7$, O and S;

or R$^1$ and R$^2$ taken together with the nitrogen atom to which they are bound form a 4-7 membered non-aromatic heterocyclyl, wherein the heterocyclyl formed may optionally include intervening heteroatoms independently selected from NH, NR$^7$, O and S;

R$^3$ is a phosphate protecting group;

R$^4$ is a -halo, —R$^5$, —NR$^7$R$^8$, —OR$^9$, —SR$^{10}$, or 2'-blocking group; or when Structural Formula Ia or Ib is:

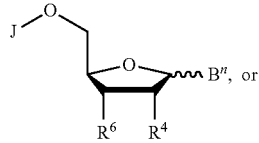 (II)

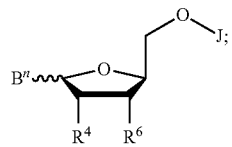 (III)

wherein R$^4$ is further selected from O—Si(R$^{11}$)$_3$ or O—CH$_2$—Si(R$^{11}$)$_3$; or when Structural Formula Ia or Ib is:

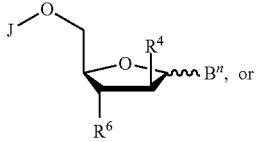 (IV)

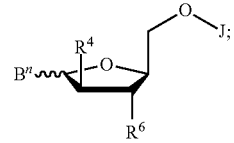 (V)

R$^4$ is further selected from —OC(=O)R$^{12}$;
each R$^5$ is independently a substituted or unsubstituted (C$_1$-C$_{12}$)alkyl group, a substituted or unsubstituted (C$_2$-C$_{12}$)alkenyl group, a substituted or unsubstituted (C$_2$-C$_{12}$)alkynyl group, or a substituted or unsubstituted phenyl, wherein the alkyl, alkenyl, alkynyl and the phenyl groups optionally includes intervening heteroatoms independently selected from NH, NR$^5$, O and S; and may optionally terminate with —NR$^7$R$^8$, (C$_1$-C$_4$)alkylamino, di(C$_1$-C$_4$)alkylamino, —OR$^9$, (C$_1$-C$_6$)alkoxy, —SR$^{10}$; or —S—(C$_1$-C$_6$)alkyl group;

$R^6$ is —H or —O—Z;

each $R^7$ is independently a fluorenylmethyloxycarbonyl;
—C(=O)—(CH$_2$)$_{1-16}$NR$^8$C(=O)CF$_3$;
—C(=O)—(CH$_2$)$_{1-16}$NR$^8$C(=O)-phthalimide;
—C(=O)—(CH$_2$)$_{1-16}$-phthalimide; NR$^8$C(=O)-phthalimide; a substituted or unsubstituted (C$_1$-C$_{12}$)alkyl group, a substituted or unsubstituted (C$_2$-C$_{12}$)alkenyl group, or a substituted or unsubstituted (C$_2$-C$_{12}$)alkynyl group;

each $R^8$ is H or a substituted or unsubstituted (C$_1$-C$_{12}$)alkyl group, a substituted or unsubstituted (C$_2$-C$_{12}$)alkenyl group, or a substituted or unsubstituted (C$_2$-C$_{12}$)alkynyl group;

each $R^9$ is independently —C(=O)—(CH$_2$)$_{1-16}$CH$_3$; a substituted or unsubstituted (C$_2$-C$_{12}$)alkenyl group, or a substituted or unsubstituted (C$_2$-C$_{12}$)alkynyl group;

each $R^{10}$ is independently —S(C$_1$-C$_6$)alkyl, —C(=O)—(CH$_2$)$_{1-16}$CH$_3$; a substituted or unsubstituted (C$_2$-C$_{12}$)alkenyl group, or a substituted or unsubstituted (C$_2$-C$_{12}$)alkynyl group;

each $R^{11}$ is independently a substituted or unsubstituted (C$_1$-C$_{12}$)alkyl group, a substituted or unsubstituted (C$_2$-C$_{12}$)alkenyl group, or a substituted or unsubstituted (C$_2$-C$_{12}$)alkynyl group; provided that if $R^4$ is —O—Si(R$^{11}$)$_3$, and two $R^{11}$ groups are both methyl, the other is not t-butyl or if $R^4$ is —O—CH$_2$—Si(R$^{11}$)$_3$, then the three $R^{11}$ groups cannot all be isopropyl;

each $R^{12}$ is independently a substituted or unsubstituted (C$_1$-C$_{12}$)alkyl group, a substituted or unsubstituted (C$_2$-C$_{12}$)alkenyl group, or a substituted or unsubstituted (C$_2$-C$_{12}$)alkynyl group, or a substituted or unsubstituted aryl group;

Z is an acid labile protecting group;

B″ is hydrogen or an optionally substituted nucleobase optionally functionalized at each exocyclic amine with an amine protecting group.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 1A-1C are graphs and tables demonstrating the purity of REV-2'-OMe-BTT-mArArCrArGrCrArUrArCrArUrCrUrCrGrArCrCmArU (SEQ ID NO: 1). (BTT is 5-Benzyl thio-1-H-tetrazole) synthesized with a coupling time of 2 minutes with the activator BTT. FIG. 1A is a graph of the trityl histogram; FIG. 1B is a graph of the capillary gel electrophoresis (CE) analysis of the crude RNA; and FIG. 1C is a table containing the crude RNA-CE analysis report.

FIGS. 2A-2D are graphs and tables demonstrating the purity of REV-2'-OMe-phosphorothioate-Oligo mArArCrArGrCrArUrArCrArUrCrUrCrGrArCrCmArU (SEQ ID NO: 2) synthesized with a coupling time of 4 minutes with the activator (0.25M) ETT (ethyl thio tetrazole). FIG. 2A is a graph of the trityl histogram; FIG. 2B is a graph of the CE analysis of the crude RNA (desalted); FIG. 2C is a table containing the CE analysis report of crude RNA; and FIG. 2D is a graph of ESI/MS (crude) Actual MW: 6971.1; Found Value: 6972.0.

FIGS. 3A-3C are graphs and tables demonstrating the purity of REV-2'-OMe-phosphodiester-Oligo mArArCrArGrCrArUrArCrArUrCrUrCrGrArCrCmArU (SEQ ID NO: 3) synthesized with a coupling time of 4 minutes. FIG. 3A is a graph of the trityl histogram; FIG. 3B is a graph of the CE analysis of the crude oligo (desalted); and FIG. 3C is a table containing the CE analysis report of the crude RNA.

FIGS. 4A-4D are graphs and tables demonstrating the purity of REV-phosphodiester-Oligo rCrArCrArGrCrArUrArCrArUrCrUrCrGrArCrCrArU (SEQ ID NO: 4) synthesized with a coupling time of 4 minutes; FIG. 4A is a graph of the trityl histogram; FIG. 4B is a graph of the CE analysis crude (desalted); FIG. 4C is a table containing CE analysis report of the crude RNA; and FIG. 4D is a graph of ESI/MS Crude RNA (desalted); Calc.: MW: 6598.9.

FIG. 5A is a graph of the trityl histogram; FIG. 5B is a table of CE analysis crude (desalted); and FIG. 5C is a table of the CE analysis report crude RNA (desalted).

FIG. 6A is a graph of the trityl histogram; and FIG. 6B is a picture of a gel of the page analysis of 76 mer phosphodiester; band #1; Bromo phenol blue; band #2; 76 mer with regular RNA; band #3; 76mer with reverse RNA; band #4; 76mer with reverse TOM RNA. TOM RNA reverse phosphoramidites: 2'-TOM-3'-O-DMT-adenosine(n-acetyl)5'-cyanoethylphosphoramidite; 2'-TOM-3'-O-DMT-cytidine(n-acetyl)5'-cyanoethylphosphoramidite; 2'-TOM-3'-O-DMT-guanosine(n-acetyl)5'-cyanoethylphosphoramidite; 2'-TOM-3'-O-DMT-uridine-5'-cyanoethylphosphoramidite.

FIGS. 11A and 11B are (a) the HPLC chromatogram and (b) the table of peak retention times of the HPLC analysis for 3'-DMT-2'-TBDMS-A(N-Bz)-5'-Phosphoramidite (lot #AL-300-2).

FIGS. 12A and 12B are (a) the HPLC chromatogram and (b) the table of peak retention times for the HPLC analysis for 3'-DMT-2'-TBDMS-G(N-iBu)-5'-Phosphoramidite (lot #NS 42-19).

FIGS. 13A and 13B are (a) the HPLC chromatogram and (b) the table of peak retention times for the HPLC analysis for 3'-DMT-2'-TBDMS-C(N—Ac)-5'-Phosphoramidite (lot #NS 143-19).

FIGS. 14A and 14B are (a) the HPLC chromatogram and (b) the table of peak retention times for the HPLC analysis for 3'-DMT-2'-TBDMS-U-5'-Phosphoramidite (lot #NS 147-19).

FIGS. 15A-15F are graphs and tables demonstrating the purity of REV-RNA-Me-THIO-mArArCrArGrCrArUrAr- CrArUrCrUrCrGrArCrCmArU (SEQ ID NO:6) synthesized with a coupling time of 6 minutes. FIG. 15A is a graph of the trityl histogram; FIG. 15B is a graph of the CE crude; FIG. 15C is table of the CE analysis; FIG. 15D is a graph showing the migration time; FIG. 15E is table of the CE report; and FIG. 15F is a graph of Mass Spectrum; Actual Value: 6971.1; Found Value: 6971.7.

FIG. 21A is a graph of an electropherogram of the crude 21-mer RNA with 3'-HEG (Hexaethyloxyglycol) made by Reverse RNA synthesis method (5'→3'-direction). Expedite model 8909-1 umole scale. Crude purity; 56.60%. FIG. 21B is a graph of an electropherogram of 21-mer RNA synthesized by reverse direction (5'→3'), followed by HEG (Hexa-ethyloxyglycol) attachment. After HPLC purification, purity by CE; 94.39%.

DETAILED DESCRIPTION OF THE INVENTION

Figure 1A:
Figure 1B:
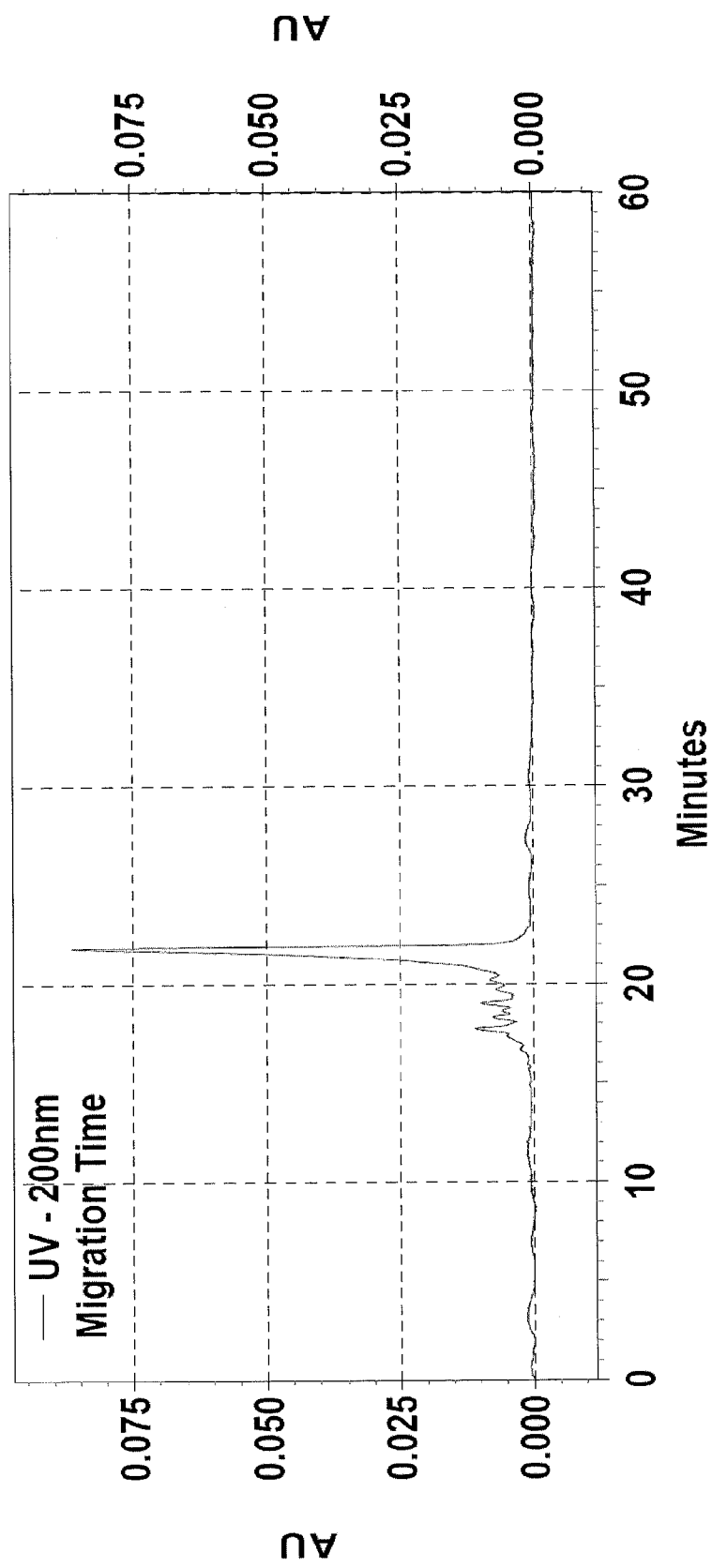
Figure 2A:
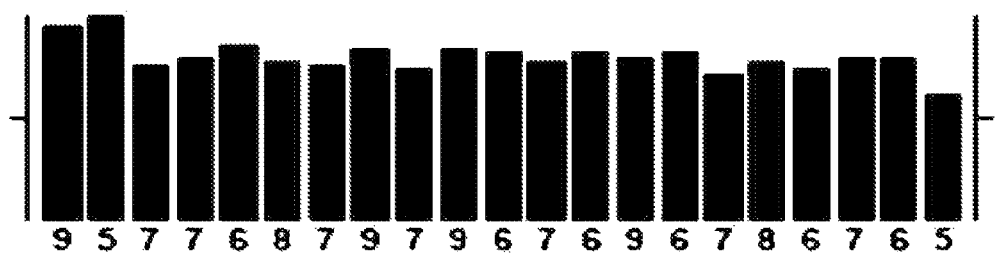
Figure 2B:
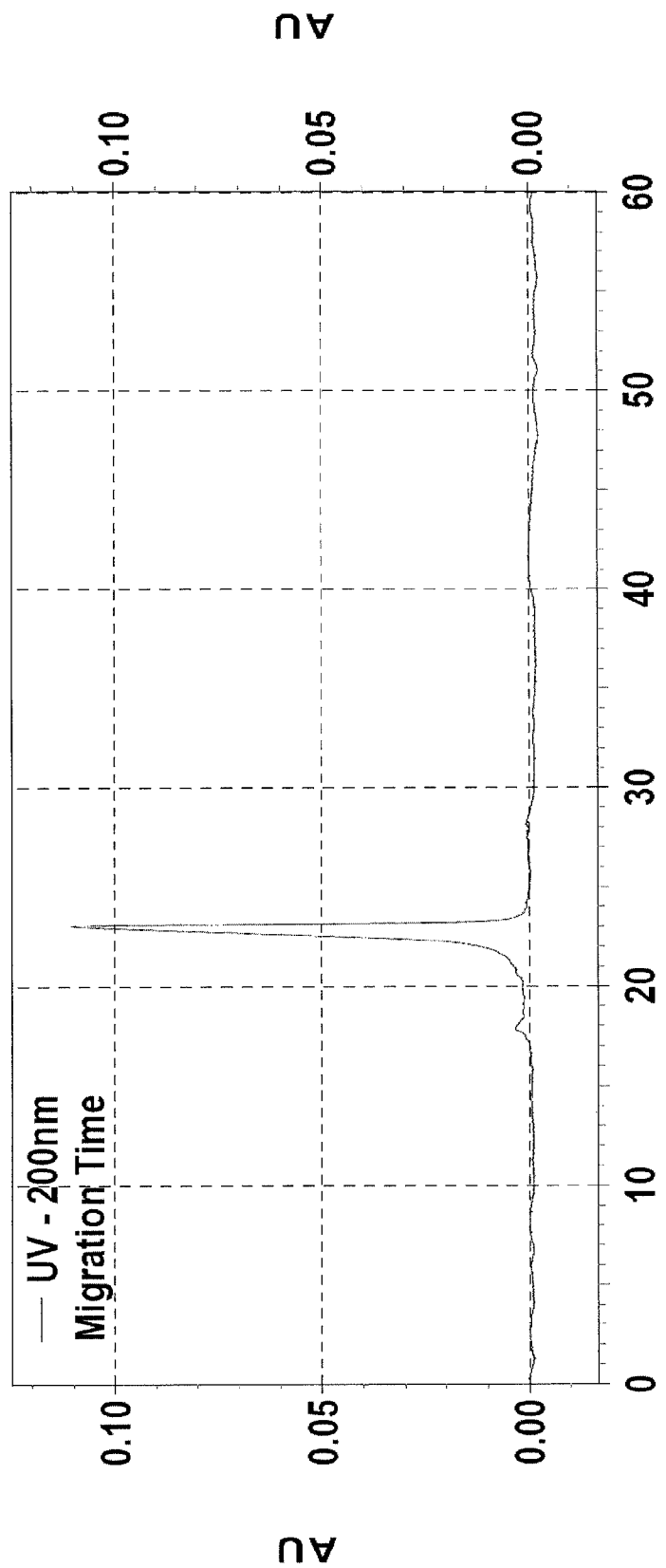
Figure 2D:
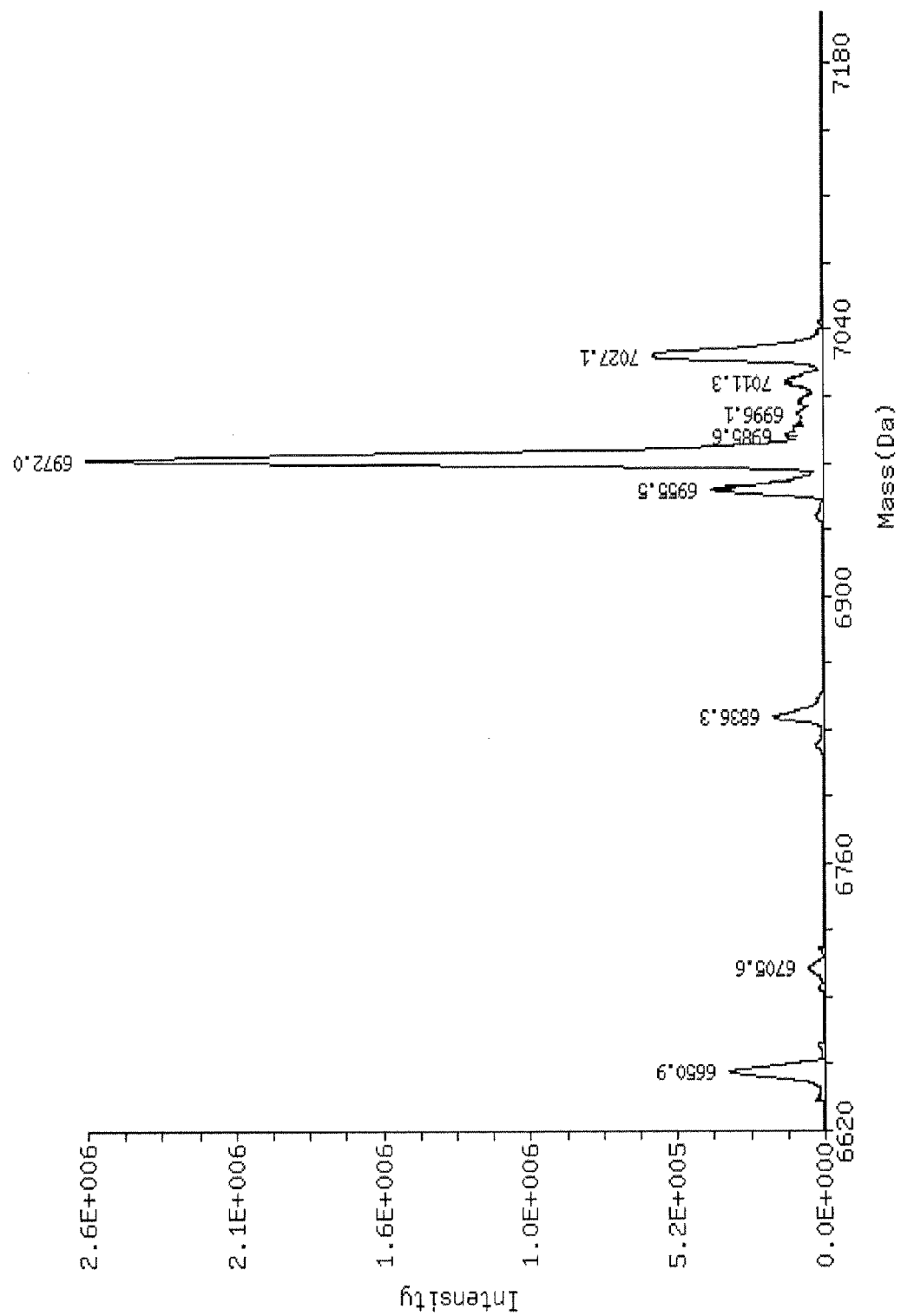
Figure 3A:
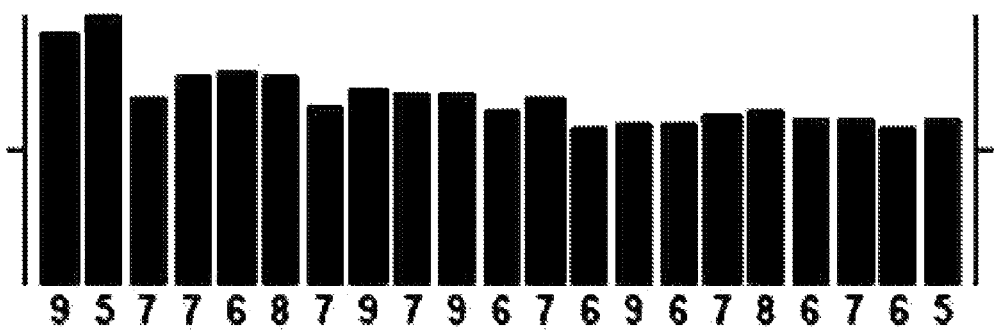
Figure 3B:
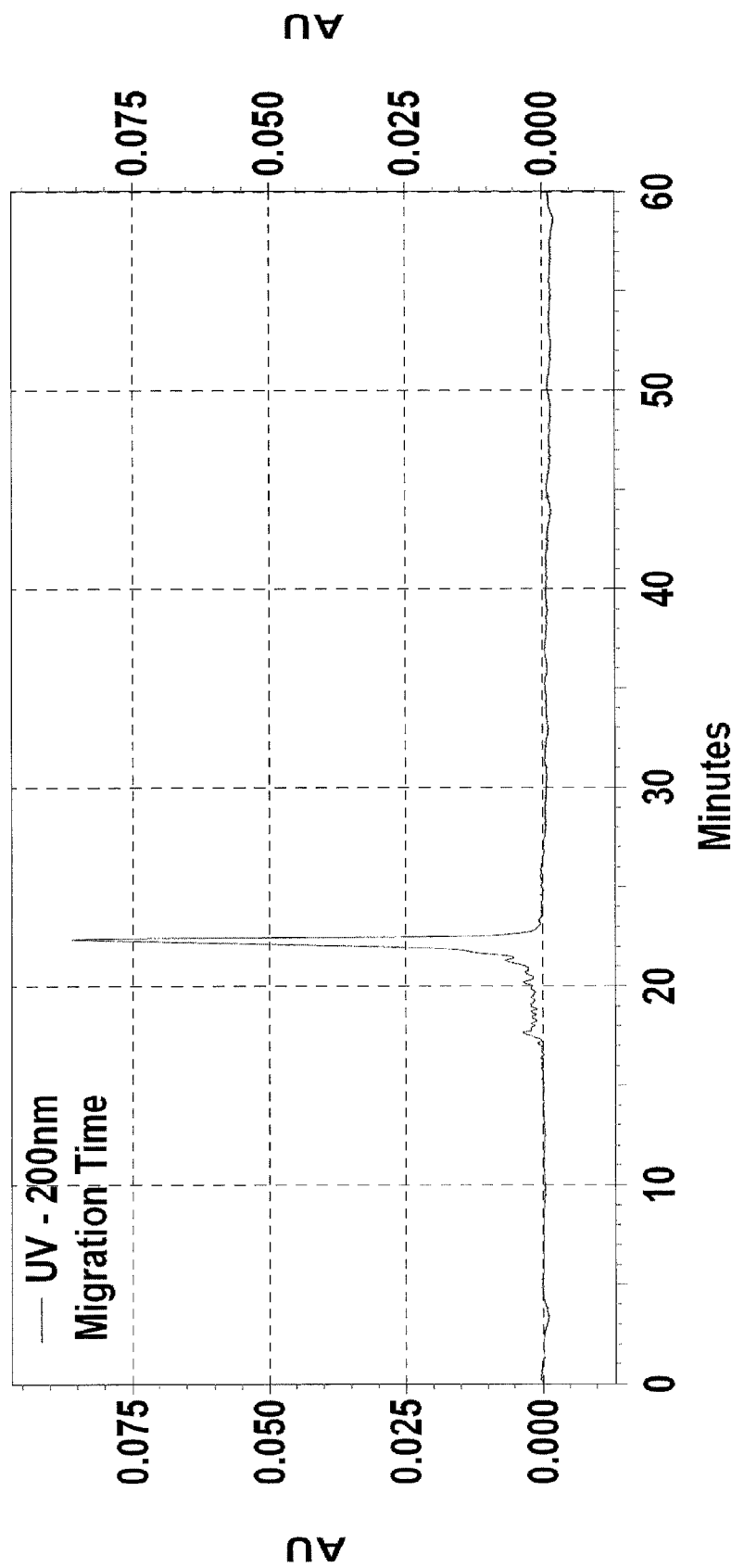
Figure 4A:
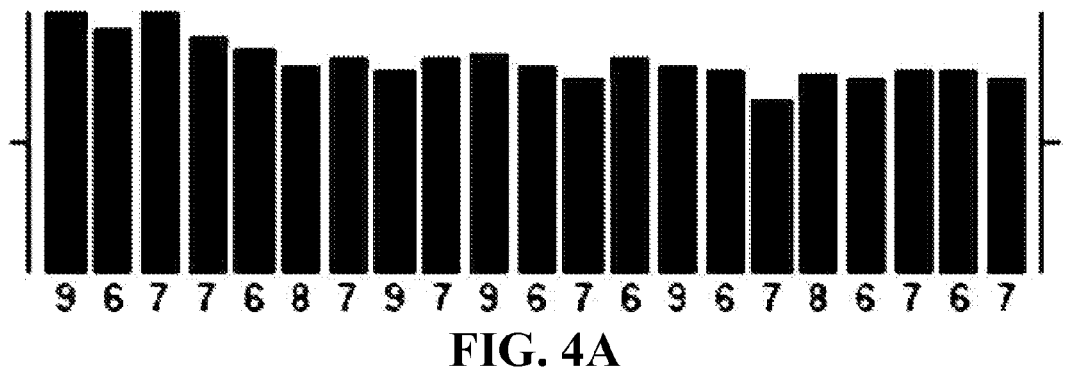
Figure 4B:
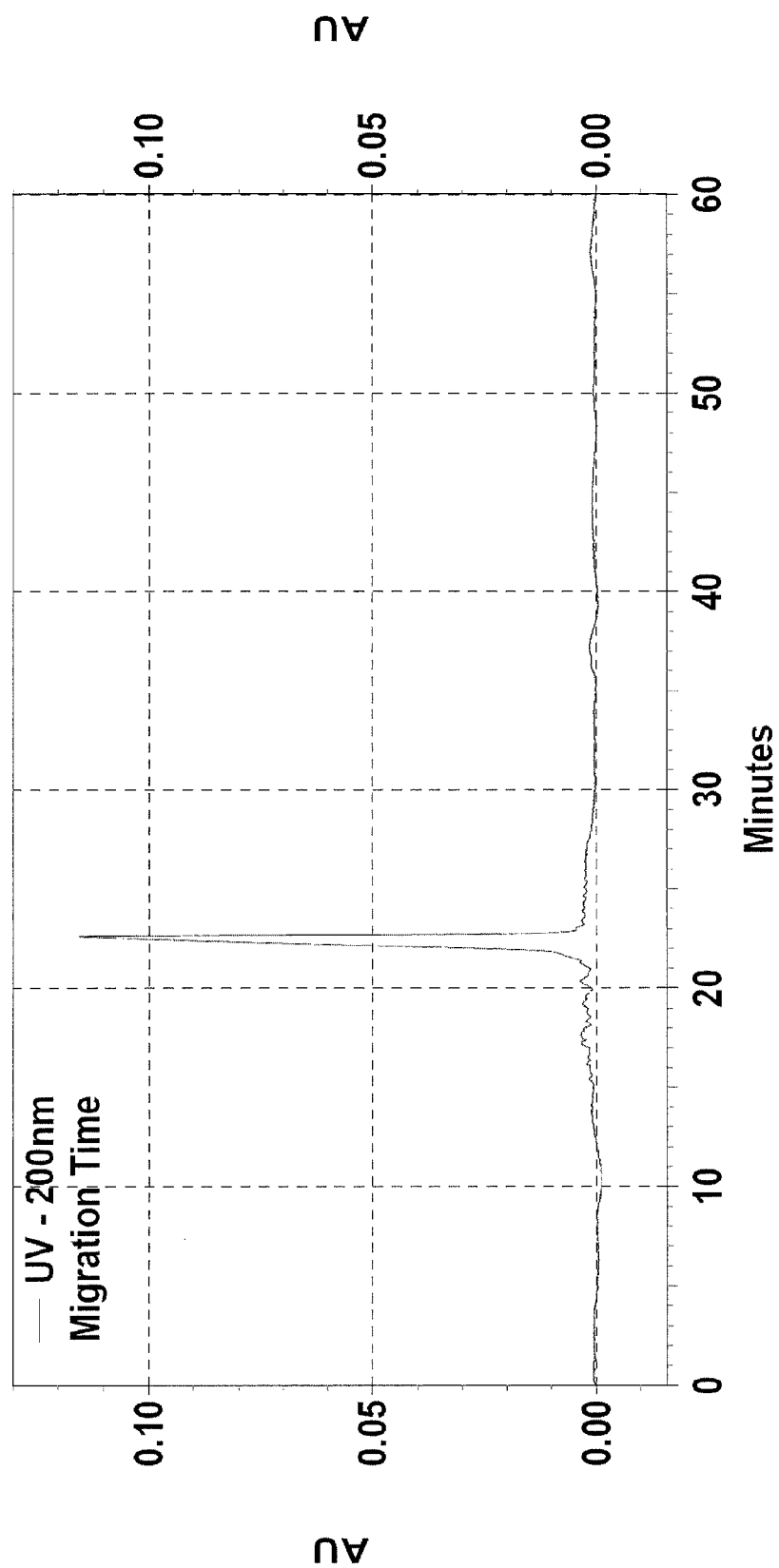
Figure 4D:
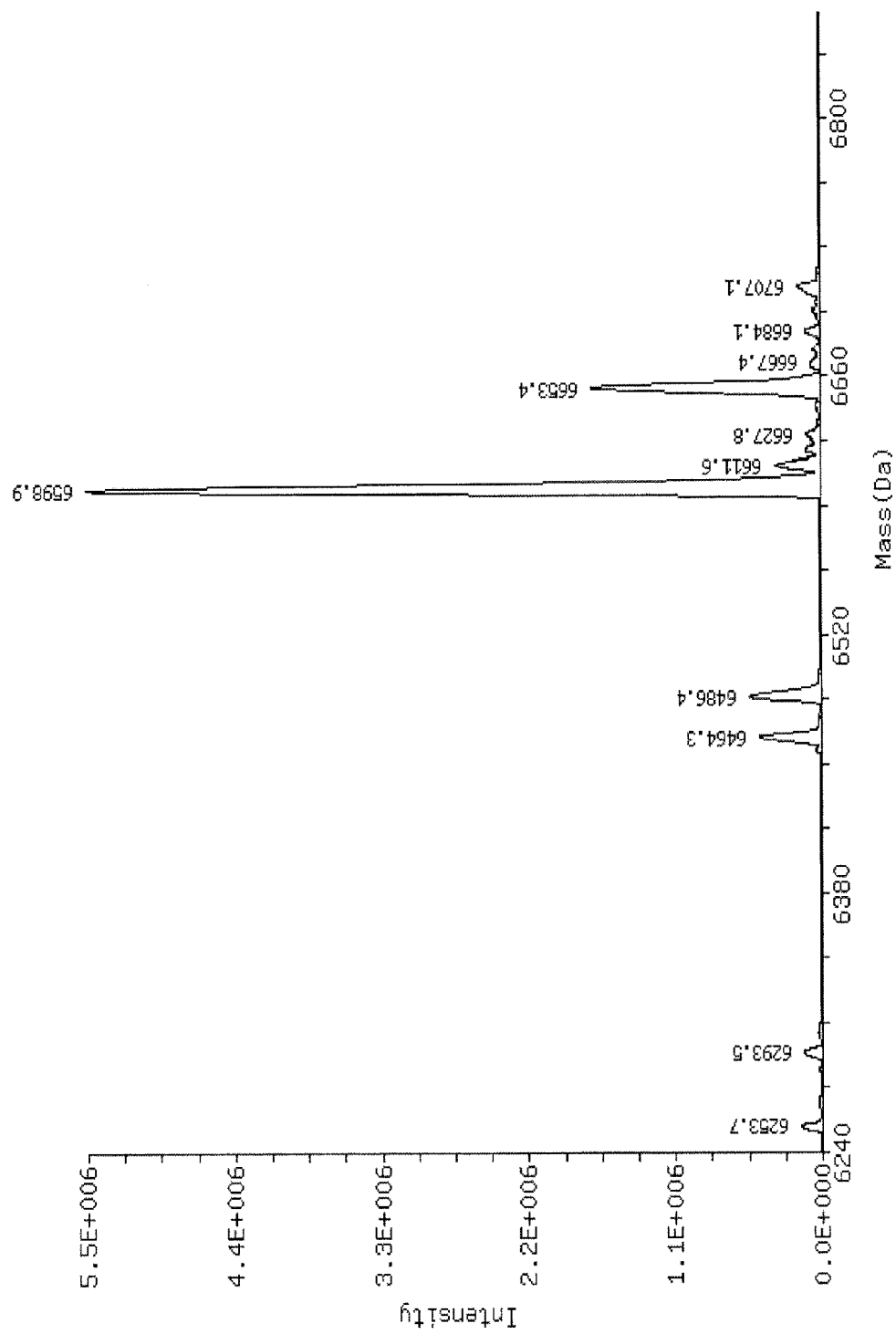
Figure 5A:
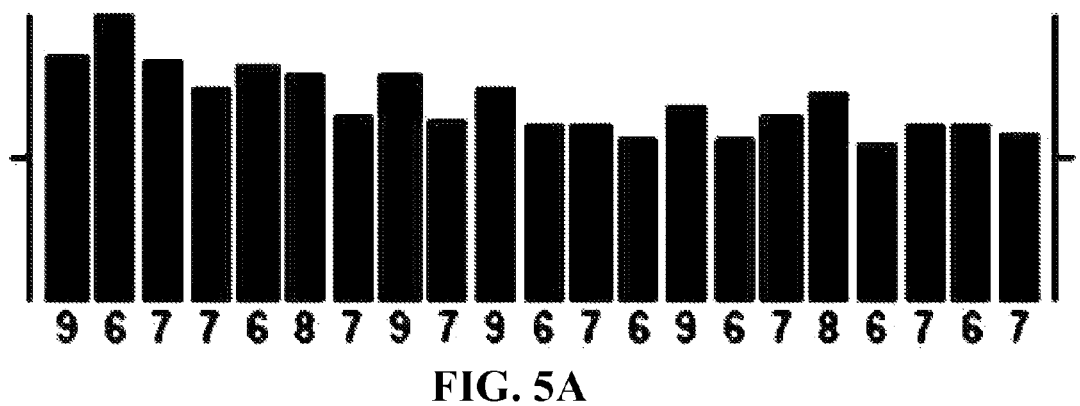
FIGS. 5A-5C are graphs and tables demonstrating the purity of REV-phosphodiester-Oligo CrArCrArGrCrArUrArCrArUrCrUrCrGrArCrCrArU (SEQ ID NO: 4) (crude desalted) using a coupling time of 6 minutes.
Figure 5B:
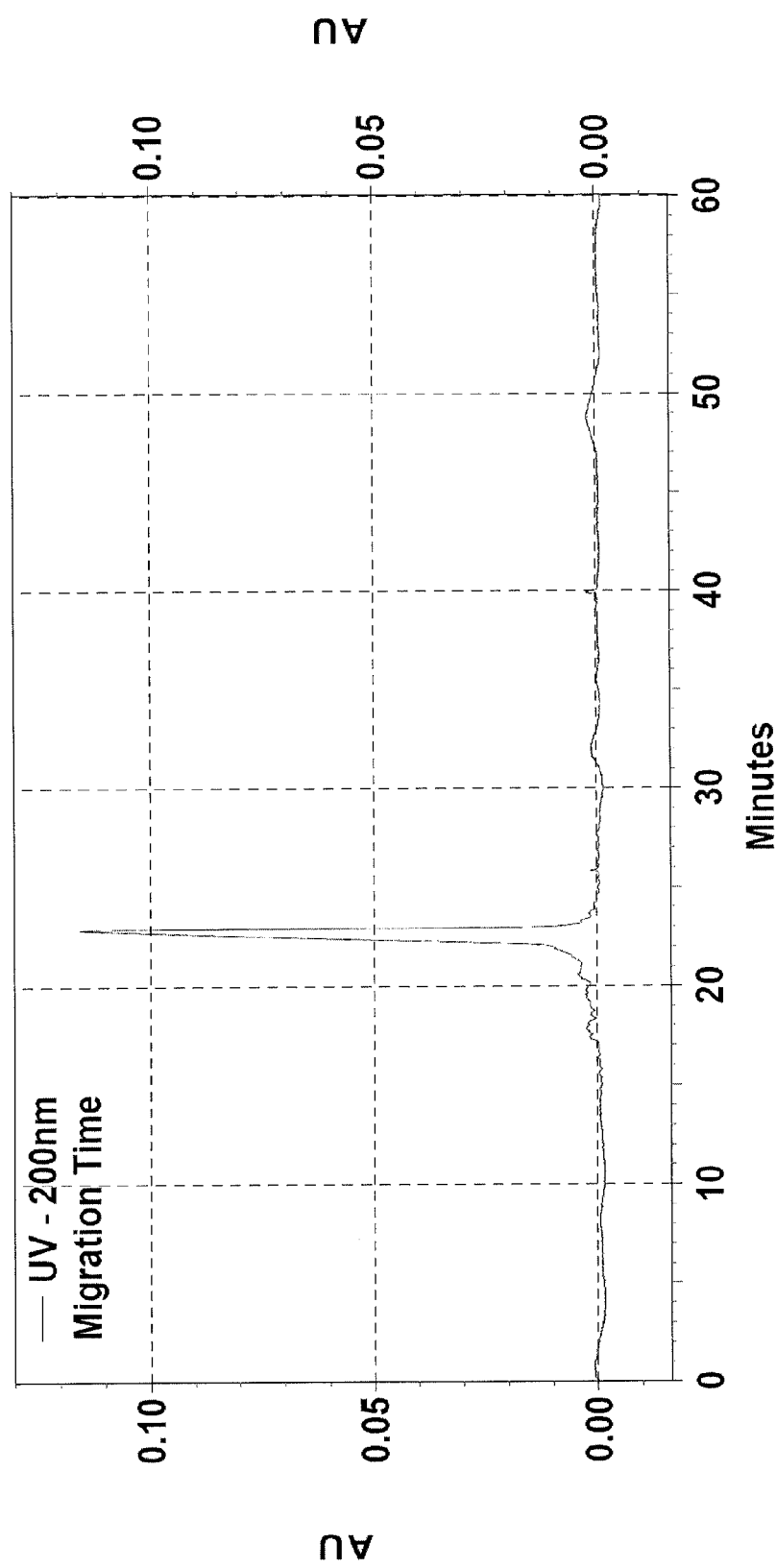
Figures 5C, 6A:
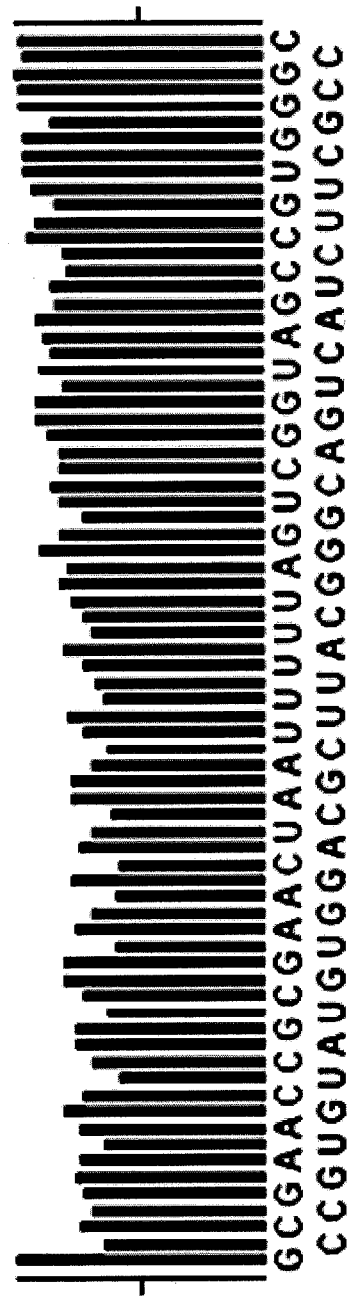
FIGS. 6A-6B is a graph and a picture of a gel demonstrating the purity of REV-phosphodiester-OLIGO-76 mer rArCrGrCrGrGrGrCrUrUrGrUrCrCrCrUrGrArArCrUrUrGrGrArCrCrUrGrGrGrArGrUrCrUrArUrUrUrUrCrArGrArGrUrArCrGrArGrArUrGrGrCrUrGrArCrUrCrGrArUrArGrGrCrCrCrG (SEQ ID NO: 5) synthesized with a coupling time of 6 minutes.
Figure 6B:
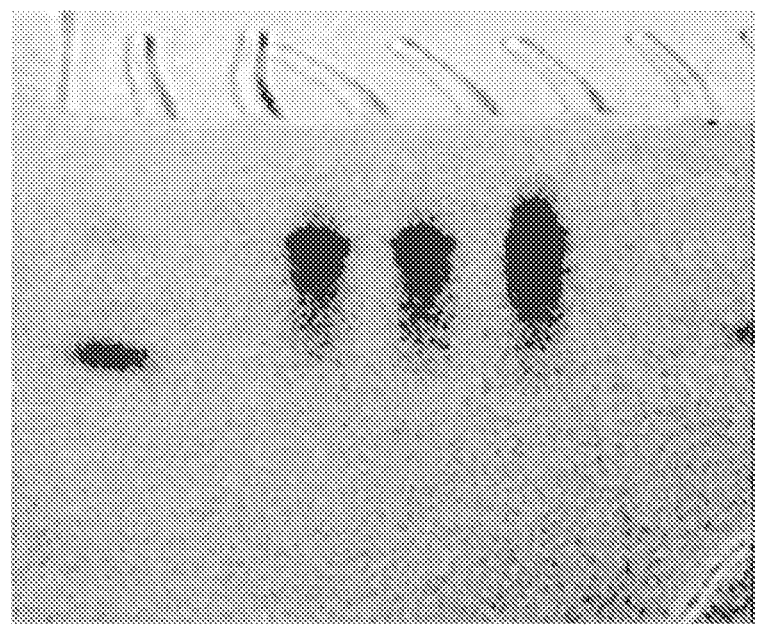
Figure 7:
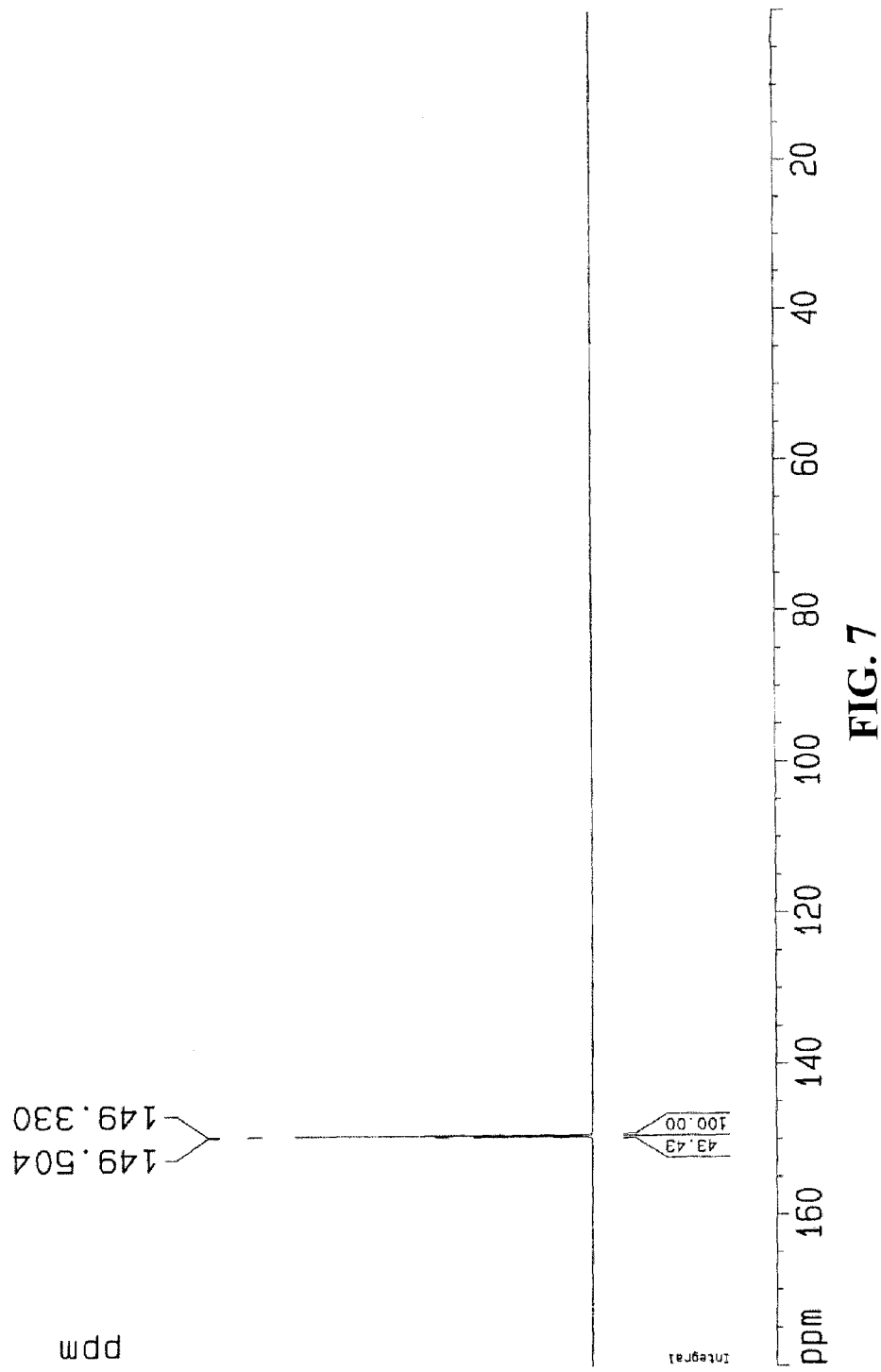
FIG. 7 is the $^{31}$P-NMR spectrum of 3'-DMT-2'-TBDMS-A(N-Bz)-5'-Phosphoramidite (lot #AL-300-2); 100% by analysis of region from 0-200 ppm.
Figure 8:
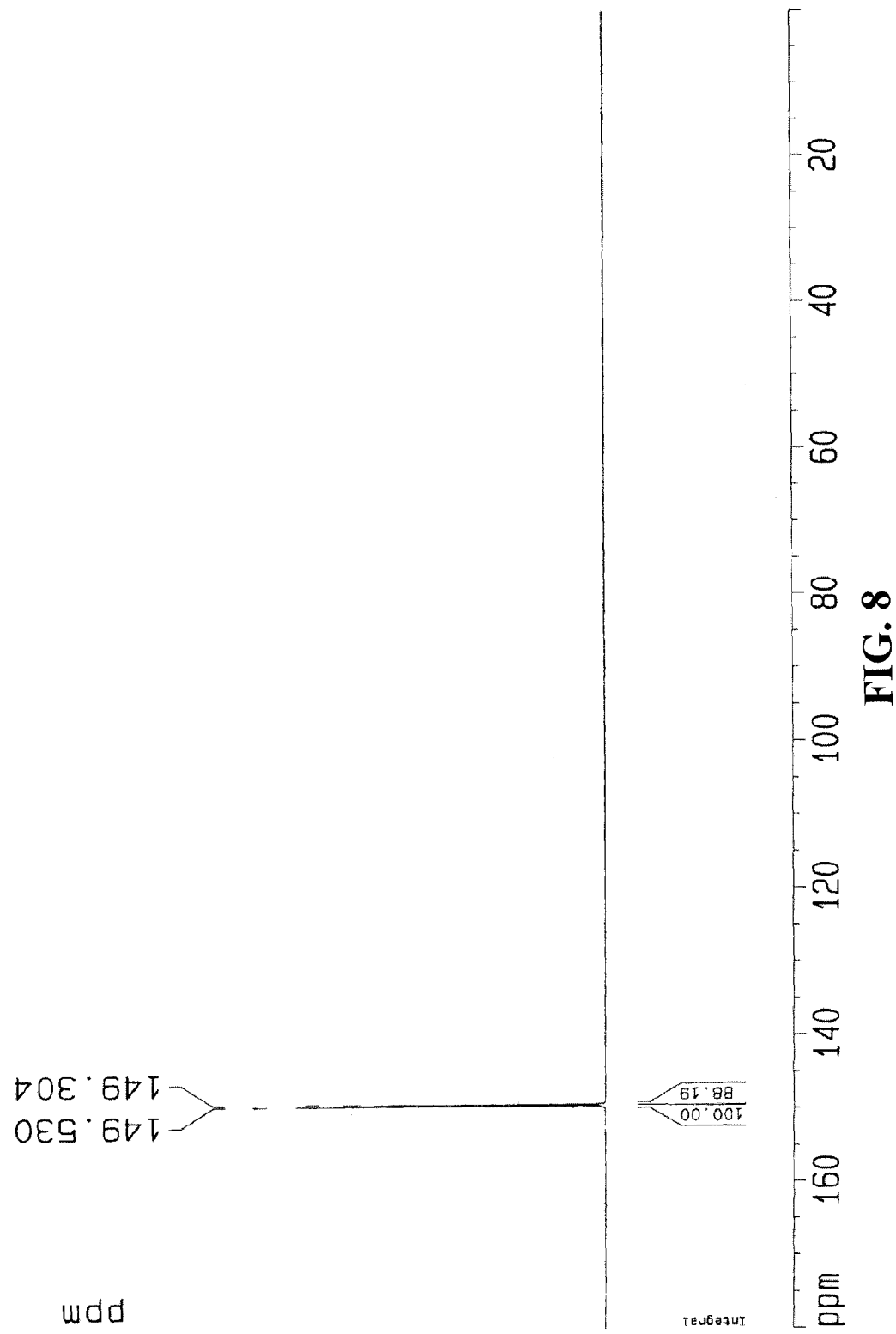
FIG. 8 is the $^{31}$P-NMR spectrum of 3'-DMT-2'-TBDMS-C—(N—Ac)-5'-Phosphoramidite (lot #NS-143-19); 100% by analysis of region from 0-200 ppm.
Figure 9:
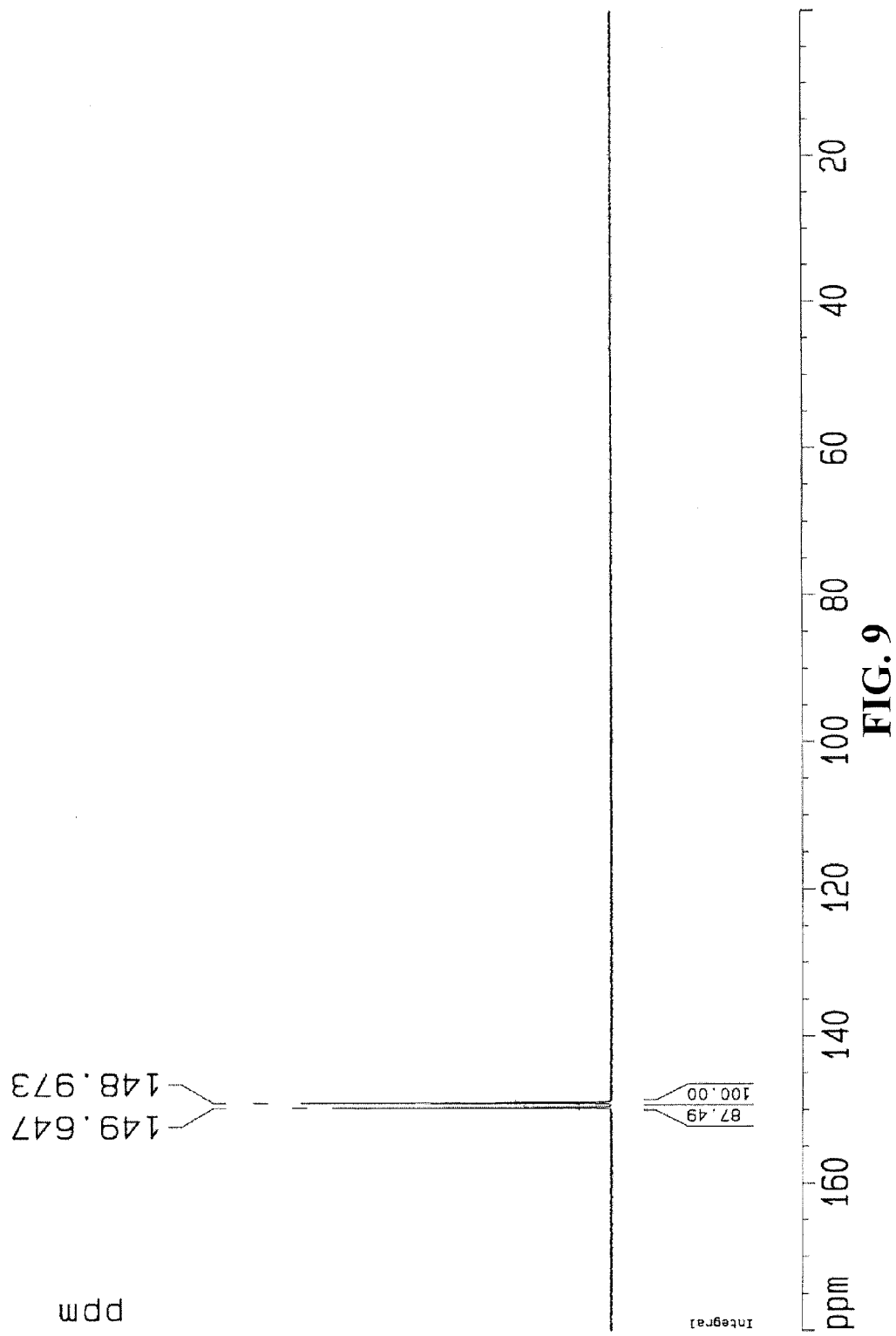
FIG. 9 is the $^{31}$P-NMR spectrum of 3'-DMT-2'-TBDMS-U-5'-Phosphoramidite (lot #NS-147-19); 100% by analysis of region from 0-200 ppm.
Figure 10:
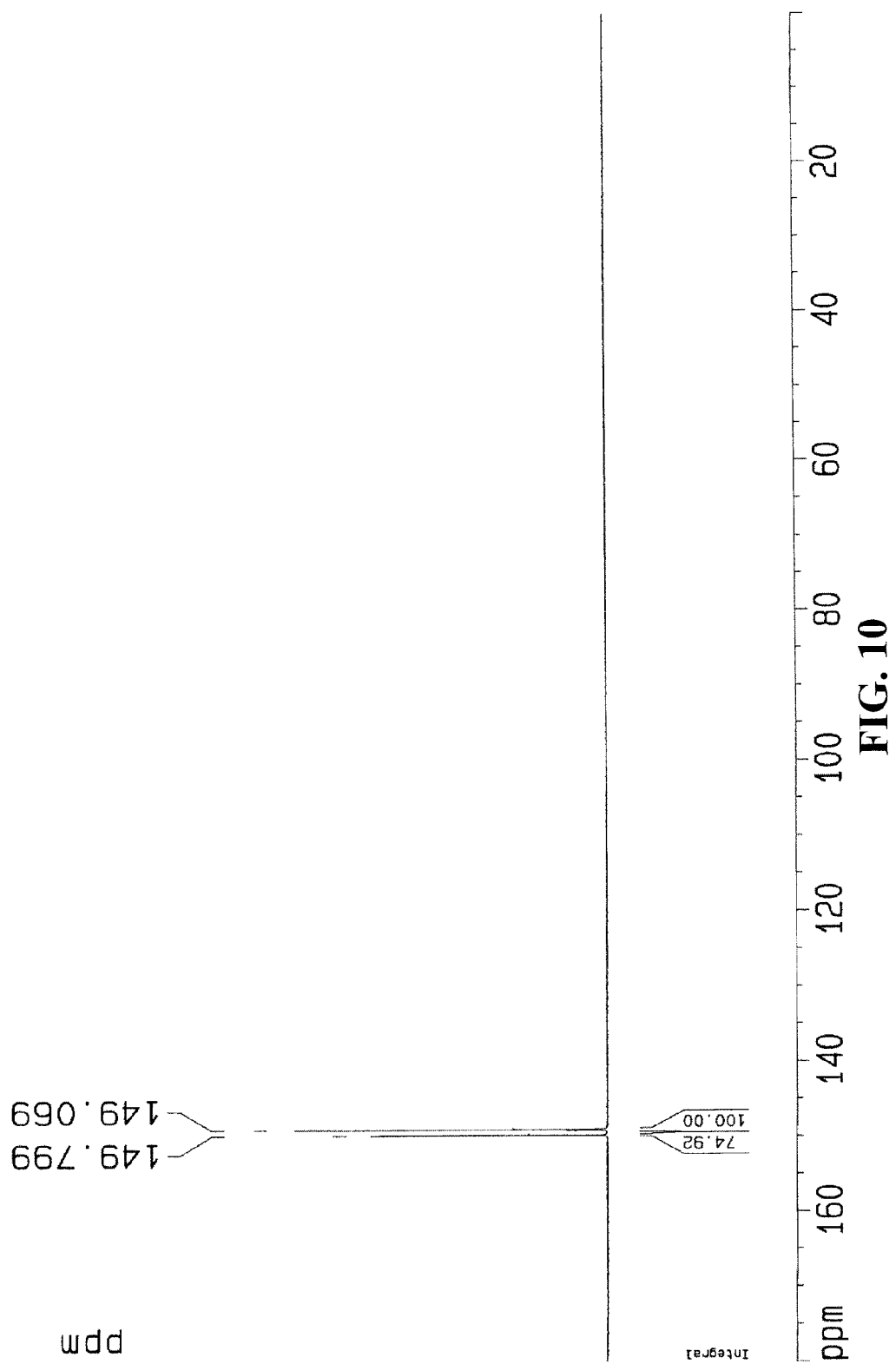
FIG. 10 is the $^{31}$P NMR spectrum of 3'-DMT-2'-TBDMS-G-(N-iBu)-5'-Phosphoramidite (lot #NS-42-19); 100% by analysis of region from 0-200 ppm.
Figure 11A:
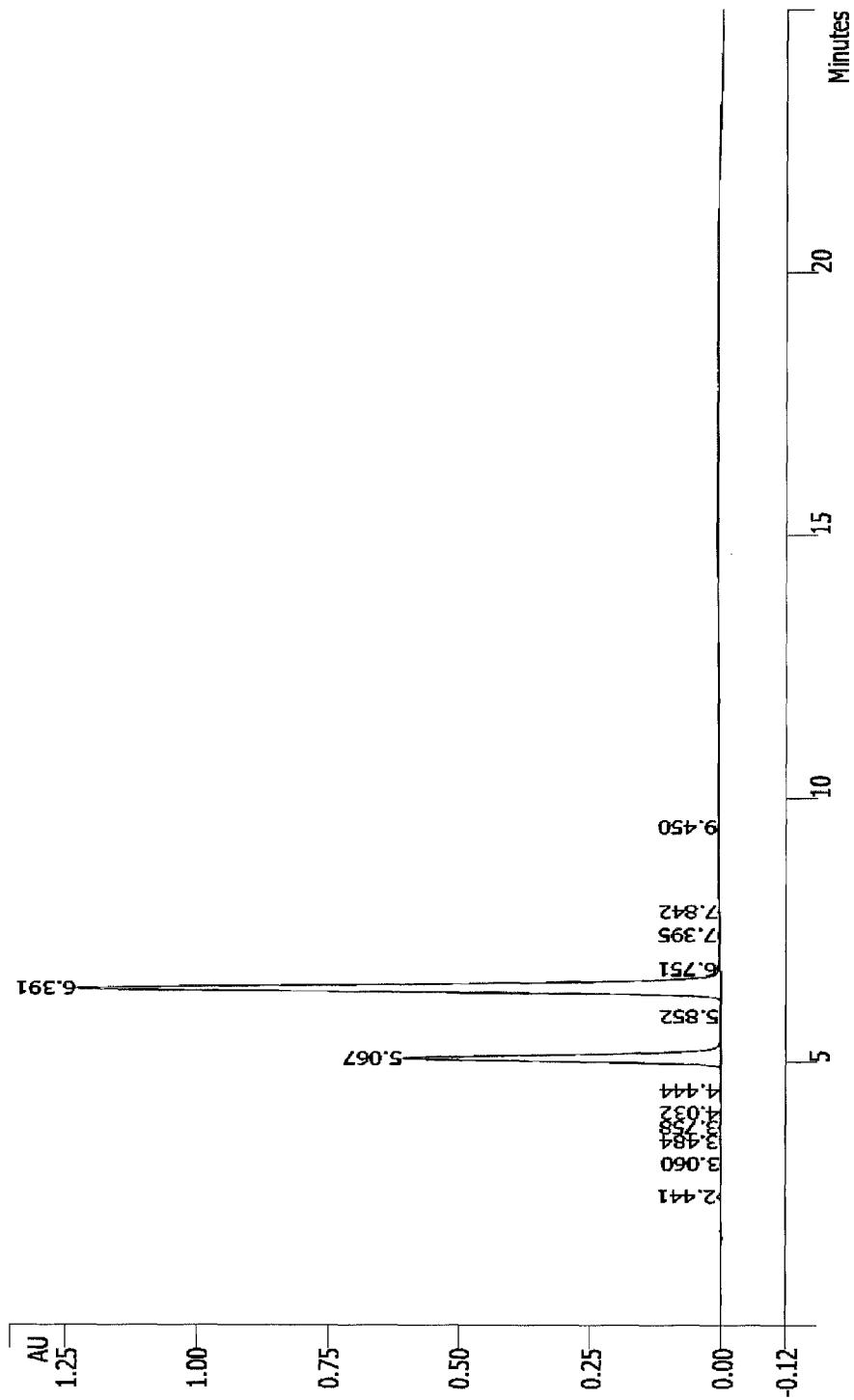
Figure 12A:
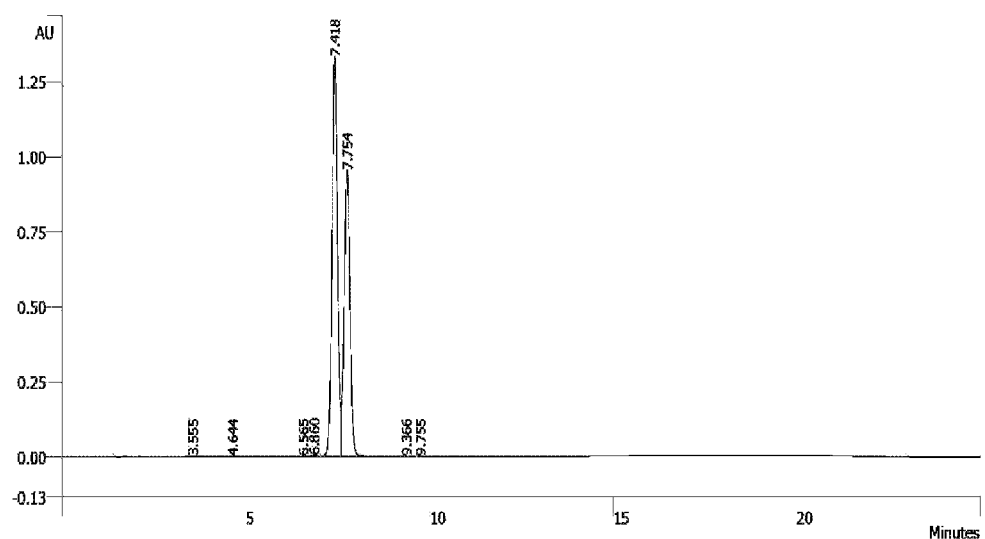
Figure 13A:
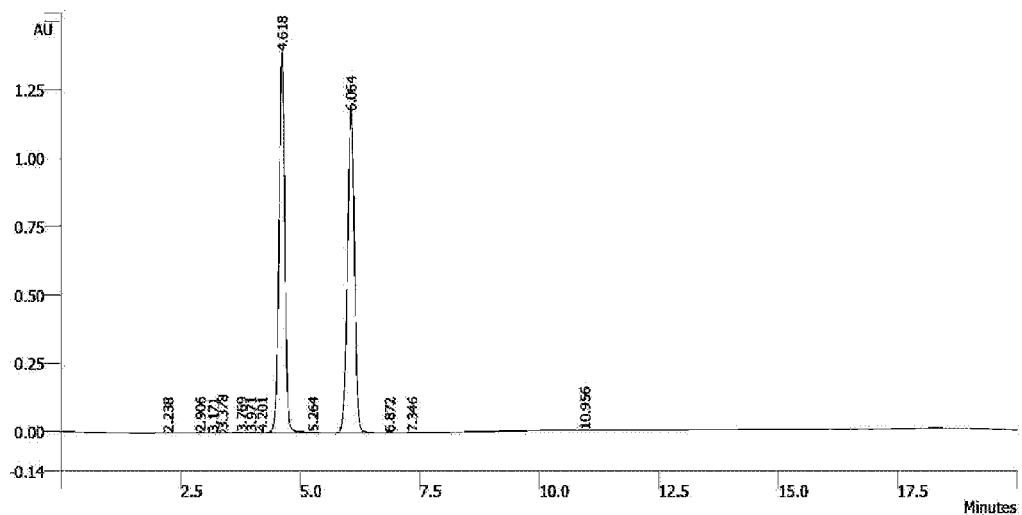
Figure 14A:
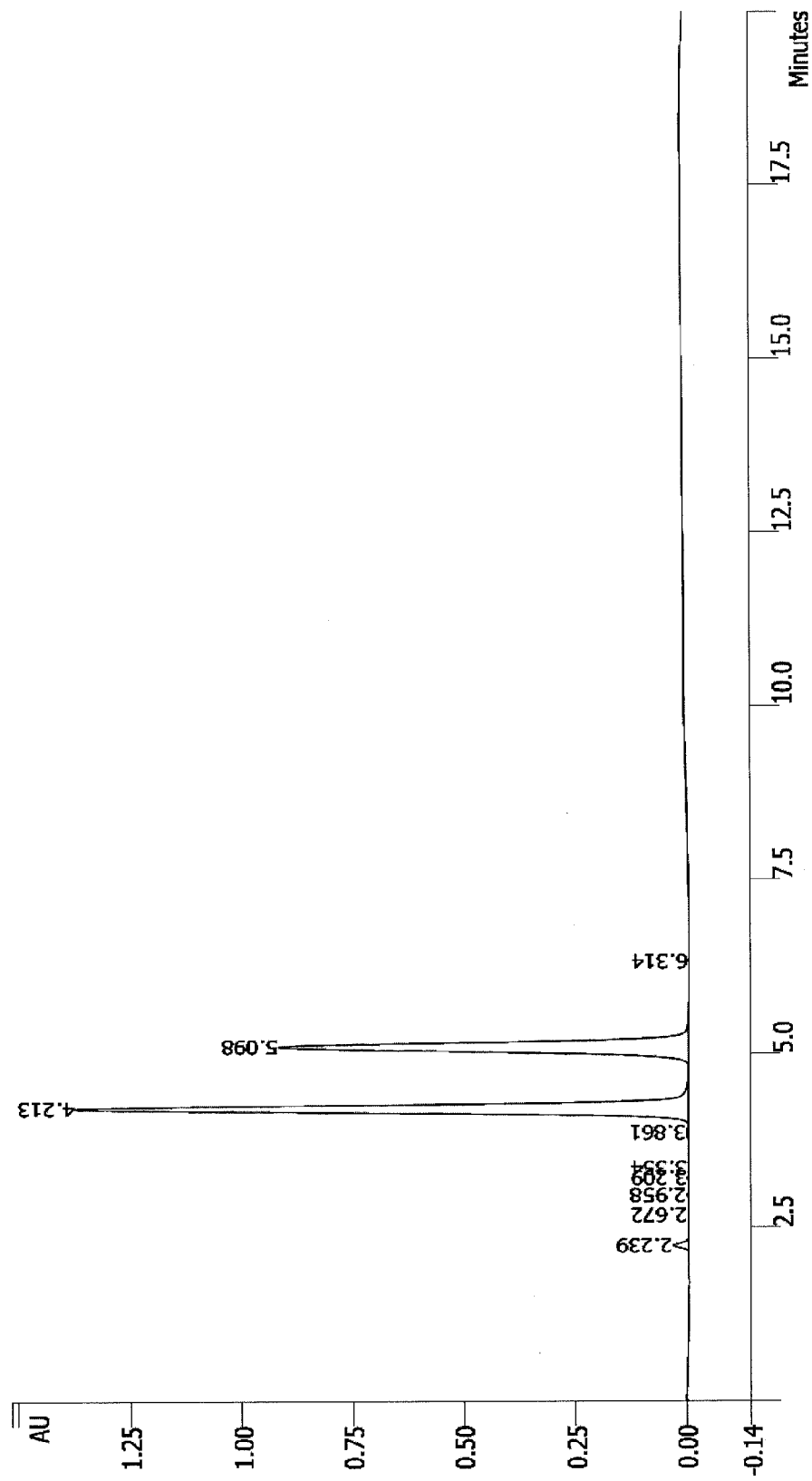
Figure 15A:
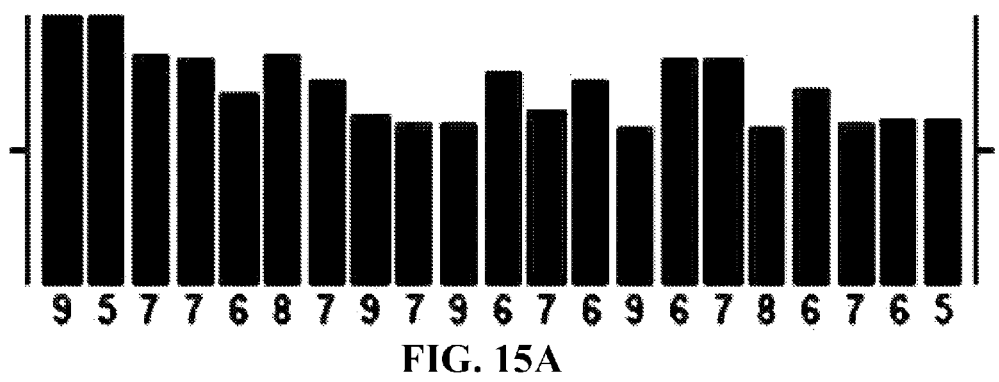
Figure 15B:
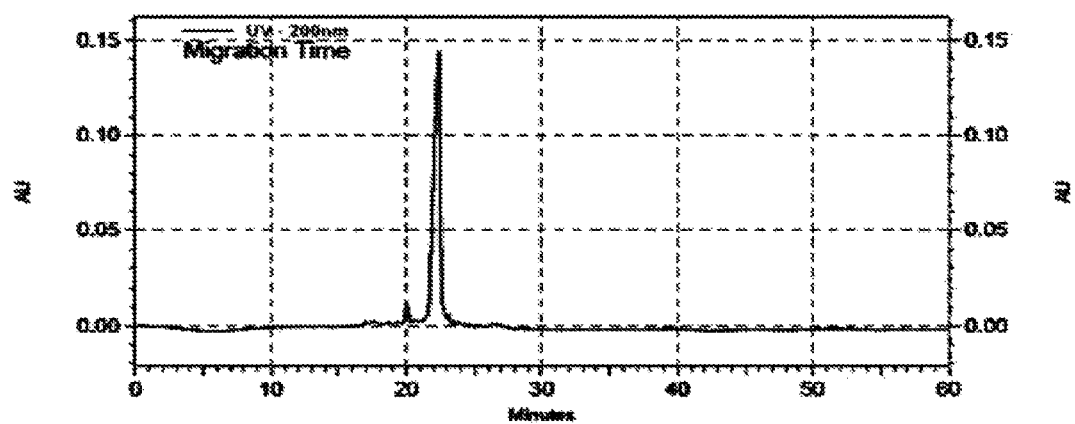
Figure 15D:
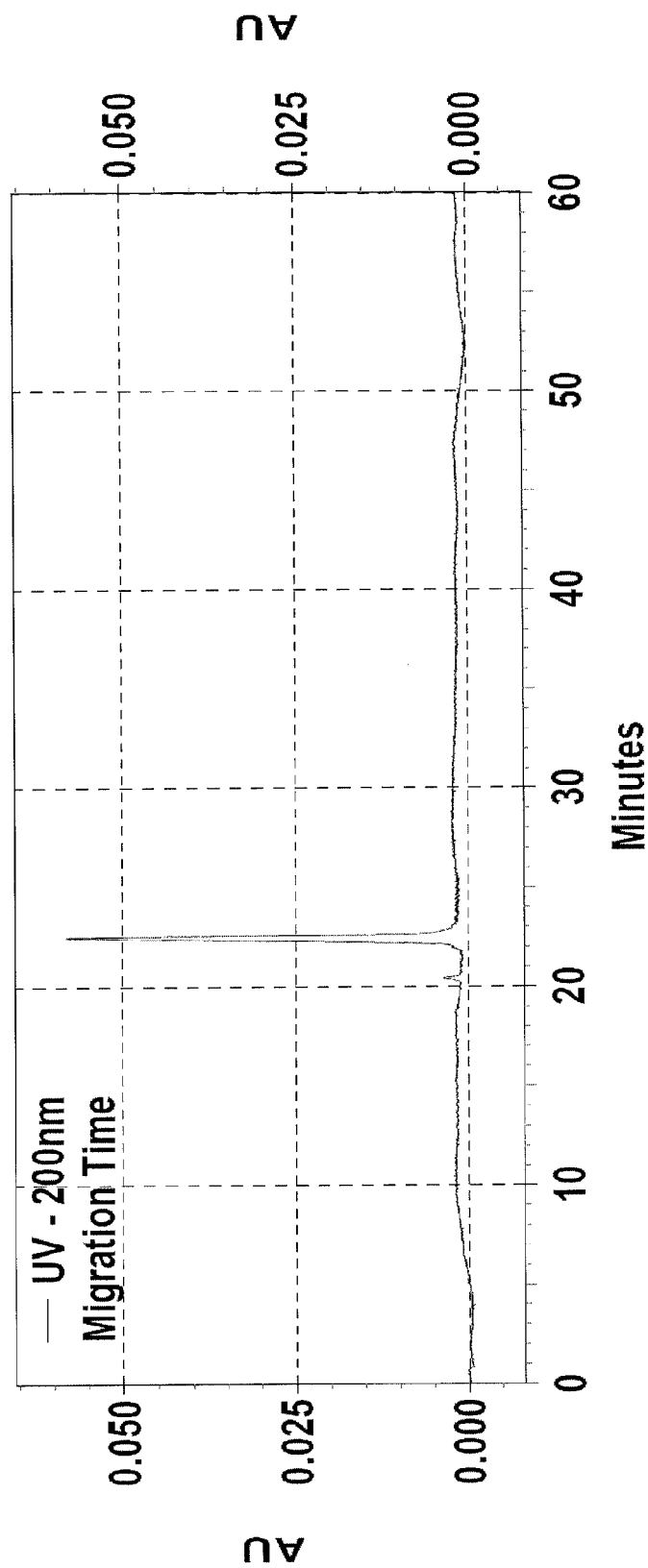
Figure 15F:
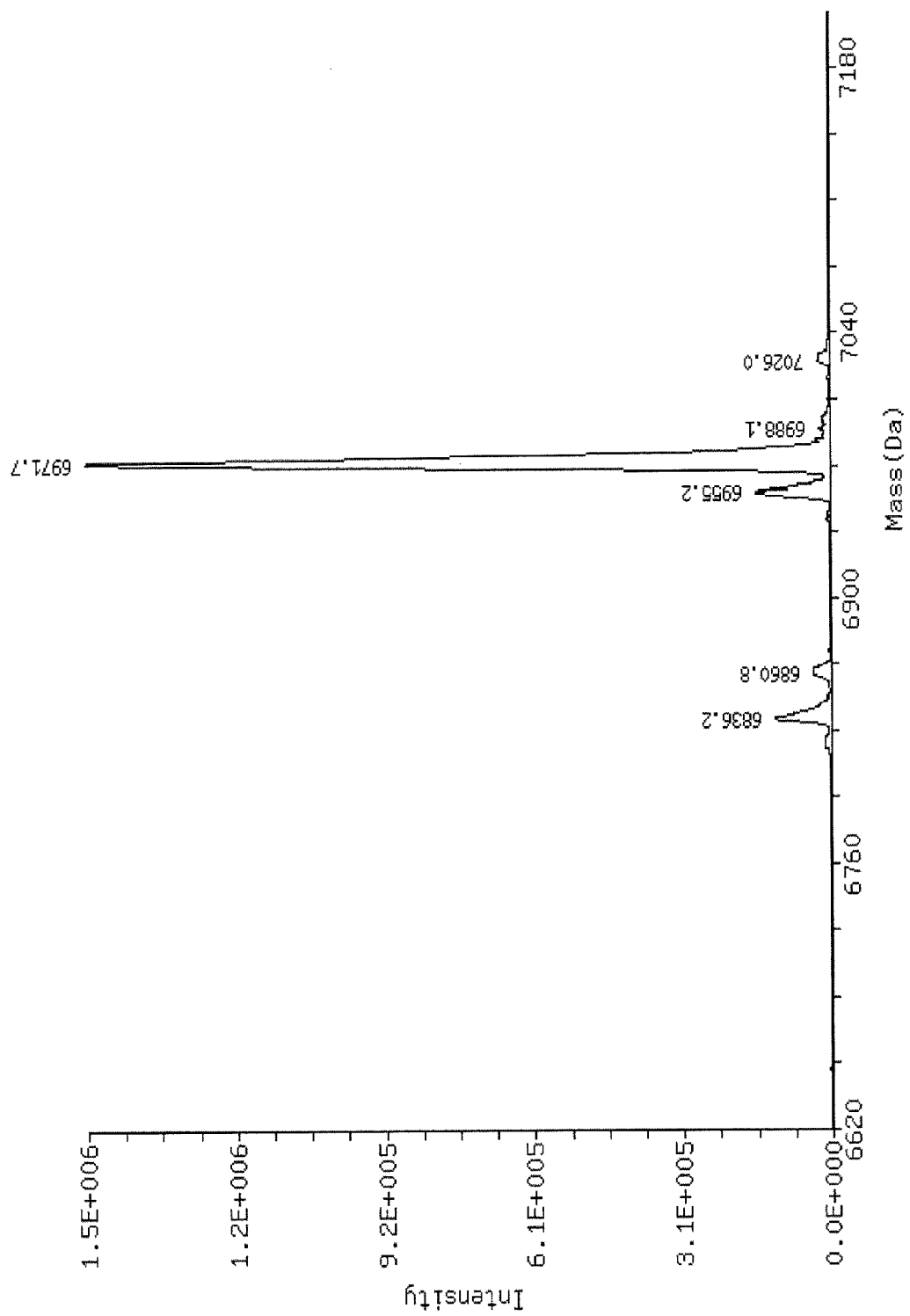
Figure 16A:
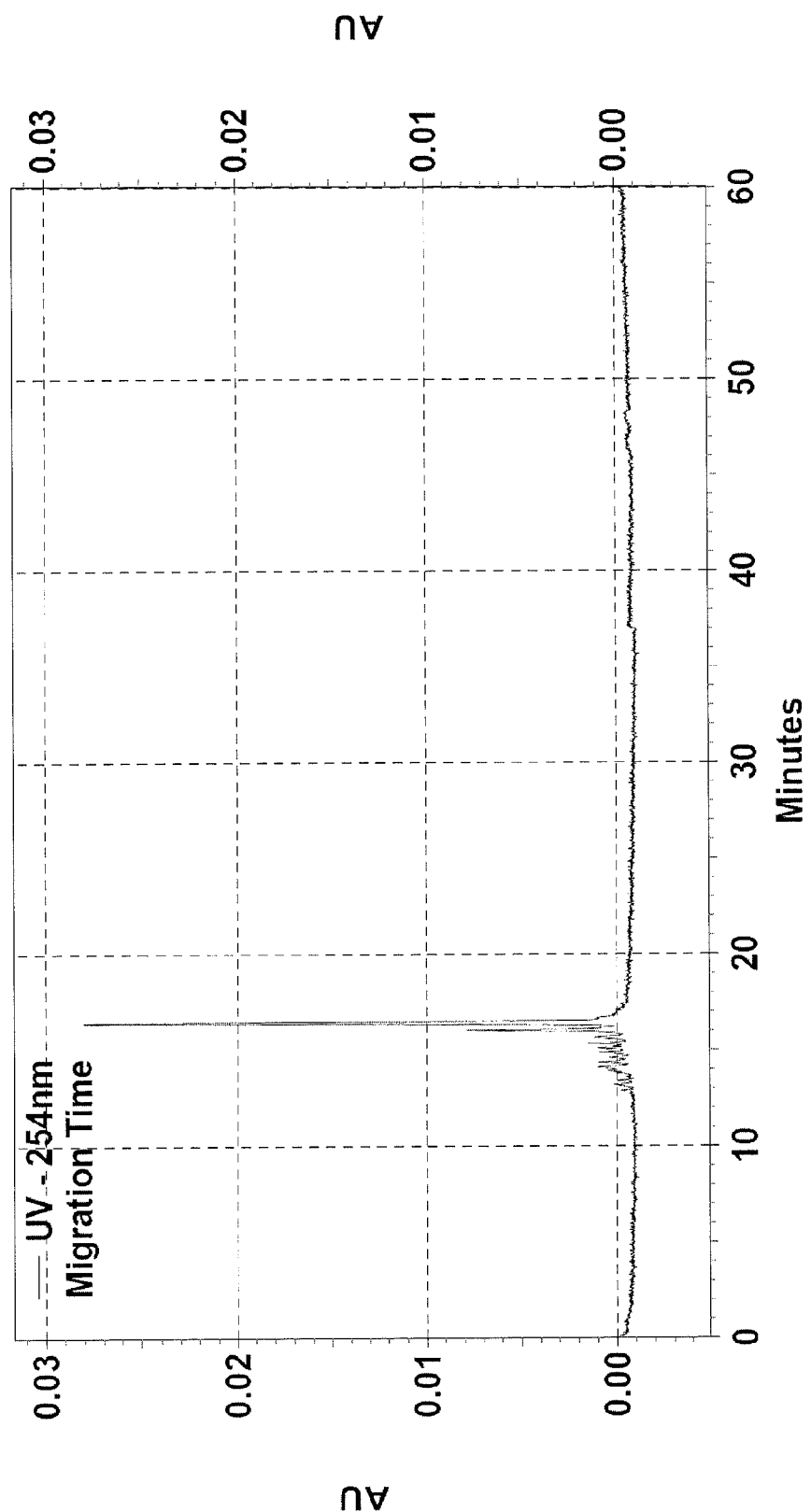
FIG. 16A is a graph of an electropherogram of the crude 21-mer RNA made by conventional method (3'45'-direction). Expedite model 8909-1 umole scale. Crude purity; 70.73%.
Figure 16B:
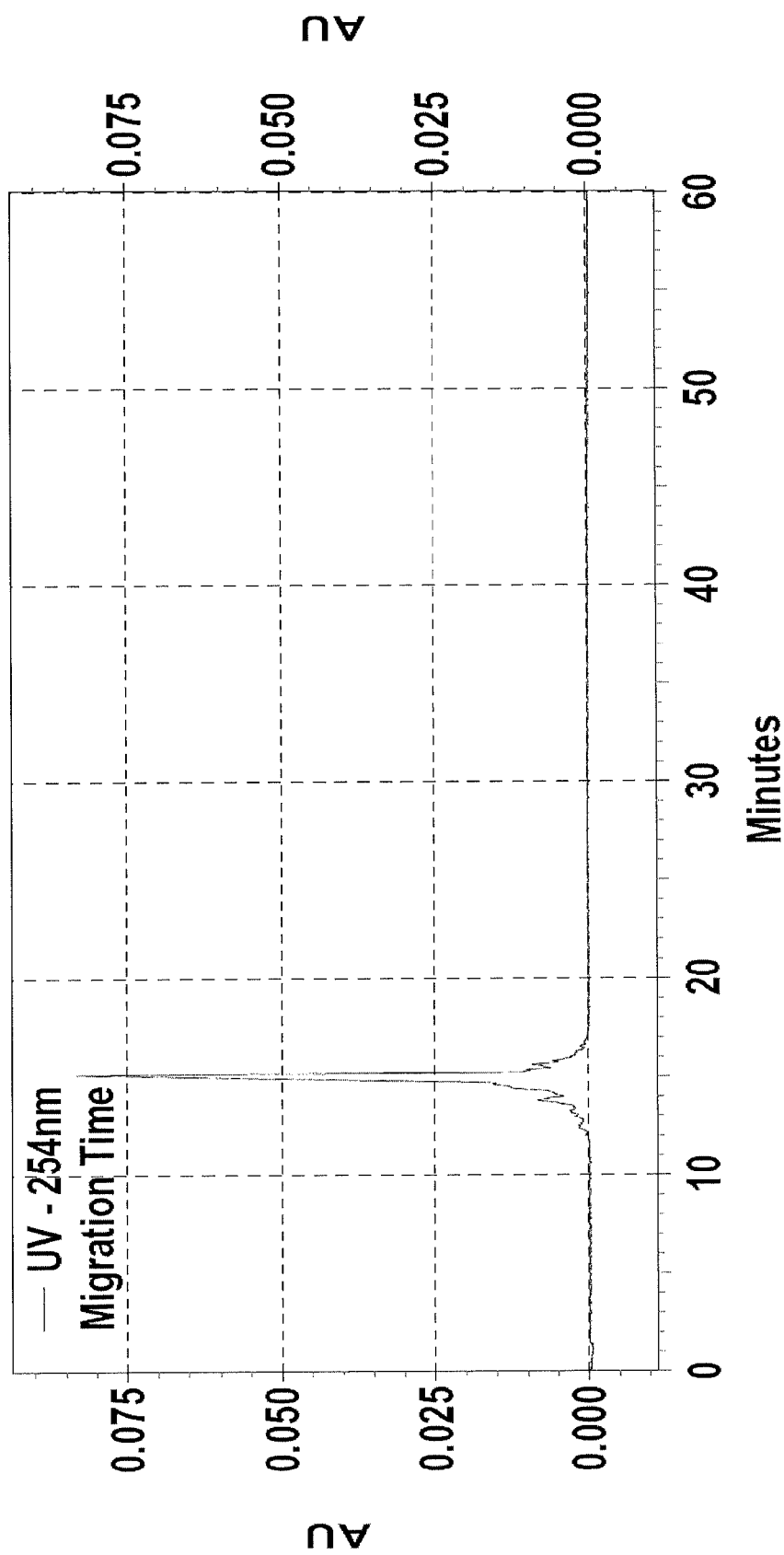
FIG. 16B is a graph of an electropherogram of the purified 21-mer RNA made by conventional method (3'→5'-direction). Expedite model 8909-1 umole scale. Crude purity; 90.78%.
Figure 17:
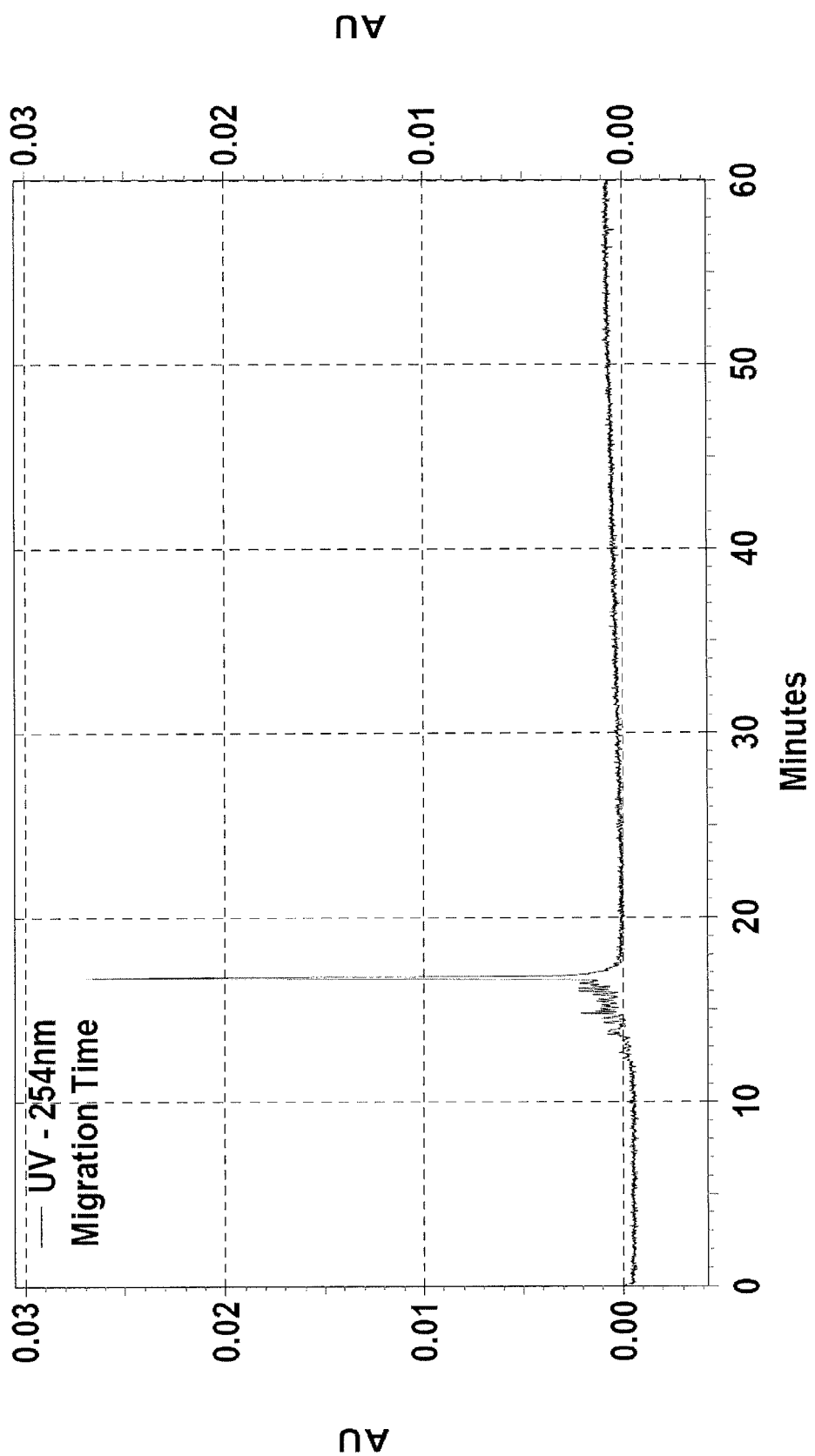
FIG. 17 is a graph of an electropherogram of the crude 21-mer RNA made by Reverse RNA synthesis method (5'→3'-direction). Expedite model 8909-1 umole scale. Crude purity; 78.55%.
Figure 18:
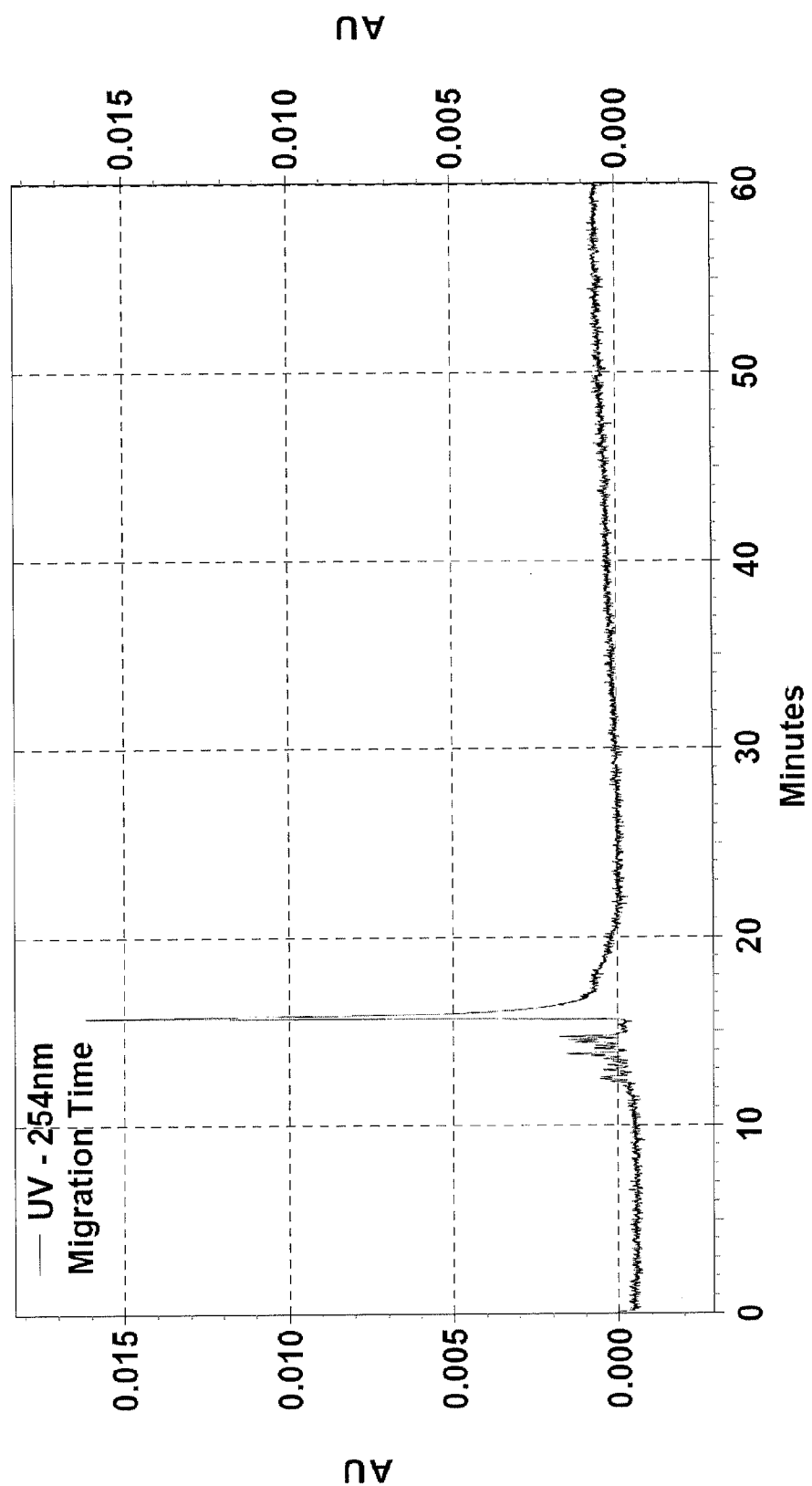
FIG. 18 is a graph an electropherogram of the crude 21-mer RNA with 3'-cholesterol CPG, made by conventional method (3'→-5'-direction). Expedite model 8909-1 umole scale. Crude purity; 82.83%.
Figure 19:
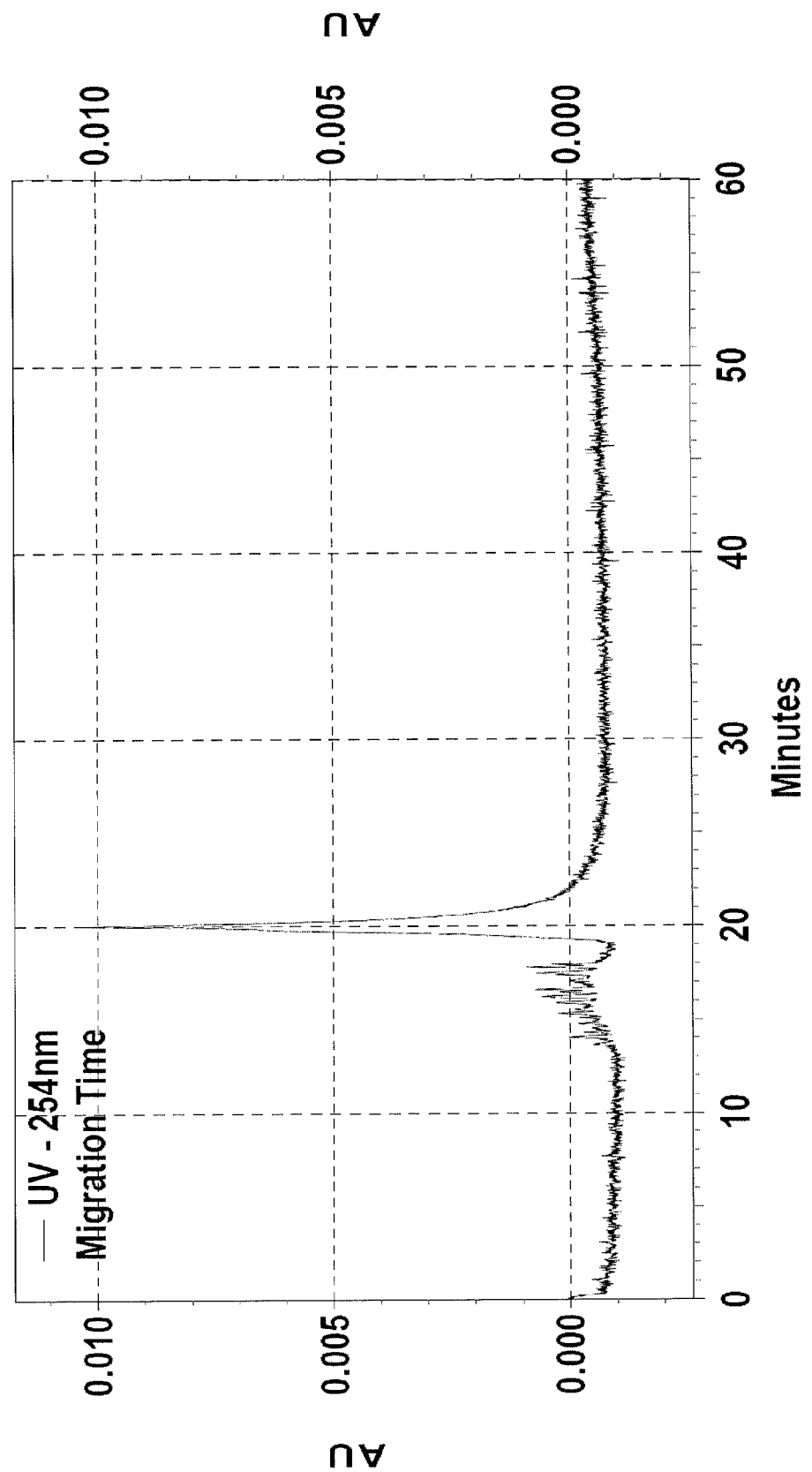
FIG. 19 is a graph of an electropherogram of the crude 21-mer RNA with 3'-Cholesterol CPG, made by Reverse RNA synthesis method (5'→3'-direction). Expedite model 8909-1 umole scale. Crude purity; 85.76%.
Figure 20:
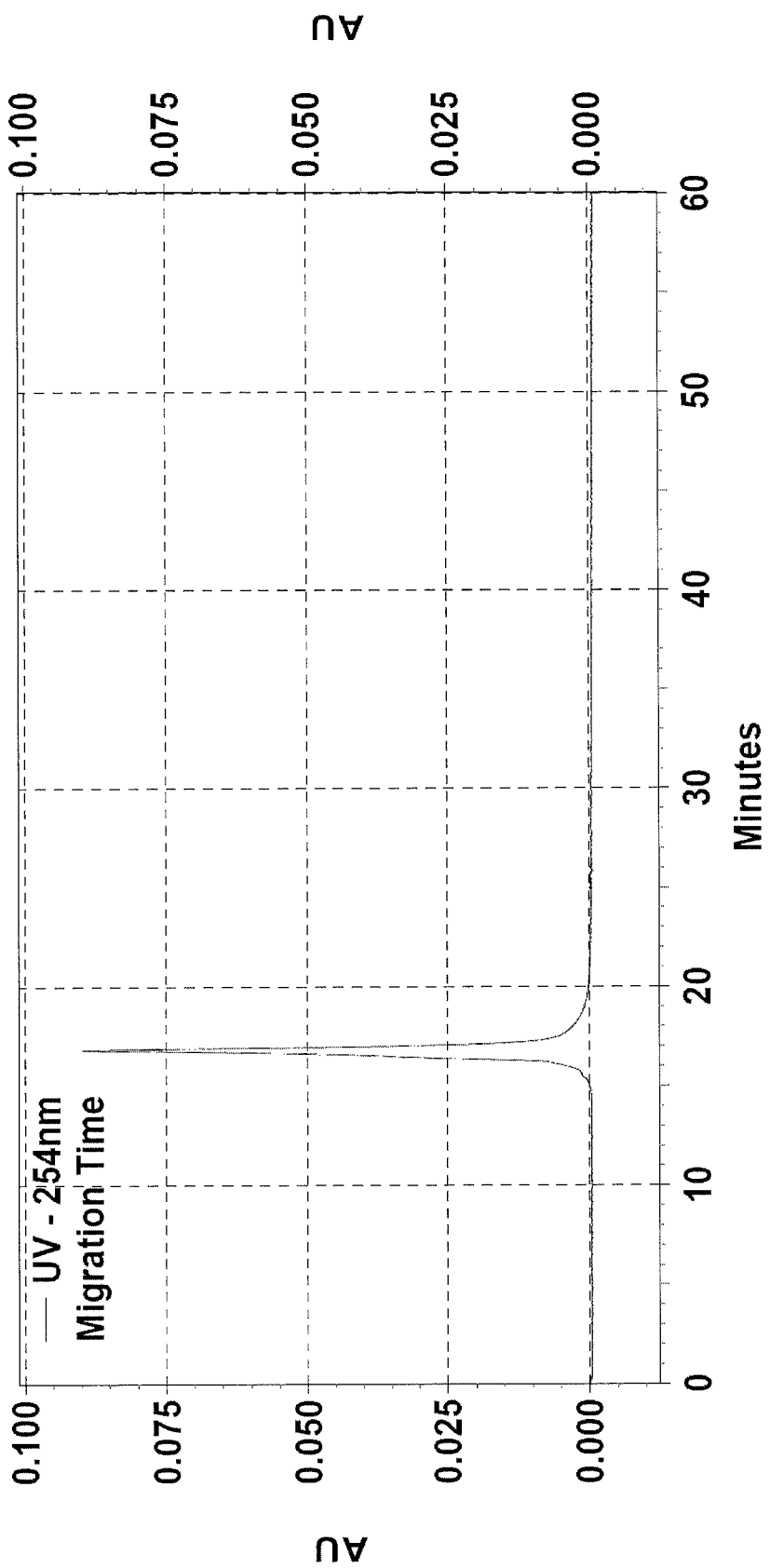
FIG. 20 is a graph of the 21-Mer RNA with 3'-Cholesterol-TEG linker. Reverse direction (5'→3') synthesis and HPLC purification. 1 umole scale. Purity; 99.9%.
Figure 21A:
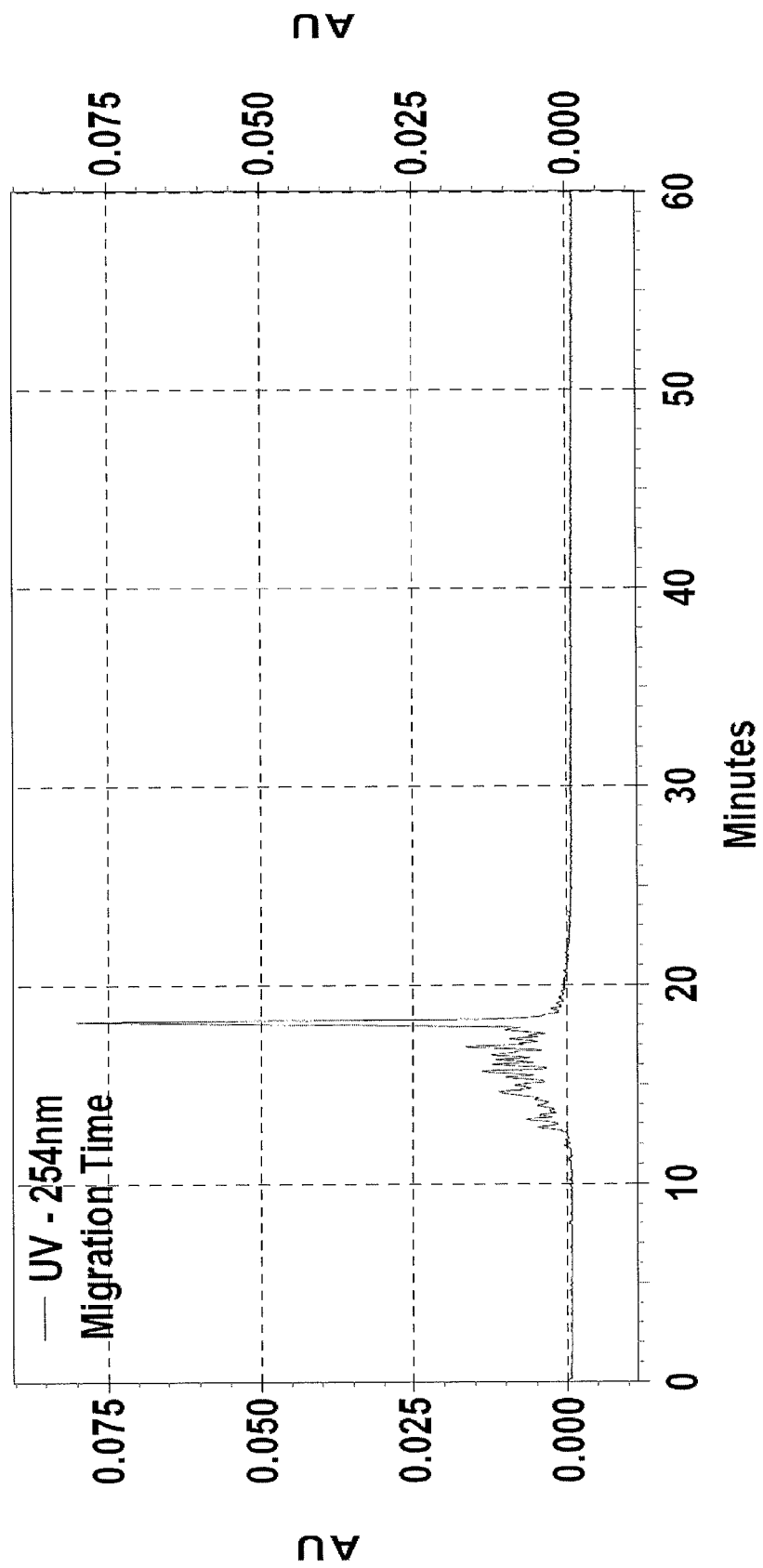
FIGS. 21A and 21B are graphs of electropherograms.
Figure 21B:
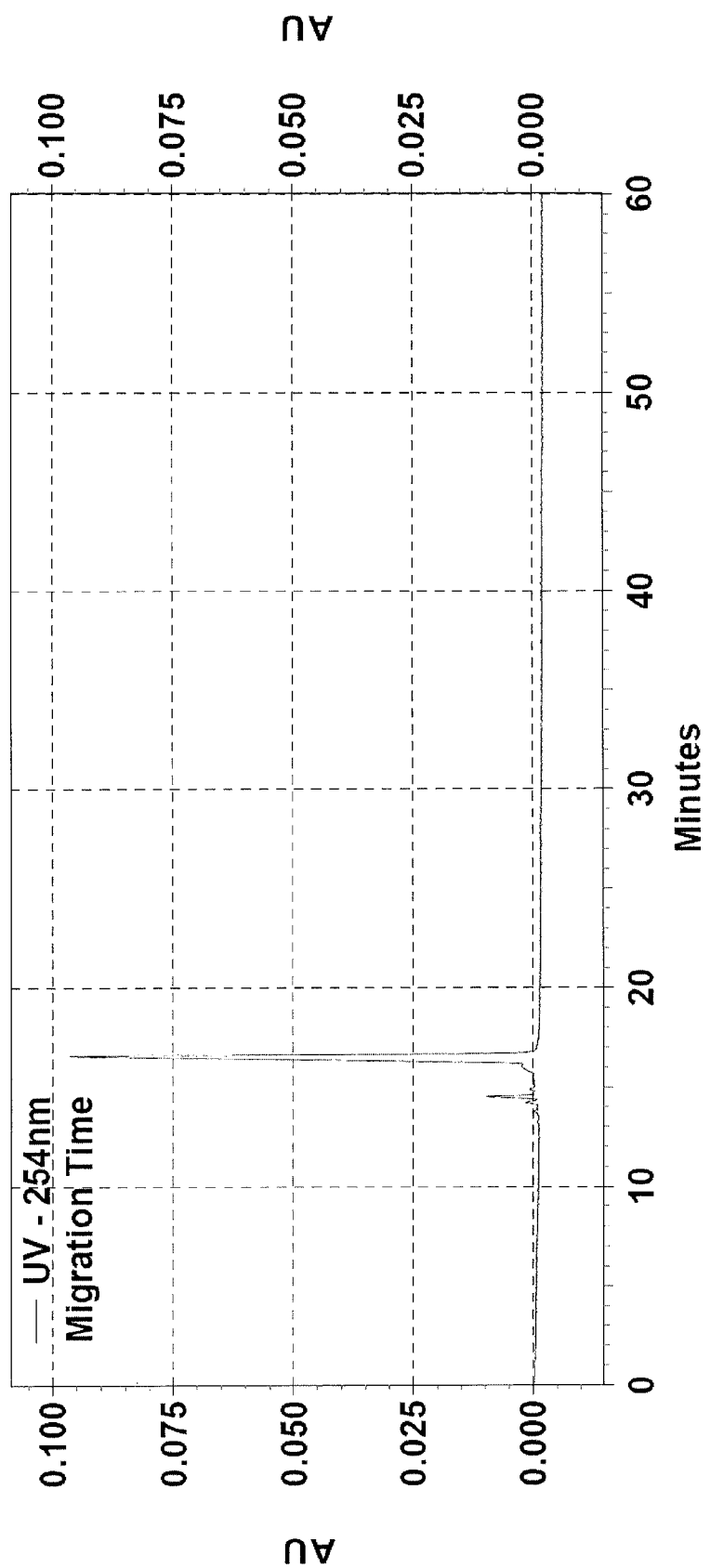
Figure 22:
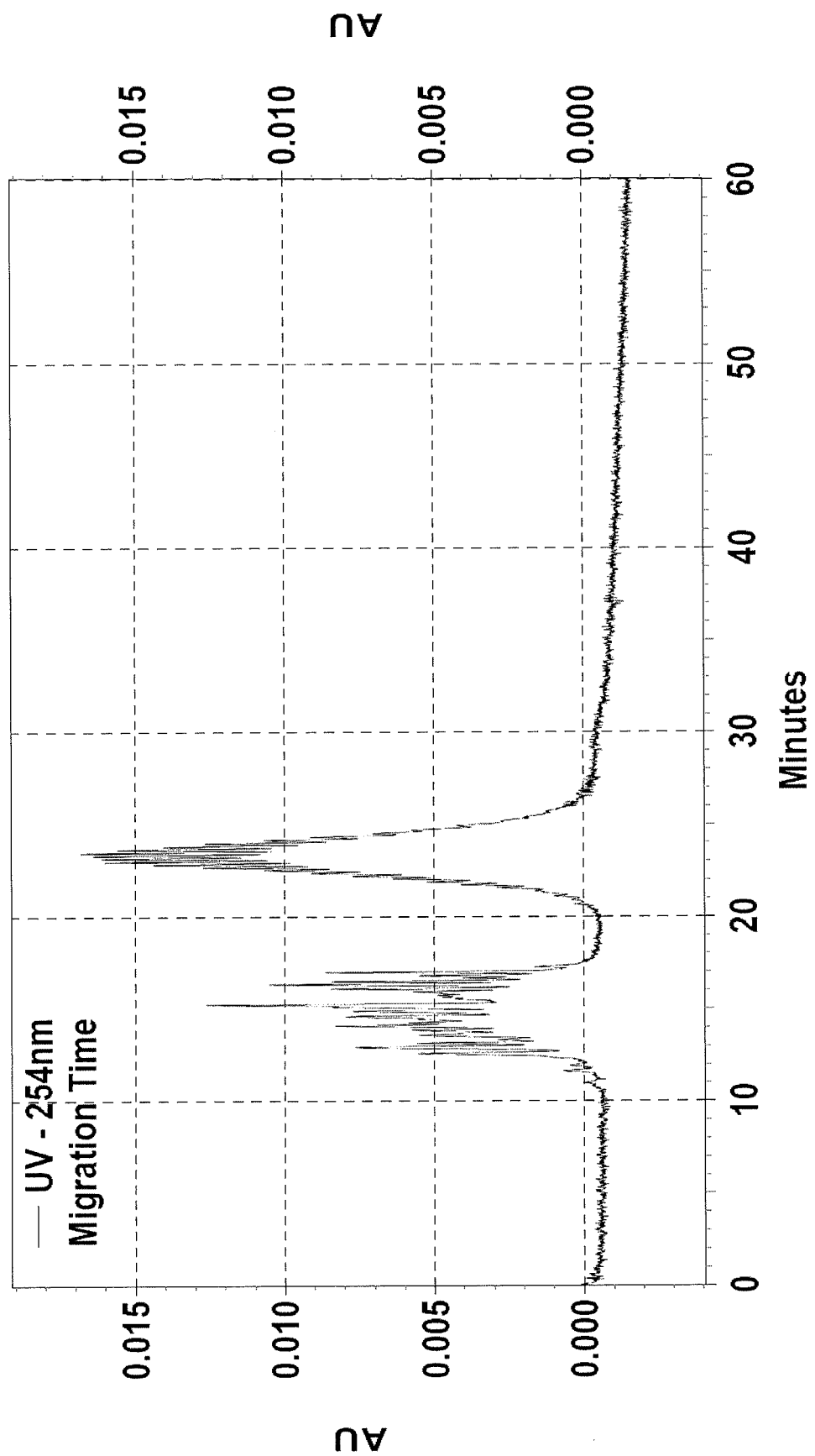
FIG. 22 is a graph of an electropherogram of the crude 21-mer RNA with 3'-PEG(Polyethylene glycol; MW 2000) made by Reverse RNA synthesis method (5'→3'-direction). Expedite model 8909-1 umole scale. Crude purity; 91.87%.
Figure 23:
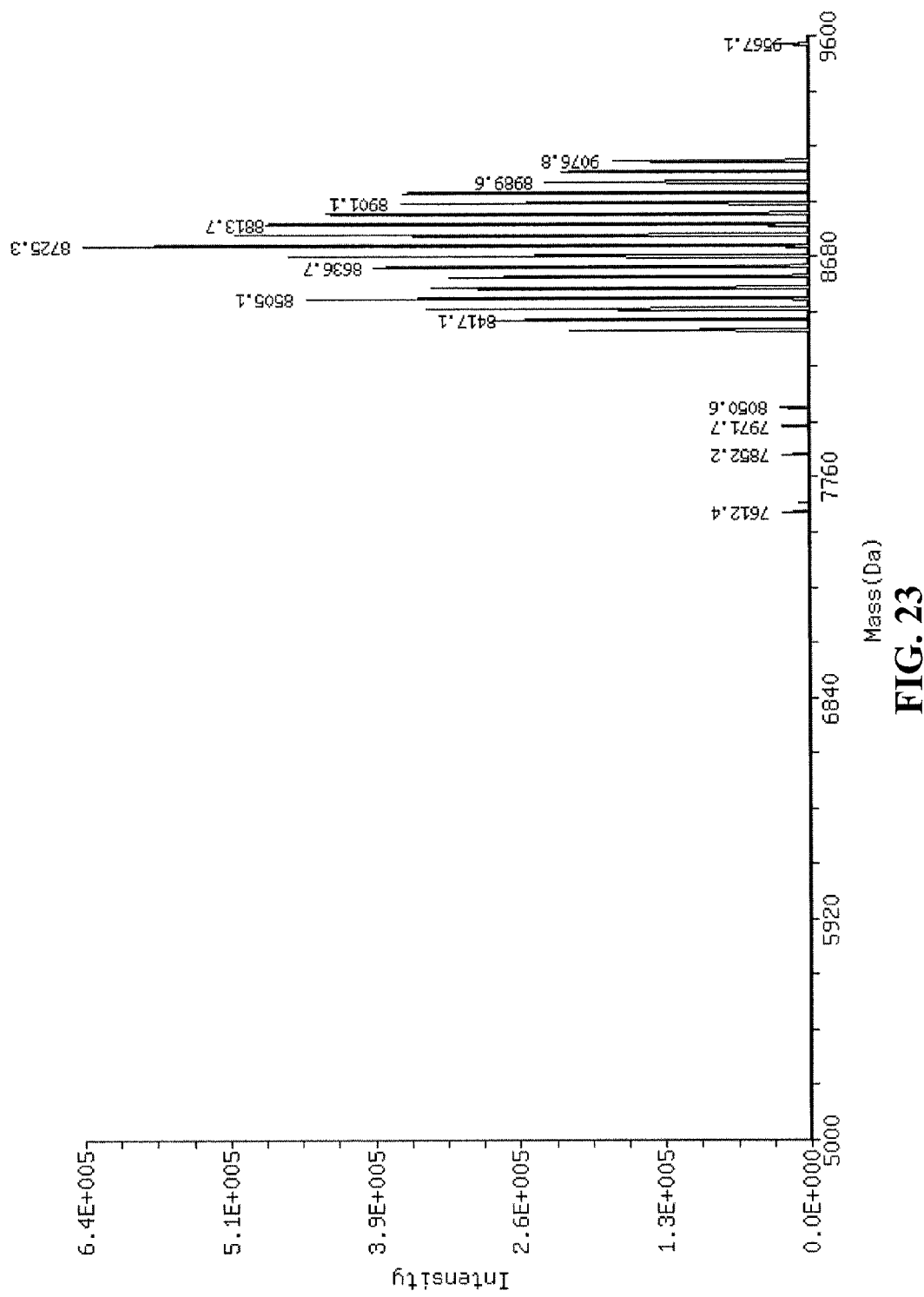
FIG. 23 is a graph of the ESI Spectral analysis of 21-mer RNA with 3'-PEG-2000 attachment, purified RNA as shown in FIG. 24. The synthesis was carried out in reverse direction (5'→3' direction). The PEG-2000 was attached as last step via the corresponding phosphoramidite, ChemGenes catalog; CLP-3119; Calculated Molecular Weight: 8684.1; and Observed Molecular Weight: 8681.1.
Figure 24:
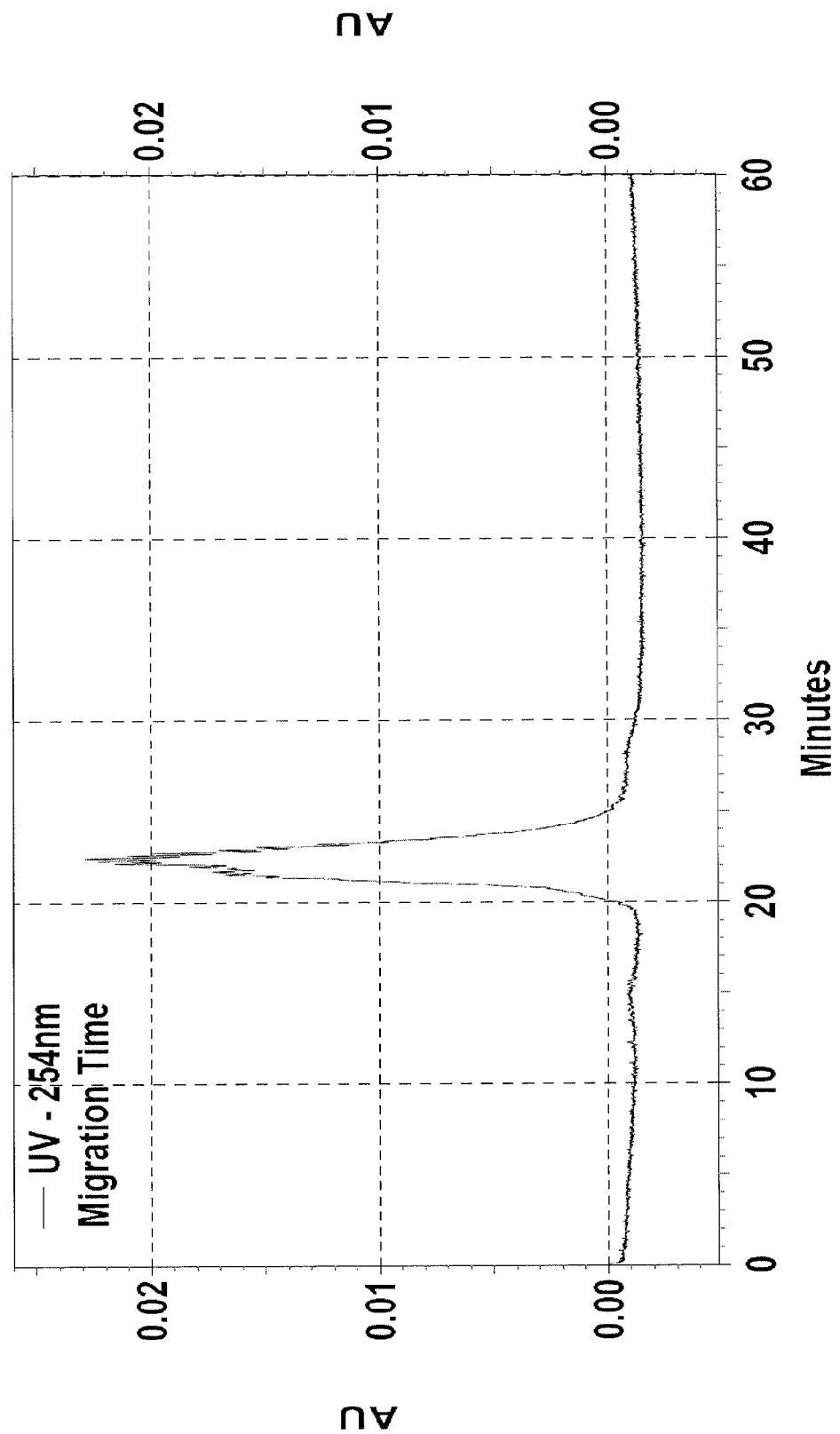
FIG. 24 is a graph of an electropherogram of the HPLC purified 21-mer RNA with 3'-PEG (Polyethyleneglycol; MW 2000). Made by Reverse RNA synthesis method (5'→3'-direction). Expedite model 8909-1 umole scale. Purity; 100%.

A description of example embodiments of the invention follows.

The teachings of all patents, published applications and references cited herein are incorporated by reference in their entirety.

In a first embodiment, the invention relates to a compound of Formula Ia, Ib, Ic, or Id:

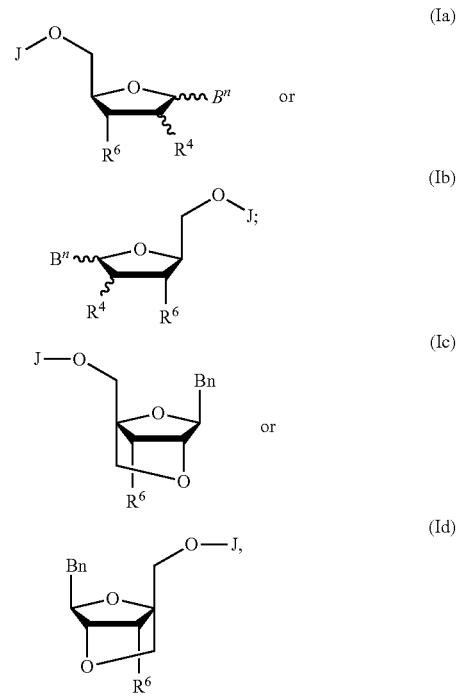

or a salt thereof, wherein
J is H,

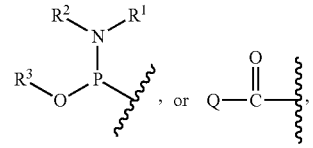

wherein ⁞ indicates where J is attached to the O atom;

Q is a) a support comprised of a linking group and a spacer that can be cleaved to form a hydroxy group; or b) an aliphatic chain, aromatic group, substituted or unsubstituted aromatic, a substituted or unsubstituted phenoxy, or levulinyl;

$R^1$ is a substituted or unsubstituted ($C_1$-$C_{12}$)alkyl group, a substituted or unsubstituted ($C_3$-$C_{20}$)cycloalkyl group, or a substituted or unsubstituted ($C_3$-$C_{20}$)cycloalkyl($C_1$-$C_{12}$)alkyl group, wherein the alkyl or cycloalkyl groups optionally include intervening heteroatoms independently selected from NH, $NR^7$, O and S;

$R^2$ is a substituted or unsubstituted ($C_1$-$C_{12}$)alkyl group, a substituted or unsubstituted ($C_3$-$C_{20}$)cycloalkyl group, or a substituted or unsubstituted ($C_3$-$C_{20}$)cycloalkyl($C_1$-$C_{12}$)alkyl group, wherein the alkyl or cycloalkyl groups optionally include intervening heteroatoms independently selected from NH, $NR^7$, O and S;

or $R^1$ and $R^2$ taken together with the nitrogen atom to which they are bound form a 4-7 membered non-aromatic heterocyclyl, wherein the heterocyclyl formed may optionally include intervening heteroatoms independently selected from NH, $NR^7$, O and S;

$R^3$ is a phosphate protecting group;
$R^4$ is a -halo, —$R^5$, —$NR^7R^8$, —$OR^9$, —Se, or 2'-blocking group; or when Structural Formula Ia or Ib is:

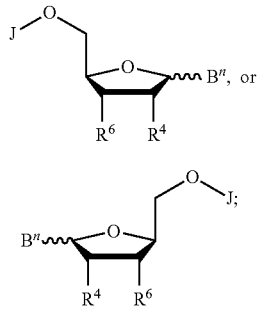

(II)

(III)

wherein $R^4$ is further selected from O—Si($R^{11}$)$_3$ or O—CH$_2$—Si($R^{11}$)$_3$; or when Structural Formula Ia or Ib is:

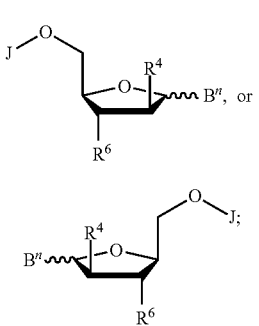

(IV)

(V)

$R^4$ is further selected from —OC(=O)$R^{12}$;
  each $R^5$ is independently a substituted or unsubstituted ($C_1$-$C_{12}$)alkyl group, a substituted or unsubstituted ($C_2$-$C_{12}$)alkenyl group, a substituted or unsubstituted ($C_2$-$C_{12}$)alkynyl group, or a substituted or unsubstituted phenyl, wherein the alkyl, alkenyl, alkynyl and the phenyl groups optionally includes intervening heteroatoms independently selected from NH, $NR^5$, O and S; and may optionally terminate with —$NR^7R^8$, ($C_1$-$C_4$)alkylamino, di($C_1$-$C_4$)alkylamino, —$OR^9$, ($C_1$-$C_6$)alkoxy, benzyl or substituted benzyl, —$SR^{10}$; or —S—($C_1$-$C_6$) alkyl group;
  $R^6$ is —H or —O—Z;
  each $R^7$ is independently a fluorenylmethyloxycarbonyl; —C(=O)—(CH$_2$)$_{1-16}$$NR^8$C(=O)CF$_3$; —C(=O)—(CH$_2$)$_{1-16}$$NR^8$C(=O)-phthalimide; —C(=O)—(CH$_2$)$_{1-16}$-phthalimide; $NR^8$C(=O)-phthalimide; a substituted or unsubstituted ($C_1$-$C_{12}$) alkyl group, a substituted or unsubstituted ($C_2$-$C_{12}$) alkenyl group, or a substituted or unsubstituted ($C_2$-$C_{12}$)alkynyl group;
  each $R^8$ is H or a substituted or unsubstituted ($C_1$-$C_{12}$)alkyl group, a substituted or unsubstituted ($C_2$-$C_{12}$)alkenyl group, or a substituted or unsubstituted ($C_2$-$C_{12}$)alkynyl group;
  each $R^9$ is independently —C(=O)—(CH$_2$)$_{1-16}$CH$_3$; a substituted or unsubstituted ($C_2$-$C_{12}$)alkenyl group, or a substituted or unsubstituted ($C_2$-$C_{12}$)alkynyl group;
  each $R^{10}$ is independently —S($C_1$-$C_6$)alkyl, —C(=O)—(CH$_2$)$_{1-16}$CH$_3$; a substituted or unsubstituted ($C_2$-$C_{12}$) alkenyl group, or a substituted or unsubstituted ($C_2$-$C_{12}$) alkynyl group;
  each $R^{11}$ is independently a substituted or unsubstituted ($C_1$-$C_{12}$)alkyl group, a substituted or unsubstituted ($C_2$-$C_{12}$)alkenyl group, or a substituted or unsubstituted ($C_2$-$C_{12}$)alkynyl group;
  each $R^{12}$ is independently a substituted or unsubstituted ($C_1$-$C_{12}$)alkyl group, a substituted or unsubstituted ($C_2$-$C_{12}$)alkenyl group, or a substituted or unsubstituted ($C_2$-$C_{12}$)alkynyl group, or a substituted or unsubstituted aryl group;
Z is an acid labile protecting group;
B″ is hydrogen or an optionally substituted nucleobase optionally functionalized at each exocyclic amine with an amine protecting group, wherein the nucleobase is selected from:
N6,N6-dimethyl adenine, N6-benzoyladenine, N-1-methyladenine, 7-deazaadenine, 7-deaza-8-azaadenine, 3-deazaadenine, ethenoadenine, isoguanine, N1-methylguanine, 7-iodo-7-deazaguanine, 7-deaza-7-iodo adenine, 7-deaza-7-iodo-6-oxopurine, 5-iodo-5-methyl-7-deazaguanine, 7-deazaguanine substituted with —C≡C(CH$_2$)$_{1-8}$-pthlamide, 7-deaza-8-azaguanine, 8-methylguanine, 8-bromoguanine, 8-aminoguanine, hypoxanthine, 6-methoxypurine, 7-deaza-6-oxopurine, 6-oxopurine, 2-aminopurine, 2,6-diaminopurine, 8-bromopurine, 8-aminopurine, 8-alkylaminopurine, 8-alkylaminopurine, thymine, N-3 methyl thymine, 5-acetoxymethylcytosine, 5-azacytosine, isocytosine, N4($C_1$-$C_6$)alkylcytosine, N-3($C_1$-$C_6$)alkylcytidine, 5-propynylcytosine, 5-iodo-cytosine, 5-($C_1$-$C_6$)alkylcytosine, 5-aryl($C_1$-$C_6$)alkylcytosine, 5-trifluoromethylcytosine, 5-methylcytosine, ethenocytosine, cytosine and uracil substituted with —CH=CH—C(=O)NH($C_1$-$C_6$)alkyl, cytosine and uracil substituted with —C≡C—CH$_2$-phthalimide, NH($C_1$-$C_6$)alkyl, 4-thiouracil, 2-thiouracil, N$^3$-thiobenzoylethyluracil, 5-propynyluracil, 5-acetoxymethyluracil, 5-fluorouracil, 5-chlorouracil, 5-bromouracil, 5-iodouracil, 4-thiouracil, N-3-($C_1$-$C_6$)alkyluracil, 5-(3-aminoallyl)-uracil, 5-($C_1$-$C_6$)alkyluracil, 5-aryl($C_1$-$C_6$)alkyluracil, 5-trifluoro methyluracil, 4-triazolyl-5-methyluracil, 2-pyridone, 2-oxo-5-methylpyrimidine, 2-oxo-4-methylthio-5-methylpyrimidine, 2-thiocarbonyl-4-oxo-5-methylpyrimidine, and 4-oxo-5-methylpyrimidine;
wherein any substitutable nitrogen atom within the nucleobase or on the exocyclic amine is optionally substituted with fluorenylmethyloxycarbonyl; —C(=O)OPh; —C(=O)($C_1$-$C_{16}$)alkyl; —C(=O)CH$_2$CH$_2$CH=CH$_2$I; —C(=O)($C_1$-$C_{16}$)alkylene-C(=O)OH; —C(=O)($C_1$-$C_{16}$)alkylene-C(=O)O($C_1$-$C_6$)alkyl; =CR$^8$N($C_1$-$C_6$)alkyl)$_2$; —C(=O)—$NR^8$—(CH$_2$)$_{1-16}$$NR^8$C(=O)CF$_3$; —C(=O)—(CH$_2$)$_{1-16}$$NR^8$C(=O)CF$_3$; —C(=O)—$NR^8$(CH$_2$)$_{1-16}$$NR^8$C(=O)-phthalimide; —C(=O)—(CH$_2$)$_{1-16}$-phthalimide; and

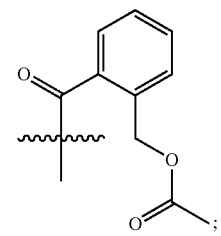

wherein any substitutable oxygen atom within the nucleobase is optionally substituted with —C(=O)N($C_1$-$C_6$alkyl)$_2$-C(=O)N(phenyl)$_2$.

In a second embodiment, the invention relates to a compound of Formula Ia, Ib, Ic, or Id:

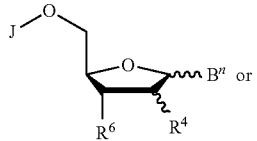

(Ia)

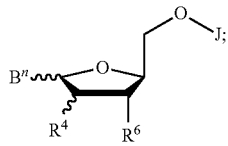

(Ib)

or a salt thereof, wherein

J is H,

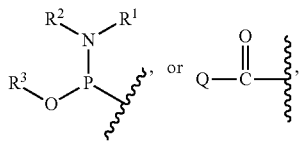

wherein ⸹ indicates where J is attached to the O atom;

Q is a) a support comprised of a linking group and a spacer that can be cleaved to form a hydroxy group; or b) an aliphatic chain, aromatic group, substituted or unsubstituted aromatic, a $R^1$ is a substituted or unsubstituted $(C_1$-$C_{12})$alkyl group, a substituted or unsubstituted $(C_3$-$C_{20})$cycloalkyl group, or a substituted or unsubstituted $(C_3$-$C_{20})$cycloalkyl$(C_1$-$C_{12})$alkyl group, wherein the alkyl or cycloalkyl groups optionally include intervening heteroatoms independently selected from NH, $NR^7$, O and S;

$R^2$ is a substituted or unsubstituted $(C_1$-$C_{12})$alkyl group, a substituted or unsubstituted $(C_3$-$C_{20})$cycloalkyl group, or a substituted or unsubstituted $(C_3$-$C_{20})$cycloalkyl$(C_1$-$C_{12})$alkyl group, wherein the alkyl or cycloalkyl groups optionally include intervening heteroatoms independently selected from NH, $NR^7$, O and S;

or $R^1$ and $R^2$ taken together with the nitrogen atom to which they are bound form a 4-7 membered non-aromatic heterocyclyl, wherein the heterocyclyl formed may optionally include intervening heteroatoms independently selected from NH, $NR^7$, O and S;

$R^3$ is a phosphate protecting group;

$R^4$ is a -halo, —$R^5$, —$NR^7R^8$, —$OR^9$, —$SR^{10}$, or 2'-blocking group; or when Structural Formula Ia or Ib is:

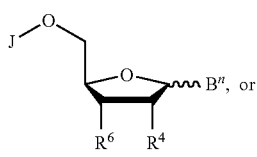

(II)

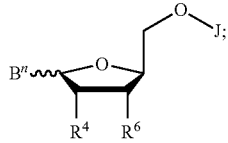

(III)

wherein $R^4$ is further selected from O—Si$(R^{11})_3$ or O—CH$_2$—Si$(R^{11})_3$; or when Structural Formula Ia or Ib is:

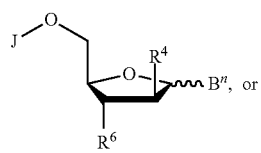

(IV)

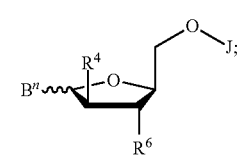

(V)

$R^4$ is further selected from —OC(=O)$R^{12}$;

each $R^5$ is independently a substituted or unsubstituted $(C_1$-$C_{12})$alkyl group, a substituted or unsubstituted $(C_2$-$C_{12})$alkenyl group, a substituted or unsubstituted $(C_2$-$C_{12})$alkynyl group, or a substituted or unsubstituted phenyl, wherein the alkyl, alkenyl, alkynyl and the phenyl groups optionally includes intervening heteroatoms independently selected from NH, $NR^5$, O and S; and may optionally terminate with —$NR^7R^8$, $(C_1$-$C_4)$alkylamino, di$(C_1$-$C_4)$alkylamino, —$OR^9$, $(C_1$-$C_6)$alkoxy, benzyl or substituted benzyl, —$SR^{10}$; or —S—$(C_1$-$C_6)$ alkyl group;

$R^6$ is —H or —O—Z;

each $R^7$ is independently a fluorenylmethyloxycarbonyl;
—C(=O)—(CH$_2$)$_{1-16}$NR$^8$C(=O)CF$_3$;
—C(=O)—(CH$_2$)$_{1-16}$NR$^8$C(=O)-phthalimide;
—C(=O)—(CH$_2$)$_{1-16}$-phthalimide; NR$^8$C(=O)-phthalimide; a substituted or unsubstituted $(C_1$-$C_{12})$ alkyl group, a substituted or unsubstituted $(C_2$-$C_{12})$ alkenyl group, or a substituted or unsubstituted $(C_2$-$C_{12})$alkynyl group;

each $R^8$ is H or a substituted or unsubstituted $(C_1$-$C_{12})$alkyl group, a substituted or unsubstituted $(C_2$-$C_{12})$alkenyl group, or a substituted or unsubstituted $(C_2$-$C_{12})$alkynyl group;

each $R^9$ is independently —C(=O)—(CH$_2$)$_{1-16}$CH$_3$; a substituted or unsubstituted $(C_2$-$C_{12})$alkenyl group, or a substituted or unsubstituted $(C_2$-$C_{12})$alkynyl group;

each $R^{10}$ is independently —S$(C_1$-$C_6)$alkyl, —C(=O)—(CH$_2$)$_{1-16}$CH$_3$; a substituted or unsubstituted $(C_2$-$C_{12})$ alkenyl group, or a substituted or unsubstituted $(C_2$-$C_{12})$ alkynyl group;

each $R^{11}$ is independently a substituted or unsubstituted $(C_1$-$C_{12})$alkyl group, a substituted or unsubstituted $(C_2$-$C_{12})$alkenyl group, or a substituted or unsubstituted $(C_2$-$C_{12})$alkynyl group; provided that if $R^4$ is —O—Si$(R^{11})_3$, and two $R^{11}$ groups are both methyl, the other is not t-butyl or if $R^4$ is —O—CH$_2$—Si$(R^{11})_3$, then the three $R^{11}$ groups cannot all be isopropyl;

each $R^{12}$ is independently a substituted or unsubstituted $(C_1-C_{12})$alkyl group, a substituted or unsubstituted $(C_2-C_{12})$alkenyl group, or a substituted or unsubstituted $(C_2-C_{12})$alkynyl group, or a substituted or unsubstituted aryl group;

Z is an acid labile protecting group;

B" is hydrogen or an optionally substituted nucleobase optionally functionalized at each exocyclic amine with an amine protecting group.

In one aspect of either the first or second embodiment, wherein J is

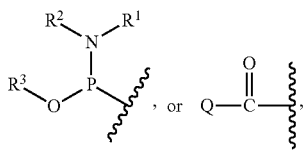

wherein ⦃ indicates where J is attached to the O atom.

In one aspect of either the first or second embodiment, wherein the compound is represented by Formula Ia or Ib:

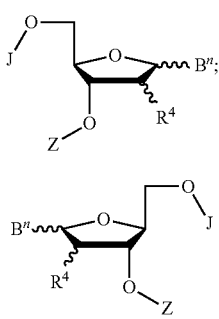

or a salt thereof.

In another aspect of either the first or second embodiment, Z is an unsubstituted or substituted aryl group, an unsubstituted or substituted triarylmethyl group, an unsubstituted or substituted trityl group, an unsubstituted or substituted tetrahydropyranyl group, or an unsubstituted or substituted 9-phenylxanthyl.

In another aspect of either the first or second embodiment, Z is di-p-anisylphenyl methyl, p-fluorophenyl-1-naphthylphenyl methyl, p-anisyl-1-naphthylphenyl methyl, di-o-anisyl-1-naphthyl methyl, di-o-anisylphenyl methyl, p-tolyldiphenylmethyl, di-p-anisylphenylmethyl, di-o-anisyl-1-naphthylmethyl, di-p-anisylphenyl methyl, di-o-anisyl phenyl methyl, di-p-anisylphenyl methyl, or p-tolyldiphenylmethyl.

In yet another aspect of either the first or second embodiment, Z is represented by the following structural formula:

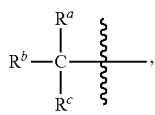

wherein ⦃ indicates attachment to the 3' oxygen atom and $R^a$, $R^b$, and $R^c$ are independently selected from the following structural formulas:

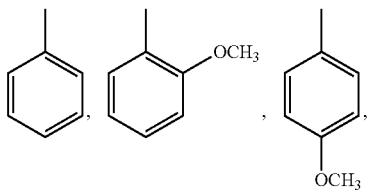

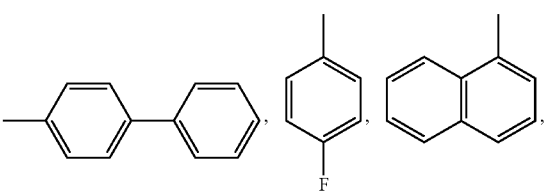

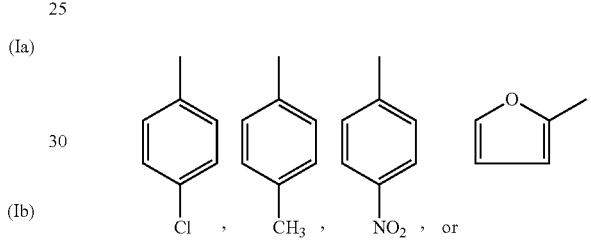

In one aspect of either the first or second embodiment, Z is 4-methoxytrityl, 4,4'-dimethoxytrityl, or 4,4',4"-trimethoxytrityl.

In another aspect of either the first or second embodiment, the substitutable nitrogen atom within the nucleobase or on the exocyclic amine is optionally substituted with =CHN(CH$_3$)$_2$; C(=O)CH(CH$_3$)$_2$; —C(=O)CH$_3$, =C(CH$_3$)N(CH$_3$)$_2$; —C(=O)OPh; —C(=O)CH$_2$CH$_2$CH=CH$_2$; —C(=O)CH$_2$CH$_2$—C(=O)O(C$_1$-C$_6$)alkyl; —C(=O)—NR$^8$—(CH$_2$)$_{1-16}$NR$^8$C(=O)CF$_3$; —C(=O)—(CH$_2$)$_{1-16}$NR$^8$C(=O)CF$_3$; —C(=O)—NR$^8$(CH$_2$)$_{1-16}$NR$^8$C(=O)-phthalimide; —C(=O)—(CH$_2$)$_{1-16}$-phthalimide and

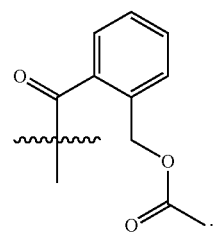

In yet another aspect of either the first or second embodiment, $R^3$ is —CH$_2$CH$_2$CN, —CH$_2$CH$_2$—Si(CH$_3$)$_2$C$_6$H$_5$, —CH$_2$CH$_2$—S(O)$_2$—CH$_2$CH$_3$, —CH$_2$CH$_2$—C$_6$H$_4$—NO$_2$, —CH$_2$CH$_2$—NH—C(O)—C$_6$H$_5$, or —CH$_2$CH$_2$—O—C$_6$H$_4$—C(O)CH$_3$, and $R^4$ is —O—Si(R$^{11}$).

In yet another aspect of either the first or second embodiment, $R^4$ is —O—Si(CH$_3$)$_2$(C(CH$_3$)$_3$) or —O—CH$_2$—Si(CH(CH$_3$)$_2$)$_3$).

In one aspect of either the first or second embodiment, the compound is represented by one of the following structural formulas:

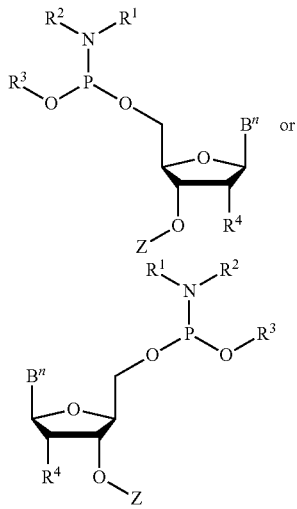

or a salt thereof.

In another aspect of either the first or second embodiment, the compound is represented by one of the following structural formulas:

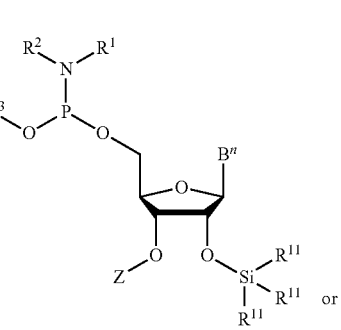

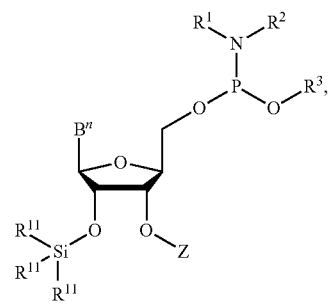

or a salt thereof.

In yet another aspect of either the first or second embodiment, $R^3$ is —CH$_2$CH$_2$CN.

In one aspect of either the first or second embodiment, the compound is represented by one of the following structural formulas:

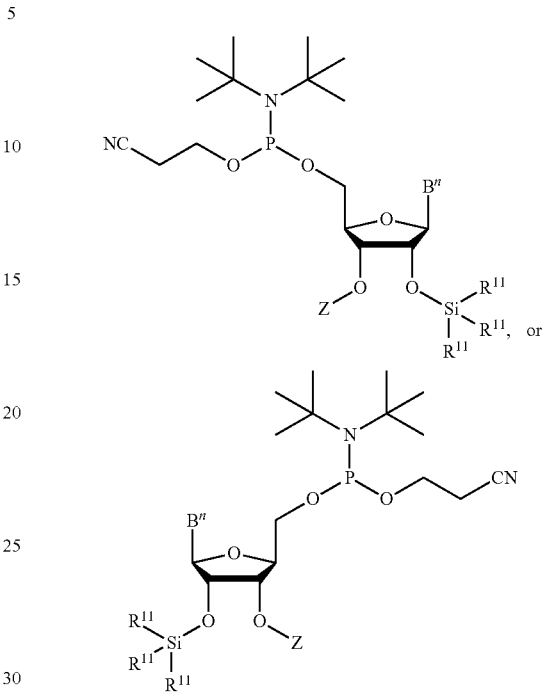

or a salt thereof.

In one aspect of either the first or second embodiment, the compound is represented by one of the following structural formulas:

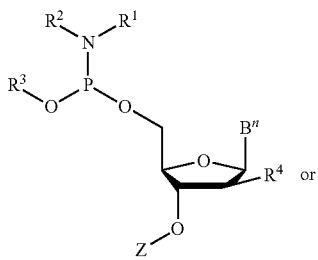

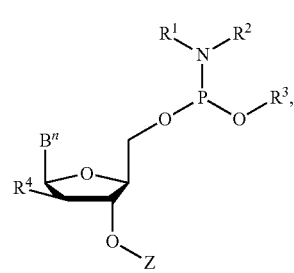

or a salt thereof.

In another aspect of either the first or second embodiment, the compound is represented by one of the following structural formula:

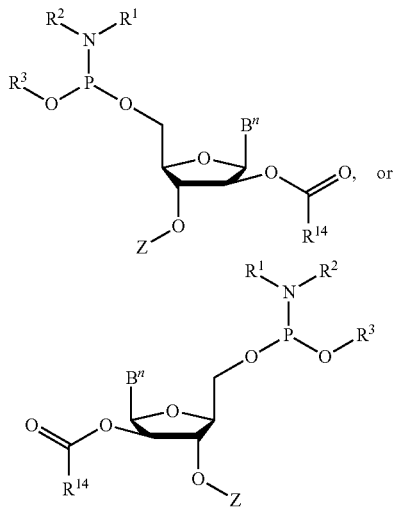

or a salt thereof.

In yet another aspect of either the first or second embodiment, $R^3$ is $CH_2CH_2CN$.

In one aspect of either the first or second embodiment, the compound is represented by one of the following structural formulas:

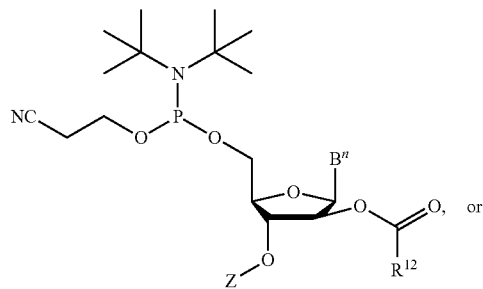

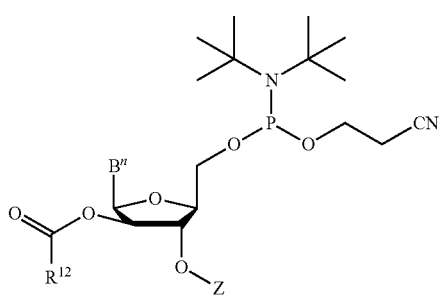

or a salt thereof.

In one aspect of either the first or second embodiment, the compound is represented by one of the following structural formulas:

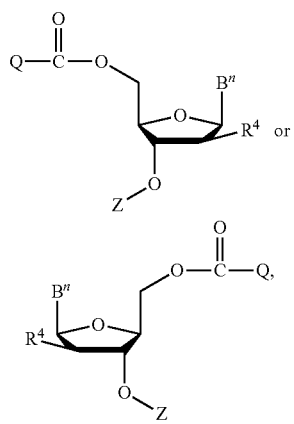

or a salt thereof.

In one aspect of either the first or second embodiment, the compound is represented by one of the following structural formulas:

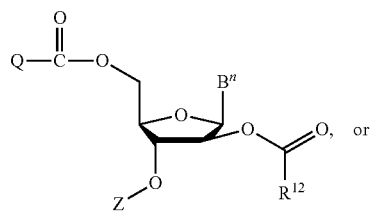

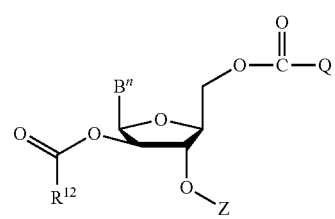

or a salt thereof.

In another aspect of either the first or second embodiment, the compound is represented by one of the following structural formulas:

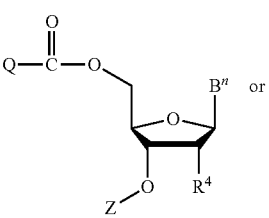

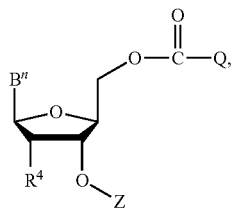

or a salt thereof.

In another aspect of either the first or second embodiment, the compound is represented by one of the following structural formulas:

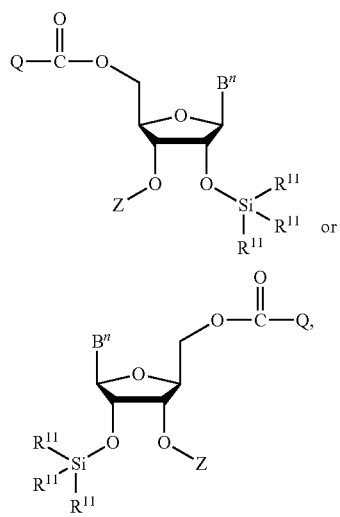

or a salt thereof.

In a third embodiment, the invention relates to a compound represented by one of the following structural formulas:

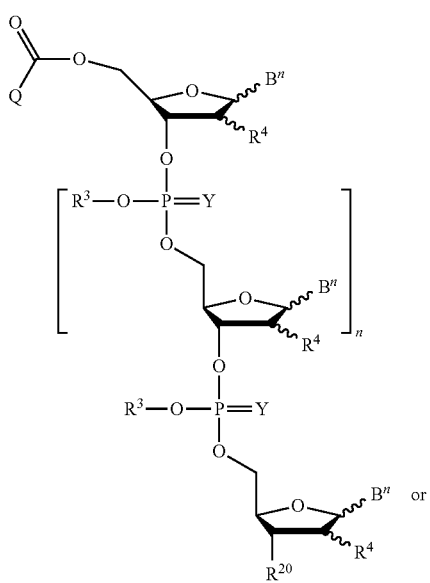

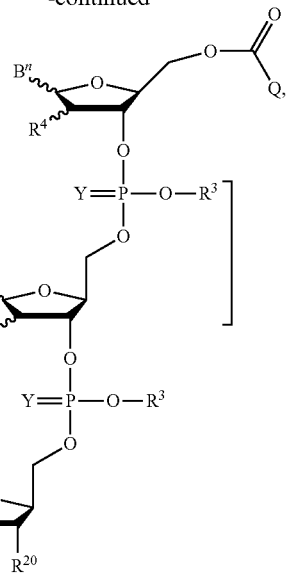

or salts thereof, wherein each Y is independently oxygen or sulfur;

Q is a) a support comprised of a linking group and a spacer that can be cleaved to form a hydroxy group; or b) an aliphatic chain, aromatic group, substituted or unsubstituted aromatic, a substituted or unsubstituted phenoxy, or levulinyl;

$R^1$ is a substituted or unsubstituted ($C_1$-$C_{12}$)alkyl group, a substituted or unsubstituted ($C_3$-$C_{20}$)cycloalkyl group, or a substituted or unsubstituted ($C_3$-$C_{20}$)cycloalkyl($C_1$-$C_{12}$) alkyl group, wherein the alkyl or cycloalkyl groups optionally include intervening heteroatoms independently selected from NH, $NR^7$, O and S;

$R^2$ is a substituted or unsubstituted ($C_1$-$C_{12}$)alkyl group, a substituted or unsubstituted ($C_3$-$C_{20}$)cycloalkyl group, or a substituted or unsubstituted ($C_3$-$C_{20}$)cycloalkyl($C_1$-$C_{12}$) alkyl group, wherein the alkyl or cycloalkyl groups optionally include intervening heteroatoms independently selected from NH, $NR^7$, O and S;

or $R^1$ and $R^2$ taken together with the nitrogen atom to which they are bound form a 4-7 membered non-aromatic heterocyclyl, wherein the heterocyclyl formed may optionally include intervening heteroatoms independently selected from NH, $NR^7$, O and S;

$R^3$ is a phosphate protecting group;

$R^4$ is a -halo, $-R^5$, $-NR^7R^8$, $-OR^9$, $-SR^{10}$, or 2'-blocking group; or when $R^4$ is in the ribose conformation, $R^4$ is further selected from $O-Si(R^{11})_3$ or $O-CH_2-Si(R^{11})_3$; or $R^4$ is in the arabinose conformation, $R^4$ is further selected from $-OC(=O)R^{12}$;

each $R^5$ is independently a substituted or unsubstituted ($C_1$-$C_{12}$)alkyl group, a substituted or unsubstituted ($C_2$-$C_{12}$) alkenyl group, a substituted or unsubstituted ($C_2$-$C_{12}$)alkynyl group, or a substituted or unsubstituted phenyl, wherein the alkyl, alkenyl, alkynyl and the phenyl groups optionally includes intervening heteroatoms independently selected from NH, $NR^5$, O and S; and may optionally terminate with $-NR^7R^8$, ($C_1$-$C_4$)alkylamino, di($C_1$-$C_4$)alkylamino, $-OR^9$, ($C_1$-$C_6$)alkoxy, benzyl or substituted benzyl, $-SR^{10}$; or $-S-(C_1-C_6)$alkyl group;

$R^6$ is $-H$ or $-O-Z$;

each $R^7$ is independently a fluorenylmethyloxycarbonyl; $-C(=O)-(CH_2)_{1-16}NR^8C(=O)CF_3$; $-C(=O)-(CH_2)_{1-16}NR^8C(=O)$-phthalimide; $-C(=O)-(CH_2)_{1-16}$- phthalimide; NR⁸C(=O)-phthalimide; a substituted or unsubstituted $(C_1-C_{12})$alkyl group, a substituted or unsubstituted $(C_2-C_{12})$alkenyl group, or a substituted or unsubstituted $(C_2-C_{12})$alkynyl group;

each $R^8$ is H or a substituted or unsubstituted $(C_1-C_{12})$alkyl group, a substituted or unsubstituted $(C_2-C_{12})$alkenyl group, or a substituted or unsubstituted $(C_2-C_{12})$alkynyl group;

each $R^9$ is independently —C(=O)—$(CH_2)_{1-16}CH_3$; a substituted or unsubstituted $(C_2-C_2)$alkenyl group, or a substituted or unsubstituted $(C_2-C_{12})$alkynyl group;

each $R^{10}$ is independently —S$(C_1-C_6)$alkyl, —C(=O)—$(CH_2)_{1-16}CH_3$; a substituted or unsubstituted $(C_2-C_{12})$alkenyl group, or a substituted or unsubstituted $(C_2-C_{12})$alkynyl group;

each $R^{11}$ is independently a substituted or unsubstituted $(C_1-C_{12})$alkyl group, a substituted or unsubstituted $(C_2-C_{12})$alkenyl group, or a substituted or unsubstituted $(C_2-C_{12})$alkynyl group;

each $R^{12}$ is independently a substituted or unsubstituted $(C_1-C_{12})$alkyl group, a substituted or unsubstituted $(C_2-C_{12})$alkenyl group, or a substituted or unsubstituted $(C_2-C_{12})$alkynyl group, or a substituted or unsubstituted aryl group;

Z is an acid labile protecting group;

B″ is hydrogen or an optionally substituted nucleobase optionally functionalized at each exocyclic amine with an amine protecting group, wherein the nucleobase is selected from:

N6,N6-dimethyl adenine, N6-benzoyladenine, N-1-methyladenine, 7-deazaadenine, 7-deaza-8-azaadenine, 3-deazaadenine, ethenoadenine, isoguanine, N1-methylguanine, 7-iodo-7-deazaguanine, 7-deaza-7-iodo adenine, 7-deaza-7-iodo-6-oxopurine, 5-iodo-5-methyl-7-deazaguanine, 7-deazaguanine substituted with —C≡C$(CH_2)_{1-8}$-pthlamide, 7-deaza-8-azaguanine, 8-methylguanine, 8-bromoguanine, 8-aminoguanine, hypoxanthine, 6-methoxypurine, 7-deaza-6-oxopurine, 6-oxopurine, 2-aminopurine, 2,6-diaminopurine, 8-bromopurine, 8-aminopurine, 8-alkylaminopurine, 8-alkylaminopurine, thymine, N-3 methyl thymine, 5-acetoxymethylcytosine, 5-azacytosine, isocytosine, N4$(C_1-C_6)$alkylcytosine, N-3$(C_1-C_6)$alkylcytidine, 5-propynylcytosine, 5-iodo-cytosine, 5-$(C_1-C_6)$alkylcytosine, 5-aryl$(C_1-C_6)$alkylcytosine, 5-trifluoromethylcytosine, 5-methylcytosine, ethenocytosine, cytosine and uracil substituted with —CH=CH—C(=O)NH$(C_1-C_6)$alkyl, cytosine and uracil substituted with —C≡C—$CH_2$-phthalimide, NH$(C_1-C_6)$alkyl, 4-thiouracil, 2-thiouracil, $N^3$-thiobenzoylethyluracil, 5-propynyluracil, 5-acetoxymethyluracil, 5-fluorouracil, 5-chlorouracil, 5-bromouracil, 5-iodouracil, 4-thiouracil, N-3-$(C_1-C_6)$alkyluracil, 5-(3-aminoallyl)-uracil, 5-$(C_1-C_6)$alkyluracil, 5-aryl$(C_1-C_6)$alkyluracil, 5-trifluoro methyluracil, 4-triazolyl-5-methyluracil, 2-pyridone, 2-oxo-5-methylpyrimidine, 2-oxo-4-methylthio-5-methylpyrimidine, 2-thiocarbonyl-4-oxo-5-methylpyrimidine, and 4-oxo-5-methylpyrimidine;

wherein any substitutable nitrogen atom within the nucleobase or on the exocyclic amine is optionally substituted with fluorenylmethyloxycarbonyl; —C(=O)OPh; —C(=O)$(C_1-C_{16})$alkyl; —C(=O)$CH_2CH_2CH=CH_{21}$; —C(=O)$(C_1-C_{16})$alkylene-C(=O)OH; —C(=O)$(C_1-C_{16})$alkylene-C(=O)O$(C_1-C_6)$alkyl; =CR⁸N$(C_1-C_6)$alkyl)₂; —C(=O)—NR⁸—$(CH_2)_{1-16}$NR⁸C(=O)CF₃; —C(=O)—NR⁸—$(CH_2)_{1-16}$NR⁸C(=O)CF₃; —C(=O)—NR⁸$(CH_2)_{1-16}$NR⁸C(=O)-phthalimide; —C(=O)—$(CH_2)_{1-16}$-phthalimide; and

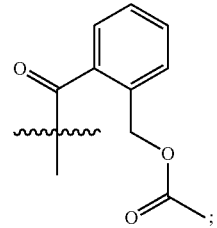

wherein any substitutable oxygen atom within the nucleobase is optionally substituted with —C(=O)N$(C_1-C_6$ alkyl)₂-C(=O)N(phenyl)₂;

$R^{20}$ is H, —O—Z, or $R^{21}$;

$R^{21}$ is 3' functional group;

Z is an acid labile protecting group; and n is 0 to 150;

or a salt thereof.

In one aspect of the third embodiment, the compound of claim 24, wherein $R^{21}$ is a) cyanoethyl phosphate-polyethylene glycols$^v$, where v is 2-100 and is number of glycol units;

b) cyanoethyl phosphate-linker attached with cholesterol, biotin, fluoresceins, cyanine dyes, psoralen, tetramethylrhodamine dye, dabcyl dye, C-3 disulfide, C-6 disulfide, symmetrical and asymmetrical hydrocarbon chain $(C_2-C_{50})$, symmetrical and asymmetrical hydrocarbon chain $(C_2-C_{50})$ with a terminal amino group protected with CF3C(=O) or phthalamido or FMOC, $(C_1-C_{16})$alkylene-amine protected with a amine protecting group, $(C_1-C_5)$alkylene-amine protected with an azide group; $(C_1-C_5)$alkylene-amine protected amine protected with an acetylene (C triple bond CH) group c) cyanoethyl phosphate-ethane-2-ol-protected with DMT group or other acid labile groups, cyanoethyl phosphate-propane-3-ol-protected with DMT group or other acid labile groups, d) $(C_1-C_{50})$alkylene with a terminal hydroxy;

e) lipids, carboxyl groups, or peptide; or f) a branched phosphoramidite.

In another aspect of the third embodiment, the compound of claim 24, wherein n is 5-75. Alternatively, n is 76-150. Alternatively, n is 10-25. Alternatively, n is 25-50. Alternatively, n is 50-75. Alternatively, n is 75-100.

In another aspect of the third embodiment, Z is an unsubstituted or substituted aryl group, an unsubstituted or substituted triarylmethyl group, an unsubstituted or substituted trityl group, an unsubstituted or substituted tetrahydropyranyl group, or an unsubstituted or substituted 9-phenylxanthyl.

In another aspect of the third embodiment, Z is di-p-anisylphenyl methyl, p-fluorophenyl-1-naphthylphenyl methyl, p-anisyl-1-naphthylphenyl methyl, di-o-anisyl-1-naphthyl methyl, di-o-anisylphenyl methyl, p-tolyldiphenylmethyl, di-p-anisylphenylmethyl, di-o-anisyl-1-naphthylmethyl, di-p-anisylphenyl methyl, di-o-anisyl phenyl methyl, di-p-anisylphenyl methyl, or p-tolyldiphenylmethyl.

In yet another aspect of the third embodiment, Z is represented by the following structural formula:

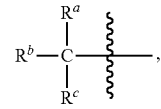

wherein ⸸ indicates attachment to the 3' oxygen atom and $R^a$, $R^b$, and $R^c$ are independently selected from the following structural formulas:

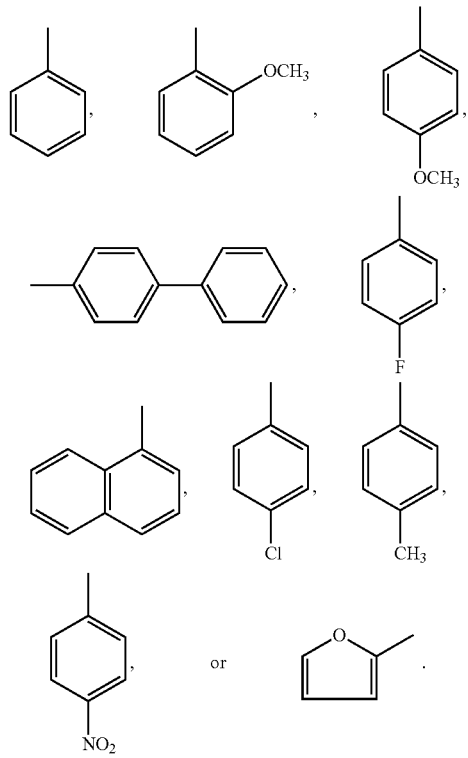

In one aspect of the third embodiment, Z is 4-methoxytrityl, 4,4'-dimethoxytrityl, or 4,4',4"-trimethoxytrityl.

In another aspect of the third embodiment, the substitutable nitrogen atom within the nucleobase or on the exocyclic amine is optionally substituted with =CHN(CH$_3$)$_2$; C(=O)CH(CH$_3$)$_2$; —C(=O)CH$_3$, =C(CH$_3$)N(CH$_3$)$_2$; —C(=O)OPh; —C(=O)CH$_2$CH$_2$CH=CH$_2$; —C(=O)CH$_2$CH$_2$—C(=O)O(C$_1$-C$_6$)alkyl; —C(=O)—NR$^8$—(CH$_2$)$_{1-16}$NR$^8$C(=O)CF$_3$; —C(=O)—(CH$_2$)$_{1-16}$NR$^8$C(=O)CF$_3$; —C(=O)—NR$^8$(CH$_2$)$_{1-16}$NR$^8$C(=O)-phthalimide; —C(=O)—(CH$_2$)$_{1-16}$-phthalimide and

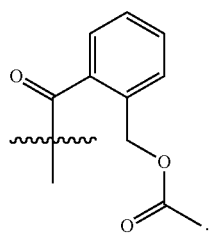 [SMILES: *C(=O)c1ccccc1COC(C)=O]

In yet another aspect of the third embodiment, $R^3$ is —CH$_2$CH$_2$CN, —CH$_2$CH$_2$—Si(CH$_3$)$_2$C$_6$H$_5$, —CH$_2$CH$_2$—S(O)$_2$—CH$_2$CH$_3$, —CH$_2$CH$_2$—C$_6$H$_4$—NO$_2$, —CH$_2$CH$_2$—NH—C(O)—C$_6$H$_5$, or —CH$_2$CH$_2$—O—C$_6$H$_4$—C(O)CH$_3$, and $R^4$ is —O—Si(R$^{11}$)$_3$.

In yet another aspect of the third embodiment, $R^4$ is —O—Si(CH$_3$)$_2$(C(CH$_3$)$_3$) or —O—CH$_2$—Si(CH(CH$_3$)$_2$)$_3$).

In yet another aspect of the third embodiment, $R^3$ is —CH$_2$CH$_2$CN.

A fourth embodiment of the invention is a synthetic RNA molecule with purity exceeding 97% and synthesized from a 5' phosphoramidite nucleoside.

The compounds of the first and the second embodiments and aspects thereof can be used in the following methods.

A fifth embodiment of the invention is a method of preparing an oligonucleotide by bond formations in the 5'- to 3'-direction for the synthesis of RNA oligomers and enantiomers thereof, said method comprises the following steps a) cleavage of the Z protecting group from a compound attached to the support represented by the following structural formula:

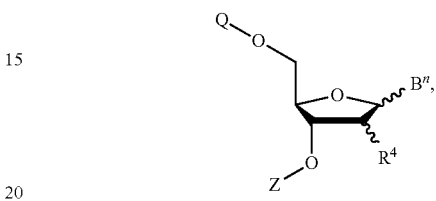

thereby forming a compound represented by structural formula (XX):

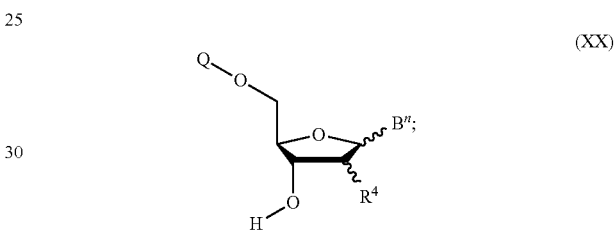

(XX)

b) reacting the compound represented by structural formula XX with a compound of structural formula XXI:

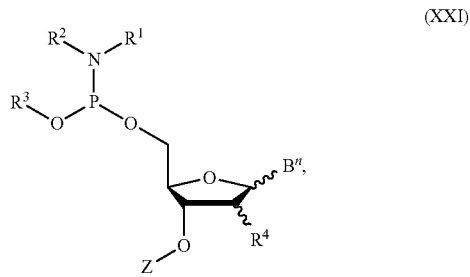

(XXI)

thereby forming 2-mer compound represented by the following structural formula:

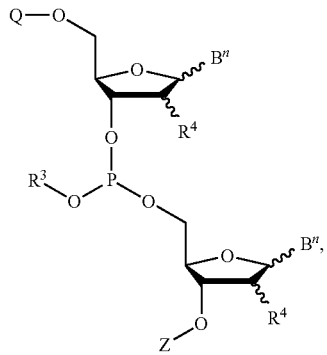

c) reacting the 2-mer with a capping agent; for example an acid anhydride to block the unreacted 3' hydroxy group d) oxidizing or sulfurization of the trivalent phosphorous group of the 2-mer compound to form a compound of structural formula XXII:

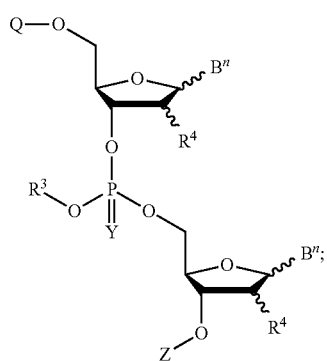

(XXII)

e) cleavage of the Z protecting group from a compound represented by the structural formula XXII, thereby forming a compound of structural formula XXIII:

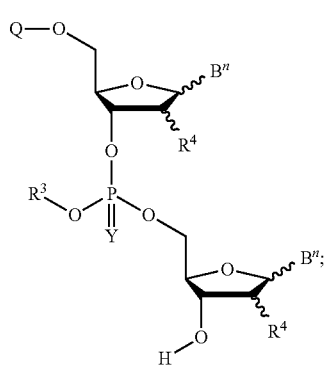

(XXIII)

f) reacting the compound represented by structural formula XXIII with a compound represented by the following structural formula:

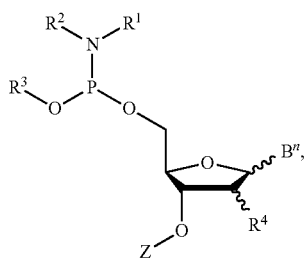

thereby forming a 3-mer after oxidation or sulfurization, represented by the following structural formula XXIV:

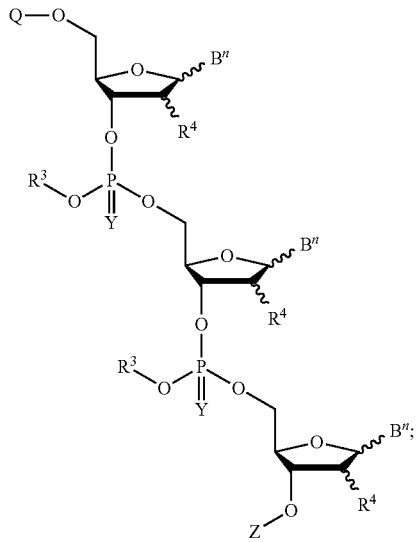

XXIV e) cleavage of the Z protecting group from a compound represented by structural formula XXIV;

g) repeating steps a) through e) n times, thereby forming a oligonucleotide represented by the following structural formula:

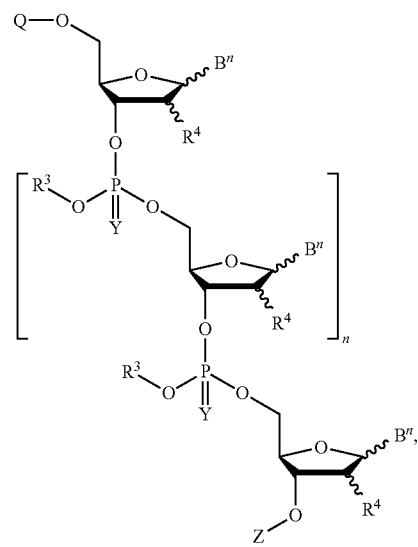

or a salt thereof, wherein

J is

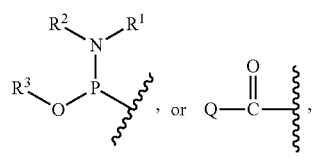

wherein $\{$ indicates where J is attached to the O atom;

Q is a) a support comprised of a linking group and a spacer that can be cleaved to form a hydroxy group; or b) an aliphatic chain, aromatic group, substituted or unsubstituted aromatic, a substituted or unsubstituted phenoxy, or levulinyl;

$R^1$ is a substituted or unsubstituted $(C_1-C_{12})$alkyl group, a substituted or unsubstituted $(C_3-C_{20})$cycloalkyl group, or a substituted or unsubstituted $(C_3-C_{20})$cycloalkyl$(C_1-C_{12})$alkyl group, wherein the alkyl or cycloalkyl groups optionally include intervening heteroatoms independently selected from NH, $NR^7$, O and S;

$R^2$ is a substituted or unsubstituted $(C_1-C_{12})$alkyl group, a substituted or unsubstituted $(C_3-C_{20})$cycloalkyl group, or a substituted or unsubstituted $(C_3-C_{20})$cycloalkyl$(C_1-C_{12})$alkyl group, wherein the alkyl or cycloalkyl groups optionally include intervening heteroatoms independently selected from NH, $NR^7$, O and S;

or $R^1$ and $R^2$ taken together with the nitrogen atom to which they are bound form a 4-7 membered non-aromatic heterocyclyl, wherein the heterocyclyl formed may optionally include intervening heteroatoms independently selected from NH, $NR^7$, O and S;

$R^3$ is a phosphate protecting group;

$R^4$ is a -halo, $-R^5$, $-NR^7R^8$, $-OR^9$, $-SR^{10}$, or 2'-blocking group; or when Structural Formula Ia or Ib is:

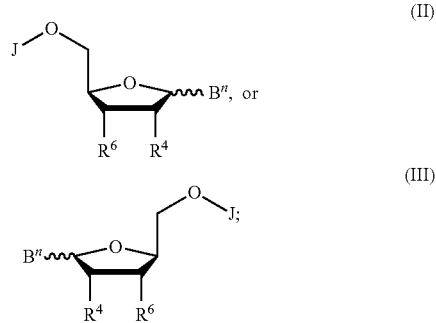

(II)

(III)

wherein $R^4$ is further selected from $O-Si(R^{11})_3$ or $O-CH_2-Si(R^{11})_3$; or when Structural Formula Ia or Ib is:

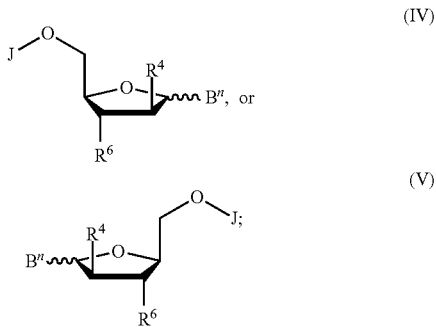

(IV)

(V)

$R^4$ is further selected from $-OC(=O)R^{12}$;

each $R^5$ is independently a substituted or unsubstituted $(C_1-C_{12})$alkyl group, a substituted or unsubstituted $(C_2-C_{12})$alkenyl group, a substituted or unsubstituted $(C_2-C_{12})$alkynyl group, or a substituted or unsubstituted phenyl, wherein the alkyl, alkenyl, alkynyl and the phenyl groups optionally includes intervening heteroatoms independently selected from NH, $NR^5$, O and S; and may optionally terminate with $-NR^7R^8$, $(C_1-C_4)$alkylamino, di$(C_1-C_4)$alkylamino, $-OR^9$, $(C_1-C_6)$alkoxy, benzyl or substituted benzyl, $-Se$; or $-S-(C_1-C_6)$alkyl group;

$R^6$ is $-H$ or $-O-Z$;

each $R^7$ is independently a fluorenylmethyloxycarbonyl; $-C(=O)-(CH_2)_{1-16}NR^8C(=O)CF_3$; $-C(=O)-(CH_2)_{1-16}NR^8C(=O)$-phthalimide; $-C(=O)-(CH_2)_{1-16}$-phthalimide; $NR^8C(=O)$-phthalimide; a substituted or unsubstituted $(C_1-C_{12})$alkyl group, a substituted or unsubstituted $(C_2-C_{12})$alkenyl group, or a substituted or unsubstituted $(C_2-C_{12})$alkynyl group;

each $R^8$ is H or a substituted or unsubstituted $(C_1-C_{12})$alkyl group, a substituted or unsubstituted $(C_2-C_{12})$alkenyl group, or a substituted or unsubstituted $(C_2-C_{12})$alkynyl group;

each $R^9$ is independently $-C(=O)-(CH_2)_{1-16}CH_3$; a substituted or unsubstituted $(C_2-C_{12})$alkenyl group, or a substituted or unsubstituted $(C_2-C_{12})$alkynyl group;

each $R^{10}$ is independently $-S(C_1-C_6)$alkyl, $-C(=O)-(CH_2)_{1-16}CH_3$; a substituted or unsubstituted $(C_2-C_{12})$alkenyl group, or a substituted or unsubstituted $(C_2-C_{12})$alkynyl group;

each $R^{11}$ is independently a substituted or unsubstituted $(C_1-C_{12})$alkyl group, a substituted or unsubstituted $(C_2-C_{12})$alkenyl group, or a substituted or unsubstituted $(C_2-C_{12})$alkynyl group;

each $R^{12}$ is independently a substituted or unsubstituted $(C_1-C_{12})$alkyl group, a substituted or unsubstituted $(C_2-C_{12})$alkenyl group, or a substituted or unsubstituted $(C_2-C_{12})$alkynyl group, or a substituted or unsubstituted aryl group;

Z is an acid labile protecting group;

$B''$ is hydrogen or an optionally substituted nucleobase optionally functionalized at each exocyclic amine with an amine protecting group, wherein the nucleobase is selected from:

N6,N6-dimethyl adenine, N6-benzoyladenine, N-1-methyladenine, 7-deazaadenine, 7-deaza-8-azaadenine, 3-deazaadenine, ethenoadenine, isoguanine, N1-methylguanine, 7-iodo-7-deazaguanine, 7-deaza-7-iodo adenine, 7-deaza-7-iodo-6-oxopurine, 5-iodo-5-methyl-7-deazaguanine, 7-deazaguanine substituted with $-C\equiv C(CH_2)_{1-8}$-pthlamide, 7-deaza-8-azaguanine, 8-methylguanine, 8-bromoguanine, 8-aminoguanine, hypoxanthine, 6-methoxypurine, 7-deaza-6-oxopurine, 6-oxopurine, 2-aminopurine, 2,6-diaminopurine, 8-bromopurine, 8-aminopurine, 8-alkylaminopurine, 8-alkylaminopurine, thymine, N-3 methyl thymine, 5-acetoxymethylcytosine, 5-azacytosine, isocytosine, N4$(C_1-C_6)$alkylcytosine, N-3$(C_1-C_6)$alkylcytidine, 5-propynylcytosine, 5-iodo-cytosine, 5-$(C_1-C_6)$alkylcytosine, 5-aryl$(C_1-C_6)$alkylcytosine, 5-trifluoromethylcytosine, 5-methylcytosine, ethenocytosine, cytosine and uracil substituted with $-CH=CH-C(=O)NH(C_1-C_6)$alkyl, cytosine and uracil substituted with $-C\equiv C-CH_2$-phthalimide, $NH(C_1-C_6)$alkyl, 4-thiouracil, 2-thiouracil, $N^3$-thiobenzoylethyluracil, 5-propynyluracil, 5-acetoxymethyluracil, 5-fluorouracil, 5-chlorouracil, 5-bromouracil, 5-iodouracil, 4-thiouracil, N-3-$(C_1-C_6)$alkyluracil, 5-(3-aminoallyl)-uracil, 5-$(C_1-C_6)$alkyluracil, 5-aryl$(C_1-C_6)$alkyluracil, 5-trifluoro methyluracil, 4-triazolyl-5-methyluracil, 2-pyridone, 2-oxo-5-methylpyrimidine, 2-oxo-4-methylthio-5-methylpyrimidine, 2-thiocarbonyl-4-oxo-5-methylpyrimidine, and 4-oxo-5-methylpyrimidine;

wherein any substitutable nitrogen atom within the nucleobase or on the exocyclic amine is optionally substituted with fluorenylmethyloxycarbonyl; $-C(=O)OPh$; $-C(=O)(C_1-C_{16})$alkyl; $-C(=O)CH_2CH_2CH=CH_2$]; $-C(=O)(C_1-C_{16})$alkylene-$C(=O)OH$; $-C(=O)(C_1-C_{16})$alkylene-$C(=O)O(C_1-C_6)$alkyl; $=CR^8N(C_1-C_6)$alkyl$)_2$; $-C(=O)-NR^8-(CH_2)_{1-16}NR^8C(=O)CF_3$; $-C(=O)-(CH_2)_{1-16}NR^8C(=O)CF_3$; $-C(=O)-NR^8(CH_2)_{1-16}NR^8C(=O)$-phthalimide; $-C(=O)-(CH_2)_{1-16}$-phthalimide; and

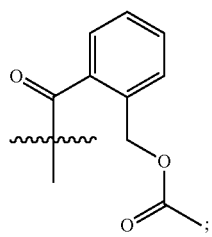 [SMILES: *C(=O)c1ccccc1COC(C)=O ; ";"]

wherein any substitutable oxygen atom within the nucleobase is optionally substituted with —C(=O)N($C_1$-$C_6$ alkyl)$_2$-C(=O)N(phenyl)$_2$; an n is 1 to 150;

or a salt thereof.

In another aspect, each Y group is independently introduced via sulfurization to form a phosphorothioate linkage or via oxidation to form a phosphate linkage.

In another aspect, wherein the $R^3$ group is eliminated after oxidation to form a phosphate linkage.

In another aspect, the $R^3$ group is eliminated after sulfurazation to form a phosphorothioate linkage.

In another aspect, the nucleobase protecting groups are deprotected with a base.

In another aspect, the base is selected from aq ammonia, methanolic ammonia, or ethanolic ammonia.

In another aspect, $R^4$ is —OSi($R^{11}$)$_3$.

In another aspect, the method further comprises the step of cleaving —OSi($R^{11}$)$_3$ with a fluoride salt.

In another aspect, the fluoride salt is tetraethylammonium fluoride.

In another aspect, further comprising the step of reacting the compound represented by the following structural formula:

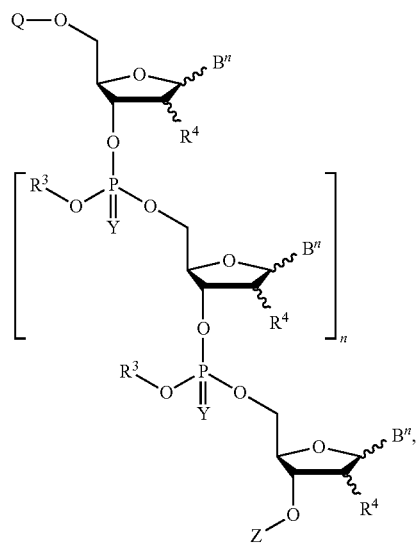

with a 3' functional group, thereby forming a compound of represented by the following structural formula;

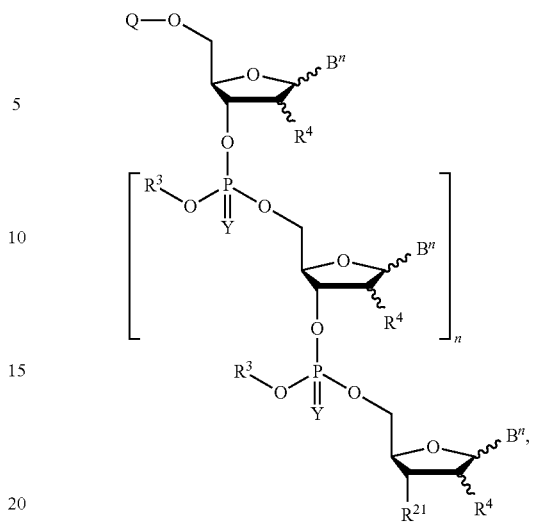

wherein $R^{21}$ is the 3' functional group or a salt thereof.

In another aspect, $R^{21}$ is a) cyanoethyl phosphate-polyethylene glycols$^v$, where v is 2-100 and is number of glycol units;

b) cyanoethyl phosphate-linker attached with cholesterol, biotin, fluoresceins, cyanine dyes, psoralen, tetramethyl-rhodamine dye, dabcyl dye, C-3 disulfide, C-6 disulfide, symmetrical and asymmetrical hydrocarbon chain ($C_2$-$C_{50}$), symmetrical and asymmetrical hydrocarbon chain ($C_2$-$C_{50}$) with a terminal amino group protected with CF3C(=O) or phthalamido or FMOC, ($C_1$-$C_{16}$)alkylene-amine protected with a amine protecting group, ($C_1$-$C_5$)alkylene-amine protected with an azide group; ($C_1$-$C_5$)alkylene-amine protected amine protected with an acetylene (C triple bond CH) group c) cyanoethyl phosphate-ethane-2-ol-protected with DMT group or other acid labile groups, cyanoethyl phosphate-propane-3-ol-protected with DMT group or other acid labile groups, d) ($C_1$-$C_{50}$)alkylene with a terminal hydroxy;

e) lipids, carboxyl groups, or peptide; or f) a branched phosphoramidite.

In another aspect, a RNA molecule made by the claimed method having a purity of 97% or greater following purification of the synthesized RNA molecule by HPLC, ion exchange, or reverse phase chromatography.

Abbreviation Summary mA=2'-O-Methyl adenosine, rA=adenosine, rC=cytidine rU=uridine rG=guanosine, 2'-OMe=2'-O-Methyl BTT=5-Benzyl thio-1-H-tetrazole, phosphorothioate=phosphorus in the pentavalent oxidized state with sulfur as P=S Me-THIO=phosphothioate CE=Capillary-Electrophoresis MW=Molecular Weight ESI/MS=Electrospray Ionisation-Mass Spectrometry DMT=4,4'-dimethoxytrityl TBDMS=tert-butyldimethylsilyl Ac=acetyl (—COCH$_3$)

Bz=benzene iBu=isobutyl (2-methylpropyl)
TOM=triisopropylsiloxymethyl
THIO=phosphorothioate, i.e., sulfur attached to phosphorus (V) (P=S)
The compounds of the invention are represented by

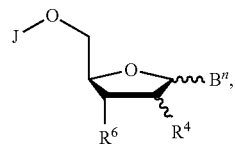

or a salt thereof.

In a specific embodiment, the compound is represented by the following structural formulas:

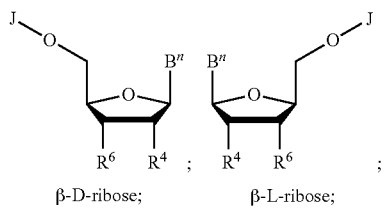

β-D-ribose;    β-L-ribose;

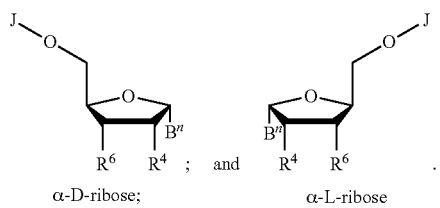

α-D-ribose;    α-L-ribose

In another embodiment, the compound is represented by the following structural formulas:

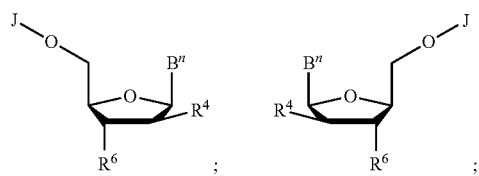

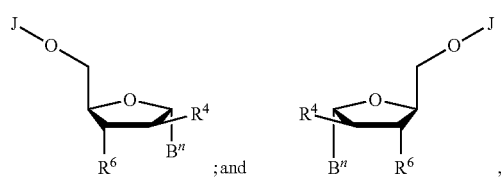

corresponding to β-D-arabinose; β-L-arabinose; α-D-arabinose; α-L-arabinose, respectively.

In one embodiment, $R^6$ is —H, or —O—Z. In a specific embodiment, $R^6$ is —O—Z and the compound is represented by the following structural formulas:

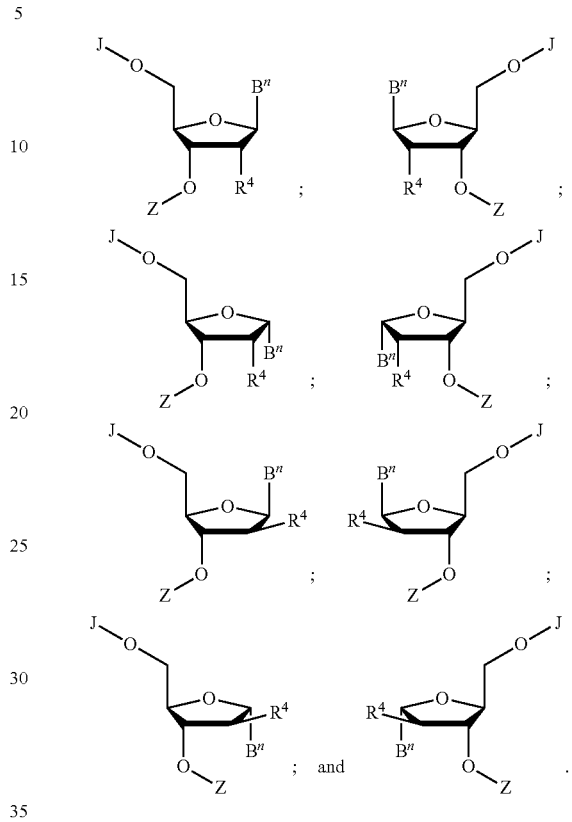

In one embodiment, Z is an acid labile protecting group. An acid labile protecting group is a protecting group which can be removed by contacting the group with a Bronsted or a Lewis acid. Acid labile protecting groups are known to those skilled in the art. Trityl groups are commonly substituted by electron donating substituents such as alkoxy groups. A preferred acid labile protecting group is a substituted or unsubstituted trityl, for example 4,4'-dimethoxytrityl (hereinafter "DMT").

In a specific embodiment, Z is an unsubstituted or substituted aryl group, an unsubstituted or substituted triarylmethyl group, an unsubstituted or substituted trityl group, an unsubstituted or substituted tetrahydropyranyl group, or an unsubstituted or substituted 9-phenylxanthyl. In a more specific embodiment, Z is selected from the following group: Trityl (triphenylmethyl, Tr), Methoxytrityl[(4-methoxyphenyl) diphenylmethyl, MMT), Dimethoxytrityl[bis-(4-methoxyphenyl)phenylmethyl, DMT], 4,4',4''-trimethoxytrityl, and 9-phenylxanthy. In another specific embodiment, Z is 4-methoxytrityl, 4,4'-dimethoxytrityl, or 4,4',4''-trimethoxytrityl.

In another embodiment, Z is di-p-anisylphenyl methyl, p-fluorophenyl-1-naphthylphenyl methyl, p-anisyl-1-naphthylphenyl methyl, di-o-anisyl-1-naphthyl methyl, di-o-anisylphenyl methyl, p-tolyldiphenylmethyl, di-p-anisylphenylmethyl, di-o-anisyl-1-naphthylmethyl, di-p-anisylphenyl methyl, di-o-anisyl phenyl methyl, di-p-anisylphenyl methyl, or p-tolyldiphenylmethyl.

In another specific embodiment, Z is represented by the following structural formula:

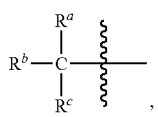

wherein ⌇ indicates attachment to the 3' oxygen atom and $R^a$, $R^b$, and $R^c$ are independently selected from the following structural formulas:

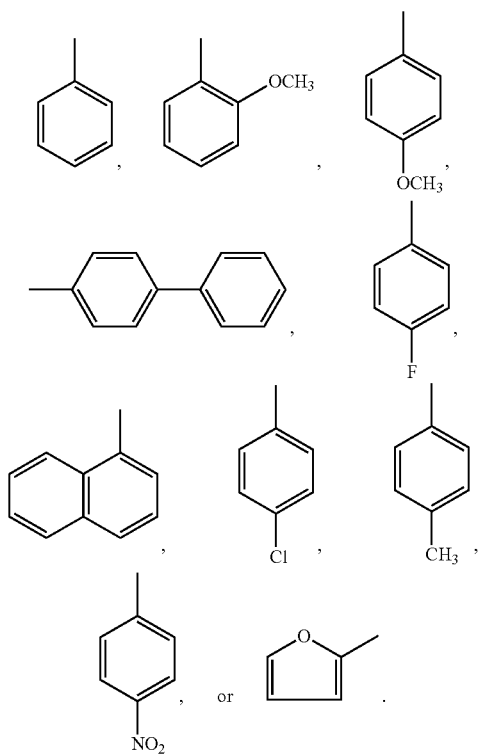

An "alkyl ester" group refers to a C1-C18 carbon chain that attaches to the rest of the molecule through a —C(O)— moiety. The carbon chain may be linear or branched, saturated or unsaturated, and may contain intervening heteroatoms such as O, NH, $NR^4$, or S.

"Aliphatic groups", as used herein, include straight chained or branched $C_1$-$C_{18}$ hydrocarbons which are completely saturated or which contain one or more unconjugated double bonds, or cyclic $C_3$-$C_{18}$ hydrocarbons which are completely saturated or which contain one or more unconjugated double bonds. Alkyl groups are straight chained or branched $C_1$-$C_8$ hydrocarbons or $C_3$-$C_8$ cyclic hydrocarbons which are completely saturated. Aliphatic groups are preferably alkyl groups.

The term "alkyl", used alone or as part of a larger moiety such as "arylalkyl" or "cycloalkylalkyl" means a straight or branched hydrocarbon radical having 1-18 carbon atoms and includes, for example, methyl, ethyl, n-propyl, isopropyl, n-butyl, sec-butyl, isobutyl, tert-butyl, n-pentyl, i-pentyl, n-hexyl, n-heptyl, n-octyl, n-nonyl, n-decyl and the like.

The term "alkylene", means a straight or branched hydrocarbon di-radical having 1-18 carbon atoms and includes, for example, methylene (—$CH_2$—), ethylene (—$CH_2CH_2$—) and the like.

The term "alkenyl", means a straight or branched hydrocarbon radical having 1-18 carbon atoms and one or more double bonds.

The term "alkynyl", means a straight or branched hydrocarbon radical having 1-18 carbon atoms and one or more triple bonds.

The term "cycloalkyl" means a monocyclic, bicyclic or tricyclic, saturated hydrocarbon ring having 3-20 carbon atoms and includes, for example, cyclopropyl, cyclobutyl, cyclopentyl, cyclohexyl, cycloheptyl, cyclooctyl, bicyclo[2.2.2]octyl, bicyclo[2.2.1]heptyl, Spiro[4.4]nonane, adamantyl and the like.

The alkyl, acetyl or cycloalkyl groups optionally include intervening heteroatoms independently selected from NH, $NR^5$, O and S. The alkyl or cycloalkyl can have up to 10 intervening heteroatoms. Specifically, the number of intervening heteroatoms can be 1, 2, 3, or 4. Alkyl groups with intervening heteroatoms include, for example —$OCH_2CH_2$—OH, —$OCH_2CH_2$—$OCH_3$, —$OCH_2CH_2$—$OCH_2CH_3$, —$OCH_2CH_2$—$OCH_2CH_2OH$, —$OCH_2CH_2$—$OCH_2CH_2OCH_3$, —$OCH_2CH_2$—$OCH_2CH_2OCH_2CH_3$, —$CH_2CH_2$—$NH_2$, —$SCH_2CH_2$—$OCH_3$, and the like. Cycloalkyl groups that include intervening heteroatoms include, for example, piperidinyl, piperazinyl, dioxanyl, morpholinyl, pyrrolidinyl, imidazolidinyl, tetrahydrofuranyl, thizaolidinyl, and the like.

"Aryl", used alone or as part of a larger moiety as in "arylalkyl", means a 6-10 membered carbocyclic aromatic monocyclic or polycyclic ring system. Examples include phenyl and naphthyl. The term "aryl" also includes phenyl rings fused to non-aromatic carbocyclic ring or to a heterocyclyl group. The term "aryl" may be used interchangeably with the terms "aromatic group", "aryl ring" "aromatic ring", "aryl group" and "aromatic group".

"Hetero" refers to the replacement of at least one carbon atom member in a ring system with at least one heteroatom selected from N, S, and O. A hetero ring may have 1, 2, 3, or 4 carbon atom members replaced by a heteroatom.

"Heterocyclyl" refers to a saturated or unsaturated, non-aromatic, monocyclic or polycyclic ring system of 3 to 20 atoms, 3 to 12 atoms, or 3 to 8 atoms, containing one to four ring heteroatoms chosen from O, N and S. Exemplary heterocyclyls include pyrrolidine, pyrrolidin-2-one, 1-methylpyrrolidin-2-one, piperidine, piperidin-2-one, 2-pyridone, 4-pyridone, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide and isothiazolidine 1,1-dioxide.

"Heterocyclyl" also includes heteroaryl groups. The term "heteroaryl" means a 5-10 membered monovalent heteroaromatic monocyclic and polycylic ring radical containing 1 to 4 heteroatoms independently selected from N, O, and S. The term "heteroaryl" also includes monocyclic heteroaryl ring fused to non-aromatic carbocyclic ring or to a heterocyclyl group. Heteroaryl groups include furyl, thienyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridinyl-N-oxide, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, quinazolinyl, benzothienyl, benzofuranyl, 2,3-dihydrobenzofuranyl, benzodioxolyl, benzimidazolyl, indazolyl, benzisoxazolyl, benzoxazolyl, benzothiazolyl, cinnolinyl, phthalzinyl, quinazolinyl, quinoxalinyl, 1,8-naphthyridinyl, 1,2,3-triazolyl, 1,2,4-triazolyl, 1,3,4-oxadiazolyl, 1,2,5-thiadiazolyl, 1,2,5-thiadiazolyl-1-oxide, 1,2,5-thiadiazolyl-1,1-dioxide, 1,3,4-thiadiazolyl, 1,2,4-triazinyl, 1,3,5-triazinyl, tetrazolyl, and pteridinyl. The terms "heteroaryl", "heteroaryl ring", and "heteroaryl group" are used interchangeably herein.

Amine, hydroxy and thiol protecting groups are known to those skilled in the art. For examples of amine protecting groups see Greene, et al., *Protective Groups in Organic Synthesis* (1991), John Wiley & Sons, Inc., pages 309-405, the teachings of which are incorporated herein by reference in their entirety. Preferably, amines are protected as amides or carbamates. For examples of hydroxy protecting groups see Id., pages 10-142, the teachings of which are incorporated herein by reference in their entirety. A preferred hydroxy protecting group is t-butyldimethylsilyl group. For examples of thiol protecting groups see Id., pages 277-308, the teachings of which are incorporated herein by reference in their entirety.

As used herein, an "exocyclic amine" refers to the amine attached to the base of the nucleoside. For example, the exocyclic amine of adenine is shown below:

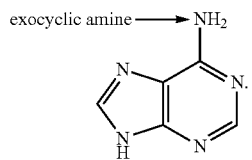

The exocylic amine can be either protected (for example, with benzoyl) or protected as formamidine (for example, —N═CH—N(CH$_3$)$_2$).

The term "oligonucleotide," as used herein, includes naturally occurring oligonucleotides, for example and ribonucleic acids (hereinafter "RNA") and nucleic acids containing modified sugar moieties, modified phosphate moieties, or modified nucleobases. Modification to the sugar moiety includes replacing the ribose ring with a hexose, cyclopentyl or cyclohexyl ring. Alternatively, the D-ribose ring of a naturally occurring nucleic acid can be replaced with an L-ribose ring or the β-anomer of a naturally occurring nucleic acid can be replaced with the α-anomer. The oligonucleotide may also comprise one or more abasic moieties. Modified phosphate moieties include phosphorothioates, phosphorodithioates, methyl phosphonates, methyl phosphates, and phosphoramidates. Such nucleic acid analogs are known to those of skill in the art. Oligonucleotides comprising mixtures of two or more of the foregoing may be prepared, for example, oligonucleotides comprising mixtures of deoxyribo- and ribonucleosides, particularly mixtures of deoxyribonucleosides and 2'-O-substituted ribonucelosides, such as 2'-O-methyl or 2'-O-methoxyethyl ribonucleosides. Examples of oligonucleotides comprising mixtures of nucleosides include ribozymes.

A chimeric oligonucleotide is an oligonucleotide that has both phosphodiester and phosphorothioate linkages and/or ribose or arabinose sugars or modified nucleoside/s within sequence such as 2'-fluoro, 2'-Omethyl, 2'-O—, 4'-C-methylene ribonucleosides, reverse abasic, reverse thymidine either within sequence or terminally.

A synthetic oligonucleotide preferably has from 2 to about 150 nucleobases. More preferably, a synthetic oligonucleotide has 2 to about 75 nucleobases. Many synthetic oligonucleotides of current therapeutic interest comprise from 8 to 40 nucleobases.

Nucleoside Bases

The compound of the invention contain a nucleoside base, represented by B″. B″ is hydrogen or an optionally substituted nucleobase optionally functionalized at each exocyclic amine with an amine protecting group.

Nucleoside bases include naturally occurring bases, such as adenine, guanine, cytosine, thymine and uracil and modified bases such as a) adenine or guanine substituted with one to 3 groups selected from halogen, hydroxy, ($C_1$-$C_6$)alkyl, ($C_2$-$C_6$) alkenyl, ($C_2$-$C_6$)alkynyl, ($C_1$-$C_6$)alkoxy, —($CH_2$)$_m$C (═O)($C_1$-$C_6$)alkyl, —($CH_2$)$_m$C(═O)O($C_1$-$C_6$)alkyl, —($CH_2$)$_m$OC(═O)($C_1$-$C_6$)alkyl, —($CH_2$)$_m$NR$^{10}$C (═O)($C_1$-$C_6$)alkyl, —($CH_2$)$_m$C(═O)($C_2$-$C_6$)alkenyl, —($CH_2$)$_m$C(═O)O($C_2$-$C_6$)alkenyl, —($CH_2$)$_m$OC(═O) ($C_2$-$C_6$)alkenyl, —($CH_2$)$_m$NR$^{10}$C(═O)($C_2$-$C_6$)alkenyl, —($CH_2$)$_m$C(═O)($C_2$-$C_6$)alkynyl, —($CH_2$)$_m$OC(═O) ($C_2$-$C_6$)alkynyl, —($CH_2$)$_m$C(═O)O($C_2$-$C_6$)alkynyl, —($CH_2$)$_m$NR$^{10}$C(═O)($C_2$-$C_6$)alkynyl, —Si(($C_1$-$C_6$) alkyl)$_3$, —O—Si(($C_1$-$C_6$)alkyl)$_3$, aryl($C_1$-$C_4$)alkyl, halo ($C_1$-$C_6$)alkyl, amino, ($C_1$-$C_6$)alkylamino, di($C_1$-$C_6$) alkylamino, triazolyl, and aminoallyl, wherein the alkyl, alkenyl or alkynyl is optionally substituted with —C(═O)NHR$^{14}$; —($CH_2$)$_m$-amino($C_1$-$C_6$)alkyl, —($CH_2$)$_m$-amino-halo($C_1$-$C_6$)alkyl, —($CH_2$)$_m$-phthalimide, b) uracil or cytosine substituted with one to 3 groups selected from halogen, hydroxy, ($C_1$-$C_6$)alkyl, ($C_2$-$C_6$) alkenyl, ($C_2$-$C_6$)alkynyl, ($C_1$-$C_6$)alkoxy, —($CH_2$)$_m$C (═O)($C_1$-$C_6$)alkyl, —($CH_2$)$_m$C(═O)O($C_1$-$C_6$)alkyl, —($CH_2$)$_m$OC(═O)($C_1$-$C_6$)alkyl, —($CH_2$)$_m$NR$^{10}$C (═O)($C_1$-$C_6$)alkyl, —($CH_2$)$_m$C(═O)($C_2$-$C_6$)alkenyl, —($CH_2$)$_m$C(═O)O($C_2$-$C_6$)alkenyl, —($CH_2$)$_m$OC(═O) ($C_2$-$C_6$)alkenyl, —($CH_2$)$_m$NR$^{10}$C(═O)($C_2$-$C_6$)alkenyl, —($CH_2$)$_m$C(═O)($C_2$-$C_6$)alkynyl, —($CH_2$)$_m$OC(═O) ($C_2$-$C_6$)alkynyl, —($CH_2$)$_m$C(═O)O($C_2$-$C_6$)alkynyl, —($CH_2$)$_m$NR$^{10}$C(═O)($C_2$-$C_6$)alkynyl, —Si(($C_1$-$C_6$) alkyl)$_3$, —O—Si(($C_1$-$C_6$)alkyl)$_3$, aryl($C_1$-$C_4$)alkyl, halo ($C_1$-$C_6$)alkyl, oxo, amino, ($C_1$-$C_6$)alkylamino, di($C_1$-$C_6$)alkylamino, triazolyl, and aminoallyl, wherein the alkyl, alkenyl or alkynyl is optionally substituted with —C(═O)NHR$^{14}$; —($CH_2$)$_m$-amino($C_1$-$C_6$)alkyl, —($CH_2$)$_m$-amino-halo($C_1$-$C_6$)alkyl, or —($CH_2$)$_m$-phthalimide, c) thymine, pyrimidine or pyridone each optionally substituted with halogen, hydroxy, ($C_1$-$C_6$)alkyl, ($C_2$-$C_6$)alkenyl, ($C_2$-$C_6$)alkynyl, ($C_1$-$C_6$)alkoxy, —($CH_2$)$_m$C(═O) ($C_1$-$C_6$)alkyl, —($CH_2$), C(═O)O($C_1$-$C_6$)alkyl, —($CH_2$)$_m$OC(═O)($C_1$-$C_6$)alkyl, —($CH_2$)$_m$NR$^{10}$C (═O)($C_1$-$C_6$)alkyl, —($CH_2$)$_m$C(═O)($C_2$-$C_6$)alkenyl, —($CH_2$)$_m$C(═O)O($C_2$-$C_6$)alkenyl, —($CH_2$)$_m$OC(═O) ($C_2$-$C_6$)alkenyl, —($CH_2$)$_n$NR$^{10}$C(═O)($C_2$-$C_6$)alkenyl, —($CH_2$)$_m$C(═O)($C_2$-$C_6$)alkynyl, —($CH_2$)$_m$OC(═O) ($C_2$-$C_6$)alkynyl, —($CH_2$)$_m$C(═O)O($C_2$-$C_6$)alkynyl, —($CH_2$)$_m$NR$^{10}$C(═O)($C_2$-$C_6$)alkynyl, —Si(($C_1$-$C_6$) alkyl)$_3$, —O—Si(($C_1$-$C_6$)alkyl)$_3$, aryl($C_1$-$C_4$)alkyl, halo ($C_1$-$C_6$)alkyl, oxo, amino, ($C_1$-$C_6$)alkylamino, di($C_1$-$C_6$)alkylamino, triazolyl, and aminoallyl, wherein the alkyl, alkenyl or alkynyl is optionally substituted with —C(=O)NHR$^{14}$; —(CH$_2$)$_m$-amino(C$_1$-C$_6$)alkyl, —(CH$_2$)$_m$-amino-halo(C$_1$-C$_6$)alkyl, or —(CH$_2$)$_m$-phthalimide, provided that the nucleobase formed is not uracil or cytosine;

d) purine, optionally substituted with halogen, hydroxy, (C$_1$-C$_6$)alkyl, (C$_2$-C$_6$)alkenyl, (C$_2$-C$_6$)alkynyl, (C$_1$-C$_6$) alkoxy, —(CH$_2$)$_m$C(=O)(C$_1$-C$_6$)alkyl, —(CH$_2$)$_m$C(=O)O(C$_1$-C$_6$)alkyl, —(CH$_2$)$_m$OC(=O)(C$_1$-C$_6$)alkyl, —(CH$_2$)$_m$NR$^{10}$C(=O)(C$_1$-C$_6$)alkyl, —(CH$_2$)$_m$C(=O)(C$_2$-C$_6$)alkenyl, —(CH$_2$)$_m$C(=O)O(C$_2$-C$_6$)alkenyl, —(CH$_2$)$_m$OC(=O)(C$_2$-C$_6$)alkenyl, —(CH$_2$)$_m$NR$^{10}$C(=O)(C$_2$-C$_6$)alkenyl, —(CH$_2$)$_m$C(=O)(C$_2$-C$_6$)alkynyl, —(CH$_2$)$_m$OC(=O)(C$_2$-C$_6$)alkynyl, —(CH$_2$)$_m$C(=O)O(C$_2$-C$_6$)alkynyl, —(CH$_2$)$_m$NR$^{10}$C(=O)(C$_2$-C$_6$)alkynyl, —Si((C$_1$-C$_6$)alkyl)$_3$, —O—Si((C$_1$-C$_6$)alkyl)$_3$, aryl(C$_1$-C$_4$)alkyl, halo(C$_1$-C$_6$)alkyl, oxo, amino, (C$_1$-C$_6$)alkylamino, di(C$_1$-C$_6$)alkylamino, triazolyl, and aminoallyl, wherein the alkyl, alkenyl or alkynyl is optionally substituted with —C(=O)NHR$^{14}$; —(CH$_2$)$_m$-amino(C$_1$-C$_6$)alkyl, —(CH$_2$)$_m$-amino-halo(C$_1$-C$_6$)alkyl, or —(CH$_2$)$_m$-phthalimide; provided that the nucleobase formed is not adenine or guanidine; or e) N6,N6-dimethyl adenine, N6-benzoyladenine, N-1-methyladenine, 7-deazaadenine, 7-deaza-8-azaadenine, 3-deazaadenine, ethenoadenine, isoguanine, N1-methylguanine, 7-iodo-7-deazaguanine, 7-deaza-7-iodo adenine, 7-deaza-7-iodo-6-oxopurine, 5-iodo-5-methyl-7-deazaguanine, 7-deazaguanine substituted with —C≡C(CH$_2$)$_{1-8}$-pthalmide, 7-deaza-8-azaguanine, 8-methylguanine, 8-bromoguanine, 8-aminoguanine, hypoxanthine, 6-methoxypurine, 7-deaza-6-oxopurine, 6-oxopurine, 2-aminopurine, 2,6-diaminopurine, 8-bromopurine, 8-aminopurine, 8-alkylaminopurine, 8-alkylaminopurine, thymine, N3 methyl thymine, 5-acroxymethylcytosine, 5-azacytosine, isocytosine, N4(C$_1$-C$_6$)alkylcytosine, N3(C$_1$-C$_6$)alkylcytidine, 5-propynylcytosine, 5-iodo-cytosine, 5-(C$_1$-C$_6$)alkylcytosine, 5-aryl(C$_1$-C$_6$)alkylcytosine, 5-trifluoromethyl-cytosine, 5-methylcytosine, ethenocytosine, cytosine and uracil substituted with —CH=CH—C(=O)NH(C$_1$-C$_6$)alkyl, cytosine and uracil substituted with —C≡C—CH$_2$-phthalimide, NH(C$_1$-C$_6$)alkyl, 4-thiouracil, 2-thiouracil, N$^3$-thiobenzoylethyluracil, 5-propynyluracil, 5-acroxymethyluracil, 5-fluorouracil, 5-chlorouracil, 5-bromouracil, 5-iodouracil, 4-thiouracil, N-3-(C$_1$-C$_6$)alkyluracil, 5-(3-aminoallyl)-uracil, 5-(C$_1$-C$_6$) alkyluracil, 5-aryl(C$_1$-C$_6$)alkyluracil, 5-trifluoro methyluracil, 4-triazolyl-5-methyluracil, 2-pyridone, 2-oxo-5-methylpyrimidine, 2-oxo-4-methylthio-5-methylpyrimidine, 2-thiocarbonyl-4-oxo-5-methylpyrimidine, and 4-oxo-5-methylpyrimidine; wherein each of which is optionally substituted with halogen, hydroxy, (C$_1$-C$_6$)alkyl, (C$_2$-C$_6$)alkenyl, (C$_2$-C$_6$)alkynyl, (C$_1$-C$_6$) alkoxy, —(CH$_2$)$_m$C(=O)(C$_1$-C$_6$)alkyl, —(CH$_2$)$_m$C(=O)O(C$_1$-C$_6$)alkyl, —(CH$_2$)$_m$OC(=O)(C$_1$-C$_6$)alkyl, —(CH$_2$)$_m$NR$^{10}$C(=O)(C$_2$-C$_6$)alkyl, —(CH$_2$)$_m$C(=O)(C$_2$-C$_6$)alkenyl, —(CH$_2$)$_m$C(=O)O(C$_2$-C$_6$)alkenyl, —(CH$_2$)$_m$OC(=O)(C$_2$-C$_6$)alkenyl, —(CH$_2$)$_m$NR$^{10}$C(=O)(C$_2$-C$_6$)alkenyl, —(CH$_2$)$_m$C(=O)(C$_2$-C$_6$)alkynyl, —(CH$_2$)$_m$OC(=O)(C$_2$-C$_6$)alkynyl, —(CH$_2$)$_m$C(=O)O(C$_2$-C$_6$)alkynyl, —(CH$_2$)$_m$NR$^{10}$C(=O)(C$_2$-C$_6$)alkynyl, C$_6$)alkyl)$_3$, —O—Si((C$_1$-C$_6$)alkyl)$_3$, aryl(C$_1$-C$_4$)alkyl, halo(C$_1$-C$_6$)alkyl, oxo, amino, (C$_1$-C$_6$) alkylamino, di(C$_1$-C$_6$)alkylamino, triazolyl, and aminoallyl, wherein the alkyl, alkenyl or alkynyl is optionally substituted with —C(=O)NHR$^{14}$; —(CH$_2$)$_m$-amino(C$_1$-C$_6$) alkyl, —(CH$_2$)$_m$-amino-halo(C$_1$-C$_6$)alkyl, or —(CH$_2$)$_m$-phthalimide;

wherein any substitutable nitrogen atom within the nucleobase or on the exocyclic amine in groups a), b), c), d) or e) is optionally substituted with (isobutyryl, phenoxyacetyl, tert butylphenoxy acetyl, isopropyl phenoxyacetyl, acetyl, —C(O)OCH$_3$, di(C$_1$-C$_6$)alkylformamidine, p-chlorobenzoyl, o-chlorobenzoyl, o-nitrobenzoyl, p-nitrobenzoyl, fluorenylmethyloxycarbonyl, nitrophenylethyl, phthaloyl, Benzyl (Bn) group, p-Methoxybenzyl (PMB), 3,4-Dimethoxybenzyl (DMPM), p-methoxyphenyl (PMP) group and =CR$^{15}$N((C$_1$-C$_6$)alkyl)$_2$, each R$^{14}$ or R$^{15}$ is a independently substituted or unsubstituted (C$_1$-C$_6$)alkyl group, a substituted or unsubstituted (C$_2$-C$_6$)alkenyl group, or a substituted or unsubstituted (C$_2$-C$_6$)alkynyl group; and each m is independently 0-12.

A protected nucleoside base is a nucleoside base in which reactive functional groups of the base are protected. Similarly, a protected heterocycle is a heterocycle in which reactive substituents of the heterocycle are protected. Typically, nucleoside bases or heterocycles have amine groups which can be protected with an amine protecting group, such as an amide or a carbamate. For example, the amine groups of adenine and cytosine are typically protected with benzoyl and alkyl ester, respectively, protecting groups, and the amine groups of guanine is typically protected with an isobutyryl group, an acetyl group or t-butylphenoxyacetyl group. However, other protection schemes may be used. For example, for fast deprotection, the amine groups of adenine and guanine are protected with phenoxyacetyl groups and the amine group of cytosine is protected with an isobutyryl group or an acetyl group. Conditions for removal of the nucleobase or heterocycle protecting group will depend on the protecting group used. When an amide protecting group is used, it can be removed by treating the oligonucleotide with a base solution, such as a concentrated ammonium hydroxide solution, N-methylamine solution or a solution of t-butylamine in ammonium hydroxide.

Nucleoside bases also include isocytidine (isoC) and isoguanosine (IsoG). IsoC and IsoG can used to exploit Watson Crick base pairing mechanism, which allow three hydrogen bonds between isoC and isoG, as shown below:

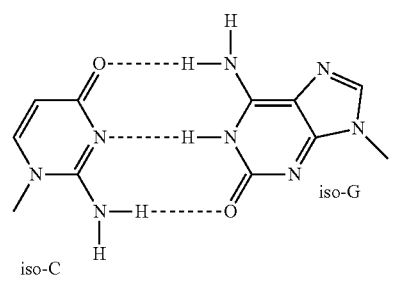

These bases can pair in both parallel and antiparallel duplex forms and as in DNA sequences they are recognized by DNA polymerases as well for chain extension, PCR etc. These molecules therefore have significant importance in as part of RNA sequences for diagnostics and therapeutic applications (See S. C. Jurczyk, et al., *Helvetica Chimica Acta.*, 81, 793-

811, 1998; and C. Roberts, et al., *Tetrahedron Lett.*, 36, 21, 3601-3604, 1995, the entire teachings of which are incorporated herein by reference).

Nucleoside bases also include 7-deaza-ribonucleosides. These 7-deaza-ribonucleosides (including 7-deaza guanosine and adenosine and inosine) can be further modified at the 7 position by introducing various substituents. For example, modification can include attachment of halogen (such as fluoro, chloro, bromo, or iodo), alkynyl, trimethylsilylalkynyl, propynylaminotrifluoromethyl, or propynylamino phthalamido. (See Xiaohua Peng and Frank Seela, International Round Table on Nucleosides, Nucleotides and Nucleic Acids, IRT-XVII, Sep. 3-7, 2006, page 82, Bern, Switzerland, the entire teachings of which are incorporated herein by reference).

Specially, 7-deaza-2'-deoxy nucleosides can be incorporated within the RNA sequence in place of a dGuanosine base to result in a decrease clamping of oligodeoxy nucleotide and hence better resolution in sequence analysis. This modification does not decrease the tm values of sequences during hybridization to complementary sequences. This modification has many significant biological properties for diagnostic and therapeutic field of DNA and RNA (See N. Ramazaeva, et al., XIII International Round Table; Nucleosides, Nucleotides and Their Biological Application, Montpellier, France Sep. 6-10, 1998, poster 304; Ramazaeva, N., et al., Helv. Chim. Acta 1997, 80, 1809 and references cited therein; Sheela, F. et al., *Helvetica Chimica Acta*, 73: 1879, 1990, the entire teachings of which are incorporated herein). In RNA, the effect of G-C base pairing is much more pronounced because RNA molecules have a strong tendency to form secondary structures. Substitution of guanosine with 7-deaza-riboguanosine has great significance in RNA therapeutics and diagnostics, 7-substituted-7-deaza-ribonucleosides have significance due to possibility of various ligand and chromophore attachments at 7-position without disturbing G-C base pairing properties.

The synthesis of 7-deaza-ribonucleosides can be achieved through the proposed synthesis of 3'-DMT-2'-TBDMS-N-protected-β-D-7-deaza-guanosine-5'-phosphoramidite (Scheme 1):

Scheme 1: Synthesis of 2'-TBDMS-3'-DMT-7-deaza-r-G(n-ibu):

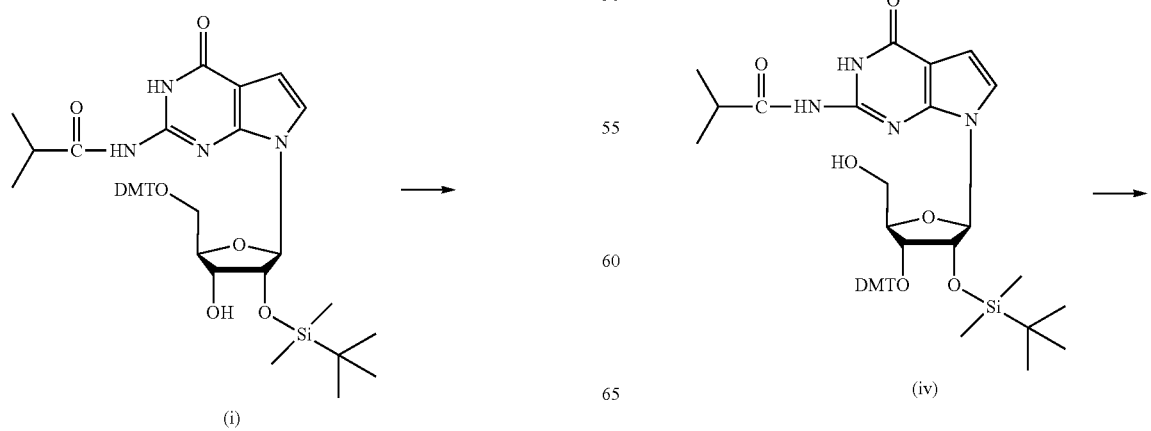

(i)

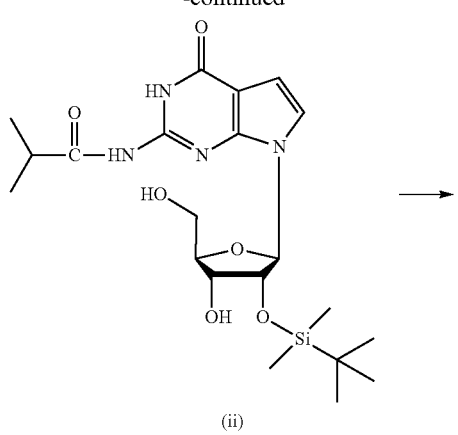

(ii)

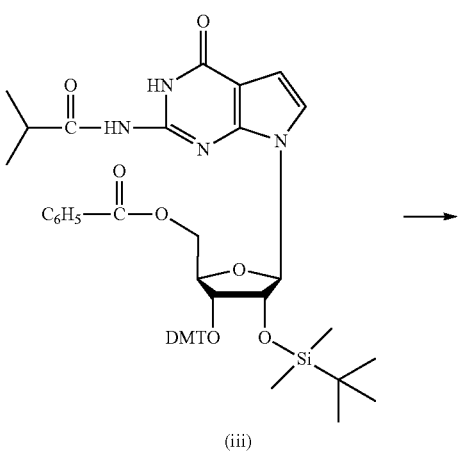

(iii)

(iv)

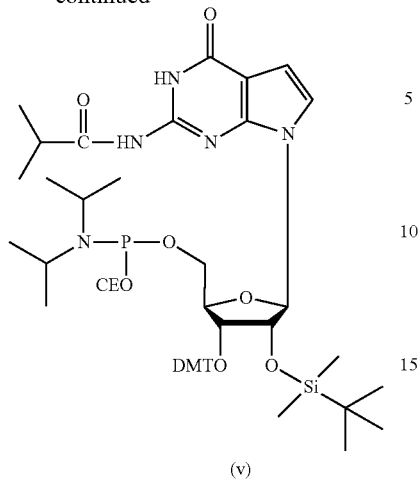

(v)

Synthesis of Compound (II); selective DMT removal from compound (i) using trichloroacetic acid and dichloromethane as solvent to obtain (ii). Compound (iii); step a; selective 5'-benzoyalation with benzoyl chloride chloride (1.1 eq)/pyridine solvent (10 fold v/v) at 0-5 C temp. leads to 5'-benzoyl group; followed by work up and column purification; (iii; step b); subsequent DMT Chloride reaction in pyridine at room temperature for 24 hours, followed by work up; subsequent column chromatography leads to compound (iii). Compound (iv); selective removal of 5'-benzoyl is achieved by selective reaction with aq. 2 N NaOH reaction by reaction of iv with aq. 2 N NaOH in pyridine as solvent, followed by neutralization with pyridinium Dowex cation exchange resin, followed by filtration to remove Dowex resin to get solution of crude iv, subsequent chromatography to get purified (iv). Compound (v). phosphitylation of (iv). with n, n-diisopropyl-2-cyanoethyl-chloro reagent (1.1 eq) in diisopropyl ethyl amine (2 eq) in THF leads to crude vi, followed by chromatography to get pure phosphoramidite (v).

The synthesis of 3'-DMT-L-ribonucleoside oligonucleotides can be achieved through of L-ribonucleosides appropriately exocyclic amine protected. A typical example of 3'-DMT-L-r-G(n-ibu)-5'-phosphoramidite is illustrated below:

The synthesis of 7-deaza-ribonucleosides can be achieved through of 3'-DMT-2'-TBDMS-N-protected-β-L-7-deaza-guanosine-5'-phosphoramidites (Scheme 2):

Scheme 2:

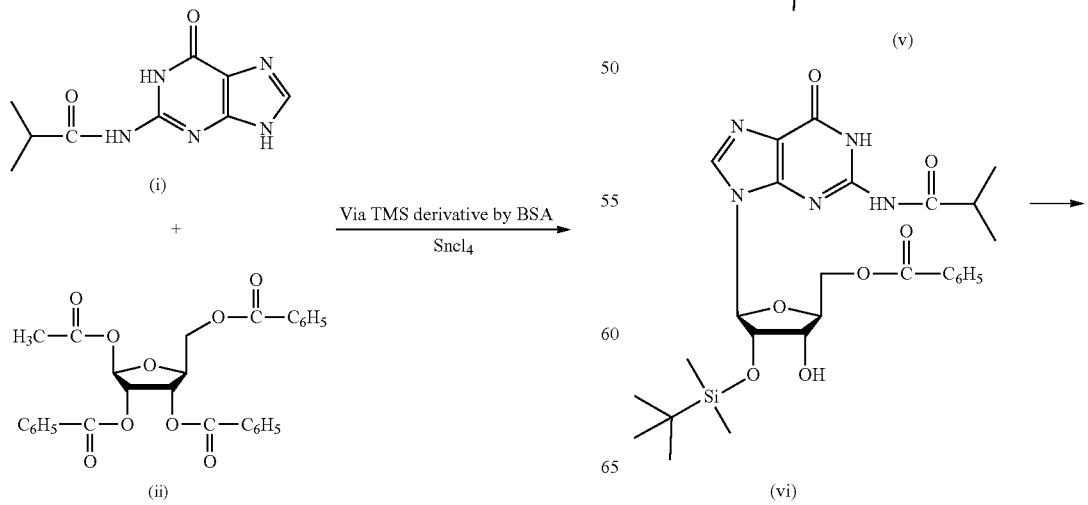

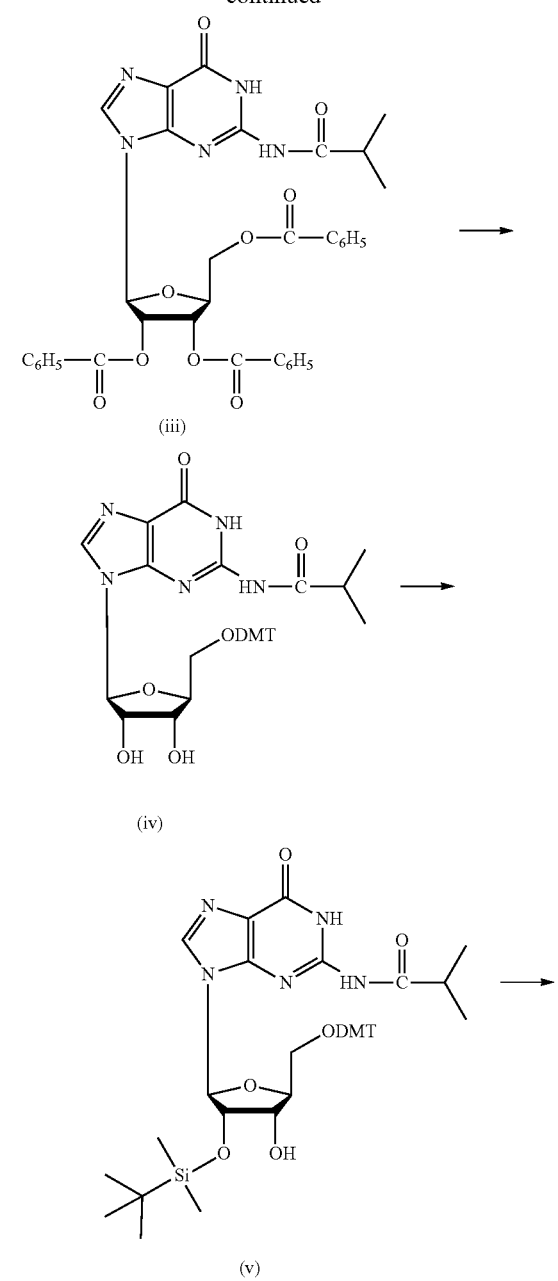

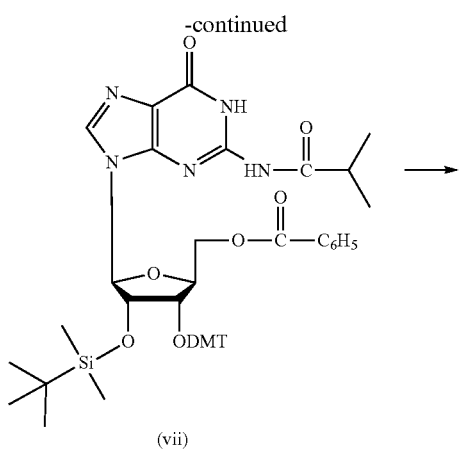

(vii)

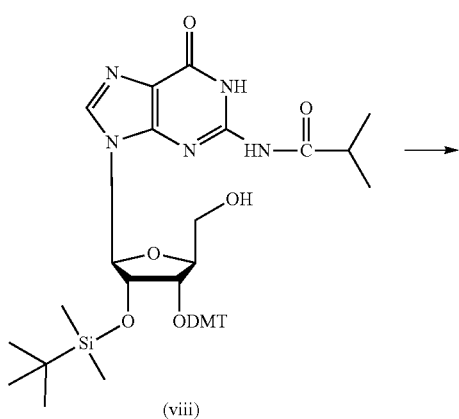

(viii)

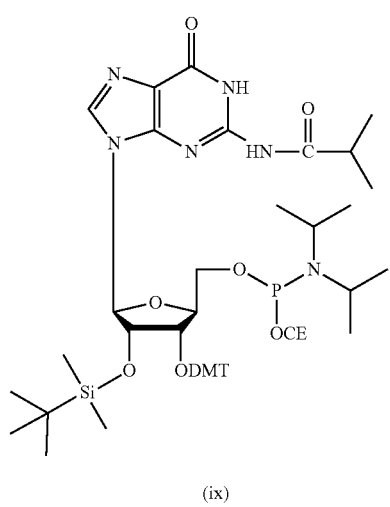

(ix)

O-Acetyl-tri-O-benzoyl-L-ribose (ii) was synthesized similar to synthesis of 1-acetyl-tri-O-benzoyl-D-ribose. N-isobutyryl guanine is first converted into silyl derivative by treatment with bissilyl trimethyl acetamidite (BSA; 5 eq) The L-sugar (iii) was then fused with silylalated n-isobutyryl-guanine in presence of $SnCl_4$ (Sn(IV) chloride) to yield fully protected crude tri-O-benzoyl-N-isobutyryl-L-guanosine. This compound was purified by column chromatography on silica gel (70-230 mesh size; Merck silica gel). The pure fully protected intermediate compound was then hydrolyzed selectively under controlled hydrolysis conditions with 2 N NaOH in pyridine/methanol (80:20) for 20 minutes at 5-10 C, followed by neutralization of reaction mixture with Dowex-pyridinium cation exchange resin to yield 5',3',2'-trihydroxy-L-guanosine (n-ibu). The crude compound was washed with ethyl acetate, followed by diethyl ether to removed solvents and benzoic acid by-products to get pure 5',3',2'-tri-hydroxy-L-guanosine (n-ibu). The dried compound subsequently treated with DMT-Chloride (DMT Chloride; 1.2 equivalent) in dry pyridine (10 fold with respect to 5',3',2'-tri hydroxy-L-guanosine (n-ibu) at 5 C for 3-4 hours to yield crude 5'-DMT-2',3'-dihydroxy-L-guanosine (n-ibu)(iv). This was purified on silica gel (70-230 mesh, Merck grade) column. The pure fractions were pooled to get pure 5'-DMT-2',3'-dihydroxy-L-guanosine (n-ibu)(iv; yield 70-75% yield from the trihydroxy compound). 2'-silylation was done to get a mixture of 2' and 3'-TBDMS protected nucleoside, from which pure 5'-DMT-2'-silyl-L-G(n-ibu) nucleoside (v) was separated by column chromatography. From this compound DMT group was selectively removed using trichloroacetic acid in dichloromethane (3% solution, v/v) at room temperature for 10 minutes. The reaction mixture was quenched with 10% aq sodium bicarbonate at zero degrees to neutralize the reaction mixture to yield crude 5,3'-dihydroxy-2'-TBDMS-L-G-(N-ibu). This compound was purified by column chromatography on silica gel (70-230 mesh; Merck grade) to provide pure 5',3'-dihydroxy-2'-TBDMS-L-G-(N-ibu). Selective 5'-benzoylation of this compound with benzoyl chloride (1.1 eq; −10 to 0 C) for 1.5 hours to yield compound (vi). This compound was similarly purified to yield pure 5'-O-benzoyl-3'-hydroxy-2'-TBDMS-L-G-(N-ibu) (compound vi). Subsequent reaction of well dried compound (vi) with DMT-chloride (2.5 eq; pyridine w/v; 1:10) was treated at room temperature for 24 hours to yield compound (vii). Purified (vii) was purified on silica gel column chromatography. The pure vii was then selectively hydrolyzed with 2 N NaOH at 5 C for 30 minutes, followed by neutralization of reaction mixture with Dowex-pyridinium cation exchange resin to yield to yield, 5'-OH, 3'-DMT-2'-TBDMS-L-rG-n-ibu (compound viii). The crude compound was purified by silica gel column (70-230 mesh, Merck silica gel) chromatography. subsequent chromatography to get purified viii was done by phosphitylation of viii. with n, n-diisopropyl-2-cyanoethyl chloro reagent (1.1 eq) in diisopropyl ethyl amine (2 eq) in THF leads to crude ix, followed by chromatography to get pure 5'-phosphoramidite (ix).

Nucleoside bases also include abasic nucleosides. Abasic sites in DNA are generated chemically or enzymatically by loss of glycolytic bond. The resulting a purinic/pyrimidinic sites lack coding information and lead to misincorporation of bases by polymerases and may play important role in mutagenesis. They eventually get converted to tetrahydrofuran derivative with a methylene group modifying the 1 position of 2'-deoxyribose. The CE phosphoramidites of both 2 deoxy and 2-hydroxyl-D-ribose with an amidite have been synthesized. A reverse RNA modification will allow efficient synthesis of such RNA, RNA/DNA chimeras, modified RNA, (See Takeshitsa, M., et al., *J. Biol. Chem.*, 1987, 262, 10171-10179; and Kalnik, M. W., et. al., *Biochemistry*, 1988, 27, 924-931, the entire teachings of which are incorporated herein by reference).

Abasic nucleosides can be synthesized by a method similarly applicable for 3'-DMT-2'-TBDMS-N-protected nucleoside phosphoramidites and is shown in the scheme below:

Scheme 1: Dihydro-D Ribose-3-DMT-2'-silyl-phosphoramidites.

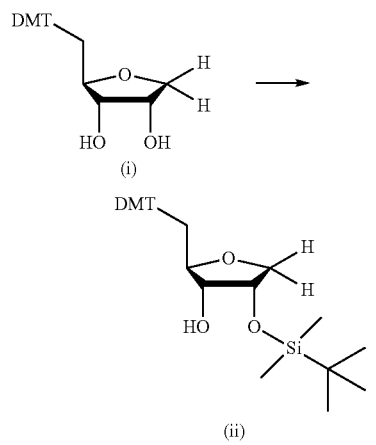

(i)

(ii)

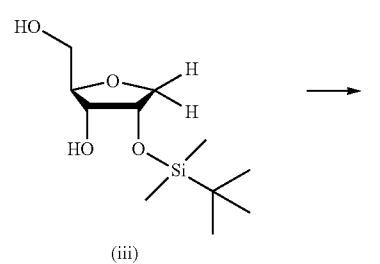

(iii)

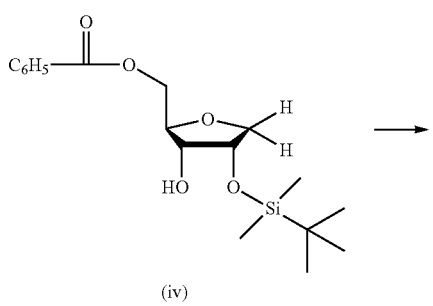

(iv)

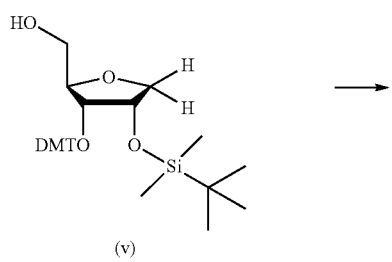

(v)

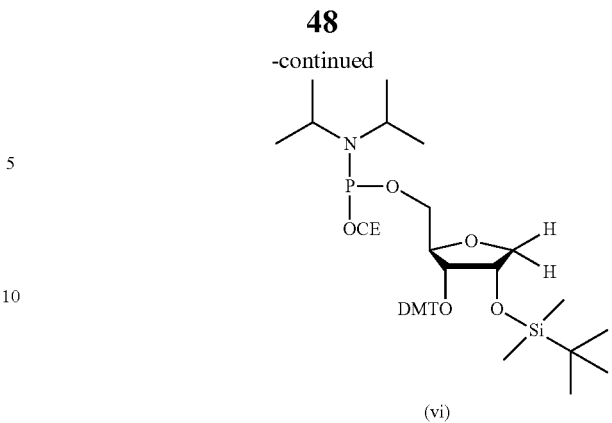

(vi)

Compound (i) from ChemGenes Corp.; (ii) selective TBDMS chloride introduction is achieved under standard condition (isomer formed at this stage can be conveniently separated); (iii) and (iv) selective 5-DMT group removal, followed by selective 5-positiobn benzoylation, (v) DMT chloride reaction leads to 3-position DMT introduction; (vi) 5-position benzoyl removal, followed by phosphorylation and purification by chromatography.

Nucleoside bases also include 2-Aminopurine nucleosides. 2-Aminopurine is a modified nucleobase analog incorporated in oligonucleotides for mutagenic studies, due to its fluorescence properties. Its structural homology to adenine and guanine make it an important tool in enzymological studies by substitution in place of adenosine or guanosine in a sequence (See Schmidt, S. et al., *Nucleosides & Nucleotides,* 14(6), 1445-1452, 1995; and McLaughlin, L. W. et al., *Nucleic Acids Res.,* 1988, 16, 5631, the entire teachings of which are incorporated herein by reference). A representative structure of a 2-aminopurine nucleoside is 2 aminopurine 3'-DMT-2'-silyl-5'-phosphoramidite, which is represented by the following structural formula:

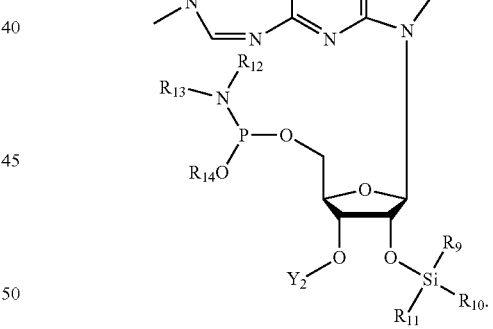

Nucleoside Modifications:

5-Hydroxymethyluridine & Cytidine are nucleoside modifications included in this invention. The 5' hydroxymethyl modification is protected with —OAc (—O—C(=O)CH$_3$) to yield 5-acetoxymethylcytosine and 5-acetoxymethyluracil.

Solid phase synthesis and restriction endonuclease cleavage of oligo deoxy nucleosides containing 5-hydroxylmethyl cytosine. has been described, see for example, "Cytosine methylation and study of its effect"; Severine Tardy-Planechaud, June Fujimoto, Susan S. Lin and Lawrence C, Sowers; *Nucleic Acids Research*, Vol. 25, No. 3, 553-558 (1997), the entire teachings of which are incorporated herein by reference.

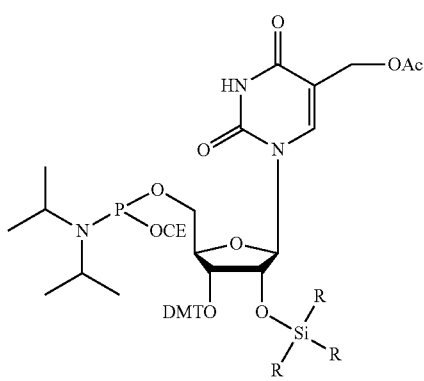

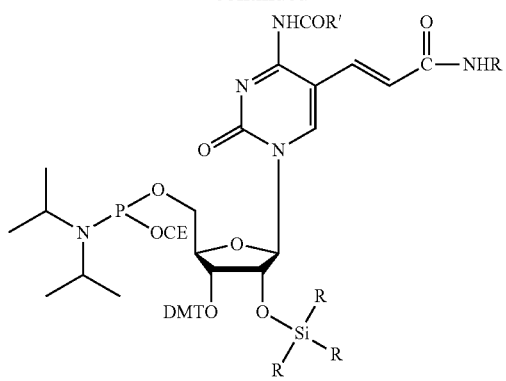

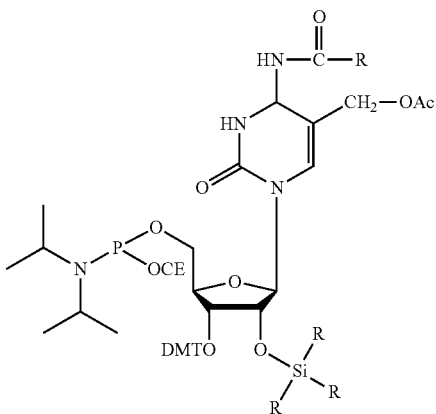

Other modified nucleobases include 1, $N^6$-ethenoadenosine, 3,$N^4$-ethenocytidine, C-5 (rU and rC) Pyrene modification, C-5 (rU and rC) Perylene modification, C-5 (rU and rC) acrylate-C-6 amino linker (TFA protected, C-5 (rU & rC) acrylate-C-2 amino linker (TFA protected), C-5 (rU and rC) acrylate-C-6 amino linker (FMOC protected), 5'-PT modifier supports, C-5 Pyrene-r-uridine, C-5 perylene-r-uridine, (5,6)-pyrrole-r-cytidine.

A representative compound of the invention including nucleobase modifications are shown below:

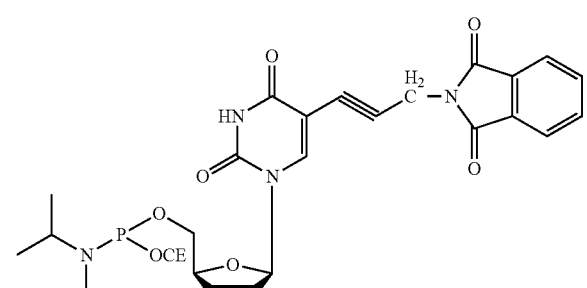

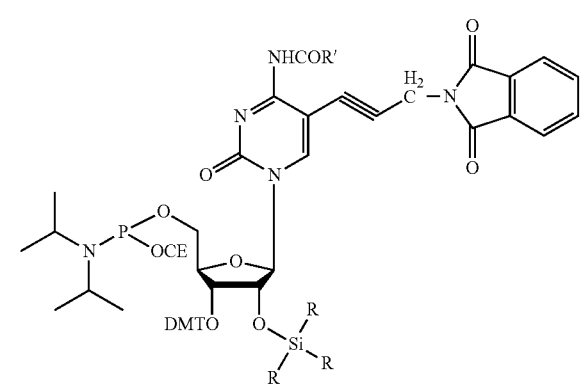

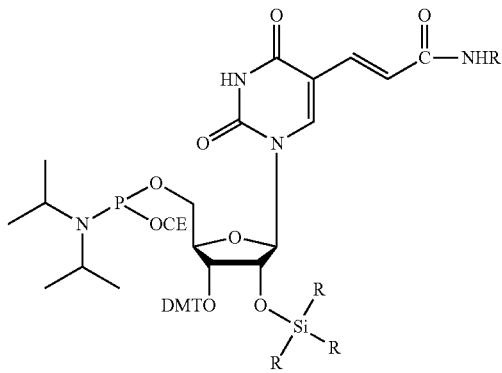

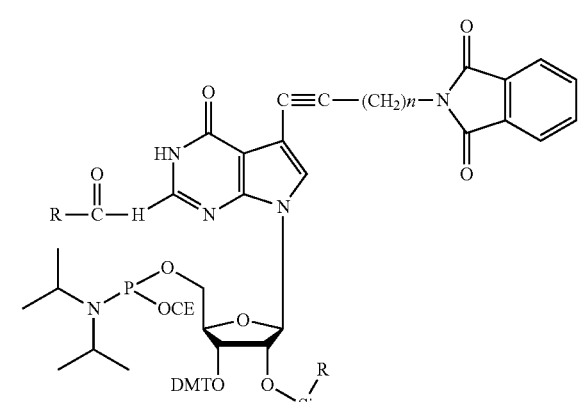

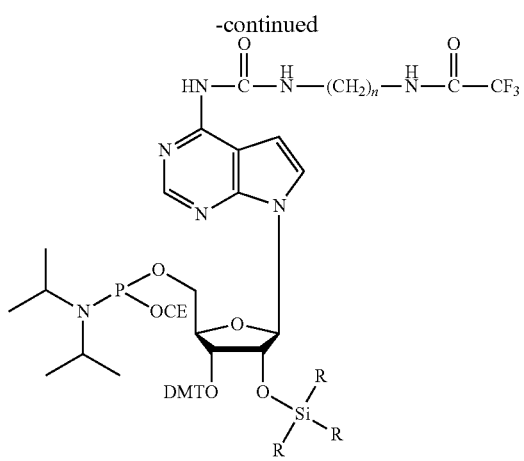

8-Methylguanosine: Several publications have reported 8-methyl guanosine as very useful modification for oligonucleotide aptamer design and Z DNA stabilizer. See for example, 8-Methylguanosine: A Powerful DNA Stabilizer; Yan Xu, Reiko Ikeda and Hiroshi Sugiyama, J.AM.Chem. Soc. 2003, 125, 13519-13524-13519, the entire teachings of which are incorporated herein by reference. A representative compound of the invention including 8-methylguanosine is shown below:

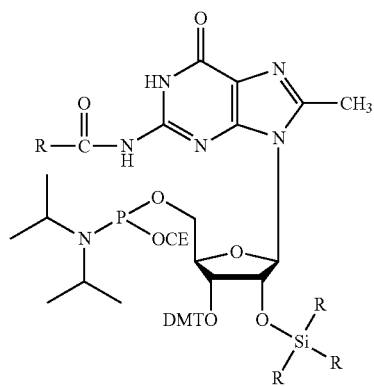

5-Aza cytidine: 5-Azacytidine is proposed to be utilized as reverse RNA synthon. 5-aza-cytidine is an well known anticancer agent.
A representative compound of the invention including 5-Azacytidine is shown below:

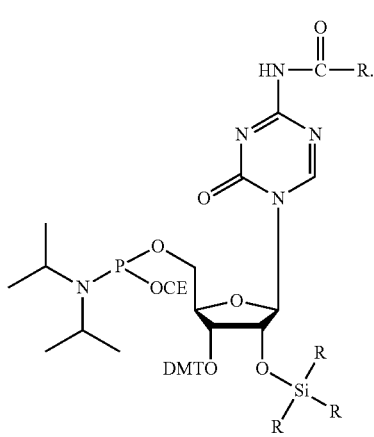

2,6-Diaminopurine riboside; See, for example, Pasternak, A., Nucleic Acids Research 2007 35(12):4055-4063, the entire teachings of which are incorporated herein by reference. The article report use of 2'-O,4'-C-methylene ribonucleosides bases in combination of 2,6-diaminopurine riboside, and the influence of 2-O-methyl-2,6-diaminopurine and LNA-2,6-diaminopurine ribosides on the thermodynamic properties of 2'-O-methyl RNA-RNA heterodulplexes, Nucleobase Protecting Groups.

Protecting groups for nucleobases are know in the art. See, for example:

1. RNA synthesis using phosphoramidites with Labile Base Protection: Users Bulletin, Applied Biosystems, Number 69, Instructions for 380B, 392 and 394 synthesizers, the entire teachings of which are incorporated herein by reference, for description of use of dimethylformamide (DMF) and n-isobutyryl protecting groups.

2. This synthesis of $N^6$ phenoxy acetyl deoxy adenosine derivatives as new reactive intermediates for preparation of linker containing oligonucleotide probes and modified LCAA (Long chain alkyl amino)-CPG (Controlled pore glass) supports was described in Edyta Krzymanska-Olejnik and Ryszard W. Adamiak, Nucleosides & Nucleotides, 10(1-3), 595-597 (1991), the entire teachings of which are incorporated herein by reference.

For the synthesis of propargyl modified oligonucleotides, 2'-propargyl-3'-DMT-5'-phosphoramidites synthons can be incorporated within sequence through the reverse synthesis process. Phosphoramidites are further postulated bearing 2'-hexyne terminal group to obtain precursor-oligonucleotides bearing free hexyl linker capable of reacting with reagents introducing various reporter probes, See U.S. Pat. No. 5,744,595 Srivastava, et al, the entire teachings of which are incorporated herein by reference.

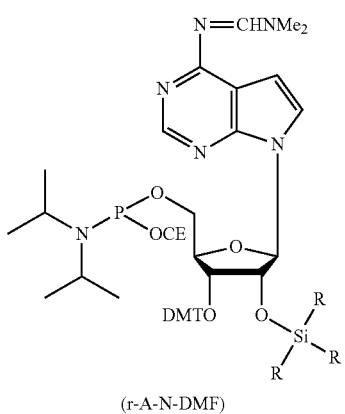

(r-A-N-DMF)

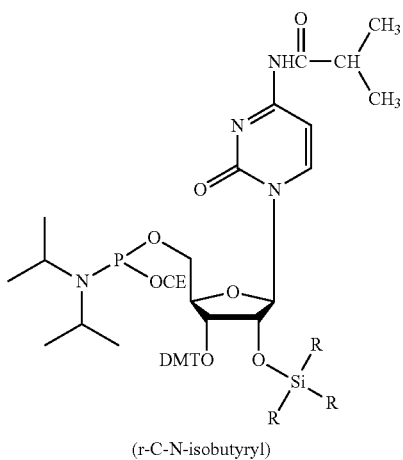

(r-C-N-isobutyryl)

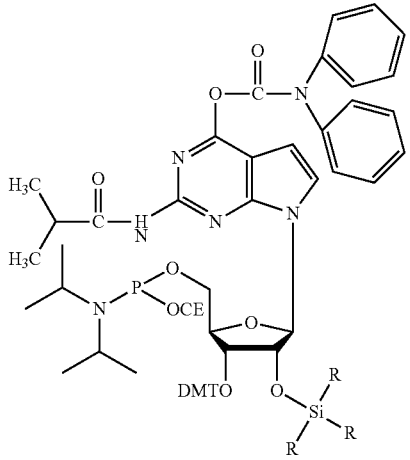

(N⁶ diphenylcarbamoyl-rG-n-ibu)

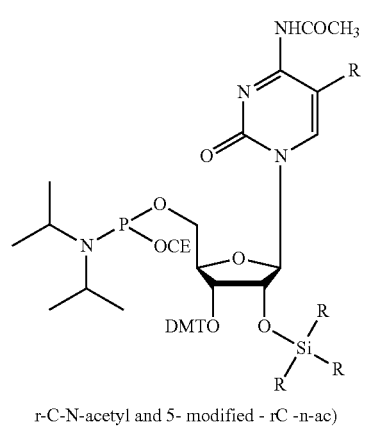

r-C-N-acetyl and 5- modified - rC -n-ac)

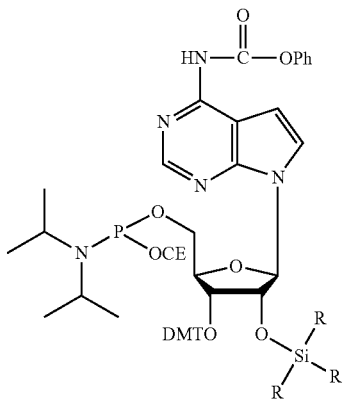

(N⁶ phenoxy carbonyl r-A)

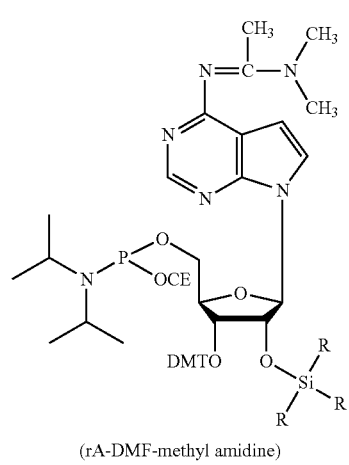

(rA-DMF-methyl amidine)

3. The use of partially methylphosphonate-modified oligodeoxy-nucleotides were synthesized on solid-phase by employing the easily removable 2-(acetoxy-methyl)benzoyl (AMB) group as base-protecting group for the synthesis of partially methylphosphonate-modified oligodeoxy-nucleotides, synthesized on solid-phase is known in the art, see for example, W. H. A. Kuijpers, et al., *Nucleic Acids Research,* 1993, Vol. 21, No. 15 3493-3500, the entire teachings of which are incorporated herein by reference. The AMB protecting group was accomplished in methanolic potassium carbonate. However, the lability of the methylphosphonate linkage towards potassium carbonate/methanol excluded the use of this deprotection reagent. Subsequently saturated ammonia solution in methanol was found to be an alternative reagent for AMB removal. It was demonstrated that the combination of the AMB protective group and ammonia/methanol as deprotection reagent significantly improves the synthesis of methylphosphonate-modified DNA fragments. A mild overnight treatment at room temperature is sufficient for complete removal of the AMB group, whereas deprotection of conventionally protected oligonucleotides requires much longer exposure to basic conditions at elevated temperatures.

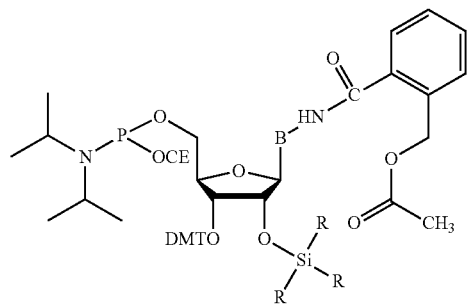

(AMB-protected nucleobase proposed for our reverse RNA synthons)

4. The following nucleobase protecting groups have been found to be very useful and are anticipated to be adopted in nucleobase protection of monomers of our invention N-pent-4-enoyl (PNT) Group As a Universal Nucleobase Protector, see, for example, "Applications in the Rapid and Facile Synthesis of Oligonucleotides, Analogs, and conjugates", Radhakrishan P. et al., *Tetrahedron*, Vol. 53, No. 8, pp. 2731-2750, 1997, the entire teachings of which are incorporated herein by reference. The synthesis of missed backbone oligonucleotides (MBOs) as antisense agents with the use of PNT nucleoside phosphoramidites in conjunction with PNT nucleoside H-phosphonates and PNT nucleoside phosphonamidites and the use of PNT group in preparation of bioreversible oligonucleotide conjugates is described therein.

The Pent-4-enoyl Group: A Novel Amine-Protecting Group; see, for example, Robert Madsen, Carmichael Roberts and Bert Fraser-Reid, *J. Org. Chem.*, 60, 7920-7926, (1995), the entire teachings of which are incorporated herein by reference. The protection of primary and secondary amines as N-pent-4-enoyl derivatives resulted in N-pent-4-enamides and were found to be highly crystalline. Deprotection was found to be rapidly and efficient under mild conditions by treatment with 3 equiv of iodine in aqueous THF solution. It shown that although an oxidizing medium is required during the deprotection, it does not effect oxidizable functionalities including p-methoxybenzyl ethers and alkyl sulfides. A representative compound of the invention including the Pent-4-enoyl group is shown below:

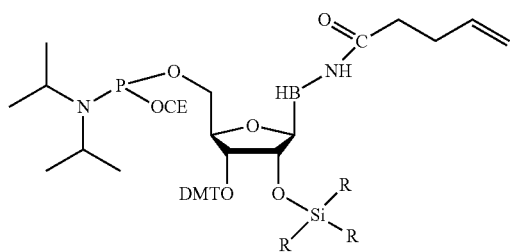

Succinyl group as exocyclic amine protecting group. Succinyl group on exocyclic amine can be utilized to further derivative/attach various supports for solid phase oligonucleotide synthesis. A representative compound of the invention including the succinyl group is shown below:

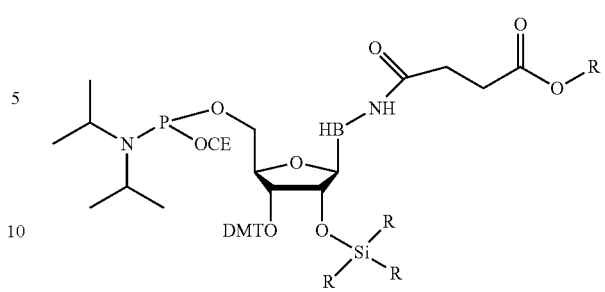

Alternatively, the exocyclic amine of 3',5' protected nucleoside can be derivatized with a succinimidyl group which can be attached to a solid support, such as structure 3 below, for synthesis in the 5'→3' direction.

(structure 3)

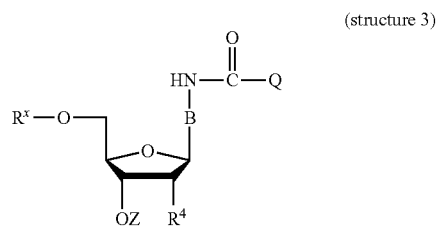

Incorporation of locked nucleic Acid™, also know as 2'-O, 4'-C-methylene ribonucleosides and phosphoramidites (LNA) via Reverse RNA synthesis process: 2'-O,4'-C-methylene ribonucleosides and phosphoramidites, a novel class of conformationally restricted oligonucleotide analogs (structure 1-6) have been shown to possess high binding ability to complementary DNA and RNA sequences. Various 2'-O,4'-C-methylene ribonucleosides and phosphoramidites are being currently evaluated for evaluation of synthetic DNA, RNA and chimeras for various therapeutic and diagnostic applications[1-5]. The most common phosphoramidite synthons used for the synthesis of defined sequence oligonucleotide are LNA-C (n-bz)-5'-DMT-3'-cyanoethyl phosphoramidites (1), LNA-C (n-ac)-5'-DMT-3'-cyanoethyl phosphoramidites (2), LNA-thymidine-5'-DMT-3'-cyanoethyl phosphoramidites (3), LNA-A (n-bz)-5'-DMT-3'-cyanoethyl phosphoramidites (4), LNA-G (n-dimethylformamidine)-5'-DMT-3'-cyanoethyl phosphoramidites (5; R; dimethylformamidine), The 2'-O,4'-C-methylene ribonucleosides and phosphoramidites oligos have been shown to help in design and efficacy of oligonucleotides for gene regulation, gene expression, antisense, si RNA, and in delivery of RNA in to cell. They have been shown to increase DNA and RNA stabilibity[1-5]. The 2'-O-4'-C-methylene ribonucleosides and phosphoramidites currently described in the art possess a 5'-DMT and 3' phosphoramidite function (6).

(1)
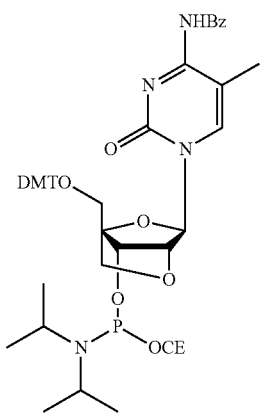

(2)
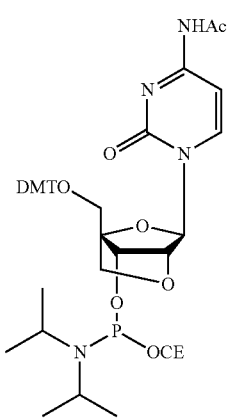

(3)
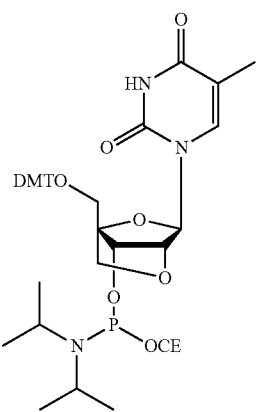

(4)
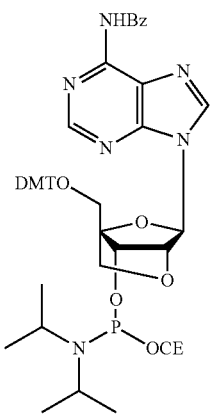

-continued (5)
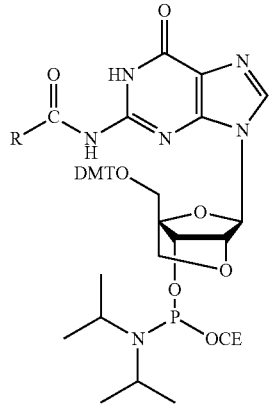

(6)
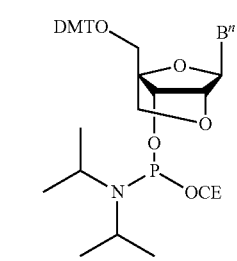

Incorporation of 2'-O-4'-C-methylene ribonucleosides proposed in our invention described in the art possess these units in oligonucleotides and the synthons to constitute a 3'-DMT and 5' phosphoramidite (structure 7), is amenable to reverse RNA synthesis according to the methods of our invention.

(7)
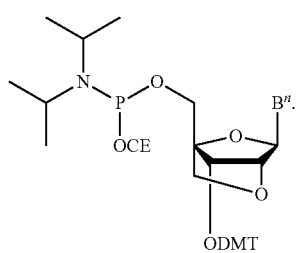

Compounds of the invention including 2'-O,4'-C-methylene ribonucleosides and phosphoramidites are shown below:

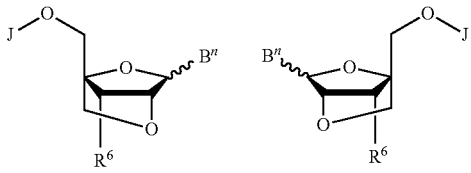

Scheme for synthesis of 2'-O-4'-C-methylene ribonucleoside-3'-DMT nucleosides, 5'-phosphoramidites and supports

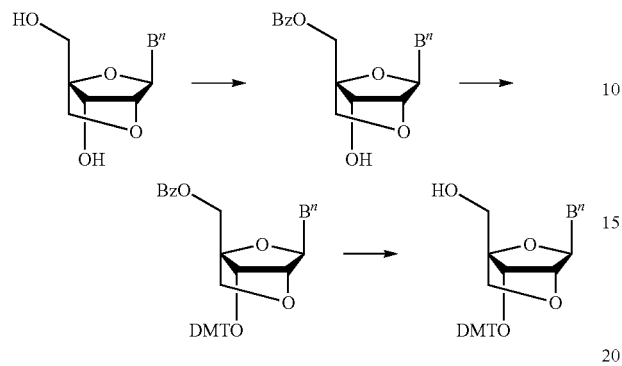

The teachings of the following references are incorporated herein by reference:

1. A. A. Koshlin, S. K. Singh, P. Nielsen, V. K. Rajwanshi, R. Kumar, M. Meldgaard, C. E. Olsen and J. Wengel, Tetrahedron, 1998 m54, 3607-3630.
2. S. K. Singh, P. Neilsen, A. A. Koshkin, and J. Wengel, Chem. Comm., 1998, (4), 455-456.
3. D. A. Braasch, D. R. Corey, Biochemistry, 2002, 41, 4503-4510.
4. J. S. Jespen, M. D. Sorensen, and J. Wengel, Oligonucleotide, 2004, 14, 130-146.
5. B. Vester and J. Wengel, Biochemistry, 2004, 43, 13233-41.
6. S. Obika, D. Nanbu, Y. Hari, J-i Andoh, K-i Morio, T. Doi, T. Imanashi, Tet. Lett., 39 (30), 5401-4, 1998.

Introduction of Sugars into Oligonucleotides

Sugars

The compounds of the invention may include, for example, ribose or arabinose. Arabinose nucleosides can be prepared through a procedure similar to that described for Ribose nucleosides. An example synthesis is shown in the scheme below:

Scheme 2'-Arabinose Reverse Amidite Synthesis:

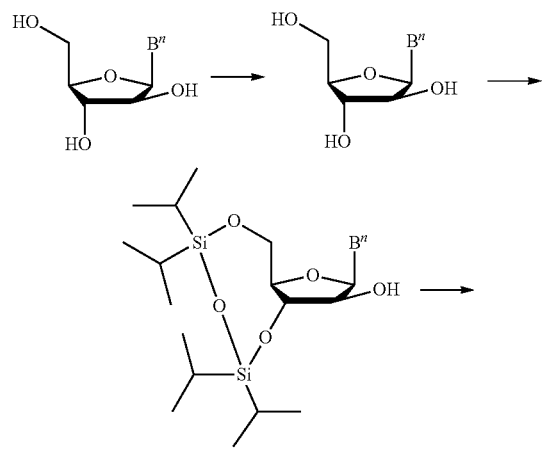

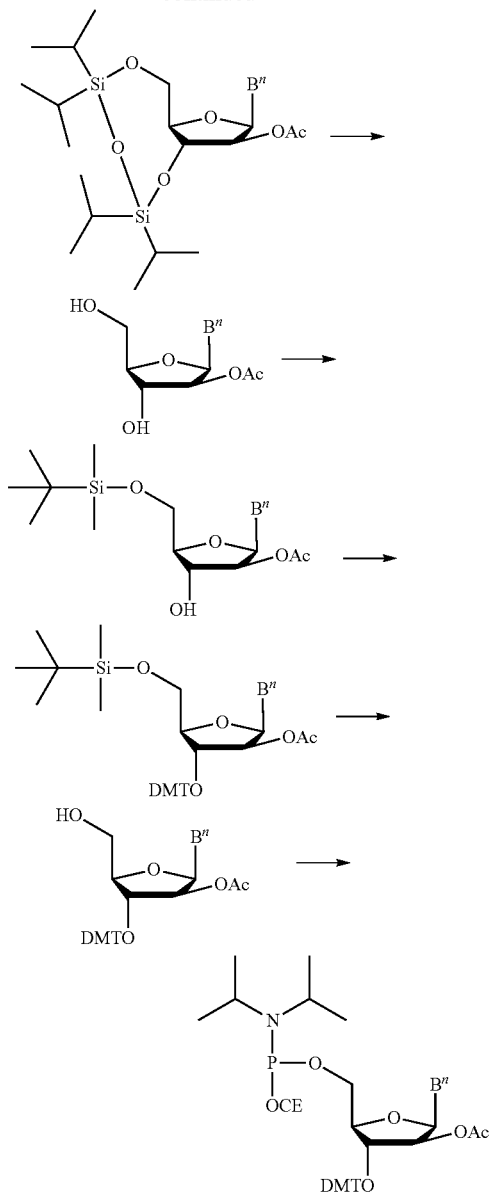

Protection of 3' Hydroxy Group:

A series of triaryl methyl groups have previously been investigated as the 5'-hydroxy protecting group of deoxy nucleosides and evaluated for trityl removal during oligonucleotide synthesis. The different color cations obtained were very useful for colorimetric monitoring and differentiation between nucleosides used in oligo synthesis, see "Color coded triarylmethyl protecting groups useful for deoxypolynucleotide synthesis"; E. F. Fisher and M. H. Caruthers, Nucleic Acids Research, Vol. 11, 5, 1589-1599 (1983), the entire teachings of which are incorporated by reference. The triarylmethyl groups for use in the invention include di-p-anisylphenyl methyl, p-fluorophenyl-1-naphthylphenyl methyl, p-anisyl-1-naphthylphenyl methyl, di-o-anisyl-1-naphthyl methyl, di-o-anisylphenyl methyl, p-tolyldiphenyl-methyl, di-p-anisylphenylmethyl, di-o-anisyl-1-naphthylmethyl, di-p-anisylphenyl methyl, di-o-anisyl phenyl methyl, di-p-anisylphenyl methyl, and p-tolyldiphenylmethyl.

In addition, triarylmethyl 3' hydroxy protecting groups are represented by the formula:

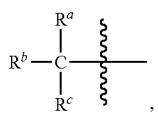

wherein ⦃ indicates attachment to the 3' oxygen atom and $R^a$, $R^b$, and $R^c$ are independently selected from the following structural formulas:

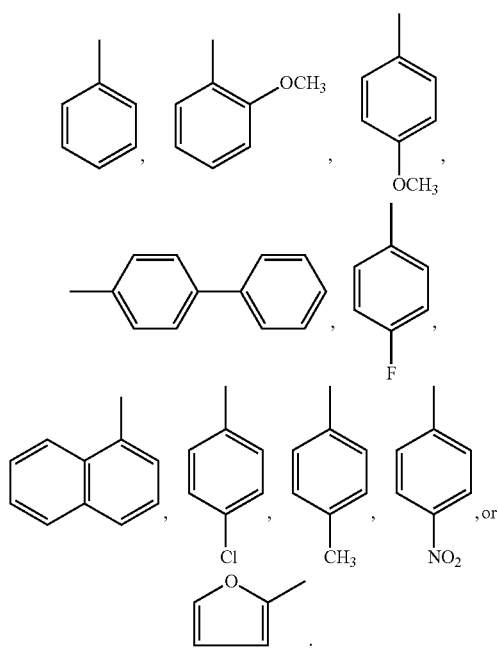

Tetrahydropyranyl and methoxytetrahydropyranyl group as a 3' hydroxy protecting agent and removal under acidic conditions. See, for example, "Synthesis of oligonucleotides with sequences identical with or analogous to the 3'-end of 16 S ribosomal RNA of *E. coli*: preparation A-C-C-U-C-C via modified phosphotriester method"; J. H. van Boom, P. M. J. Boom, P. M. J. Burgers, G. van der Marel, C. H. M. Verdegaal and Mrs. G. Wille, the entire teachings of which are incorporated herein by reference. A representative 3' methoxytetrahydropyranyl group is shown below:

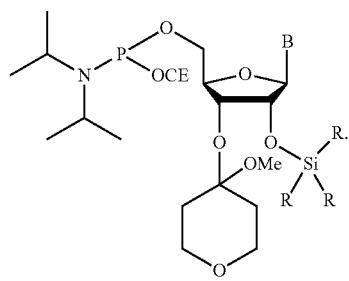

Phosphate Protecting Groups (Represented by $R^3$)

As used herein, the term "phosphate protecting group" refers to a moiety that, when present in a molecule of the invention, is eliminated following the formation of oligonucleotide. For example, the phosphate moiety can be protected by a cyanoethyl protecting group. It is well known that the cyanoethyl protecting group for internucleotide phosphate formation is eliminated by β-elimination mechanism leading to acrylonitrile and phosphodiester oligonucleotides. (Scheme 3

Scheme 3. Elimination of cyanoethyl phosphate group via base :B.

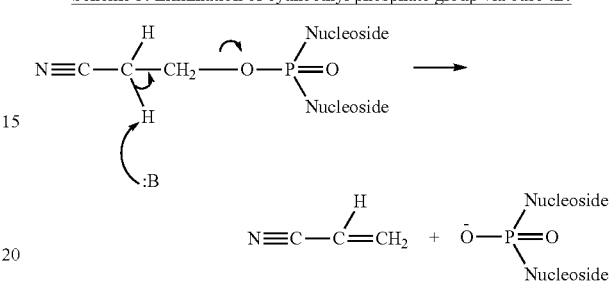

Phosphate protecting groups include —$CH_2CH_2CN$, —$CH_2CH_2$—$Si(CH3)_2C_6H_5$, —$CH_2CH_2$—$S(O)_2$—$CH_2CH_3$, —$CH_2CH_2$—$C_6H_4$—$NO_2$, —$CH_2CH_2$—NH—C(O)—$C_6H_5$, or —$CH_2CH_2$—O—$C_6H_4$—$C(O)CH_3$, and $R^4$ is —O—$Si(R^5)_3$. Other Phosphate protecting groups are known in the art and include (2-Acetoxyphenoxy)ethyl (APOE) (See Cheruvallath, Z. S., et. al; *Org. Process Res. Dev.*, 2006, 10 (2), pp 251-256, the entire teachings of which are incorporated herein by reference), and 2-Benzamidoethyl group (See Guzaev A P, *J. Am. Chem. Soc.* 2001 Feb. 7; 123(5):783-93, the entire teachings of which are incorporated herein by reference).

A 2'-blocking group is a 2-O-anhydro nucleobase represented by the following structural formula:

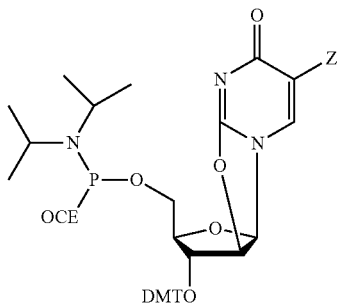

3' Functional Groups

The present invention is directed to the synthesis of high purity RNAs, specifically to introduce selected groups at the 3'-end of oligonucleotides of synthetic RNAs. Such RNA molecules have applications in therapeutics, diagnostics, drug design and selective inhibition of an RNA sequence within cellular environment, blocking a function of different types of RNA present inside cell.

Oligonucleotides have been shown to be taken up by mammalian cells rather easily. Uptake has been shown to result in nuclear accumulation. Attachment of lipophilic molecules to oligonucleotides has been shown to increase their uptake properties considerably. Specifically, attachment of cholesterol and poly-L-lysine have been studied in detail.

Other RNA conjugates include peptide-RNA conjugates. Peptide transfer RNA molecules are key molecules for the biosynthesis of proteins taking place in ribosomes, and in translation of genetic code to functional proteins. They generally play important role in anchoring RNA to compartmentalization and concentrate in liposomes (See Lazar, A. et al., International Round Table on Nucleosides, Nucleotides and Nucleic Acids, IRT-XVII, Sep. 3-7, 2006, page 47, Bern, Switzerland, the teachings of which are incorporated herein by reference.)

The peptide attachment of these functional groups generally takes place at the 3'-end, and are referred to as a "3' Functional Group".

As used herein, a "3' Functional Group" refers to moieties attached to the 3' end of the RNA molecule. The Reverse Synthesis Method described herein provides for attachment of a moiety at the end of the oligonucleotide chain. The 3' functional group may include lipids such as fatty acids and cholesterol, steroids, peptides, enzymes and labels, including moieties that are fluorescent, chemiluminescent, or radiolabelled.

The 3' functional groups may be introduced through the reaction of a phosphoramidite linkers shown below:

1. The attachment of the 3' functional group to the RNA leads to amphiphilic 3'-peptidyl-RNA conjugates. Such molecules mimic natural peptide-transfer RNA. Synthesis of such RNA have been done on solid support by the above referenced authors. The RNA was joined to a peptide via an amide linkage to a variety of peptides. For example, the compound represented by the following structural formula can be attached at the 3' end using the Reverse Synthetic method disclosed herein:

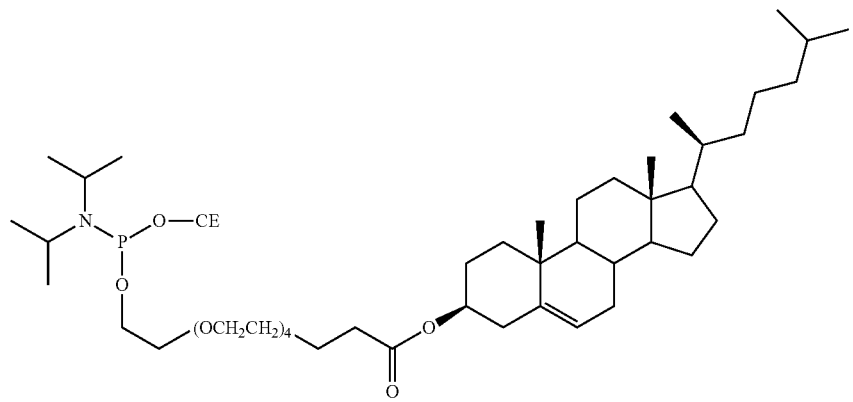

2. Biotin Attachment at 3'-End of an RNA

3'-Biotin attachment via biotin amidite is possible in a single step and avoids the use of biotin CPG. Generally, a protected biotin amidite is used to attach biotin by solid phase oligonucleotide synthesis in order to get high purity oligonucleotides. A "protected biotin" is known in the art, see, for example, U. Pieles, B. S. Sproat and G. M. Lamm, *Nucleic Acids Research, Vol.* 18, No. 15, 4355 (1990), the entire teachings of which are incorporated herein by reference. A representative protected biotin that can be used in the invention is as follows:

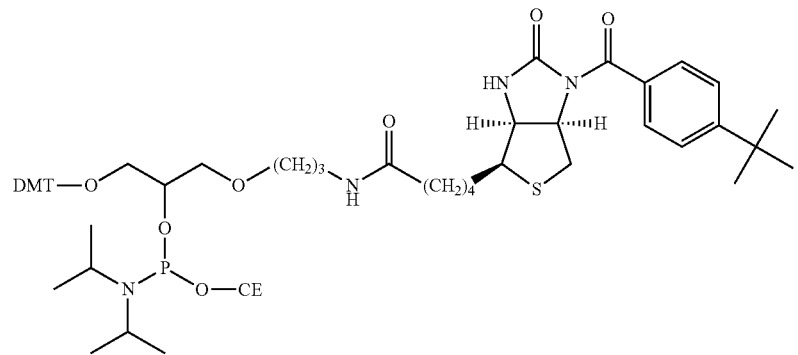

3. Disulfide Linker for 3' Functional Groups.

The oligonucleotides of our invention can be derivatized at the 3'-end by a disulfide linker, which can generate an —SH group. Subsequent coupling to an enzyme carrying a terminal SH function or an activated sulfide to lead to disulfide linked oligo-enzyme conjugate. A representative disulfide linker is as follows:

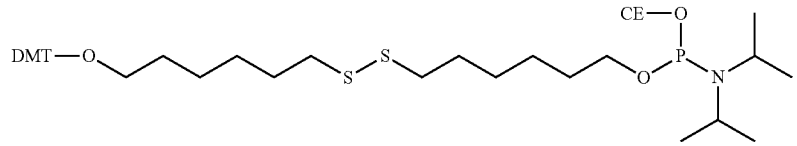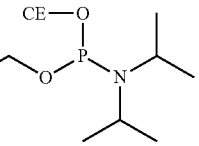

These disulfide linker phosphoramidite can be conveniently attached to the 3'-terminal of an oligonucleotide. The attached disulfide attached via a phosphate at 3'-end can then be conjugated to various peptides, enzymes via sulfide coupling or exchange reaction known in the art.

For attachment of 3'-thiol modification, 3'-disulphides from readily available amidites, viz., C-3 disulfide, C-6 disulfide can be used. Oligonucleotides containing a free sulphhydryl group and subsequent attachment of thiol specific probes have been previously described and can be modified for attachment of the thio group at the 3' end. (See Connolly, B. A. NAR, 13, 12, 4485, 1985, the teachings of which are incorporated herein by reference). Oligonucleotide probes containing a free sulphydryl group at their 5'-terminal have been synthesized and further derivatized with thio specific probes. S-triphenyl-O-cyanoethyl phosphoramidite-2-mercapto ethanol and other alkyl chains can be synthesized and incorporated in an oligonucleotide at the 3'-end.

4. 3'-Branched Linkers for Multiple Group Attachment

The synthesis of branched oligonucleotides as signal amplification multimers in nucleic acid assay is described in T. Horn, et al., *Nucleotides and Nucleotides*, 895&6), 875-877 (1989), the entire teachings of which are incorporated herein by reference.

Enzyme probes are described in "Highly sensitive detection of DNA using enzyme linked DNA-probes using colorimetric and fluorometric detection", Akira Murakai, et al., *Nucleic Acids Research*, Vol. 17, No. 14, 5587 (1989), the entire teachings of which are incorporated herein by reference.

Branching phosphoramidite can be attach to oligonucleotide terminals. The branched phosphoramidite can be utilized to attach various reporter molecules, chromophores, enzymes, ligands, polyethylene glycols, peptides, or other 3' functional groups described herein. A branched oligonucleotide is prepared by reacting the 3'-hydroxy of the sugar with a compound of the following structural formula:

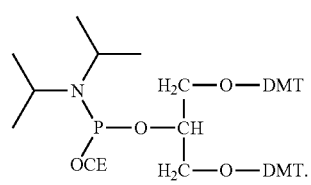

The DMT protecting group can be replaced with other appropriate hydroxy protecting groups as described herein.

In addition, a vast number of applications are possible for attachment at the 3'-end of an oligonucleotide. Bulky molecules can be attached via direct coupling at the 3'-end of the RNA, such as cholesterol, long chain aliphatic chains such as C-18, triethylene glycols, hexaethylene glycols.

Polyethylene Glycols, such as PEG 2000 amide and PEG 4000 amidites at the 3'-end of an RNA have been achieved.

The modification of the overhang of the sense strand (3'-End) of SiRNA is not expected to affect targeted mRNA recognition, as the antisense SiRNA strand guides target recognition. Useful modification for improvement of delivery of SiRNA can be designed.

Non radioisotopic hybridization assay methods and diagnostic applications using fluorescent, chemiluminescent and enzyme labeled oligonucleotide probes are known in the art. (See Urdea, M. et al., *NAR*, 16, 11, 1988, the entire teachings of which are incorporated herein by reference). In addition, radiolabelled polynucleotide probes have been extensively applied for detection of complementary nucleic acids by specific hybridization. The reverse synthesis method disclosed herein can be used to label long oligonucleotides (such as those including 100 bases). Examples of labels that can be attached via the reverse synthetic method disclosed herein include, for example, Fluoresceine; Texas red; rhodamine; chemiluminiscent molecules such as isoluminol; enzymes such as horseradish peroxidase; alkaline phosphatase labels; and enzymes.

2' Substituents

The 2'-silyl ethers have been developed extensively and they are known to have remarkable stability. Solvolysis of silyl ethers have been extensively studied and it is known that bulky alkyl silyl ethers have a high degree of stability; (See Bazani, B. and Chvalowski, V., Chemistry of Organosilicon Compounds, Vol. 1, Academic Press, New York, 1965, the entire teachings of which are incorporated herein by reference). Extensive research work was subsequently done by Ogilvie and coworkers as 2'-hydroxy protecting group for oligo ribonucleotide synthesis (See Ogilvie, K. K., et al., *Tetrahedron Letters*, 15: 2861-2864, 1974; and Ogilvie, K. K., et al. *J. Carbohydrate Nucleosides Nucleotides*, 3: 197-227, 1976; Ogilvie, K. K. Proceedings of the 5th International Round Table on Nucleosides, Nucleotides and Their Biological Applications, Rideout, J. L., Henry, D. W., and Beacham L. M., III, eds., Academic, London, pp. 209-256, 1983, the entire teachings of which are incorporated herein by reference).

The t-butyldimethyl silyl protecting group on 2'-hydroxyl of ribonucleosides has been the group of choice for making 3'-phosphoramidites and for utilizing them for oligonucleotide synthesis which have been shown to migrate to 3'-hydroxyl position rather easily. (See Ogilvie, K. K., and Entwistle, D. W. *Carbohydrate Res.*, 89: 203-210, 1981; and Wu, T., and Ogilvie, K. K. *J. Org. Chem.*, 55: 4717-4734, 1990, the entire teachings of which are incorporated herein by reference). Such migration complicates the synthesis of the desired phosphoramidites and requires an efficient method of purification that clearly resolves corresponding isomers and prevents any contamination of the final monomer. In contrast, the migration to the 3' hydroxyl is not a factor for during Reverse (5'→3') Synthesis.

Representative 2' amino protecting groups include compounds represented by the following structural formulas:

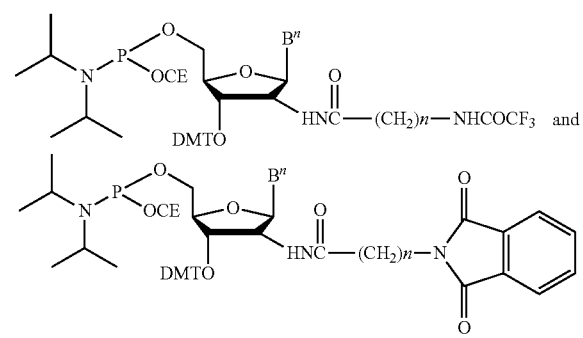

2'-Fluoro-3'-DMT-nucleoside-5'-phosphoramidites.

The 2'-Fluoro substituent can be incorporated through the following proposed synthesis of 3'-DMT-2'-fluoro-N-protected-nucleoside-5'-phosphoramidites:

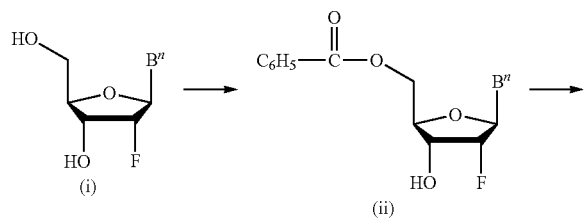

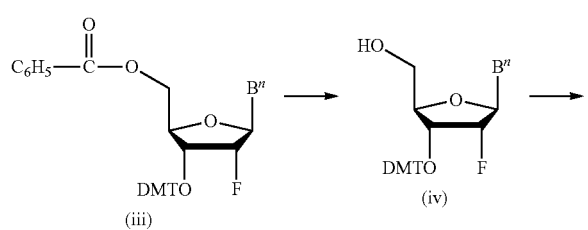

Alternatively, the 2'-Fluoro substituent can be incorporated through the following proposed synthesis of 2'-Fluoro-3'-DMT-N-protected (with fast deprotecting groups) nucleoside-5'-phosphoramidites:

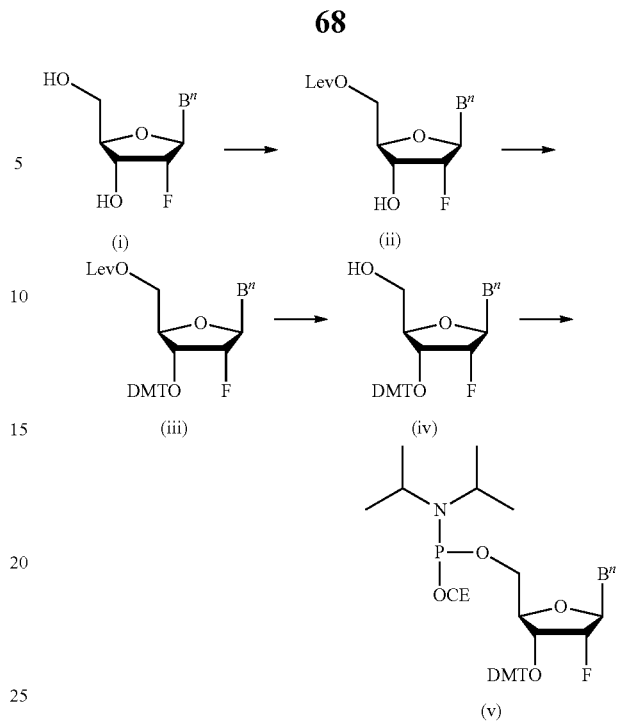

Selective 5'-levulinyl protection followed by crystallization to yield compound (II); DMT-Cl reaction to yield compound (iii), followed by reaction with ammonia for 4-5 min to yield compound (iv) The 5'-phosphoramidites can then be synthesized by standard phosphitylation chemistry process to yield (v The standard Jones process can be utilized to prepare 2'-arabinose fluoro nucleosides (FANA) as well. The process includes: Conversion of (i) to (ii) steps; a; transient protection with TMS chloride; followed by reaction with phenoxyacetyl chloride/pyridine; b; 2-4 minutes aq ammonia treatment to selectively remove TMS groups; c; crystallization of phenoxyacetyl protected-2'-fluoro nucleosides.

The 2'-fluoro modification of sugar portion of nucleosides, either 2'-ribo fluoro-2'-deoxy or 2'-arabino fluoro-2'-deoxy-nucleosides (FANA) have found significant application in design of various class of DNA and RNA such as antisense, microRNA, siRNA, aptamers. The selective introduction of such units into an oligonucleotides requires careful deprotection after solid phase oligonucleotide synthesis. It has been demonstrated that if harsh ammonia deprotection is carried out there is depyrimidation of oligonucleotides and loss of fluorine from sugar moiety. Thus, the development of optimized protecting group of the nucleoside exocyclic functional group is required in general is required to ensure all modified nucleosides units within an oligonucleotide will be compatible with mild base deprotection.

Several protecting groups such as FMOC, phenoxyacetyl, tertiary butyl phenoxyacetyl (t-BPAC), isopropyl phenoxy acetyl (isoPrPAC) and guanosine N-2 nitrogen protected with acetyl (N-acetyl guanosine) are therefore being utilized to minimize either loss of fluorine from the fluoronucleoside units. The reverse RNA synthesis units therefore need to be protected with labile protecting group so they can be removed under mild deprotection conditions after oligonucleotide synthesis. Similarly mild phosphate deprotecting groups, such as cyanoethyl phosphoramidite chemistry are being currently used in present state of the art in this technology in DNA and RNA synthesis.

Deprotection of FMOC protecting group has been carried out under various very mild basic reaction conditions. (See Heikkila, J. and Chattopadhyaya, J., *Acta Chem, Scand. B* 37, No. 3, 263-265, 1983, the entire teachings of which are incorporated herein by reference.) It is possible to utilize either aqueous ammonia condition deprotection, which results in nucleophilic displacement of FMOC protecting group, or by a Non-nucleophilic base such as triethylamine, which causes B-elimination of FMOC-active hydrogen group, as seen in the scheme below:

Scheme Showing FMOC-β-Elimination

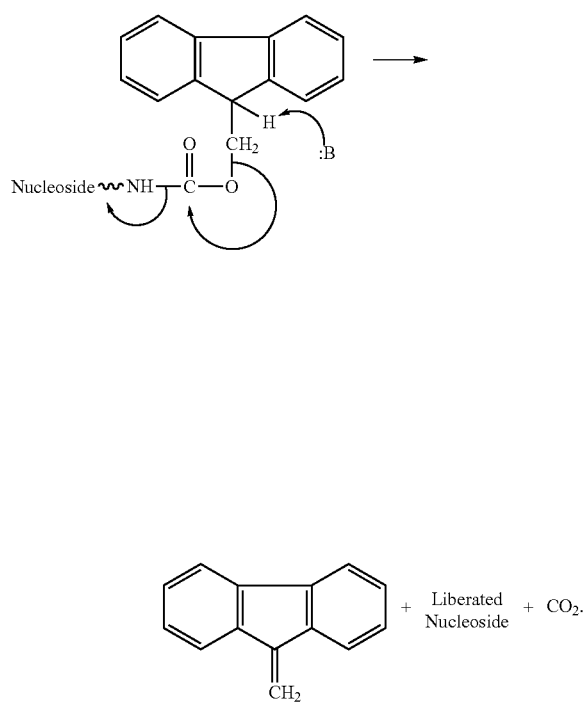

It is therefore possible to modulate the FMOC protecting group removal conditions from oligonucleotides, and the FMOC as base protecting group can be removed by the process of β-elimination, just like the β-elimination process to remove cyanoethyl group. Other protecting groups, for example, including phenoxyacetyl or alkylated phenoxyacetyl groups, can also be utilized in the reverse synthesis method described herein to generate highly pure deprotected oligonucleotides.

This process therefore offers very attractive potential to use ammonia free oligo synthesis. This process furthermore has potentials to offer deoxyoligonucleotides for complete deprotection of oligos on solid supports. This technology or process has potential to offer ribonucleotides such as required for chip based technology as well high purity oligonucleotides for microRNA, Si RNA, RNA chips These base protecting groups in conjunction with cyanoethyl phosphate protecting group therefore provide the opportunity to remove both N-protecting groups and cyanoethyl groups from the synthesized deoxy and ribo oligonucleotides on the support cleanly, preferably with non aqueous bases, and on support for many diagnostics application.

The FMOC protecting group is very well established in peptide synthesis and one of the preferred reagent for amino group protection of alpha-amino group of amino acids for step wise peptide synthesis (See Carpino, L. A., and Han, G. Y., *J. Amer. Chem. Soc.,* 92: 5748, 1970, the entire teachings of which are incorporated herein by reference). Another N-protecting group is 2-nitrophenyl sulfenyl (NPS) for the protection of amino function of cytidine, adenosine, guanosine and the corresponding 2'-deoxyribo nucleosides. (See J. Heikkila, J. et al., *Acta Chem. Scand B* 37: 857-864, 1983, the entire teachings of which are incorporated herein by reference). The attachment of NPS to an exocyclic amine is represented by the following structural formula:

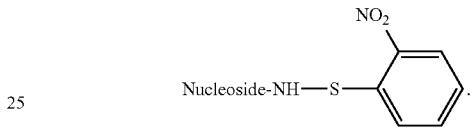

Phosphoramidite

Studies on the formation of the internucleotode n bond in RNA Synthesi using dialkylamino phosphoramidites; G. Gasparutto, D. Molko & R. Teoule, Nucleosides & Nucleotides, 9(8), 1087-1098 (1990), the entire teachings of which are incorporated herein by reference. Among various 5'-DMT-2'-TBDMS-U-3'-n, n-dialkyl amino cyanoethyl phosphoramidites tested during olignucleotide synthesis, it was found by the above authors that n,n-diethyl and n-ethyl, n-methylamino protection gave the best coupling result of average 97% after 4 minutes of coupling to form homopolyme of rU. For example, 5' diethylamino-cyanoethyl can be used in the invention disclosed herein.

Addition of 2' or 3' Functional Groups Using Click Chemistry Via Reverse RNA Synthesis Process Copper (I) catalyzed Huisgen 1,3-dipolar cycloaddition of azides with terminal alkynes is a well established example of a click reaction used in click chemistry (See Broggl, J., et al., International Round Table Conference on Nucleosides, Nucleotides and Nucleic acids, Sep. 3-7, 2006, Bern, Switzerland, p. 348, the entire teachings of which are herein incorporated by reference).

The 3'-DMT-2'-alkyne-5'-phosphoramidite compounds of the invention would offer further advantage of modification and attachment of various macromolecules at 3'-terminal of an RNA. Reverse RNA synthesis process would allow introduction of various modifications at 3'-end of oligos, as well as internal positions during solid phase oligo nucleotide synthesis:

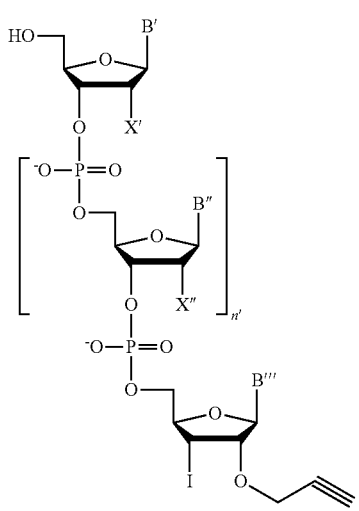

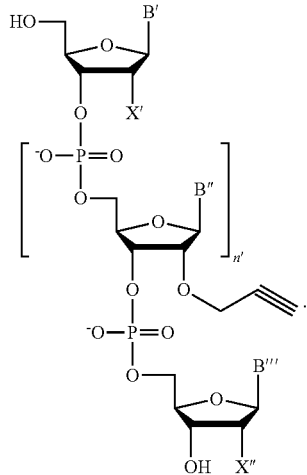

With 5'-solid support the reverse amidites, viz., 3'-DMT-2'-alkyne-5'-phosphoramidites would undergo oligo synthesis. Macromolecules such as, chromophores, ligands, biologically significant polypeptides, cholesterol and polyethyleneglycols can be regiospecifically attached via click chemistry:

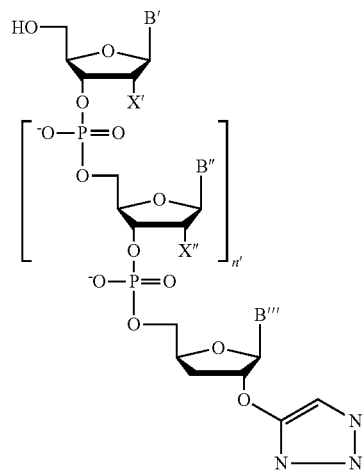

The click chemistry process on solid phase support allows clean cycloaddition products in which all the reactants are washed out, followed by liberation of oligonucleotide. The modifications include highly efficient quencher dyes for use in molecular sensors and attached to oligonucleotides via "click chemistry". A proposed synthesis for compounds of the invention that can be used in click chemistry is depicted in the scheme below:

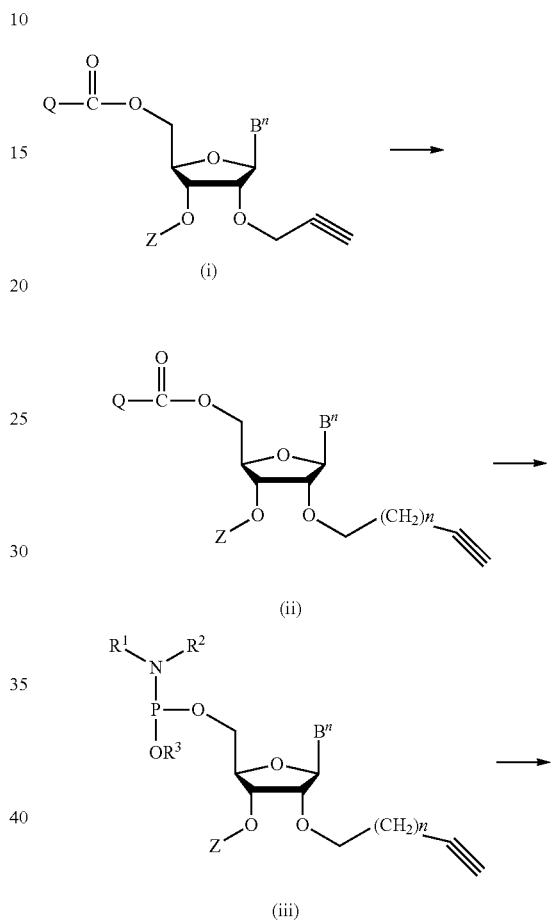

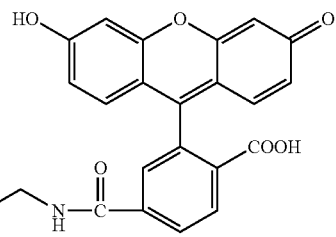

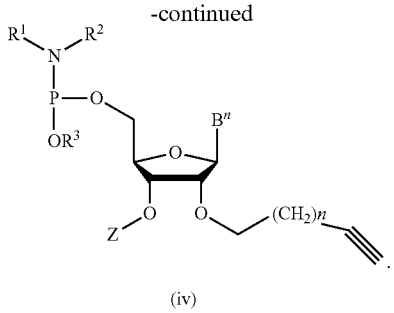

(iv)

n is 2 to 16

Building blocks for combinatorial "click chemistry" have been developed; multiple cycles of click reaction have been performed leading to oligonucleotides bearing single or multiple units of various chromophores and other macromolecules. We have improved the catalytical 1,3-cycloaddition efficiency for "click" reactions for synthesis of high purity DNA/RNA based probes on automated solid support based oligonucleotide synthesis. We have also developed novel highly efficient quencher dyes for use in molecular sensors and attached to oligonucleotides via click chemistry. The teachings of the following citations are incorporated herein by reference:

1. V. V. Rostovtsev, L. G. Green, V. V. Fokin, K. B. Sharpless, Angew. Chem. Int. Ed., 2002, 41, 2596-2599.
2. A. V. Ustinov, et al, *Tetrahedron,* 2007, 64, 1467-1473.
3. Agnew, B. et al., US Patent application 20080050731/A1.
4. X. Ming, P. Leonard, D. Heindle and F. Seela, Nucleic Acid Symposium Series No, 52, 471-472, 2008.
5. Srivastava, S. et al., U.S. Pat. No. 5,744,595
6. M. Manoharan, K. L. Tivel, and P. D. Cook, *Tetrahedron Lett.,* 1995, 36, 3651-3654.
7. G. S. Rule, J. Frim, J. E. Thompson, J. R. Lepock, and J. Kruuv, *Cryobiology,* 1978 15, 408-414.
8. C. J. Yu, Y. Wan, H. Yowanto, J. In, C. Tao, M. D. James, C. L. Tan, G. F. Blackburn, and T. J. Meade, *J. Am. Chem. Soc.,* 2001, 123, 11155-11161.

Biotin Attachment at 3'-End of an RNA

Generally, a protected biotin amidite is used to attach biotin by solid phase oligonucleotide synthesis in order to get high purity oligonucleotides. A "protected biotin" is known in the art, see, for example, U. Pieles, B. S. Sproat and G. M. Lamm, *Nucleic Acids Research,* Vol. 18, No. 15, 4355 (1990), the entire teachings of which are incorporated herein by reference.

Protection of 3'-Hydroxy:

1. Additional triaryl methyl protecting groups: See for example, "Color coded triarylmethyl protecting groups useful for deoxypolynucleotide synthesis"; E. F. Fisher and M. H. Caruthers, *Nucleic Acids Research,* Vol. 11, 5, 1589-1599 (1983), the entire teachings of which are incorporated herein by reference. Triarylmethyl Groups reported include di-p-anisylphenyl methyl, p-fluorophenyl-1-naphthylphenyl methyl, p-anisyl-1-naphthylphenyl methyl, di-o-anisyl-1-naphthyl methyl, di-o-anisylphenyl methyl, p-tolyldiphenylmethyl, di-p-anisylphenylmethyl, di-o-anisyl-1-naphthylmethyl, di-p-anisylphenyl methyl, di-o-anisyl phenyl methyl, di-p-anisylphenyl methyl, p-tolyldiphenylmethyl. Additional triaryl methyl protecting groups are represented by the following structural formula:

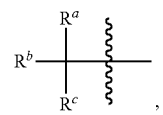

wherein ⟨ indicates attachment to the 3' oxygen atom and $R^a$, $R^b$, and $R^c$ are independently selected from the following structural formulas:

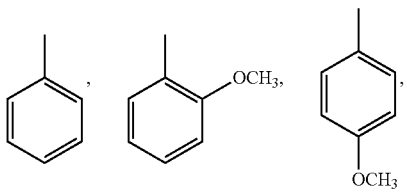

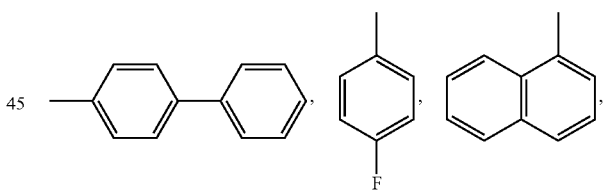

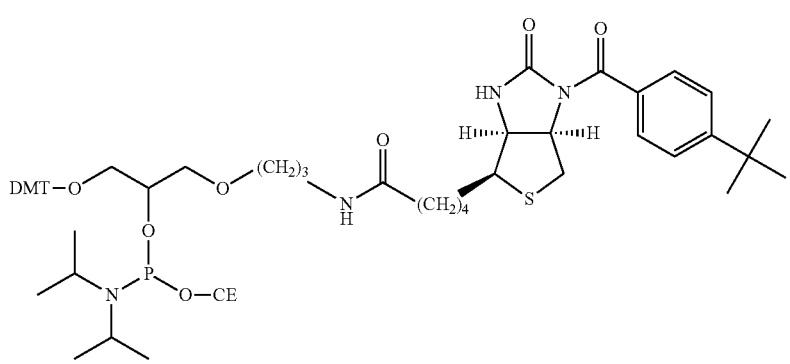

2. Use of tetrahydropyranyl and methoxytetrahydropyranyl group as protecting agent and removal under acidic conditions for the 3'-protecting group. This protecting group which can be removed under acidic conditions, see for example, "Synthesis of oligonucleotides with sequences identical with or analogous to the 3'-end of 16 S ribosomal RNA of *E. coli*: preparation A-C-C-U-C-C via modified phosphotriester method"; J. H. van Boom, P. M. J. Boom, P. M. J. Burgers, G. van der Marel, C. H. M. Verdegaal and Mrs. G. Wille, the entire teachings of which are incorporated herein by reference. A representative compound of the invention including methoxytetrahydropyranyl is shown below:

Advantages of Reverse RNA Method

We have synthesized full length oligos with a coupling time of 2 minutes using BTT as activator. The crude oligo purity obtained was 78.95% by HPLC. Using ETT as an activator, a 4.0 minute coupling time was possible, resulting in the crude oligo purity obtained to be 89.09%. The crude oligo purity by reverse process has been generally in the range of 90%. Using the reverse RNA method on a large scale synthesis (12 umol scale) we achieved similar results (crude oligo was approx. 92% and purified oligo was approx. 98%.), using a 6 minutes coupling time. We were able to synthesize phosphorothioate oligonucleotides and mixed phosphorothioate/phosphate backbone without loss of coupling efficiency or oligonucleotide quality. In contrast, the convention (3'→5') direction synthesis resulted in crude oligo purity in the range of 80%, requiring several purifications to increase the purity to approx. 90%. The conventional RNA synthesis results in impurities on both the sides of desired band. While the reverse RNA synthesis, even with 2' coupling time does not give any N+1 impurities and HPLC trace shows right hand side of the peak is fairly straight. Previously, reverse RNA synthesis; 5'→3' showed that crude purity of oligonucleotides was approx. 80% by HPLC. Currently, reverse RNA synthesis; 5'→3' crude oligo purity to the extent of 90% due to perhaps to increased purity of the monomer synthons, and/or the reduced coupling time of 4 minutes of coupling time with ETT as activator, as compared to 10 minutes.

Representative Examples of Chrompohores and Quencher Dye Attachment to Oligo Nucleotides Using Reverse RNA Synthesis Approach:

1. Reverse RNA synthesis utilizing 2'-Propargyl synthons and an azide linked quencher dye (ChemGene's proprietary quencher bis azo dye):

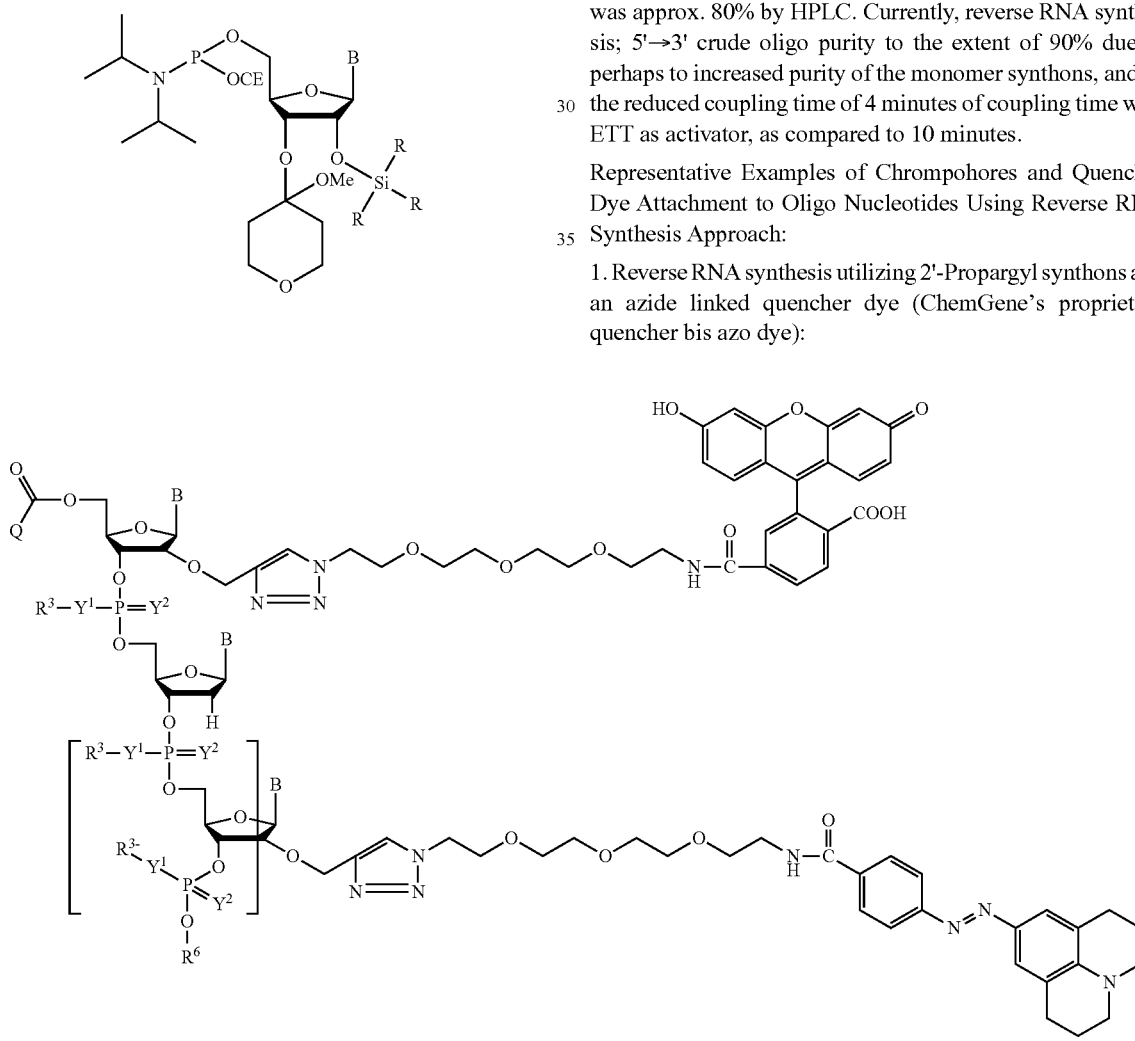

2. Reverse RNA synthesis utilizing 2'-Propargyl synthons and an azide linked chromophore(6-FAM) multiple internal incorporation:
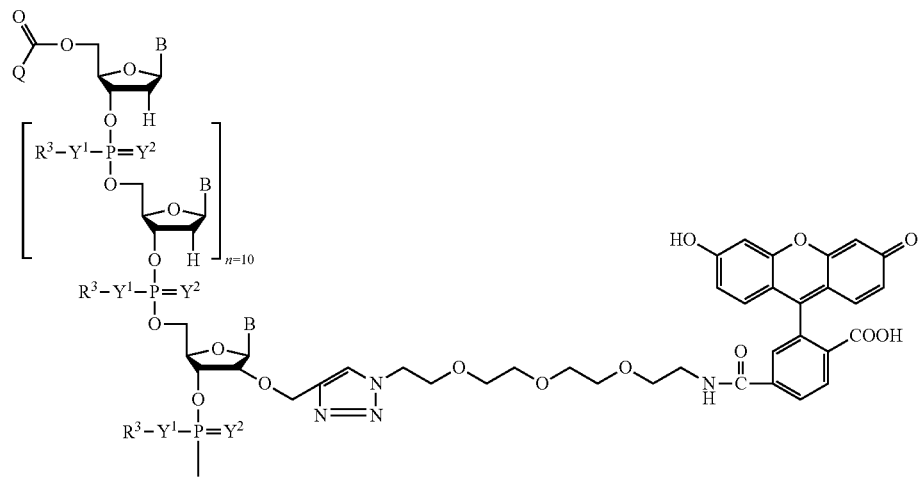
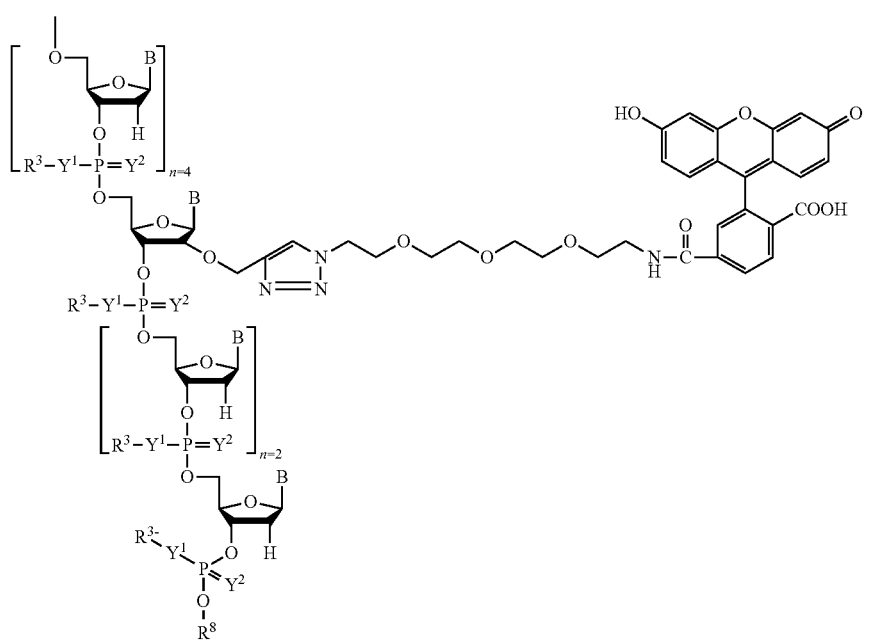

2. Reverse RNA synthesis utilizing 2'-Propargyl synthons and an azide linked chromophore, Ferrocine; 3'-End attachment
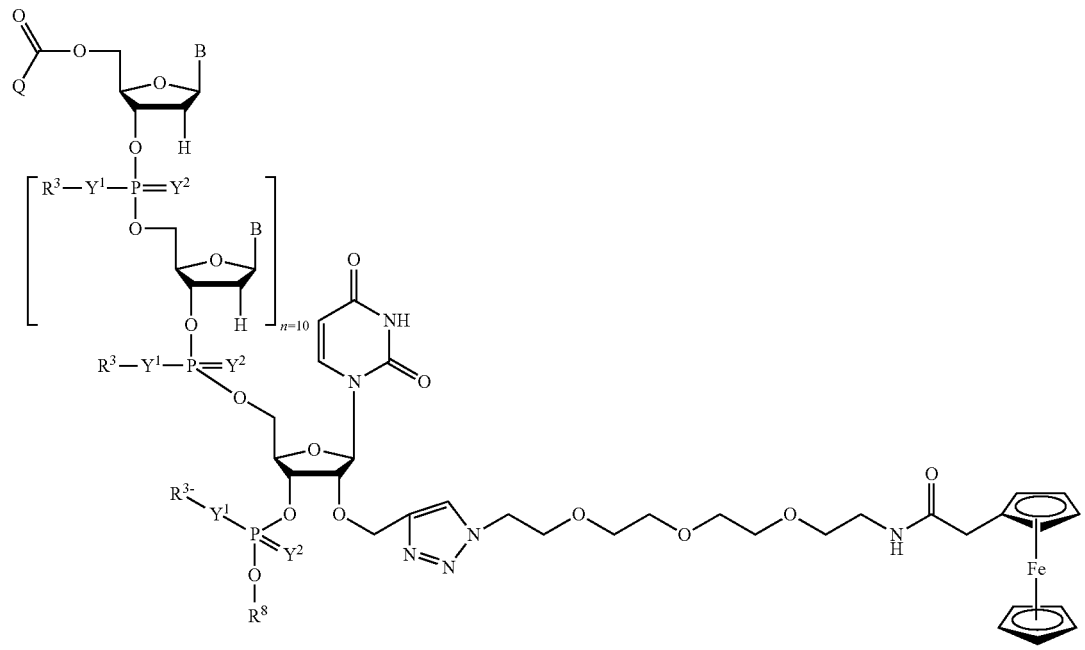
4. Reverse RNA synthesis utilizing 2'-Propargyl synthons and an azide linked chromophore(6-FAM) (single internal incorporation:
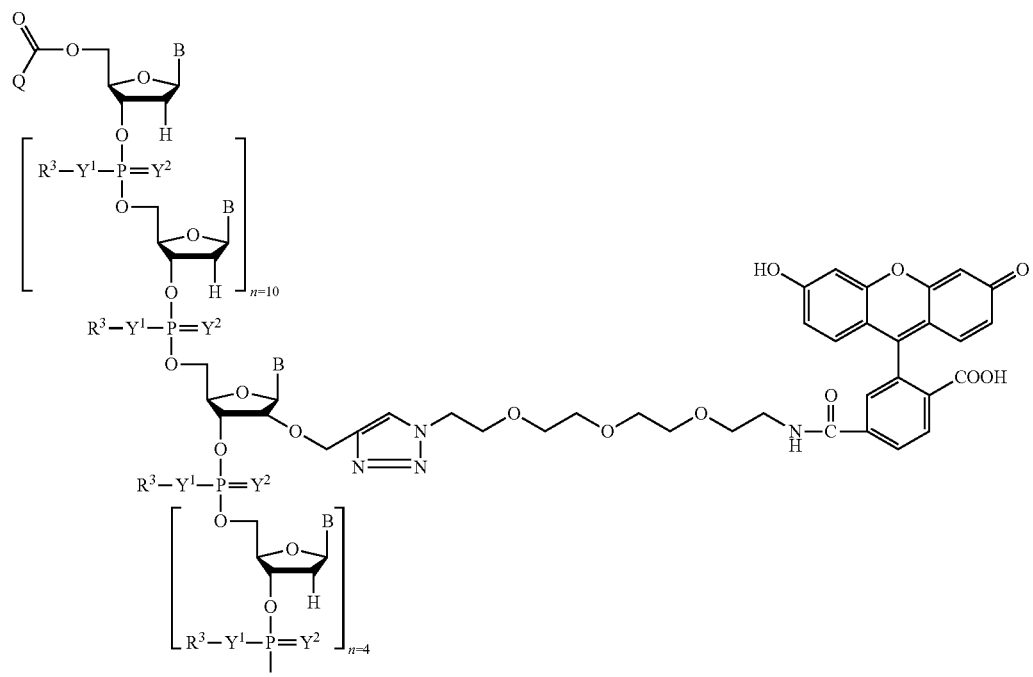

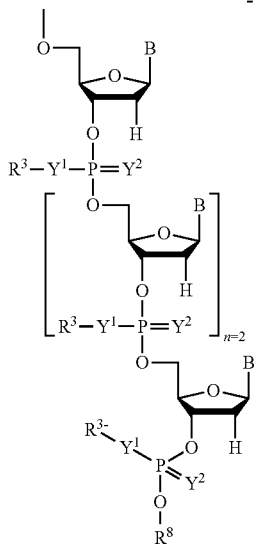

5. Linker (L) can be attached via two step process (a); The 3'-end base has a protecting group which can be conveniently removed to lead to free 3'-hydroxyl group, (b) activation of the free 3'-hydroxyl group via succinmidyl carbonate and subsequent reaction of the succinimidyl carbonate with an amine terminated linker) to lead to compound of structure 2. The structure 1 is derived by last coupling with a linker having a phosphoramidite function.

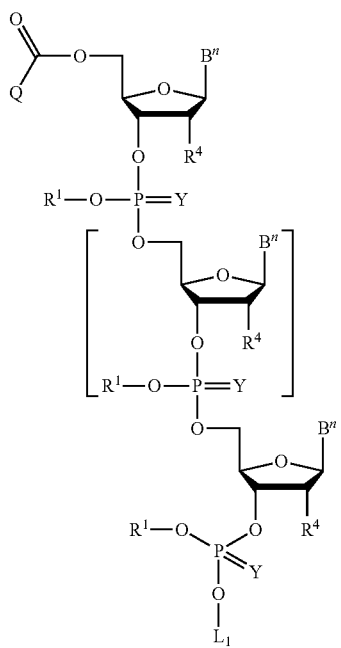
(structure 1)

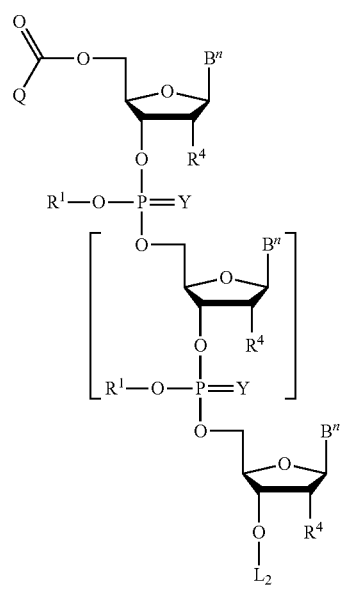
(structure 2)

List of Linkers, Chromophores (Designated as $L_1$ and $L_2$)

The L's could be derived from a Linker, chromophores, fluorescent dyes, fluorescent nucleosides, fluorescent molecule attached to a nucleoside and can be coupled as a phosphoramidite or they could be derived from an active ester, such as NHS ester. The list include as follows:

Functional Groups for Further Derivatization of an Oligo at 3'-End or Internal Position;

amino modifier C-3, amino modifier (C-6), amino modifier C-12, amino modifier C-5-dU, amino modifier C-5-dU, 3'-thiol modifier (C-6 spacer), thiol modifier (C6-disulphide), carboxy modifier (with spacer), carboxy modifier (C-10 spacer), C-8 (amino modifier-C6-spacer)-r-adenosine, FMOC protected amino modifier-5-r cytidine (spacer), FMOC protected amino modifier-C-5 uridine (spacer), 3'-thiol modifier (C-3 spacer) disulphide, 3'-Chemical phosphorylation of an oligonucleotide Phosphate-on-phosphorylating reagent (sulfonyl diethanol mono DMT, mono phosphoramidite), biscyanoethyl phosphorylating reagent 3'-aldehyde attachment to an oligonucleotide:

3'-Aldehyde modifier C-2 spacer, formyl indole,

Spacer Attachment to Oligonucleotides:

To generate space between the end of an oligonucleotide and subsequent attachment of a molecule of interest such as peptides, amino acids, chromophores, polyethylene glycols, asymmetric doubler, symmetrical doubler, long trebler, trebler, Chromophores, Dyes Attachment at 3' End on or within a Sequence:

Chromophores, dye and spacer attachment in internal position or 3'-end of an oligonucleotide synthesized via our process can be conveniently achieved;

Dabcyl with a spacer, dabcyl —C-5 uridine or 2'-deoxy uridine, biotin with a spacer, biotin with tetraethylene glycol spacer, biotin —C-5 deoxy thymidine, biotin —C-5 uridine, biotin (tetraethylene glycol spacer), 5-(spacer) fluorosceine, 6-(Spacer) fluoresceine (6-FAM), 5-(spacer) hexachlorofluoresceine, 5-(spacer) tetrachlorofluoresceine, 6-(spacer) hexachlorofluoresceine, 6-(spacer) tetrachlorofluoresceine, fluoresceine-C-5 deoxy thymidine, fluoresceine —C-5-rU, tetramethyl rhodamine (TAMRA), Cy5™, Cy 5.5™ Cy 3™, Cy 35™ (cy dyes are trade mark of General Electric; GE-Amersham), Epoch Richmond Red™, Epoch Kokimo Yellow™, Epoch Gig Harbor Green™, Epock Eclipse Quencher™, (Eclipse dyes are trade mark of Epoch Biosciences Inc.), BHQ-0™, BHQ-1™, BHQ-2 ™, BHQ-3™ (BHQ dyes are trade mark of Biosearch Technologies, Inc.).

Various other dye attachment such as C-5 Pyrene-r-uridine, C-5 perylene-r-uridine, (5,6)-pyrrole-r-cytidine, Acridine dye attached to a spacer, dinitrophenyl amine attached to a spacer, cholesterol tetraethylene glycol attached to a spacer via 3-OH, psoralen attached to a spacer via furan ring, Ethylene diamine tetraacetic acid (EDTA) attached via spacer, puromycin.

Other linkers include: C-5 (rU and rC) acrylate Biotin, C-5 (rU and rC) fluoresceine, 6-FAM, 5-FAM, Tamra, rhodamine, acrylate.

Use of an activator. An activator may be added during the coupling step in the method forming an oligonucleotide bond between the 5'-phosphoramidites of our invention and a hydroxyl group. The activator is chosen and is capable of activation and subsequent protonation of the amidite nitrogen. The activator could be selected from tetrazole, benzyl thio tetrazole, ethyl thio tetrazole, dicyanodiimidazole. The activators which lead to activation of the amidite bond for reaction coupling with an hydroxyl group top form phosphate.

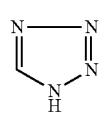
(Tetrazole)

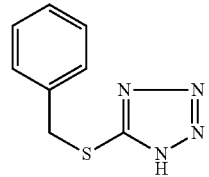
(BTT)

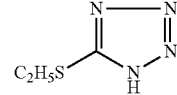
(ETT)

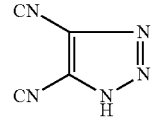
(DCI)

Application of Reverse RNA Synthesis in MicroRNA Synthesis microRNAs (miRNA) are generally non-coding RNAs highly conserved, having a length of 20 to 25 nucleotides in length that regulate expression of target genes through sequence specific hybridization to the 3' untranslated region (UTR) of messenger RNAs and either block translation or direct degradation of their target messenger RNAs and are present in plants and animal alike. This novel class of RNAs was first discovered in *C. elegans* in 1993 by the laboratory of Dr. Victor Ambrose, (Lee R. C., et al. (1993), 14. *Cell* 75: 843-854, the entire teachings of which are incorporated herein by reference). They have now been identified in almost every species including the discovery of microRNAs in humans (Lim L. P., et al. (2003), *Science* 299: 1540, the entire teachings of which are incorporated herein by reference) Each miRNA is thought to regulate multiple genes, and since hundreds of miRNA genes are predicted to be present in higher eukaryotes, the potential regulatory circuitry afforded by miRNA is enormous. Several research groups have provided evidence that miRNAs may act as key regulators of processes as diverse as early development (Reinhart 2000), cell proliferation and cell death (Brennecke 2003), apoptosis and fat metabolism (Xu 2003). microRNAs have been shown to play an integral role in numerous biological processes including the immune response, cell-cycle control, metabolism, viral replication, stem cell differentiation and human development. Many microRNAs are conserved across multiple species indicating the evolutionary importance of these molecules as modulators of critical biological pathways. However microRNA expression or function is significantly altered in many disease states, including cancer, heart failure, and viral infections. Targeting pathways of human disease with miRNA-based drugs represents a potentially powerful new therapeutic approach.

The reverse RNA synthesis approach present an opportunity to synthesize such RNAs, to include modifications for stability of such RNA in intracellular environment and to incorporate ligands or delivery agents for uptake and therapeutic development.

Application of Reverse RNA synthesis in RNAi synthesis

Silencing gene expression with RNA interference (RNAi) has become a well studied approach offering potential for selective gene inhibition and application in the control and management of various biochemical and pharmacological processes. Early studies by, showed that RNA interference in *Caenorhabditis elegans* is mediated by 21 and 22 nucleotide RNA sequences. (See Fire et al., *Nature,* 391: 806-811, 1998, the entire teachings of which are incorporated herein by reference). This was further confirmed as a general phenomenon of specific inhibition of gene expression by small double stranded RNA's being mediated by 21 and 22 nucleotide RNAs, (See *Genes Dev.,* 15: 188-200, 2001, the entire teachings of which are incorporated herein by reference). Subsequently a vast amount of research led to the confirmation of above studies and established RNAi as a powerful tool for selective, and very specific gene inhibition and regulation. (See Nishikura, K., *Cell,* 107, 415-418, 2001; and Nykanen, A., et al., *Cell,* 107: 309-321, 2001; and Tuschl, T., *Nat. Biotechnol.,* 20: 446-448, 2002; and Mittal, V., *Nature Rev.,* 5, 355-365, 2004; *Proc. Natl. Acad. Sci, USA,* 99, 6047-6052, 2002; and Donze, O. & Picard, D., *Nucl. Acids. Res.,* 30, e46, 2002; and Sui, G., et al., *Proc. Natl. Acad. Sci. USA,* 99, 5515-5520, 2002; and Paddison, P. J. et al., *Genes Dev.,* 16, 948-959, 2002, the entire teachings of which are incorporated herein by reference). Besides the natural double stranded (ds) RNA sequences, chemically modified RNA have been shown to cause similar or enhanced RNA interference in mammalian cells using 2'-deoxy-2'-fluoro-β-D-arabinonucleic acid (FANA) into sequences for siRNA activities. (See Dowler, T., et al., *Nucl. Acids Res.,* 34, 1669-1675, 2006, the entire teachings of which are incorporated herein by reference).

Various other modifications to improve siRNA properties have been pursued, which include alteration in backbone chemistry, 2'-sugar modifications, and nucleobase modifications, some of which have been recently reviewed. (See Nawrot, B, and Sipa, K., *Curr. Top. Med. Chem.,* 6: 913-925, 2006; and Manoharan, M., *Curr. Opin. Chem. Biol.,* 8, 570-579, 2004, the entire teachings of which have been incorporated herein by reference). The PS modifications of siRNA are well tolerated, although some reports indicate increased toxicity and somewhat reduced efficacy. (See Harborth, J, *Antisense Nucleic Acid Drug Dev.,* 13, 83-105, 2003, the entire teachings of which are incorporated herein by reference). Among these is also the 2'-O-Methyl modification, although it maintains A form (RNA like) helix, and has been shown to be either retaining or reducing siRNA activity depending on the number of such modifications within a sequence. (See Chiu, Y. L., Rana, T. M., *RNA,* 9:1034-1048, 2003, the entire teachings of which have been incorporated herein by reference). It has also been shown that extensive 2'-O-Methyl modification of a sequence can be made in the sense strand without loss of siRNA activity. (See Kraynack, B. A., Baker, B. F., *RNA,* 12: 163-176, 200, the entire teachings of which are incorporated herein by reference).

Support and Linking Groups

The support material (represented in the structural formulas herein as "Q") is a non-swellable solid support. The support material could be solid, liquid, or in gel form. The "linking group" is a moiety such as a carbonyl that connects the nucleoside to the support and suitable linking groups are described in the following paragraphs. The support material Q is a) a support comprised of a linking group and a spacer, for example, succinyl, hydroquinolyl, oxalyl, that can be cleaved to form a hydroxy group; or b) an aliphatic chain, aromatic group, substituted or unsubstituted aromatic, a substituted or unsubstituted phenoxy, or levulinyl. Alternatively, an irreversible linker can be used.

The "linking group and spacer" is a moiety such as a carbonyl that connects the nucleoside to the support and suitable linking groups are described in the following paragraphs.

The two most often used solid-phase materials are Controlled Pore Glass (CPG) and macroporous polystyrene (MPPS). CPG is commonly defined by its pore size. In oligonucleotide chemistry, pore sizes of 500, 1000, 1500, 2000, and 3000 Å are used to allow the preparation of about 50, 80, 100, 150, and 200-mer oligonucleotides, respectively. To make native CPG suitable for further processing, the surface of the material can be treated with (3-aminopropyl)triethoxysilane to give Aminopropyl CPG. The aminopropyl arm may be further extended to result in Long Chain Aminoalkyl (LCAA) CPG. The amino group is then used as an anchoring point for linkers suitable for oligonucleotide synthesis. MPPS suitable for oligonucleotide synthesis is a low-swellable, highly cross-linked polystyrene obtained by polymerization of divinylbenzene (min 60%), styrene, and 4-chloromethylstyrene in the presence of a porogeneous agent. The macroporous chloromethyl MPPS obtained is converted to aminomethyl MPPS.

To make the support material suitable for oligonucleotide synthesis, non-nucleosidic linkers (universal supports) or nucleoside succinates are covalently attached to the reactive amino groups in the solid support material by routine methods. The remaining unreacted amino groups are capped with acetic anhydride. For example, the synthesis starts with the universal support where a non-nucleosidic linker is attached to the support material. A phosphoramidite respective to the 5'-terminal nucleoside residue is coupled to the universal support in the first synthetic cycle of oligonucleotide chain assembly using the standard protocols. The chain assembly is then continued until the completion, after which the support-bound oligonucleotide is deprotected. The characteristic feature of the universal solid supports is that the release of the oligonucleotides occurs by the hydrolytic cleavage of a P—O bond that attaches the 5'-O of the 5'-terminal nucleotide residue to the universal linker. The critical advantage of this approach is that the same support is used irrespectively of the sequence of the oligonucleotide to be synthesized.

Alternatively, the 5'-hydroxy group of the 5'-terminal nucleoside residue is attached to the support via, most often, 5'-O-succinyl arm. The oligonucleotide chain assembly starts with the coupling of a phosphoramidite building block respective to the nucleotide residue second from the 5'-terminus. The 5'-terminal hydroxy group in oligonucleotides synthesized on nucleosidic supports is deprotected under the conditions somewhat milder than those applicable for universal supports.

Another linking group includes Q-support, which is a hydroquinone spacer, conveniently cleaved as compared to succinyl supports (See University Technologies International, LP(UTI) & Publication; R. T. Pon and S. Y. Yu, *Tetrahedron Lett.,* 1997, 38, 3327-3330, the teachings of which are incorporated herein by reference.). The structural formula is as follows: Support-NH—C(=O)—CH2-O—C6H4-O—CH2-C(=O)—O-5'-nucleoside, and is represented by the following structural formula:

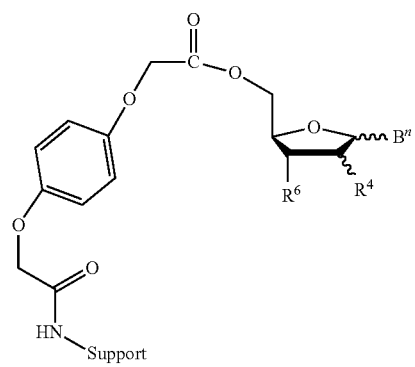

There are vast variety of supports currently available for oligonucleotide synthesis with choice to adopt to different types of oligonucleotides. Some of the key support technologies and descriptions are noted in the following paragraphs.

See Richard T. Pon; Current Protocols in Nucleic Acid Chemistry, Unit 31, February 2000, the entire teachings of which are incorporated herein by reference. The physical & chemical properties of supports are described in this manual and suitability for various chemistries of oligonucleotide synthesis.

Universal support have found significant application in oligonucleotides. UnyLinker technology as developed by Isis Pharmaceuticals, allows synthesis of oligonucleotides using single molecule as compared to derivatization of individual DNA or RNA bases. The cleavage of Unylinker molecules takes place smoothly to include a free 3'-end hydroxyl group on the 3'-end nucleoside. Our invention proposed to introduce such Unylinker molecule at the 5'-end of an oligonucleotide of our 5'-→3'-oligonucleotide synthesis process. After solid phase oligonucleotide synthesis the Universal support can be conveniently removed to generate free 5'-end hydroxy group. Isis Pharmaceutical technology has an intellectual property to covers this molecule for carrying out 3'-→5'-oligonucleotide synthesis and is covered by the following patents; the entire teachings of which are incorporated herein by reference: U.S. patent application 60/520,179 (DVCM0009US.L), filed Nov. 13, 2003 and entitled Supports for oligomer synthesis; U.S. patent application 60/530,477 (DVCM0010US.L), filed Dec. 16, 2003 and entitled Supports for oligomer synthesis. A subsequent publication by Isis Pharmaceutical scientists on this Universal support technology was reported.

A universal support has been described by AM Chemicals, LLC. The company described a convertible solid support which allows introduction of variety of ligands, functional groups at 3'-terminal. Our invention proposed to utilize this solid support for incorporated in our process for functionalization at 5'-position. A publication describing universal support described by AM Chemicals, LLC outlines application in detail of 3'-→5'-direction oligonucleotide synthesis; A conformationally Preorganized Universal Support for Efficient Oligonucleotide Synthesis, Andre P. Guzaev & Muthiah Manoharan, J. Am. Chem. Soc., 2003, 125, 2380-2381, the entire teachings of which are incorporated herein by reference.

Nitto Phase$^R$ (a trade mark of Nitto Denko Technical Corporation). Nitto phase$^R$ support has been demonstrated to have potential for use in the synthesis of therapeutic grade DNA and RNA. Nitto Phase$^R$ support, marketed through Kinovate Life Sciences, a wholly owned subsidiary of Nitto Denko Corp. This can be utilized as a support in our process and invention as a support for 5'-position attachment of nucleosides. With our superior process for RNA synthesis in reverse direction, and combination with this support we anticipate synthesis of high quality oligonucleotides. Prime Synthesis Inc., reports (see Website of Prime Synthesis Inc.) use of controlled pore glass (CPG) of various linker/spacers for attachment to CPG bead surface.

GE Health Care, a division of GE (General Electric) has described a custom support for oligonucleotide synthesis, known as Primer Support 200 (apczech.cz/pdf/df-primer support.pdf). The support has been shown by GE Health Care, suitable for DNA synthesis, RNA synthesis, custom base addition during oligonucleotide synthesis and growing oligonucleotide chain, labeling of various chromophores such as fluoresceine, dabsyl, phosphate-ON reagents etc. Primer support has been loaded to from 20-250 umole/g level. However no 5'-→3' direction RNA synthesis has been known or proposed to best of our knowledge.

The following compounds are not compounds of the present invention:

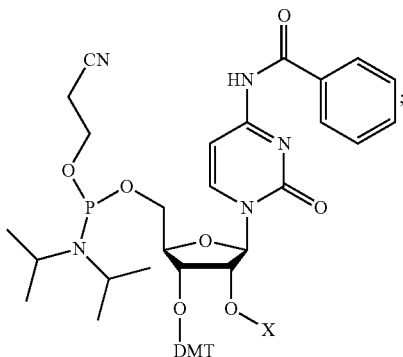

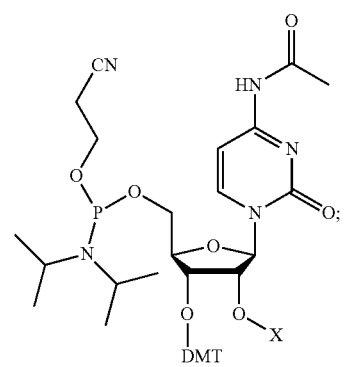

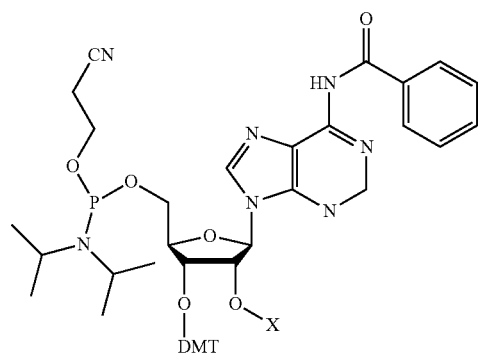

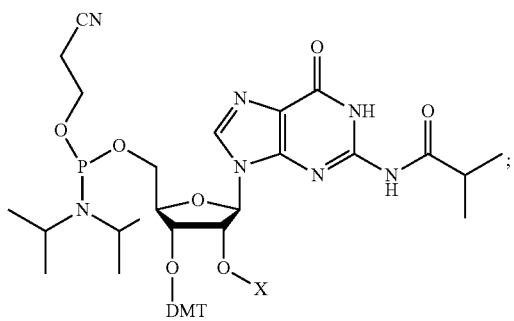

89
-continued
90
-continued
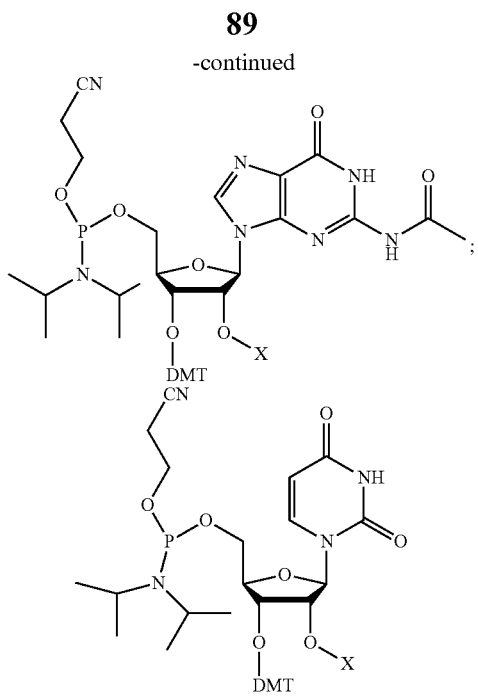
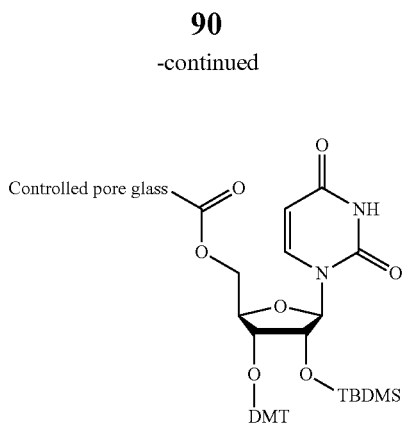
X = t-butyldimethylsilyl (TBDMS) or triisopropylsiloloxymethyl (TOM)
EXEMPLIFICATION
The details of synthesis scheme are outlined in the Scheme 1:
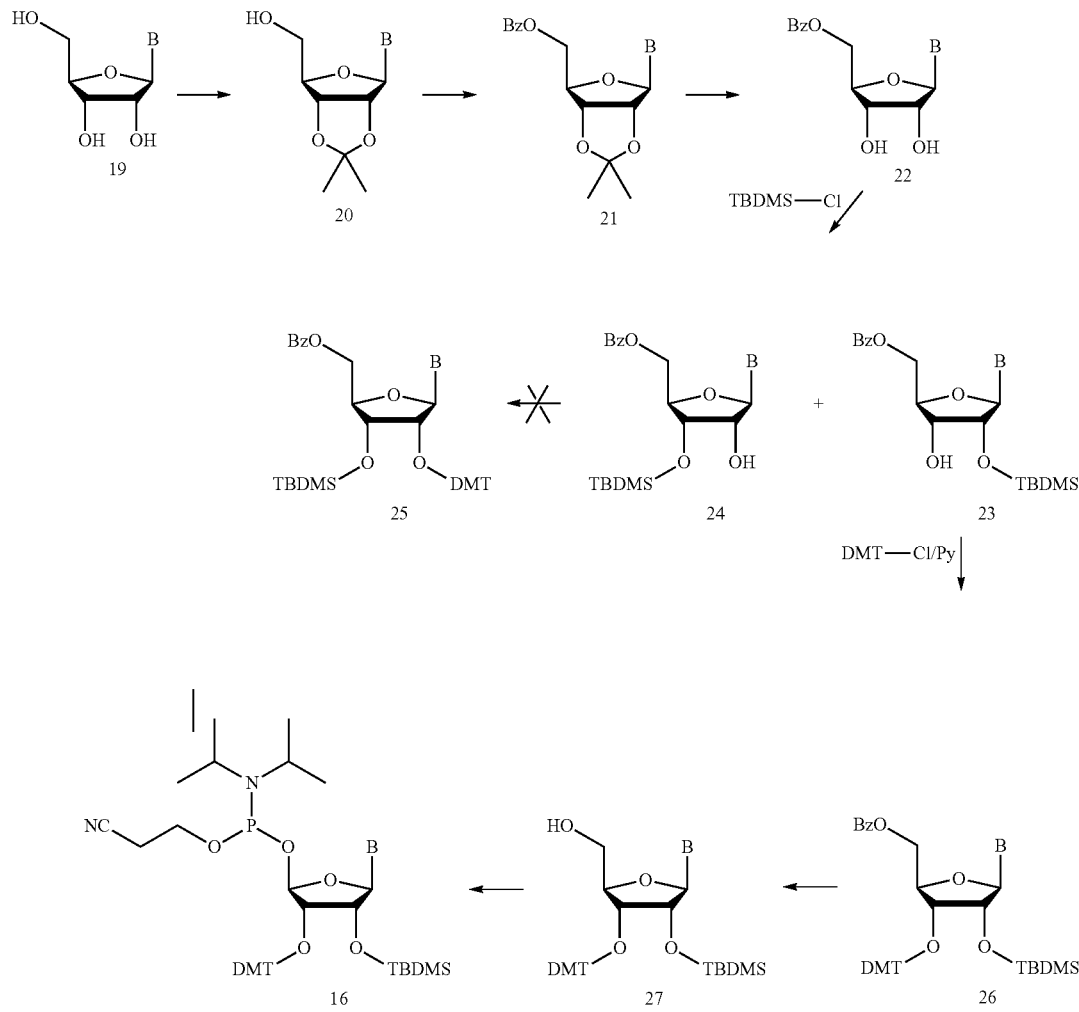

The 2',3'-Isopropylidene function is utilized to protect the 2',3' hydroxyl groups of ribose of n-protected ribonucleosides. A number of preferred n-protecting groups are shown in the Scheme (1). The 5'-hydroxyl group is subsequently protected, preferably with benzoyl group to obtain compounds of general structure 21. The isopropylidene group is then selectively removed under mild acidic conditions well known in the art. This step leads to compounds of general formula 22. Subsequent reaction with TBDM Silyl chloride (tert-butyl dimethyl silyl chloride) leads to mono silyl compound of general formula 23. The present inventors have observed that 3'-TBDMS group, i.e., the formation of compound structure 24 is not preferred in this process. In most of the cases they observed a clean product whose structure was confirmed to be 23 by chemical and analytical methods.

Purification is carried out at each step either via crystallization or column chromatography at each of the steps of the process mentioned above. Subsequent reaction with dimethoxytrityl chloride (DMT-chloride) in pyridine leads to 3'-DMT-2'-TBDMS-n-protected nucleosides of the general structure 26. Each of the compounds were fully purified by column chromatography.

TBDMS-n-protected nucleosides (structure 27) were purified by silica gel column chromatography. The purified compounds (structure 27) were subsequently phosphorylated with phosphorylating reagents, such as n,n-diisopropylamino cyanoethyl phosphonamidic chloride or 2-cyanoethyl,n,n,n, n-tetraisopropyl phosphane to yield the corresponding phosphoramidites (structures 16). Both the phosphorylating reagents, n,n-diisopropylamino cyanoethyl phosphonamidic chloride or 2-cyanoethyl, n,n,n,n-tetraisopropyl phosphane are readily available in the market Manufactured by Chem-Genes Corp., and the methods of phosphorylation to produce corresponding phosphoramidites are well known in the art.

Large Scale synthesis of high purity 3'-DMT-2'-TBDMS-nucleoside-5'-phosphoramidites for Reverse RNA synthesis. Typical synthesis of 70-100 g quantity of the phosphoramidites is illustrated in the following examples. Each of the phosphoramidite synthesis process demonstrate purity of 100% by 31 P NMR and greater than 98% purity by high pressure liquid chromatography (HPLC) analysis. The quality control data are presented in separate table.

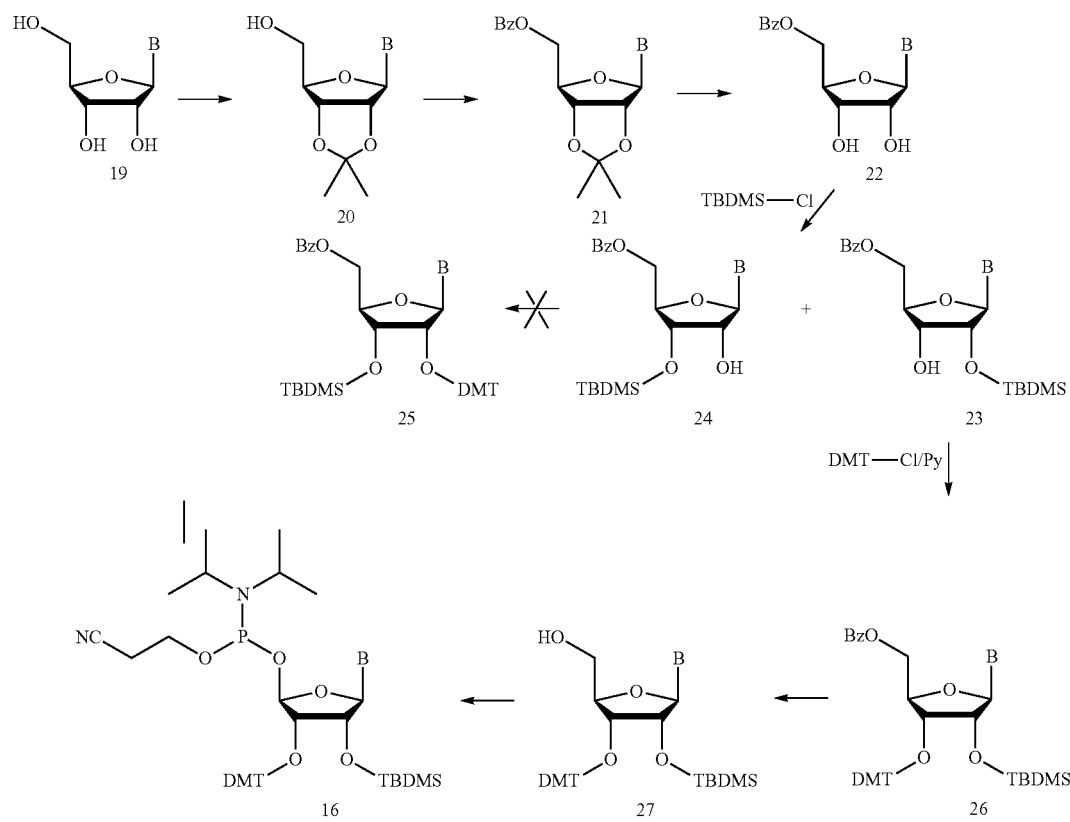

Where B = a) A(N—Bz), b) C (N—Bz), c) C (N—Ac), d) G (N—iBu)
e) A (N—tBPac), f) C (N —tBPac), g) G (N—tBPac),
h) A (N—Pac), i) C (N—Pac), j) G (N—Pac), k) U.

Although they utilized TBDMS group to produce 2'-TBDMS ether, other silyl ethers can be utilized at this step. A careful aqueous/methanolic NaOH hydrolysis resulted in compounds with free 5'-hydroxyl group, general structure 27. Selective 5'-benzoyl removal with aqueous or methanolic base is well known in the art. The compounds 3'-DMT-2'-

Synthesis of 3'-ODMT-2' OTBDMS-7-deaza rG (n-ibu)-5'-OP

Step (a): 5'ODMT-2' TBDMS-7-deaza rG (n-ibu)
Step (b): 5'OH-2'-TBDMS-7-deaza rG-(n-ibu)
Step (c): 5'-OBZ-2'TBDMS-7-deaza rG-(n-ibu)

Step (d): 5'-OBZ-3'-ODMT-2'-TBDMS-7-deaza rG (n-ibu)
Step (e): 5'-; OH-3'-ODMT-2'-TBDM S-7-deaza rG (n-ibu)
Step (f): 3'-ODMT-2'-TBDMS-7-deaza rG(n-ibu)-5'-cyano-ethyl phosphoramidite
Step (a): 5'ODMT-2' TBDMS-7-deaza rG (n-ibu) was produced by known procedure as published in literature
Step (b): 5'OH-2'-TBDMS-7-deaza rG-(n-ibu):
5'-O-DMT-2'-TBDMS-7-deaza rG (n-ibu); 30 gm was taken in trichloroacetic acid in dichloromethane (3% solution, w/v; 2 eq) for selective DMT group removal from 5'-position. The mixture was shaken vigorously to get clear solution which get dark purple as the reaction proceeds. The solution was further stirred at room temperature for 10 minutes. The reaction mixture was then quenched with 10% aq sodium bicarbonate solution (precooled to 05 C) at zero degree to neutralized reaction to get pH between 7-8. The organic layer was washed with saturated brine once, followed by passing through anhydrous sodium sulfate and concentrated in vacuo. The residue was purified by column chromatography on silica gel (70-230 mesh; Merck grade) to get pure 5',3'-dihydroxy-2'-TBDMS-7deaza rG (n-ibu); yield 15 gm (85%); tlc rf. 0.2 (Solvent system (5:3:2): Chl: Hex:Acetone
Step (c): 5'-OBz-2'TBDMS-7-deaza rG-(n-ibu):
5'OH-2'-TBDMS-7-deaza rG-(n-ibu) was benzoylated at 5'-position selectively. 5'OH-2'-TBDMS-7-deaza rG-(n-ibu) (15 gm) was taken in dry pyridine (10 fold w/v; 150 ml), brought to −10 C to 0 under anhydrous conditions. Benzoyl chloride (1.1 eq, 4.10 ml) was added in one portion and the mixture stirred for 1.5 hours at the same temperature. The mixture was quenched with cold methanol, followed by removal of solvent in vacuo. The mixture was extracted in chloroform, washed with saturated aq bicarbonate, followed by washing once with saturated brine solution. The organic layer passed through anhydrous sodium sulfate, followed by removal of solvent under low vacuum. The residue was purified by crystallization in ethyl ether and ethyl acetate mixture to get 17 gm pure compound. HPLC purity 99%. rf. 0.5. (Solvent system (5:3:2): Chl: Hex:Acetone.
Step (d): 5'-OBz-3'-ODMT-2'-TBDMS-7-deaza rG (n-ibu)
The previous step compound; 5'-OBz-2'TBDMS-7-deaza rG-(n-ibu) (17 g) was dried with anhydrous pyridine twice, followed by taking in pyridine w/v; 1:10, 170 ml) and the solution was protected from moisture and brought to 0-5 C. DMT-chloride (25.2 g; 2.5 eq was added to the solution and the reaction mixture was stirred at room temperature for 24 hours, followed by quenching the reaction with chilled methanol. The solution was vacuum evaporated and worked up by extraction in ethyl acetate. The organic layer was washed with saturated sodium bicarbonate, followed by saturated brine solution, followed by passing the organic layer over anhydrous sodium sulfate. The solution was concentrated and residue was purified by column chromatography (Silica gel 70-230 mesh E. Merck), yield 9 gm pure, purity 98% by HPLC, and unreacted starting material (8 gm) was also recovered.
Step (e): 5'-; OH-3'-ODMT-2'-TBDM S-7-deaza rG (n-ibu):
The compound (6.0 g) obtained after preceding step was hydrolyzed selectively under control hydrolysis condition 2N NaOH in pyridine:MeOH 60 ml (80:20) for 30 minutes at 5-10 O c. followed by neutralization of reaction mixture with Dowex-pyridinium cation exchange resin, followed by filtration to remove Dowex resin to get crude product. The solvents were pumped and the residue was subsequently purified by column chromatography to get pure compound, yield 4.0 g. HPLC purity 98.5%. Mass and 1H NMR Step (f): 3'-ODMT-2'-TBDMS-7-deaza rG(n-ibu)-5'-cyano-ethyl phosphoramidite:
The compound obtained in the preceding step was thoroughly dried with anhydrous acetonitrile twice. The dried product was taken in dry distilled tetrahydrofuran. Diisopropyl ethyl amine (2.o eq) was subsequently added to reaction mixture while stirring under anhydrous conditions. To the reaction mixture was added diisopropyl 2-cyano ethyl chloro reagent (1.1 eq). The mixture was allowed to stir for 2.0 hours at room temperature. To crude reaction mixture was quenched with saturated sodium bicarbonate (chilled to zero C), followed by dilution with excess ethyl acetate. The organic layer was washed once with saturated brine solution. The organic layer was passed through anhydrous sodium sulfate. The solvent removed under vacuo, and the crude reaction mixture was purified by column chromatography (Silicagel 230-400 mesh, E. Merck grade); solvent system for purification; 45:45:10::Chloroform:ethylacetate:triethylamine) to get pure phosphoramidite. HPLC purity>98%. 31p nmr, 1H NMR, MASShnmr mass hplc.

Coupling efficiency test showed >98% coupling

Synthesis of 3'-O-DMT-2'-TBDMS-L-rU phosphoramidite

Step (a) 1-O Ac-2,3,5-tri-O-bz-L-ribose (using silylated uracil)
Step (b) 2',3',5'-tri-O-bz-L-uridine
Step (c) L-uridine
Step (d) 2',3'-isopropylidine-L-rU
Step (e) 5'-O-Bz-2',3'-isopropylidine-L-rU
Step (f) 5'-O-Bz-L-rU
Step (g) 5'-O-Bz-2'-TBDMS-L-rU
Step (h) TBDMS-3'-O-DMT-L-rU
Step (i) 5'-OH-2'-TBDMS-3'-O-DMT-L-rU
Step (j): 3'-O-DMT-2'-TBDMS-L-rU-5'-cyanoethyl phosphoramidite
Step (a):
1-O-Acetyl-tri-O-benzoyl-L-ribose (i) was synthesized similar to synthesis of 1-acetyl-tri-O-benzoyl-D-ribose which is well known in the art.
Step (b):
2',3',5'-Tri-O-benzoyl-L-uridine.
The silylated uracil was made by treatment with hexamethyl disilazane (Hexamethyldisilazane; HMDS; 20 eq). The silylated uracil was then fused with 1-O-Acetyl-tri-O-benzoyl-L-ribose in presence of tin (IV) chloride (SnCl4 as catalyst). The crude product was worked up by neutralization by solid sodium bicarbonate, followed by filtration with acetonitrile. The solid was discarded. The filtrate was pumped out under vacuum. This crude compound was purified by column chromatography on Silicagel column (E. Merck; 70-230 mesh). The pure fractions were pumped and the product was characterized by HPLC, UV and ESI/MS.
Step (c):
2,3,5-Tri-hydroxy-L-uridine (L-uridine):
The pure fully protected intermediate compound obtained in step (b) was the hydrolyzed with aq ammonia (29%) in pyridine (50:50; v/w) for 36 hours at 37 degree C. to yield crude product. The crude compound was washed with diethyl ether followed by washing with ethylacetate to remove solvent and benzoic acid. The compound is subsequently crystallized in ethanol. The pure dried product, yield 80%. The product was analyzed by HPLC, UV and ESI/MS.

Step (d):
2',3'-isopropylidine-L-rU
The dried compound was taken in take in distilled acetone (6 fold with respect to the weight of dried weight. Of the precursor), The mixture was stirred at room temperature after addition of catalytic amount of H2SO4, followed by addition of 2,2, di methoxy propane (4 eq. with respect L-rU), and further diluted with acetone & stirred for 1 hr. After this period sodium carbonate was added to the reaction mixture to bring pH to neutral. The mixture was filtered to remove solid, and the filtrate concentrated in vacuo. The crude (2',3' isopropylidene LrU) was purified on by column chromatography (Silica gel 70-230 mesh size), solvent system; CHCl3: MeoH (90:10), yielded pure compound, yield 85%. The product was characterized by UV, JPLC and ESI/MS. Tlc; CHCl$_3$:MeOH (9:1); rf. 0.45); purity>98%. of the dried compound.

Step (e) 5'-O-Bz-2',3'-isopropylidine-L-rU:
The product obtained after step (d) was taken in dry pyridine (10 fold) and benzoyl Chloride (1.1 eq) was added at 0-5 degree C., and the reaction mixture was stirred at 0-5 C. for 1.5 hours. The crude reaction mixture was worked up after quenching the reaction mixture with cold methanol, followed by removal of solvent. The crude reaction product was subsequently purified by column chromatography in solvent system (Chl: Hexane: acetone: 50:30:20). Pure dried product was characterized by UV, HPLC, ESI/MS. Yield; 80%.

Step (f) 5'-O-Bz-L-rU
The product obtained in the preceding step was taken in dioxane (5 fold with respect to the pure dried solid) and 2 N HCl (5 fold V; V) was added. The mixture was stirred overnight at room temperature. The mixture was quenched with solid sodium bicarbonate at 0 C till pH is neutral. The solvent was filtered and filtrate was pumped to dryness. The residue was crystallized in acetonitrile, pure product was dried and characterized by UV, HPLC, ESI/MS, yield 75%.

Step (g) 5'-O-Bz-2'-TBDMS-L-rU:
The preceeding product was taken in dry tetrahydrofuran (10 fold w/v) was added to silver nitrate/pyridine complex under stirring and under dry conditions, followed by addition of TBDMS-chloride (1.1 eq). The reaction mixture was stirred for 8 hours at room temperature.
The crude tlc indicated formation of two major spots. The reaction mixture was worked up by dilution with 100 fold excess ethylacetate. The organic layer was washed with saturated bicarbonate, followed by saturated brine solution. The organic layer was filtered through anhydrous sodium sulfate. The organic layer was then pumped to dryness and residue was purified by column chromatography. The pure band was characterized by UV, HPLC 1H NMR and ESI/MS. Yield of desired 2'-isomer, approx. 55%.

Step (h) 5'-O-Bz-2'-TBDMS-3'-O-DMT-L-rU
The preceding step well dried compound was taken in dry pyridine (10 fold; w/v) and to the solution was added DMT-Chloride (DMT Chloride; 2.5 equivalent). The reaction mixture was stirred for 24 hours to yield crude product. The reaction was quenched with chilled methanol (2 eq with respect to DMT-Chloride used in the reaction). The crude mixture was then concentrated in vacuum and the residue was purified by column chromatography (Silicagel; 230 400 mesh Merck grade). The pure fractions were pooled, concentrated and the product obtained was characterized by UV, HPLC, 1H NMR and ESI/MS. Yield; 85%.

Step (i) TBDMS-3'-O-DMT-L-rU
The pure product obtained in the preceding step was taken in pyridine/methanol (50:50 V; V) and treated with 2 N NaOH at 5 degree C. for 30 minutes, while pH was maintained at 12.5-13. After 30 minutes the reaction mixture was neutralized by addition of Dowex-pyridinium cation exchange resin to yield crude product to yield. The crude compound was purified by silica gel column chromatography Silica gel 230-400 mesh E. Merck grade). The pure fractions were pooled and solvent removed. The dried product was analyzed and characterized by HPLC, UV, 1-H NMR, and ESI/MS. Yield; 90%.

Step (j): 3'-O-DMT-2'-TBDMS-L-rU-5'-cyanoethyl phosphoramidite
The pure dry product was phosphitylated with n, n-diisopropyl-2-cyanoethyl chloro reagent (1.1 eq) in diisopropyl ethyl amine (2 eq) in THF for 1.5 hours reaction at room temperature. The crude reaction was worked in usual way, followed by column chromatography to get pure product. The product was analyzed & characterized by UV, HPLC, 1H NMR, ESI/MS and 31 P NMR.

Oligonucleotide 1 Synthesis: Oligonucleotide 1 was synthesized using 5'→3' directed REV-RNA phosphoramidite chemistry in 1 mmol scale. The synthesis were performed on Expedite 8900 synthesizer using standard RNA 1 mmol cycle and coupling time of the monomers with solid support 4.0 minute.

Amidites used (see table for activator used):
(1) $N^6$-Benzoyl-2'-O-TBDMS-3'-O-DMT-adenosine-5'-cyanoethyl-N,N-diisopropyl-phosphoramidite (A-N-Bz). LOT #AL300-2
(2) $N^4$-Acetyl-2'-O-TBDMS-3'-O-DMT-cytidine-5'-cyanoethyl-N,N-diisopropyl-phosphoramidite (C—N—Ac). LOT #NS143-19
(3) $N^2$-Isobutryl-2'-O-TBDMS-3'-O-DMT-guanosine-5'-cyanoethyl-N,N-diisopropyl-phosphoramidite (G-N-Ibu). LOT #NS42-19
(4) 2'-O-TBDMS-3'-O-DMT-Uridine-5'-cyanoethyl-N,N-diisopropyl-phosphoramidite. LOT #NS147-19

Products Used:
(5) 2'-O-TBDMS-3'-O-DMT-Uridine-5'-Succinyl CPG 1000A. Trityl Value; 28.4 um/gm LOT #NS24-19
(6) DDTT ((Dimethylamino-methylidene)amino)-3H-1,2,4-dithiazoline-3-thione), lot #AG015
(7) Ethyl thio tetrazole (ETT); (0.25M), lot #DP 152-4

General Procedure for 1.0 umol Phosphodiester and Phosphorothioate:
The aforementioned amidites (solid) were each individually taken in 20 mL expedite bottle and dissolved in a quantity of dry acetonitrile to make the solution 0.075M. The bottles were flushed with Argon and shaken after sealing the screw cap promptly to dissolve solid completely. Due to the limited solubility of G-N-Ibu in dry acetonitrile, G-N-Ibu was dissolved in 50% anhydrous dichloromethane followed by addition of dry acetonitrile to make a 50:50 dichloromethane: acetonitrile solution. The monomer solution bottles were then screwed in to the synthesizer as follows: Amidite No. 1 on port #6; Amidite No. 2 on port #7; Amidite No. 3 on port #8; and Amidite No. 4 on port #9. In addition, 1.0 um expedite column with Product No. 5 was prepared and attached to the synthesizer.

After completion of the synthesis per summary key features as listed in the table, the controlled pore glass (CPG) solid support was washed with 3.0 ml diethyl ether and transferred to a 2 ml microfuge tube. Oligonucleotide 1 were cleaved from the CPG and deprotected by incubation for 30 min at 65° C. in 1 ml of 40% methylamine solution in water. The supernatant was removed and the CPG was washed with 1 ml of water; supernatants were pooled and dried. The t-butyl-dimethylsilyl protecting group was removed from the RNA residue by treatment with 500 ul of fresh 12.0% solution of tetraethyl ammonium fluoride in DMSO, at 45 C in ultrasonic bath for 1 hour. Oligonucleotide 1 was precipitated with 1.5 ml of n-butanol; the sample was cooled at −20° C. for 1 hour then centrifuged at 10,000 g for 10 minutes. The supernatant was decanted, the pellet was washed with n-butanol one more time and finally washed with 500 ul ethanol and then again centrifuge at 10000 rpm for 5 minutes, the supernatant was decanted. The pellet was dissolved in 1000 ul M.Q water and check the OD's (Crude desalt). Oligonucleotide 1 was then purified by Ion-Exchange HPLC using a linear gradient of in buffer A=(10.0%, 0.5M TRIS and 10.0% ACN) pH 7.5 and buffer B=1.0 M Lithium Chloride in buffer A.

The entire sample was loaded on a Source 15Q column (1.0 cm×25 cm) and eluted with a linear 5% to 75% acetonitrile gradient over 40 minutes. Samples were monitored at 260 nm and peaks corresponding to the desired oligonucleotide species were collected, and precipitated by adding 5.0 volume of (2% $LiClO_4$, in acetone), followed by centrifuging at 10,000 g for 10 minutes. The supernatant was decanted, and the pellet was washed with ethanol.

Oligonucleotide 2:

Oligonucleotide 2 was synthesized using 5'→3' directed REV-RNA phosphoramidite chemistry in 1 μmole scale. The synthesis was performed on Expedite 8900 synthesizer using standard RNA 1 μmole cycle and coupling time of the monomers with solid support 4.0 minute.

Amidites used (see table for activator used):

(1.) $N^6$-Benzoyl-2'-O-TBDMS-3'-O-DMT-adenosine-5'-cyanoethyl-N,N-diisopropyl-phosphoramidite (rA), LOT #AL300-2

(2.) $N^4$-Acetyl-2'-O-TBDMS-3'-O-DMT-cytidine-5'-cyanoethyl-N,N-diisopropyl-phosphoramidite (rC), LOT #NS143-19

(3.) $N^2$-Isobutryl-2'-O-TBDMS-3'-O-DMT-guanosine-5'-cyanoethyl-N,N-diisopropyl-phosphoramidite(rG), LOT #NS42-19

(4.) 2'-O-TBDMS-3'-O-DMT-Uridine-5'-cyanoethyl-N,N-diisopropyl-phosphoramidite(rU), LOT #NS147-19

(5.) $N^6$-Benzoyl-2'-O-Me-3'-O-DMT-adenosine-5'-cyanoethyl-N,N-diisopropyl-phosphoramidite, LOT #133-8SS (6.) 2'-O-TBDMS-3'-O-DMT-Uridine-5'-Succinyl CPG 1000A (rU), TV-8.4 um/gm, LOT #NS24-19 addition of dry acetonitrile to make a 50:50 dichloromethane: acetonitrile solution. The monomer solution bottles are then screwed in to the synthesizer as follows: Amidite No. 1 on port #6; Amidite No. 2 on port #7; Amidite No. 3, on port #8 and Amidite No. 4 on port ft 9; and Amidite No. 5 on port #5. In addition, 1.0 um expedite column with Product No. 6 was prepared and attached to the synthesizer. For oligonucleotide 2, the sulfurizing reagent Dimethylamino-methylidene) amino)-3H-1,2,4-dithiazoline-3-thione(DDTT) was dissolved in a pyridine:acetonitrile (90:10) to make 0.1M solution. This reagent was put on the auxillary port of the synthesizer.

Following synthesis, the controlled pore glass (CPG) solid support was washed with 3.0 mL diethyl ether and transferred to a 2 mL microfuge tube. Oligonucleotides were cleaved from the CPG and deprotected by incubation for 30 min at 65° C. in 1 ml of 40% methylamine solution in water. The supernatant was removed and the CPG was washed with 1 ml of water; supernatants were pooled and dried. The t-butyl-dimethylsilyl protecting group was removed from the RNA residue by treatment with 500 uL of fresh 12.0% solution of tetraethyl ammonium fluoride in DMSO, at 45 C in ultrasonic bath for 1 hours. The oligonucleotide was precipitated by 1.5 mL of n-butanol; the sample was cooled at −20° C. for 1 hour then centrifuged at 10,000 g for 10 minutes. The supernatant was decanted, the pellet was washed with n-butanol one more time and washed with 500 ul ethanol and centrifuged at 10000 rpm for 5 minutes. Following centrifugation, the supernatant was decanted. The pellet was dissolve in 1000 ul M.Q water and the OD's was checked (Crude desalt).

The oligonucleotides were then purified by Ion-Exchange HPLC using a linear gradient of A=(10.0%, 0.5M TRIS and 10.0% ACN) pH 7.5. Buffer B=1.0M Lithium Chloride in buffer A. The entire sample was loaded on a Source 15Q column (1.0 cm×25 cm) and eluted with a linear 15% to 95% gradient over 40 minutes. Samples were monitored at 260 nm and peaks corresponding to the desired oligonucleotide species were collected, and precipitated by adding 5.0 volume of (2% $LiClO_4$, in acetone), followed by centrifuging at 10,000 g for 10 minutes. The supernatant was decanted, and the pellet was washed with ethanol.

| Oligonucleotide sequences synthesized by Reverse Synthesis method. | |
|---|---|
| Oligonucleotide 1 Phosphodiester Oligonucleotide | rCrArCrArGrCrArUrArCrArUrCrUrCrGrArCrArU (SEQ ID NO: 4) rA is $N^6$-Benzoyl-2'-O-TBDMS-3'-O-DMT-adenosine-OP rC is $N^4$-Acetyl-2'-O-TBDMS-3'-O-DMT-cytidine-OP rG is $N^2$-Isobutryl-2'-O-TBDMS-3'-O-DMT-guanosine-OP rU is 2'-O-TBDMS-3'-O-DMT-Uridine-OP |
| Oligonucleotide 2 Phosphorothioate oligonucleotide sequence with 2'-O-methyl bases on terminal | mA(ps)-rArCrArGrCrArUrArCrArUrCrUrCrGrArCrCmArU (SEQ ID NO: 7) Phosphorothioate rA is $N^6$-Benzoyl-2'-O-TBDMS-3'-O-DMT-adenosine-OP; rC is $N^4$-Acetyl-2'-O-TBDMS-3'-O-DMT-cytidine-OP; rG is is $N^2$-Isobutryl-2'-O-TBDMS-3'-O-DMT-guanosine-OP rU is 2'-O-TBDMS-3'-O-DMT-Uridine-OP; mA is $N^6$-Benzoyl-2'-O-Me-3'-O-DMT-adenosine-OP; DDTT |

(7.) Ethyl thio tetrazole (ETT); (0.25M), lot #DP 152-4

The aforementioned amidites (solid) were each individually taken in 20 mL expedite bottle and dissolved in a quantity of dry acetonitrile to make the solution 0.075M. Due to the limited solubility of G-N-Ibu in dry acetonitrile, G-N-Ibu was dissolved in 50% anhydrous dichloromethane followed by Large Scale Oligonucleotide Synthesis:

12 umol scale phosphorothioate oligonucleotide synthesis bearing terminal 2'-O-methyl bases (seq #2) was carried out. The following data are included;

(a) Trityl Histogram; (b) CE (capillary Gel electrophoresis) of crude oligo synthesized; (c) CE & HPLC of purified oligonucleotide (d) ESI-MS analysis for molecular weight determination, General Procedure 12.0 umol phosphorothioate oligonucleotide:

The amidites and products were prepared and the synthesis was performed on Expedite 8900 synthesizer as described above for Oligonucleotides 1 and 2. The Scale, Monomers Coupling Time, Activator, and DDTT/Iodine reagent were as described in the table below.

Table of Oligo Synthesis Conditions for 4 Min and 6 Min Coupling Time.

| Monomers in dry ACN (0.075M) | Scale | Monomers Coupling Time | Activator | DDTT/ Iodine reagent/ Time | OD'S Crude (desalt) | CE Analysis Crude (desalted) |
|---|---|---|---|---|---|---|
| Rev-RNA amidites (21 MER) | 1.0 umol | 4.0 min | 0.25M (ETT) | Iodine Oxidizer, 0.02M | 82.0 OD'S (21-mer) | 95.29% |
| Rev-RNA with 2'-OMe (21 MER) | 1.0 umol | 4.0 min | 0.25M (ETT) | Iodine Oxidizer, 0.02M | 90.0 OD'S (21-mer) | 89.03% |
| Rev-RNA with 2'-OMe-Phosphorothioate | 1.0 umol | 4.0 min | 0.25M (ETT) | DDTT, (2.0 min) 0.1M in Py:ACN (90:10) | 93.0 OD'S (21-mer) | 89.09% |
| Rev-RNA amidite (21 MER) | 1.0 umol | 6.0 min | 0.25M (ETT) | Iodine Oxidizer, 0.02M | 79.0 OD'S | 93.69% |
| Rev-RNA amidite (76 Mer) | 1.0 umol | 6.0 min | 0.25M (ETT) | Iodine Oxidizer, 0.02M | 190.0 OD'S | GEL Traces |
| Rev-RNA-2'-OMe-phosphorothioate | 12.0 umol | 6.0 min | 0.25M (ETT) | DDTT (2.0 min; 0.1M in Pyr:ACN | 1427 OD's | 92.63% |

After completion of the synthesis per summary key features as listed in the table, the controlled pore glass (CPG) solid support was washed with 15 mL diethyl ether and transferred to a 8×2 ml microfuge tube. Oligonucleotides were cleaved from the CPG and deprotected by incubation for 30 min at 65° C. in 1 mL of 40% methylamine solution in water. The supernatant was removed and the CPG was washed with 1 ml of water; supernatants were pooled and dried. The t-butyl-dimethylsilyl protecting group was removed from the RNA residue by treatment with 500 ul of fresh 12.0% solution of tetraethyl ammonium fluoride in DMSO, at 45 C in ultrasonic bath for 1 hour. The oligonucleotide was precipitated with 1.5 ml of n-butanol; the sample was cooled at −20° C. for 1 hour then centrifuged at 10,000 g for 10 minutes. The supernatant was decanted, the pellet was washed with n-butanol one more time and finally washed with 500 ul ethanol and then again centrifuge at 10000 rpm for 5 minutes, the supernatant was decanted. The pellet was dissolve in 1000 ul M.Q water and check the OD's (Crude desalt).

Crude RNA purity is obtained above is in the range of 90-92% by HPLC or CE analysis. Subsequent purification is done by either ion-exchange or reverse phase HPLC. The purification results in purified RNA ranging in 92% to 98% purity.

Details of Purification:

The oligonucleotide was then purified by Ion-Exchange HPLC using a linear gradient of in buffer A=(10.0%, 0.5M TRIS and 10.0% ACN) pH 7.5. Buffer B=1.0M Lithium Chloride in buffer A.

The entire sample was loaded on a Source15Q column (1.0 cm×25 cm) and eluted with a linear 60% to 100% buffer B gradient over 40 minutes. Samples were monitored at 260 nm and peaks corresponding to the desired oligonucleotide peak was collected, and precipitated by adding 5.0 volume of (2% LiClO$_4$, in acetone), followed by centrifuging at 10,000 g for 10 minutes. The supernatant was decanted, the pellet was washed with ethanol, yield; 343.0 OD (260 nm); purity (analyzed by CE); 98.01%.

Abbreviations:

mA; (2'-Omethyl-r-adenosine);

rC; (r-cytidine);

rG (r-guanosine);

rU (r-uridine)

Sequence Listings:

REV-RNA-Me-SEQ (With Methoxy)
(SEQ ID NO: 8)
SEQ: rUmrArCrCrArGrCrUrCrUrArCrArUrArCrGrArCrAmrA REV-RNA-Me-THIO-4Min Coupling Time
(SEQ ID NO: 9)
SEQ: rU-p(s)mrA-p(s)rC-p(s)rC-p(s)rA-p(s)rG-p(s)

rC-p(s)rU-p(s)rC-p(s)rU-p(s)rA-p(s)rC-p(s)rA-p(s)

rU-p(s)rA-p(s)rC-p(s)rG-p(s)rA-p(s)rC-p(s)rA-p(s)

mrA-p(s)

REV-RNA-4Min Coupling Time (Without Methoxy)
(SEQ ID NO: 10)
SEQ: rUrArCrCrArGrCrUrCrUrArCrArUrArCrGrArCrArC 76 MER
(SEQ ID NO: 11)
SEQ: rGrCrC rCrGrG rArUrA rGrCrU rCrArG rUrCrG rGrUrA rGrArG rCrArUrCrArG rArCrU rUrUrU rUrArU rCrUrG rArGrG rGrUrC rCrArG rGrGrUrUrCrA rArGrU rCrCrC rUrGrU rUrCrG rGrGrC rGrCrC rA While this invention has been particularly shown and described with references to example embodiments thereof, it will be understood by those skilled in the art that various changes in form and details may be made therein without departing from the scope of the invention encompassed by the appended claims.

What is claimed is:

1. A compound of Formula Ia or Ib:

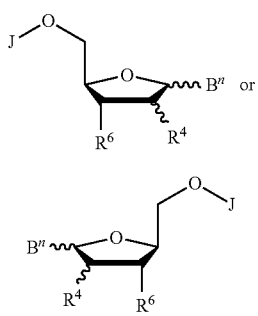

or a salt thereof, wherein:
J is H,

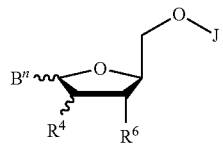

wherein § indicates where J is attached to the O atom;
Q is a support comprised of: a) a linking group and a spacer that can be cleaved to form a hydroxy group; or b) an aliphatic chain, aromatic group, substituted or unsubstituted aromatic, a substituted or unsubstituted phenoxy, or levulinyl;

$R^1$ is a substituted or unsubstituted $(C_1-C_{12})$alkyl group, a substituted or unsubstituted $(C_3-C_{20})$cycloalkyl group, or a substituted or unsubstituted $(C_3-C_{20})$cycloalkyl$(C_1-C_{12})$alkyl group, wherein the alkyl or cycloalkyl groups optionally include intervening heteroatoms independently selected from NH, $NR^7$, O and S;

$R^2$ is a substituted or unsubstituted $(C_1-C_{12})$alkyl group, a substituted or unsubstituted $(C_3-C_{20})$cycloalkyl group, or a substituted or unsubstituted $(C_3-C_{20})$cycloalkyl$(C_1-C_{12})$alkyl group, wherein the alkyl or cycloalkyl groups optionally include intervening heteroatoms independently selected from NH, $NR^7$, O and S;

or $R^1$ and $R^2$ taken together with the nitrogen atom to which they are bound form a 4-7 membered non-aromatic heterocyclyl, wherein the heterocyclyl formed may optionally include intervening heteroatoms independently selected from NH, $NR^7$, O and S;

$R^3$ is a phosphate protecting group;

$R^4$ is a -halo, —$R^5$, —$NR^7R^8$, —$OR^9$, —$SR^{10}$, or 2'-blocking group; or when Structural Formula Ia or Ib is:

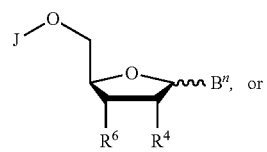

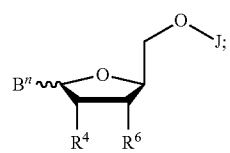

wherein $R^4$ is further selected from O—Si$(R^{11})_3$ or O—CH$_2$—Si$(R^{11})_3$; or when Structural Formula Ia or Ib is:

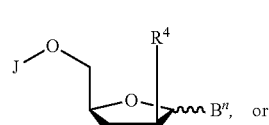

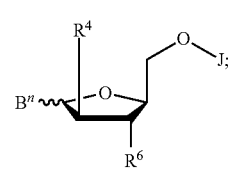

$R^4$ is further selected from —OC(=O)$R^{12}$;

each $R^5$ is independently a substituted or unsubstituted $(C_1-C_{12})$alkyl group, a substituted or unsubstituted $(C_2-C_{12})$alkenyl group, a substituted or unsubstituted $(C_2-$ $C_{12}$)alkynyl group, or a substituted or unsubstituted phenyl, wherein the alkyl, alkenyl, alkynyl and the phenyl groups optionally includes intervening heteroatoms independently selected from NH, $NR^5$, O and S; and may optionally terminate with —$NR^7R^8$, ($C_1$-$C_4$)alkylamino, di($C_1$-$C_4$)alkylamino, —$OR^9$, ($C_1$-$C_6$)alkoxy, benzyl or substituted benzyl, —$SR^{10}$; or —S—($C_1$-$C_6$) alkyl group;

$R^6$ is —H or —O—Z;

each $R^7$ is independently a fluorenylmethyloxycarbonyl; —C(=O)—($CH_2$)$_{1-16}$$NR^8$C(=O)$CF_3$; —C(=O)—($CH_2$)$_{1-16}$$NR^8$C(=O)-phthalimide; —C(=O)—($CH_2$)$_{1-16}$-phthalimide; $NR^8$C(=O)-phthalimide; a substituted or unsubstituted ($C_1$-$C_{12}$)alkyl group, a substituted or unsubstituted ($C_2$-$C_{12}$)alkenyl group, or a substituted or unsubstituted ($C_2$-$C_{12}$)alkynyl group;

each $R^8$ is H or a substituted or unsubstituted ($C_1$-$C_{12}$)alkyl group, a substituted or unsubstituted ($C_2$-$C_{12}$)alkenyl group, or a substituted or unsubstituted ($C_2$-$C_{12}$)alkynyl group;

each $R^9$ is independently —C(=O)—($CH_2$)$_{1-16}$$CH_3$; a substituted or unsubstituted ($C_2$-$C_{12}$)alkenyl group, or a substituted or unsubstituted ($C_2$-$C_{12}$)alkynyl group;

each $R^{10}$ is independently —S($C_1$-$C_6$)alkyl, —C(=O)—($CH_2$)$_{1-16}$$CH_3$; a substituted or unsubstituted ($C_2$-$C_{12}$) alkenyl group, or a substituted or unsubstituted ($C_2$-$C_{12}$) alkynyl group;

each $R^{11}$ is independently a substituted or unsubstituted ($C_1$-$C_{12}$)alkyl group, a substituted or unsubstituted ($C_2$-$C_{12}$)alkenyl group, or a substituted or unsubstituted ($C_2$-$C_{12}$)alkynyl group;

each $R^{12}$ is independently a substituted or unsubstituted ($C_1$-$C_{12}$)alkyl group, a substituted or unsubstituted ($C_2$-$C_{12}$)alkenyl group, or a substituted or unsubstituted ($C_2$-$C_{12}$)alkynyl group, or a substituted or unsubstituted aryl group;

Z is an unsubstituted or substituted aryl group, an unsubstituted or substituted triarylmethyl group, an unsubstituted or substituted trityl group, an unsubstituted or substituted tetrahydropyranyl group, or an unsubstituted or substituted 9-phenylxanthyl;

$B^n$ is hydrogen or an optionally substituted nucleobase optionally functionalized at each exocyclic amine with an amine protecting group, wherein the nucleobase is selected from:

N6,N6-dimethyl adenine, N-1 methyladenine, 7-deazaadenine, 7-deaza-8-azaadenine, 3-deazaadenine, ethenoadenine, isoguanine, N1-methylguanine, 7-iodo-7-deazaguanine, 7-deaza-7-iodoadenine, 7-deaza-7-iodo-6-oxopurine, 5-iodo-5-methyl-7-deazaguanine, 7-deazaguanine substituted with —C≡C($CH_2$)$_{1-8}$-pthlamide, 7-deaza-8-azaguanine, 8-methylguanine, 8-bromoguanine, 8-aminoguanine, hypoxanthine, 6-methoxypurine, 7-deaza-6-oxopurine, 6-oxopurine, 2-aminopurine, 2,6-diaminopurine, 8-bromopurine, 8-aminopurine, 8-alkylaminopurine, 8-alkylaminopurine, thymine, N-3 methyl thymine, 5-acetoxymethylcytosine, 5-azacytosine, isocytosine, N-4($C_1$-$C_6$)alkylcytosine, N-3($C_1$-$C_6$)alkylcytidine, 5-propynylcytosine, 5-iodo-cytosine, 5-($C_1$-$C_6$)alkylcytosine, 5-aryl($C_1$-$C_6$) alkylcytosine, 5-trifluoromethylcytosine, 5-methylcytosine, ethenocytosine, cytosine and uracil substituted with —CH=CH—C(=O)NH($C_1$-$C_6$)alkyl, cytosine and uracil substituted with —C≡C—$CH_2$-phthalimide, NH($C_1$-$C_6$)alkyl, 4-thiouracil, 2-thiouracil, $N^3$-thiobenzoylethyluracil, 5-propynyluracil, 5-acetoxymethyluracil, 5-fluorouracil, 5-chlorouracil, 5-bromouracil, 5-iodouracil, thiouracil, N-3-($C_1$-$C_6$)alkyluracil, 5-(3-aminoallyl)-uracil, 5-($C_1$-$C_6$)alkyluracil, 5-aryl($C_1$-$C_6$) alkyluracil, 5-trifluoromethyluracil, 4-triazolyl-5-methyluracil, 2-pyridone, 2-oxo-5-methylpyrimidine, 2-oxo-4-methylthio-5-methylpyrimidine, 2-thiocarbonyl-4-oxo-5-methylpyrimidine, and 4-oxo-5-methylpyrimidine;

wherein any substitutable nitrogen atom within the nucleobase or on the exocyclic amine is optionally substituted with fluorenylmethyloxycarbonyl; —C(=O)OPh; —C(=O)($C_1$-$C_{16}$)alkyl; —C(=O) $CH_2CH_2CH$=$CH_2$—; —C(=O)($C_1$-$C_{16}$)alkylene-C(=O)OH; —C(=O)($C_1$-$C_{16}$)alkylene-C(=O)O($C_1$-$C_6$)alkyl; =$CR^8N$(($C_1$-$C_6$)alkyl)$_2$; —C(=O)—$NR^8$—($CH_2$)$_{1-16}$$NR^8$C(=O)$CF_3$; —C(=O)—($CH_2$)$_{1-16}$$NR^8$C(=O)$CF_3$; —C(=O)—$NR^8$ ($CH_2$)$_{1-16}$$NR^8$C(=O)-phthalimide; —C(=O)—($CH_2$)$_{1-16}$-phthalimide; and

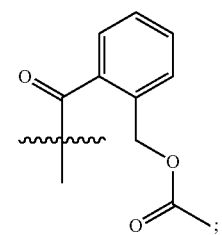

wherein any substitutable oxygen atom within the nucleobase is optionally substituted with —C(=O)N($C_1$-$C_6$alkyl)$_2$ or —C(=O)N(phenyl)$_2$.

2. A compound of Formula Ia or Ib:

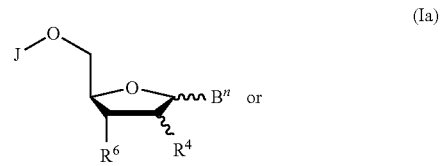

(Ia)

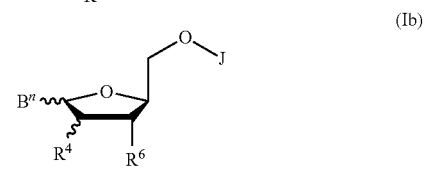

(Ib)

or a salt thereof, wherein:
J is H or

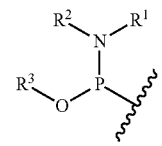

$R^1$ is a substituted or unsubstituted ($C_1$-$C_{12}$)alkyl group, a substituted or unsubstituted ($C_3$-$C_{20}$)cycloalkyl group, or a substituted or unsubstituted ($C_3$-$C_{20}$)cycloalkyl($C_1$-$C_{12}$)alkyl group, wherein the alkyl or cycloalkyl groups optionally include intervening heteroatoms independently selected from NH, $NR^7$, O and S;

$R^2$ is a substituted or unsubstituted $(C_1-C_{12})$alkyl group, a substituted or unsubstituted $(C_3-C_{20})$cycloalkyl group, or a substituted or unsubstituted $(C_3-C_{20})$cycloalkyl$(C_1-C_{12})$alkyl group, wherein the alkyl or cycloalkyl groups optionally include intervening heteroatoms independently selected from NH, $NR^7$, O and S;

or $R^1$ and $R^2$ taken together with the nitrogen atom to which they are bound form a 4-7 membered non-aromatic heterocyclyl, wherein the heterocyclyl formed may optionally include intervening heteroatoms independently selected from NH, $NR^7$, O and S;

$R^3$ is a phosphate protecting group;

$R^4$ is a -halo, $-R^5$, $-NR^7R^8$, $-OR^9$, $-SR^{10}$, or 2'-blocking group; or when Structural Formula Ia or Ib is:

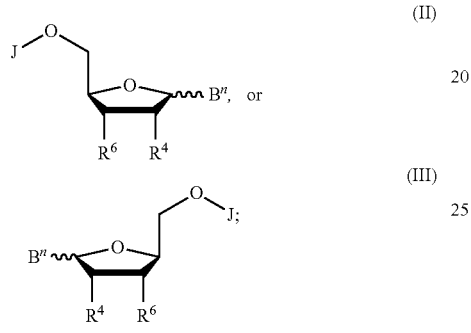

wherein $R^4$ is further selected from $O-Si(R^{11})_3$ or $O-CH_2-Si(R^{11})_3$; or when Structural Formula Ia or Ib is:

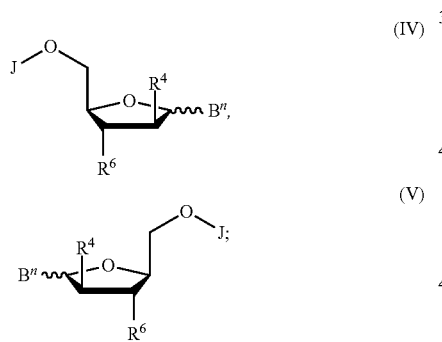

$R^4$ is further selected from $-OC(=O)R^{12}$;

each $R^5$ is independently a substituted or unsubstituted $(C_1-C_{12})$alkyl group, a substituted or unsubstituted $(C_2-C_{12})$alkenyl group, a substituted or unsubstituted $(C_2-C_{12})$alkynyl group, or a substituted or unsubstituted phenyl, wherein the alkyl, alkenyl, alkynyl and the phenyl groups optionally includes intervening heteroatoms independently selected from NH, $NR^5$, O and S; and may optionally terminate with $-NR^7R^8$, $(C_1-C_4)$alkylamino, di$(C_1-C_4)$alkylamino, $-OR^9$, $(C_1-C_6)$alkoxy, benzyl or substituted benzyl, $-SR^{10}$; or $-S-(C_1-C_6)$alkyl group;

$R^6$ is $-H$ or $-O-Z$;

each $R^7$ is independently a fluorenylmethyloxycarbonyl; $-C(=O)-(CH_2)_{1-16}NR^8C(=O)CF_3$; $-C(=O)-(CH_2)_{1-16}NR^8C(=O)$-phthalimide; $-C(=O)-(CH_2)_{1-16}$-phthalimide; $NR^8C(=O)$-phthalimide; a substituted or unsubstituted $(C_1-C_{12})$alkyl group, a substituted or unsubstituted $(C_2-C_{12})$alkenyl group, or a substituted or unsubstituted $(C_2-C_{12})$alkynyl group;

each $R^8$ is H or a substituted or unsubstituted $(C_1-C_{12})$alkyl group, a substituted or unsubstituted $(C_2-C_{12})$alkenyl group, or a substituted or unsubstituted $(C_2-C_{12})$alkynyl group;

each $R^9$ is independently $-C(=O)-(CH_2)_{1-16}CH_3$; a substituted or unsubstituted $(C_2-C_{12})$alkenyl group, or a substituted or unsubstituted $(C_2-C_{12})$alkynyl group;

each $R^{10}$ is independently $-S(C_1-C_6)$alkyl, $-C(=O)-(CH_2)_{1-16}CH_3$; a substituted or unsubstituted $(C_2-C_{12})$alkenyl group, or a substituted or unsubstituted $(C_2-C_{12})$alkynyl group;

each $R^{11}$ is independently a substituted or unsubstituted $(C_1-C_{12})$alkyl group, a substituted or unsubstituted $(C_2-C_{12})$alkenyl group, or a substituted or unsubstituted $(C_2-C_{12})$alkynyl group; provided that if $R^4$ is $-O-Si(R^{11})_3$, and two $R^{11}$ groups are both methyl, the other is not t-butyl or if $R^4$ is $-O-CH_2-Si(R^{11})_3$, then the three $R^{11}$ groups cannot all be isopropyl;

each $R^{12}$ is independently a substituted or unsubstituted $(C_1-C_{12})$alkyl group, a substituted or unsubstituted $(C_2-C_{12})$alkenyl group, a substituted or unsubstituted $(C_2-C_{12})$alkynyl group, or a substituted or unsubstituted aryl group;

Z is an unsubstituted or substituted aryl group, an unsubstituted or substituted triarylmethyl group, an unsubstituted or substituted trityl group, an unsubstituted or substituted tetrahydropyranyl group, or an unsubstituted or substituted 9-phenylxanthyl;

$B^n$ is hydrogen or an optionally substituted nucleobase optionally functionalized at each exocyclic amine with an amine protecting group, provided that the compound is not represented by one of the following structural formulas:

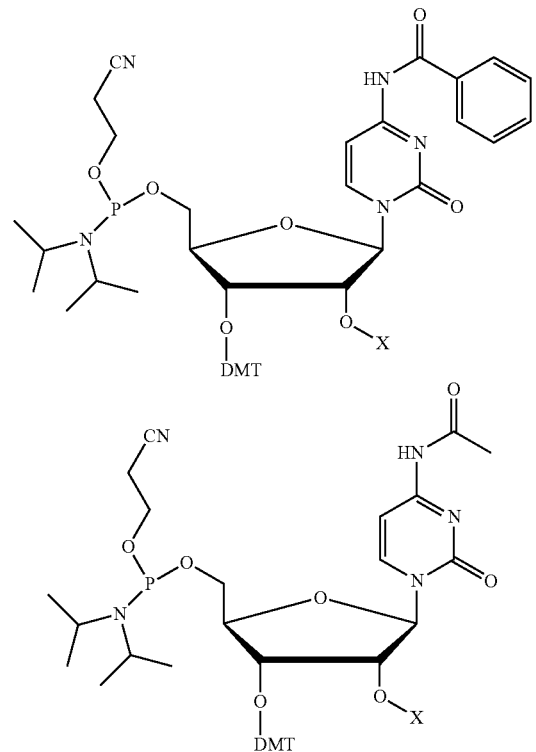

-continued

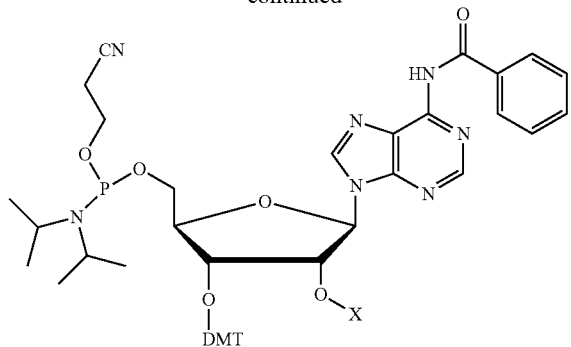

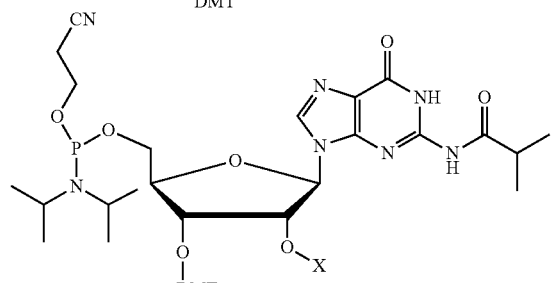

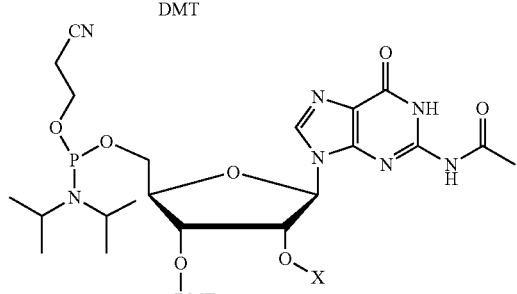

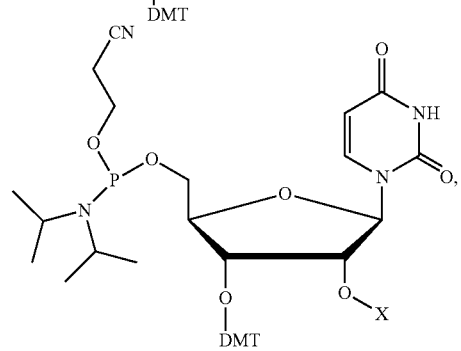

wherein X is tert-butyldimethylsilyl or triisopropyl-siloloxymethyl.

3. The compound of claim 1, wherein J is

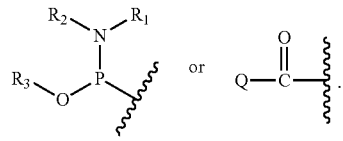

4. The compound of claim 1, wherein Z is di-p-anisylphenyl methyl, p-fluorophenyl-1-naphthylphenyl methyl, p-anisyl-1-naphthylphenyl methyl, di-o-anisyl-1-naphthyl methyl, di-o-anisylphenyl methyl, p-tolyldiphenylmethyl, di-p-anisylphenylmethyl, di-o-anisyl-1-naphthylmethyl, di-p-anisylphenyl methyl, di-o-anisyl phenyl methyl, di-p-anisylphenyl methyl, or p-tolyldiphenylmethyl.

5. The compound of claim 1, wherein Z is represented by the following structural formula:

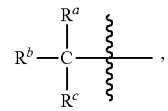

wherein ⌇ indicates attachment to the 3' oxygen atom and $R^a$, $R^b$, and $R^c$ are independently selected from the following structural formulas

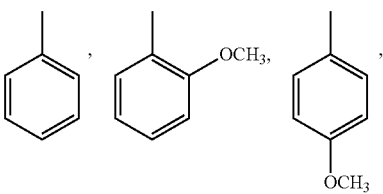

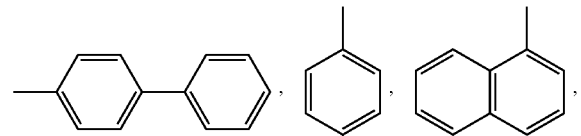

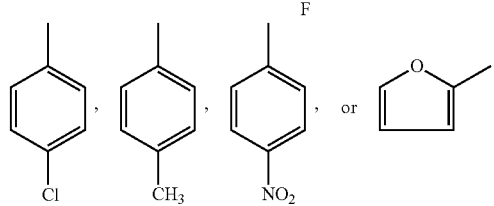

6. The compound of claim 1, wherein Z is 4-methoxytrityl, 4,4'-dimethoxytrityl, or 4,4',4''-trimethoxytrityl.

7. The compound of claim 1, wherein the substitutable nitrogen atom within the nucleobase or on the exocyclic amine is optionally substituted with =CHN(CH$_3$)$_2$; C(=O)CH(CH$_3$)$_2$; —C(=O)CH$_3$, =C(CH$_3$)N(CH$_3$)$_2$; —C(=O)OPh; —C(=O)CH$_2$CH$_2$CH=CH$_2$; —C(=O)CH$_2$CH$_2$—C(=O)O(C$_1$-C$_6$)alkyl; —C(=O)—NR$^8$—(CH$_2$)$_{1-16}$NR$^8$C(=O)CF$_3$; —C(=O)—(CH$_2$)$_{1-16}$NR$^8$C(=O)CF$_3$; —C(=O)—NR$^8$(CH$_2$)$_{1-16}$NR$^8$C(=O)-phthalimide; —C(=O)—(CH$_2$)$_{1-16}$-phthalimide and

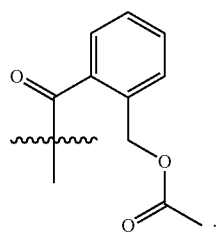 [SMILES: *C(=O)c1ccccc1COC(C)=O ; "."]

8. The compound of claim 1, wherein R$^3$ is —CH$_2$CH$_2$CN, —CH$_2$CH$_2$—Si(CH$_3$)$_2$C$_6$H$_5$, —CH$_2$CH$_2$—S(O)$_2$—CH$_2$CH$_3$, —CH$_2$CH$_2$—C$_6$H$_4$—NO$_2$, —CH$_2$CH$_2$—NH—C(O)—C$_6$H$_5$, or —CH$_2$CH$_2$—O—C$_6$H$_4$—C(O)CH$_3$, and R$^4$ is —O—Si(R$^{11}$)$_3$ or —O—CH$_2$—Si(R$^{11}$)$_3$.

9. The compound of claim 8, wherein R⁴ is —O—Si(CH₃)₂(C(CH₃)₃) or —O—CH₂—Si(CH(CH₃)₂)₃.

10. The compound of claim 1, wherein the compound is represented by one of the following structural formulas:

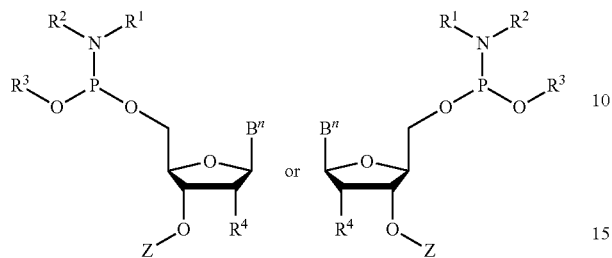

or a salt thereof.

11. The compound of claim 10, wherein the compound is represented by one of the following structural formulas:

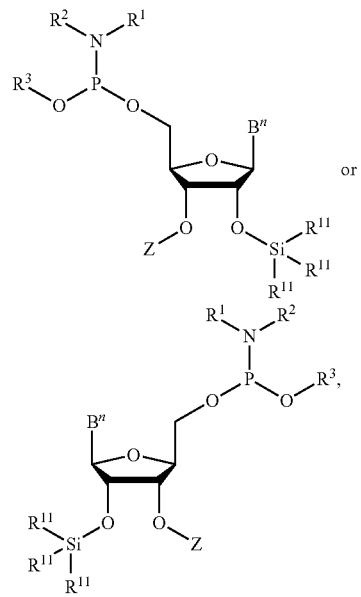

or a salt thereof.

12. The compound of claim 11, wherein R³ is —CH₂CH₂CN.

13. The compound of claim 12, wherein the compound is represented by one of the following structural formulas:

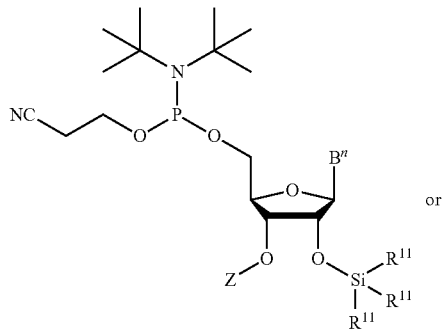

-continued

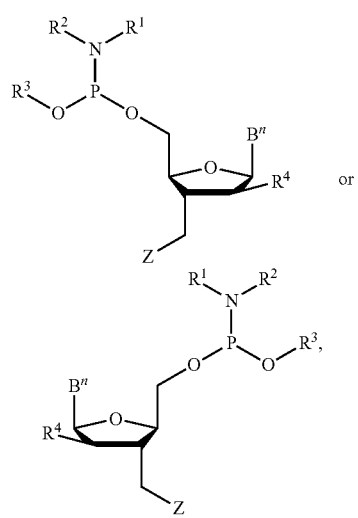

or a salt thereof.

14. The compound of claim 1, wherein the compound is represented by one of the following structural formulas:

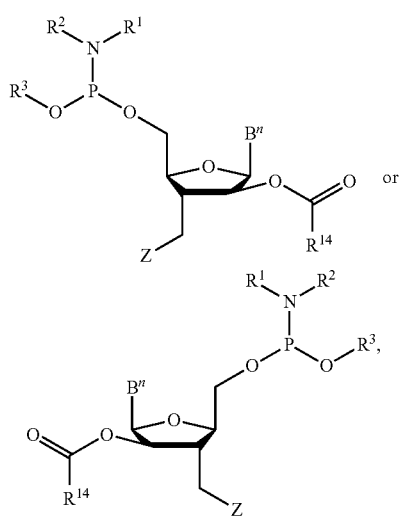

or a salt thereof.

15. The compound of claim 14, wherein the compound is represented by one of the following structural formula:

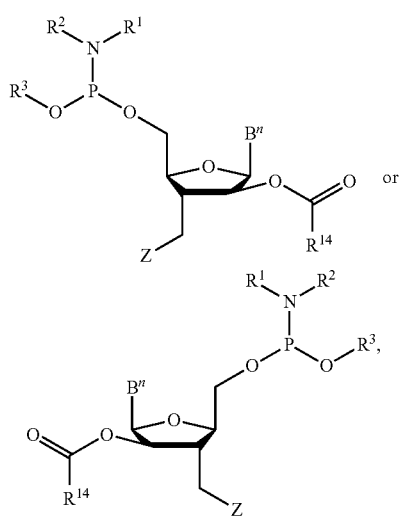

or a salt thereof.

16. The compound of claim 15, wherein $R^3$ is —CH$_2$CH$_2$CN.

17. The compound of claim 16, wherein the compound is represented by one of the following structural formulas:

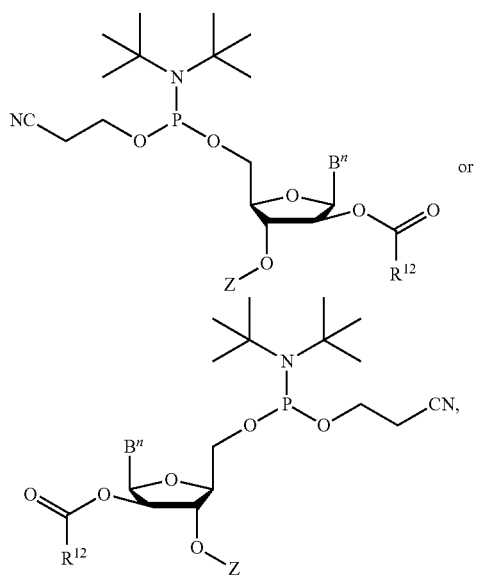

or a salt thereof.

18. The compound of claim 1, wherein the compound is represented by one of the following structural formulas:

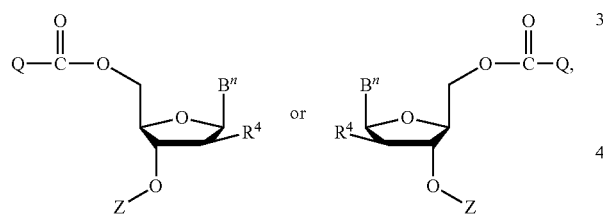

or a salt thereof.

19. The compound of claim 18, wherein the compound is represented by one of the following structural formulas:

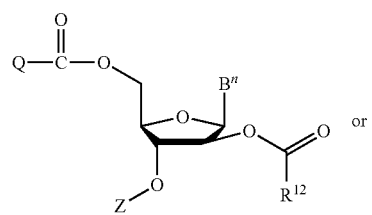

or a salt thereof.

20. The compound of claim 1, wherein the compound is represented by one of the following structural formulas:

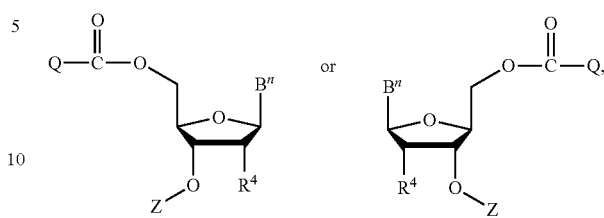

or a salt thereof.

21. The compound of claim 20, wherein the compound is represented by one of the following structural formulas:

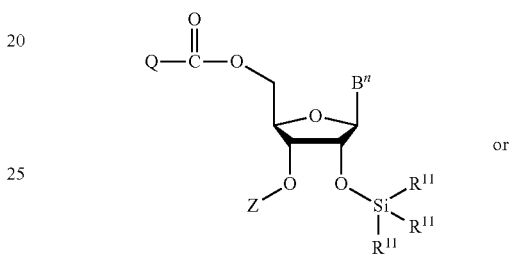

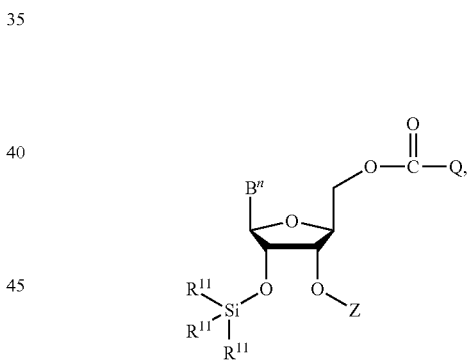

or a salt thereof.

22. A method of preparing an oligonucleotide by bond formations in the 5'- to 3'-direction for the synthesis of RNA oligomers and enantiomers thereof, said method comprises the following steps a) cleavage of Z from a compound represented by the following structural formula:

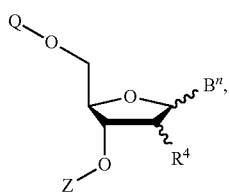

thereby forming a compound represented by structural formula (XX):

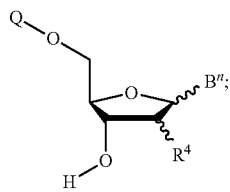

(XX)

b) reacting the compound represented by structural formula XX with a compound of structural formula XXI:

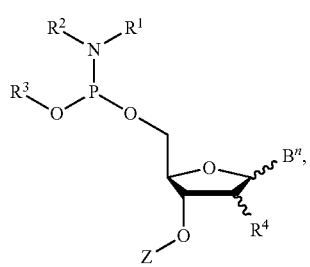

(XXI)

thereby forming 2-mer compound represented by the following structural formula:

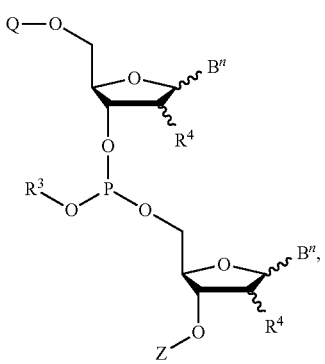

c) reacting the 2-mer compound with a capping agent;

d) oxidizing or sulfurizing the trivalent phosphorous group of the 2-mer compound to form a compound of structural formula XXII:

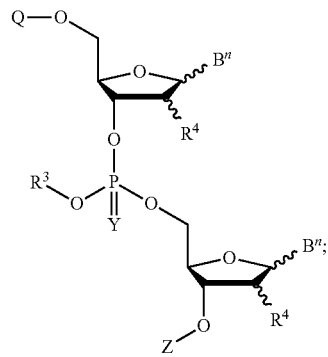

(XXII)

e) cleavage of Z from the compound represented by structural formula XXII, thereby forming a compound of structural formula XXIII:

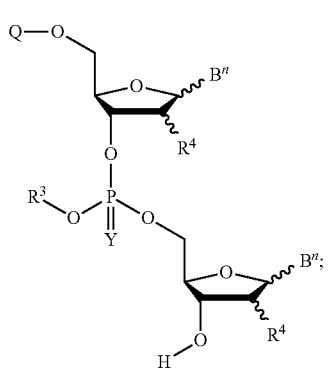

(XXIII)

f) reacting the compound represented by structural formula XXIII with a compound represented by the following structural formula:

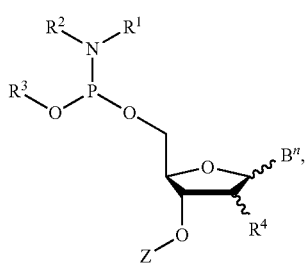

thereby forming a 3-mer represented by the following structural formula XXIV:

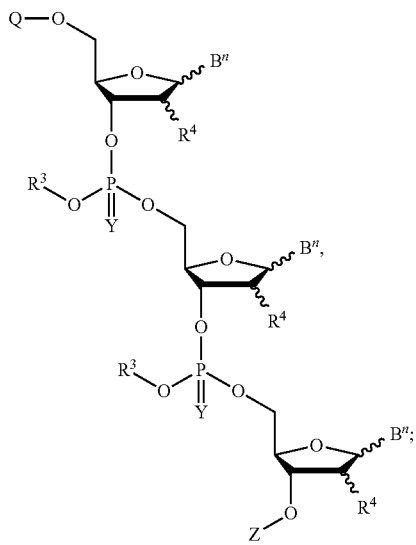

g) cleavage of Z from the compound represented by structural formula XXIV;

h) repeating steps a) through g) n times, thereby forming a oligonucleotide represented by the following structural formula:

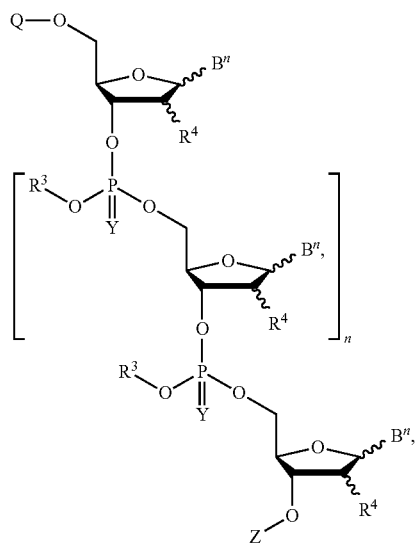

or a salt thereof, wherein:

Q is a support comprised of: a) a linking group and a spacer that can be cleaved to form a hydroxy group; or b) an aliphatic chain, aromatic group, substituted or unsubstituted aromatic, a substituted or unsubstituted phenoxy, or levulinyl;

each $R^1$ is independently a substituted or unsubstituted $(C_1\text{-}C_{12})$alkyl group, a substituted or unsubstituted $(C_3\text{-}C_{20})$cycloalkyl group, or a substituted or unsubstituted $(C_3\text{-}C_{20})$cycloalkyl$(C_1\text{-}C_{12})$alkyl group, wherein the alkyl or cycloalkyl groups optionally include intervening heteroatoms independently selected from NH, $NR^7$, O and S;

each $R^2$ is independently a substituted or unsubstituted $(C_1\text{-}C_{12})$alkyl group, a substituted or unsubstituted $(C_3\text{-}C_{20})$cycloalkyl group, or a substituted or unsubstituted $(C_3\text{-}C_{20})$cycloalkyl$(C_1\text{-}C_{12})$alkyl group, wherein the alkyl or cycloalkyl groups optionally include intervening heteroatoms independently selected from NH, $NR^7$, O and S;

or each occurrence of $R^1$ and $R^2$ taken together with the nitrogen atom to which they are bound independently forms a 4-7 membered non-aromatic heterocyclyl, wherein the heterocyclyl formed may optionally include intervening heteroatoms independently selected from NH, $NR^7$, O and S;

each $R^3$ is independently a phosphate protecting group;

each $R^4$ is independently a -halo, $-R^5$, $-NR^7R^8$, $-OR^9$, $-SR^{10}$, or 2'-blocking group; or when a 1-mer is in the β-D-ribose, β-L-ribose, α-D-ribose or α-L-ribose configuration, wherein $R^4$ is further selected from $O-Si(R^{11})_3$ or $O-CH_2-Si(R^{11})_3$; or when a 1-mer is in the β-D-arabinose, β-L-arabinose, α-D-arabinose or α-L-arabinose configuration, $R^4$ is further selected from $-OC(=O)R^{12}$;

each $R^5$ is independently a substituted or unsubstituted $(C_1\text{-}C_{12})$alkyl group, a substituted or unsubstituted $(C_2\text{-}C_{12})$alkenyl group, a substituted or unsubstituted $(C_2\text{-}C_{12})$alkynyl group, or a substituted or unsubstituted phenyl, wherein the alkyl, alkenyl, alkynyl and the phenyl groups optionally includes intervening heteroatoms independently selected from NH, $NR^S$, O and S; and may optionally terminate with $-NR^7R^8$, $(C_1\text{-}C_4)$alkylamino, di$(C_1\text{-}C_4)$alkylamino, $-OR^9$, $(C_1\text{-}C_6)$alkoxy, benzyl or substituted benzyl, $-SR^{10}$; or $-S-(C_1\text{-}C_6)$alkyl group;

each $R^7$ is independently a fluorenylmethyloxycarbonyl; $-C(=O)-(CH_2)_{1-16}NR^8C(=O)CF_3$; $-C(=O)-(CH_2)_{1-16}NR^8C(=O)$-phthalimide; $-C(=O)-(CH_2)_{1-16}$-phthalimide; $NR^8C(=O)$-phthalimide; a substituted or unsubstituted $(C_1\text{-}C_{12})$alkyl group, a substituted or unsubstituted $(C_2\text{-}C_{12})$alkenyl group, or a substituted or unsubstituted $(C_2\text{-}C_{12})$alkynyl group;

each $R^8$ is independently H or a substituted or unsubstituted $(C_1\text{-}C_{12})$alkyl group, a substituted or unsubstituted $(C_2\text{-}C_{12})$alkenyl group, or a substituted or unsubstituted $(C_2\text{-}C_{12})$alkynyl group;

each $R^9$ is independently $-C(=O)-(CH_2)_{1-16}CH_3$; a substituted or unsubstituted $(C_2\text{-}C_{12})$alkenyl group, or a substituted or unsubstituted $(C_2\text{-}C_{12})$alkynyl group;

each $R^{10}$ is independently $-S(C_1\text{-}C_6)$alkyl, $-C(=O)-(CH_2)_{1-16}CH_3$; a substituted or unsubstituted $(C_2\text{-}C_{12})$alkenyl group, or a substituted or unsubstituted $(C_2\text{-}C_{12})$alkynyl group;

each $R^{11}$ is independently a substituted or unsubstituted $(C_1\text{-}C_{12})$alkyl group, a substituted or unsubstituted $(C_2\text{-}C_{12})$alkenyl group, or a substituted or unsubstituted $(C_2\text{-}C_{12})$alkynyl group;

each $R^{12}$ is independently a substituted or unsubstituted $(C_1\text{-}C_{12})$alkyl group, a substituted or unsubstituted $(C_2\text{-}C_{12})$alkenyl group, or a substituted or unsubstituted $(C_2\text{-}C_{12})$alkynyl group, or a substituted or unsubstituted aryl group;

each Z is independently an unsubstituted or substituted aryl group, an unsubstituted or substituted triarylmethyl group, an unsubstituted or substituted trityl group, an unsubstituted or substituted tetrahydropyranyl group, or an unsubstituted or substituted 9-phenylxanthyl;

each $B''$ is independently hydrogen or an optionally substituted nucleobase optionally functionalized at each exocyclic amine with an amine protecting group, wherein the nucleobase is independently selected from:

N6,N6-dimethyl adenine, N1 methyladenine, 7-deazaadenine, 7-deaza-8-azaadenine, 3-deazaadenine, ethenoadenine, isoguanine, N1-methylguanine, 7-iodo-7-deazaguanine, 7-deaza-7-iodoadenine, 7-deaza-7-iodo-6-oxopurine, 5-iodo-5-methyl-7-deazaguanine, 7-deazaguanine substituted with —C≡C(CH$_2$)$_{1-8}$-pthlamide, 7-deaza-8-azaguanine, 8-methylguanine, 8-bromoguanine, 8-aminoguanine, hypoxanthine, 6-methoxypurine, 7-deaza-6-oxopurine, 6-oxopurine, 2-aminopurine, 2,6-diaminopurine, 8-bromopurine, 8-aminopurine, 8-alkylaminopurine, 8-alkylaminopurine, thymine, N-3 methyl thymine, 5-acetoxymethylcytosine, 5-azacytosine, isocytosine, N-4(C$_1$-C$_6$)alkylcytosine, N-3(C$_1$-C$_6$)alkylcytidine, 5-propynylcytosine, 5-iodo-cytosine, 5-(C$_1$-C$_6$)alkylcytosine, 5-aryl(C$_1$-C$_6$) alkylcytosine, 5-trifluoromethylcytosine, 5-methylcytosine, ethenocytosine, cytosine and uracil substituted with —CH=CH—C(=O)NH(C$_1$-C$_6$)alkyl, cytosine and uracil substituted with —C≡C—CH$_2$-phthalimide, NH(C$_1$-C$_6$)alkyl, 4-thiouracil, 2-thiouracil, N$^3$-thiobenzoylethyluracil, 5-propynyluracil, 5-acetoxymethyluracil, 5-fluorouracil, 5-chlorouracil, 5-bromouracil, 5-iodouracil, N-3-(C$_1$-C$_6$)alkyluracil, 5-(3-aminoallyl)-uracil, 5-(C$_1$-C$_6$)alkyluracil, 5-aryl(C$_1$-C$_6$)alkyluracil, 5-trifluoromethyluracil, 4-triazolyl-5-methyluracil, 2-pyridone, 2-oxo-5-methylpyrimidine, 2-oxo-4-methylthio-5-methylpyrimidine, 2-thiocarbonyl-4-oxo-5-methylpyrimidine, and 4-oxo-5-methylpyrimidine;

wherein any substitutable nitrogen atom within the nucleobase or on the exocyclic amine is optionally and independently substituted with fluorenylmethyloxycarbonyl; —C(=O)OPh; —C(=O)(C$_1$-C$_{16}$)alkyl; —C(=O) CH$_2$CH$_2$CH=CH$_2$I; —C(=O)(C$_1$-C$_{16}$)alkylene-C(=O)OH; —C(=O)(C$_1$-C$_{16}$)alkylene-C(=O)O(C$_1$-C$_6$)alkyl; =CR$^8$N(C$_1$-C$_6$)alkyl)$_2$; —C(=O)—NR$^8$—(CH$_2$)$_{1-16}$NR$^8$C(=O)CF$_3$; —C(=O)—(CH$_2$)$_{1-16}$NR$^8$C(=O)CF$_3$; —C(=O)—NR$^8$—(CH$_2$)$_{1-16}$NR$^8$C(=O)-phthalimide; —C(=O)—(CH$_2$)$_{1-16}$-phthalimide; and

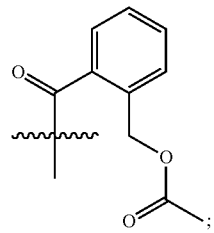

wherein any substitutable oxygen atom within the nucleobase is optionally and independently substituted with —C(=O)N(C$_1$-C$_6$alkyl)$_2$-C(=O)N(phenyl)$_2$; and n is 1 to 150.

23. The method of claim 22, wherein each Y group is independently introduced via sulfurization to form a phosphorothioate linkage or via oxidation to form a phosphate linkage.

24. The method of claim 23, wherein the R$^3$ group is eliminated after oxidation to form a phosphate linkage.

25. The method of claim 23, wherein the R$^3$ group is eliminated after sulfurization to form a phosphorothioate linkage.

26. The method of claim 25, wherein the nucleobase protecting groups are deprotected with a base.

27. The method of claim 26, wherein the base is selected from aqueous ammonia, methanolic ammonia, or ethanolic ammonia.

28. The method of claim 26, wherein R$^4$ is —OSi(R$^{11}$)$_3$.

29. The method of claim 28, wherein the method further comprises the step of cleaving —Si(R$^{11}$)$_3$ from —OSi(R$^{11}$)$_3$ with a fluoride salt.

30. The method of claim 29, wherein the fluoride salt is tetraethylammonium fluoride.

31. The method of claim 22, further comprising the step of reacting the compound represented by the following structural formula:

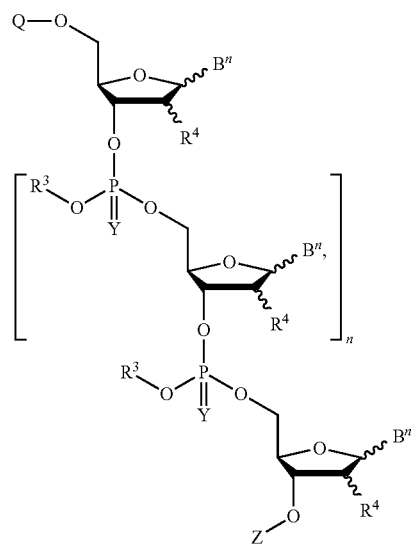

with a 3' functional group, thereby forming a compound represented by the following structural formula:

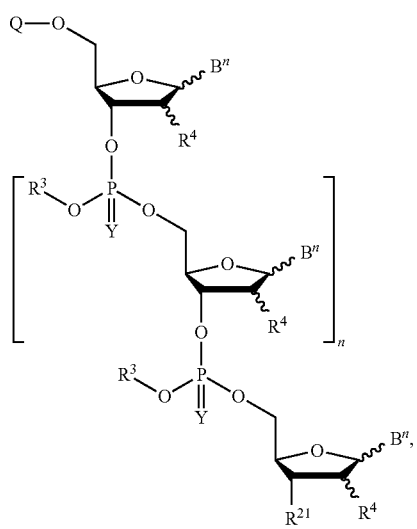

wherein R$^{21}$ is the 3' functional group or a salt thereof.

32. The method of claim 31, wherein $R^{21}$ is
a) cyanoethyl phosphate-polyethylene glycols', where v is 2-100 and is number of glycol units;
b) cyanoethyl phosphate-linker attached with cholesterol, biotin, fluorescein, cyanine dye, psoralen, tetramethylrhodamine dye, dabcyl dye, C-3 disulfide, C-6 disulfide, symmetrical and asymmetrical hydrocarbon chain ($C_2$-$C_{50}$), symmetrical and asymmetrical hydrocarbon chain ($C_2$-$C_{50}$) with a terminal amino group protected with $CF3C(=O)$ or phthalamido or FMOC, ($C_1$-$C_{16}$)alkylene-amine protected with a amine protecting group, ($C_1$-$C_5$)alkylene-amine protected with an azide group; ($C_1$-$C_5$)alkylene-amine protected with a C≡CH group;
c) cyanoethyl phosphate-ethane-2-ol-protected with DMT group or other acid labile group, cyanoethyl phosphate-propane-3-ol-protected with DMT group or other acid labile group;
d) ($C_1$-$C_{50}$)alkylene with a terminal hydroxy;
e) lipid, carboxyl group, or peptide; or
f) a branched phosphoramidite.

\* \* \* \* \*

UNITED STATES PATENT AND TRADEMARK OFFICE
CERTIFICATE OF CORRECTION

PATENT NO. : 8,541,569 B2
APPLICATION NO. : 12/708827
DATED : September 24, 2013
INVENTOR(S) : Suresh C. Srivastava and Naveen P. Srivastava It is certified that error appears in the above-identified patent and that said Letters Patent is hereby corrected as shown below:

In the Claims:

Claim 1, Column 113, Line 46, delete "N-1 methyladenine" and insert -- N-1-methyladenine --.

Claim 1, Column 114, Line 12, delete "—" before the ";".

Claim 3, Column 117, Lines 54 - 60, delete the structures and replace them with:

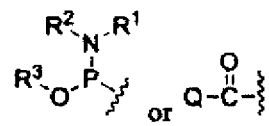

Claim 14, Column 120, Lines 20 - 40, delete the structures and replace them with:

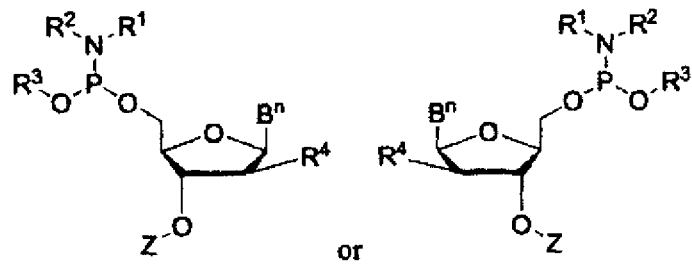

Claim 15, Column 120, Lines 45 - 65, delete the structures and replace them with:

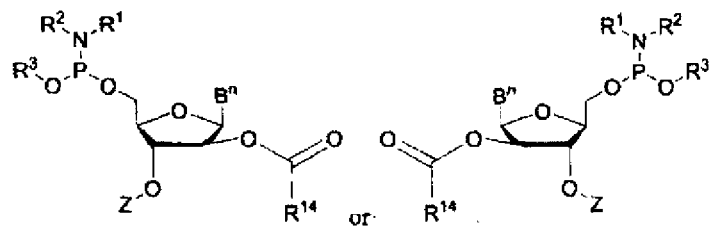

Signed and Sealed this
First Day of July, 2014

Michelle K. Lee
*Deputy Director of the United States Patent and Trademark Office*

CERTIFICATE OF CORRECTION (continued)
U.S. Pat. No. 8,541,569 B2

Claim 22, Column 126, Line 33, delete "$NR^S$" and insert -- $NR^5$ --.

Claim 22, Column 127, Line 7, delete "N1 methyladenine" and insert -- N1-methyladenine --.

Claim 32, Column 129, Line 2, delete "glycols'" and insert -- $glycols^v$ --.